United States Patent
Dower et al.

(10) Patent No.: US 11,999,771 B2
(45) Date of Patent: *Jun. 4, 2024

(54) IL-7Rαγc LIGAND IMMUNOGLOBULIN FUSION PROTEINS

(71) Applicant: MEDIKINE, INC., Menlo Park, CA (US)

(72) Inventors: William J. Dower, Menlo Park, CA (US); Ronald W. Barrett, Menlo Park, CA (US); Michael C. Needels, Menlo Park, CA (US); Steven E. Cwirla, Menlo Park, CA (US); Alice V. Bakker, Menlo Park, CA (US); Inkyung Park, Menlo Park, CA (US)

(73) Assignee: Medikine, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,567

(22) Filed: Dec. 5, 2022

(65) Prior Publication Data

US 2023/0322880 A1 Oct. 12, 2023

Related U.S. Application Data

(60) Provisional application No. 63/328,700, filed on Apr. 7, 2022.

(51) Int. Cl.
| | | |
|---|---|---|
| *C07K 14/54* | (2006.01) | |
| *A61K 38/20* | (2006.01) | |
| *A61K 38/00* | (2006.01) | |
| *C07K 7/08* | (2006.01) | |
| *C07K 14/715* | (2006.01) | |

(52) U.S. Cl.
CPC ...... *C07K 14/5418* (2013.01); *A61K 38/2046* (2013.01); *A61K 38/00* (2013.01); *C07K 7/08* (2013.01); *C07K 14/7155* (2013.01); *C07K 2319/30* (2013.01)

(58) Field of Classification Search
CPC ............ C07K 14/5418; C07K 14/7155; C07K 2319/30; A61K 38/204
See application file for complete search history.

(56) References Cited

U.S. PATENT DOCUMENTS

| | | | |
|---|---|---|---|
| 5,635,597 A | 6/1997 | Barrett et al. | |
| 9,861,705 B2 | 1/2018 | Bossard et al. | |
| 10,035,836 B1 | 7/2018 | Greve | |
| 10,689,417 B2 | 6/2020 | Dower et al. | |
| 10,703,776 B2 | 7/2020 | Dower et al. | |
| 11,248,030 B2 | 2/2022 | Dower et al. | |
| 11,254,729 B2 | 2/2022 | Dower et al. | |
| 11,746,139 B2 | 9/2023 | Dower et al. | |
| 2003/0166163 A1 | 9/2003 | Gillies | |
| 2005/0054054 A1 | 3/2005 | Foss et al. | |
| 2006/0141581 A1 | 6/2006 | Gillies et al. | |
| 2009/0104218 A1 | 4/2009 | Tettelin et al. | |
| 2011/0243887 A1 | 10/2011 | Lauder et al. | |
| 2013/0330296 A1 | 12/2013 | Khaled | |
| 2017/0327555 A1 | 11/2017 | Greve | |
| 2018/0125941 A1 | 5/2018 | Greve | |
| 2018/0162919 A1 | 6/2018 | Greve et al. | |
| 2018/0362655 A1 | 12/2018 | Wang et al. | |
| 2019/0119346 A1 | 4/2019 | Garcia et al. | |
| 2019/0153058 A1 | 5/2019 | Greve | |
| 2019/0194255 A1 | 6/2019 | Tagaya et al. | |
| 2019/0202881 A1 | 7/2019 | Greve | |
| 2019/0202882 A1 | 7/2019 | Greve | |
| 2020/0040034 A1 | 2/2020 | Dower et al. | |
| 2020/0040036 A1 | 2/2020 | Dower et al. | |
| 2020/0291066 A1 | 9/2020 | Dower et al. | |
| 2020/0291067 A1 | 9/2020 | Dower et al. | |
| 2021/0130424 A1 | 5/2021 | Dower et al. | |
| 2021/0198336 A1 | 7/2021 | Dower et al. | |
| 2021/0253669 A1 | 8/2021 | Dower et al. | |
| 2021/0253670 A1 | 8/2021 | Dower et al. | |
| 2022/0119465 A1 | 4/2022 | Dower et al. | |
| 2022/0119492 A1 | 4/2022 | Dower et al. | |
| 2022/0119493 A1 | 4/2022 | Dower et al. | |
| 2023/0357358 A1 | 11/2023 | Dower et al. | |

FOREIGN PATENT DOCUMENTS

| | | |
|---|---|---|
| JP | 2017528444 | 9/2017 |
| TW | 201833137 | 9/2018 |
| WO | 2010/099084 | 9/2010 |
| WO | 2017/068421 | 4/2017 |
| WO | 2017/136818 | 8/2017 |
| WO | 2020/033312 A1 | 2/2020 |
| WO | 2021/092075 A1 | 5/2021 |
| WO | 2021/092081 A1 | 5/2021 |
| WO | WO-2021122866 A1 | 6/2021 |
| WO | 2021/158619 A1 | 8/2021 |
| WO | 2021/158623 A1 | 8/2021 |
| WO | 2022/098890 A1 | 5/2022 |
| WO | WO-2023196876 A1 | 10/2023 |

OTHER PUBLICATIONS

International Preliminary Report on Patentability for Application No. PCT/US2020/035747, dated Dec. 7, 2021, 11 pages.
International Preliminary Report on Patentability for Application No. PCT/US2020/058963, dated May 10, 2022, 7 pages.
International Preliminary Report on Patentability for Application No. PCT/US2019/045109, dated Feb. 9, 2021, 10 pages.
International Preliminary Report on Patentability for Application No. PCT/US2021/016356, dated Jul. 28, 2022, 7 pages.
International Preliminary Report on Patentability for Application No. PCT/US2021/016361, dated Jul. 28, 2022, 6 pages.
International Preliminary Report on Patentability for Application No. PCT/US2020/058969, dated May 10, 2022, 8 pages.

(Continued)

*Primary Examiner* — Zachary C Howard
(74) *Attorney, Agent, or Firm* — COOLEY LLP

(57) ABSTRACT

IL-7Rαγc ligands and IL-7Rαγc IgG-Fc fusion proteins are disclosed. The IL-7Rαγc ligands and IL-7Rαγc IgG-Fc fusion proteins are IL-7R agonists.

29 Claims, 37 Drawing Sheets
Specification includes a Sequence Listing.

(56) References Cited

OTHER PUBLICATIONS

International Preliminary Report on Patentability for Application No. PCT/US2021/058085, dated May 8, 2023, 8 pages.
Burtea et al., "Screening for peptides targeted to IL-7Ra for molecular imaging of rheumatoid arthritis synovium", Arthritis Research & Therapy, Oct. 2016, vol. 18, No. 1, 230, 19 pages.
Partial International Search for PCT Application No. PCT/US2019/045109, dated Nov. 5, 2019, 17 pages.
International Search Report and Written Opinion for PCT Application No. PCT/US2019/045109, dated Jan. 14, 2020, 20 pages.
International Search Report and Written Opinion for PCT Application No. PCT/US2020/058963, dated Apr. 7, 2021, 12 pages.
International Search Report and Written Opinion for PCT Application No. PCT/US2021/016356, dated Jul. 13, 2021, 12 pages.
International Search Report and Written Opinion for PCT Application No. PCT/US2021/016361, dated Jul. 15, 2021, 12 pages.
International Search Report and written Opinion for PCT Application No. PCT/US2020/058969, dated Apr. 6, 2021, 14 pages.
International Search Report and Written Opinion for PCT Application No. PCT/US2021/058085, dated Jun. 2, 2022, 14 pages.
Betts et al., "Chapter 14: Amino Acid Properties and Consequences of Substitutions, Bioinformatics for Geneticists", 2003, Barnes and Gray Eds., 28 pages.
Burtea et al., "Screening for peptides targeted to IL-7Ra for molecular imaging of rheumatoid arthritis synovium", Arthritis Res Therapy, Oct. 2016, vol. 18, No. 1, 230, 19 pages.
Chen et al., "Fusion Protein Linkers: Property, Design and Functionality", Advanced Drug Delivery Reviews, Oct. 2013, vol. 65, No. 10, pp. 1357-1369.
Dower et al., "MDK/MDK-701: A potent fully efficacious peptidyl agonist of IL-7Rαγc, designed with no reference to cytokine or receptor structure and unrelated to IL-7, fused to an FC-domain for PK enhancement", Journal for ImmunoTherapy of Cancer, 2020, vol. 8, Issue 3, pp. A341-A342.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," OncoImmunology, 2017, vol. 6, No. 3, e1277306, 15 pages.
Levin et al., "Exploiting a natural conformational switch to engineer an interleukin-2 'superkine'," Nature, Apr. 2012, vol. 484, p. 529-533.
McElroy et al., "Structural reorganization of the interleukin-7 signaling complex", PNAS, 2012, vol. 109, No. 7, pp. 2503-2508.
Mitra et al., "Interleukin-2 Activity can be Fine-Tuned with Engineered Receptor Signaling Clamps," Immunity, May 2015, vol. 42, No. 5, 29 pages.
Moors et al., "Interneukin-7 (IL-7) and IL-7 splice variants affect differentiation of human neural progenitor cells", Genes and Immunity, 2010, vol. 11, pp. 11-20.
Pulliam et al., "Common gamma chain cytokines in combinatorial immune strategies against cancer," Immunology Letters, 2016, vol. 169, p. 61-72.

Rodriguez et al., "Hypothetical protein EBU92_10635 [Betaproteobacteria bacterium]", Genbank online entry, National Center for Biotechnology Information, retrieved from URL [ https://www.ncbi.nlm.nih.gov/protein/NBO41957.1 ] retrieved on Jan. 12, 2020, 2 pages.
Silva et al., "De novo design of potent and selective mimics of IL-2 and IL-15", Nature, Jan. 2019, 565(7738), pp. 186-191.
UNIPROTKB Accession No. A0A227JM75, Oct. 25, 2017, retrieved from URL [https://www.uniprot.org/uniprot/A0A227JM75], entire document retrieved on Mar. 22, 2021, 5 pages.
UNIPROTKB Accession No. A0A444GHQ1, May 8, 2019, retrieved from URL [https://www.uniprot.org/uniprot/A0A444GHQ1], entire document retrieved on Jun. 12, 2021, 3 pages.
UNIPROTKB Accession No. A0A0N1IMW7, Dec. 9, 2015, retrieved from URL [https://www.uniprot.org/uniprot/A0A0N1IMW7], entire document retrieved on Jun. 12, 2021, 3 pages.
UNIPROTKB Accession No. A0A2D7IYS8, Apr. 25, 2018, retrieved from URL [https://www.uniprot.org/uniprot/A0A2D7IYS8], entire document retrieved on Mar. 19, 2021, 3 pages.
UNIPROTKB Accession No. A0A1D1ZF92, Nov. 30, 2016, retrieved from URL [https://www.uniprot.org/uniprot/A0A1D1ZF92], retrieved on Mar. 19, 2021, 3 pages.
Cooper M, et al., "A Long-Acting Pharmacological Grade Interleukin-7 Molecule Logarithmically Accelerates Cart Proliferation, Differentiation, and Tumor Killing", Biol Blood Marrow Transplant, 25(3 Suppl), 223, 2019, pp. S163-S164.
International Search Report and Written Opinion for PCT Application No. PCT/US2023/065402, dated Apr. 8, 2023, 14 pages.
Kim, Ji-Hae et al., "Hybrid Fc-fused interleukin-7 induces an inflamed tumor microenvironment and improves the efficacy of cancer immunotherapy," Clin Transl Immunology. (2020); 9(9):e1168, 16 pages.
McElroy C A et al., "Structural and Biophysical Studies of the Human IL-7/IL-7Ralpha Complex", Structure, 17(1), 2009, pp. 54-65.
NCBI Reference Sequence: NP_000197.1, "cytokine receptor common subunit gamma precursor [*Homo sapiens*]," Nov. 27, 2023 [retrieved online Dec. 9, 2023] https://www.ncbi.nlm.nih.gov/protein/NP_000197.1/, 4 pages.
NCBI Reference Sequence: NP_002176.2: interleukin-7 receptor subunit alpha isoform 1 precursor [*Homo sapiens*], Dec. 25, 2023; [retrieved online Dec. 26, 2023] URL: https://www.ncbi.nlm.nih.gov/protein/NP_002176.2/, 4 pages.
NCBI Reference Sequence: XP_005593949.1: cytokine receptor common subunit gamma [Macaca fascicularis], Dec. 8, 2021; ; [retrieved online Dec. 26, 2023] URL: https://www.ncbi.nlm.nih.gov/protein/XP_005593949, 2 pages.
Park, Angie I., et al.; "Abstract 2066: In vitro and in vivo properties of MDK703: An Fc-peptide fusion IL-7Rαγc agonist unrelated in structure to IL-7," Cancer Res (2022) 82 (12_Supplement):2066, 1 page.
UniProtKB/Swiss-Prot: P16871.3, Interleukin-7 receptor subunit alpha, Nov. 3, 2023, [retrieved online Dec. 27, 2023] URL: https://www.ncbi.nlm.nih.gov/protein/P16871, 8 pages.

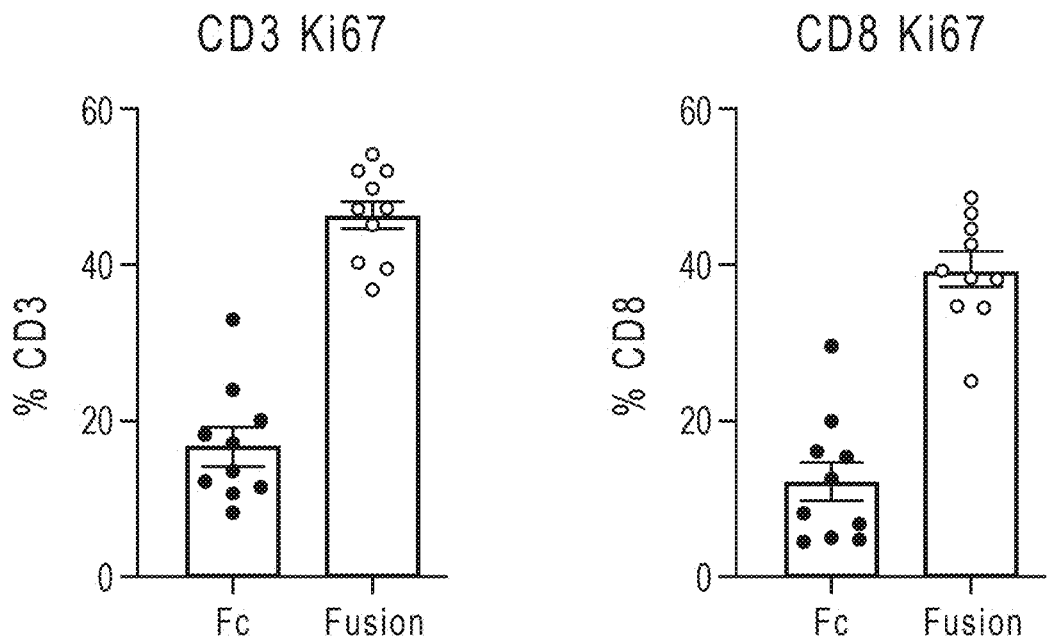
FIG. 18A
FIG. 18B
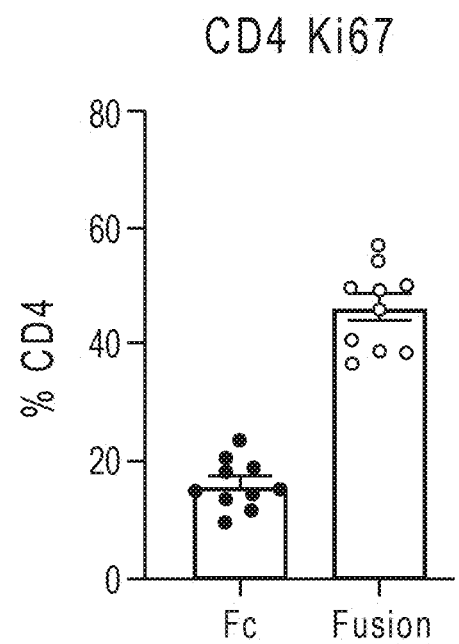
FIG. 18C

IL-7Rαγc LIGAND IMMUNOGLOBULIN FUSION PROTEINS

This application claims the benefit under 35 U.S.C. § 119(e) of U.S. Provisional Application No. 63/328,700 filed on Apr. 7, 2022, which is incorporated by reference in its entirety.

FIELD

The present disclosure relates to IL-7Rαγc ligands and IL-7Rαγc IgG-Fc fusion proteins. The IL-7Rαγc ligands and IL-7Rαγc IgG-Fc fusion proteins are IL-7R agonists.

SEQUENCE LISTING

The present application contains a Sequence Listing which is included with this application and a copy of the Sequence Listing will be submitted electronically in XML format and is incorporated by reference in its entirety. The XML copy, created on Nov. 16, 2022, is named 62AJ-001410US-362859_SL.xml and is 207,077 bytes in size.

BACKGROUND

Interleukin-7 (IL-7) is required for the development and maintenance of T-cell homeostasis and plays an important role in the establishment of the B-cell repertoire. Unlike most interleukins, IL-7 is primarily produced by non-hematopoietic stromal cells rather than leukocytes. Under normal conditions, free IL-7 levels are limiting, but accumulate during lymphopenia, leading to increased T cell proliferation and replenishment of T-cell populations. Under certain physiological conditions, recombinant human IL-7 administered to humans, non-human primates, and mice produces widespread T cell proliferation, increased T cell numbers, modulation of peripheral T cell subsets, and increased T cell receptor repertoire diversity. These effects may be therapeutically useful in a variety of clinical settings.

IL-7 is a member of the common γ chain (γc, CD132) family of cytokines that includes interleukin-2 (IL-2), IL-4, IL-7, IL-9, IL-15, and IL-21. IL-7 signals via an active complex formed with its unique α-receptor, IL-7Rα (CD127), and the common γc receptor (Rγc). Receptor activation leads to signaling through an array of pathways, including JAK-STAT, P13K-AKT, and Src kinases.

The IL-7Rα receptor subunit exists in two states: a full-length membrane-bound form that, with Rγc, mediates IL-7R signal transduction; and soluble (alternatively-spliced, secreted, or shed) forms of the extracellular domain that may provide regulation of extracellular IL-7 levels and modulation of IL-7R signaling.

The cell surface signaling-competent form of IL-7Rα is expressed on most resting T-cells and is down regulated upon T-cell activation, while naïve memory T-cells continue to express IL-7Rα; and regulatory cells typically express very low levels of IL-7Rα. IL-7R signaling is necessary for long-term maintenance of T cell populations, in part, by modulating apoptosis. Both CD4+ and CD8+ memory T-cells are dependent on IL-7 for long-term survival.

Emerging evidence suggests IL-7R agonists may be useful in immuno-oncology therapy. For example, IL-7 is effective in increasing cytotoxic CD8+ T lymphocytes (CD8+ T-cell), and long-term tumor antigen-specific CD8+ T-cell responses are enhanced by IL-7 treatment.

IL-7 exhibits inhibitory effects in tumors such as glioma, melanoma, lymphoma, leukemia, prostate cancer, and glioblastoma; and administration of IL-7 in murine tumor models has shown decreased cancer cell growth. IL-7 has been shown to enhance the antitumor effect of interferon-γ (IFNγ) in rat glioma tumors, and can induce the production of IL-1α, IL-1β, and TNF-α by monocytes, which can inhibit tumor growth.

IL-7 has been shown to have potential in the treatment of lymphopenias, septic shock, and infectious disease as well immune deficiencies of aging (immuno-senescence), and enhancement of response to vaccination. IL-7 prevents or reverses T-cell exhaustion and induces rejuvenation and increased activity of transferred CAR-T cells. IL-7 is currently being studied to prevent or reverse lymphopenia associated with COVID-19. IL-7/IL-7R signaling has also been implicated in autoimmune diseases, chronic inflammatory diseases, and cancer, and therefore therapeutic targeting of the IL-7/IL-7R pathway is expected to have clinical benefit.

Importantly, the administration of recombinant IL-7 has been found to be well tolerated in clinical trials.

SUMMARY

According to the present invention, IL-7Rαγc ligands comprise an Il-7Rα ligand comprising an amino acid sequence of SEQ ID NO: 1 or an amino acid sequence having greater than 70% sequence similarity to any one of SEQ ID NO: 1; and an Rγc ligand comprising an amino acid sequence of SEQ ID NO: 11 or an amino acid sequence having greater than 70% sequence similarity to SEQ ID NO: 11.

According to the present invention, IL-7Rαγc IgG-Fc fusion proteins comprise an IgG-Fc fragment bound to an IL-7Rαγc ligand according to the present invention.

According to the present invention, pharmaceutical compositions comprise an IL-7Rαγc ligand according to the present invention.

According to the present invention, pharmaceutical compositions comprise an IL-7Rαγc IgG-Fc fusion protein according to the present invention.

According to the present invention, methods of treating a cancer, an inflammatory disease, an autoimmune disease, or a viral disease in a patient comprise administering to a patient in need of such treatment a therapeutically effective amount of an IL-7Rαγc ligand according to the present invention, or an IL-7Rαγc IgG-Fc fusion protein according to the present invention.

According to the present invention, methods of treating a cancer, an inflammatory disease, an autoimmune disease, or a viral disease in a patient comprise administering to a patient in need of such treatment a therapeutically effective amount of an IL-7Rαγc ligand according to the present invention, or an IL-7Rαγc IgG-Fc fusion protein according to the present invention.

According to the present invention, nucleic acids encode for an IL-7Rαγc ligand according to the present invention.

According to the present invention, nucleic acids encode for an IL-7Rαγc IgG-Fc fusion protein according to the present invention.

BRIEF DESCRIPTION OF THE DRAWINGS

The drawings described herein are for illustration purposes only. The drawings are not intended to limit the scope of the present disclosure.

FIGS. 18A-18E show T-cell and NK cell subpopulations in Ki-67+ cells from humanized mice treated with either a control Fc fragment or the IL-7Rαγc IgG2-Fc fusion protein having SEQ ID NO: 45.

DETAILED DESCRIPTION

Figure 1:
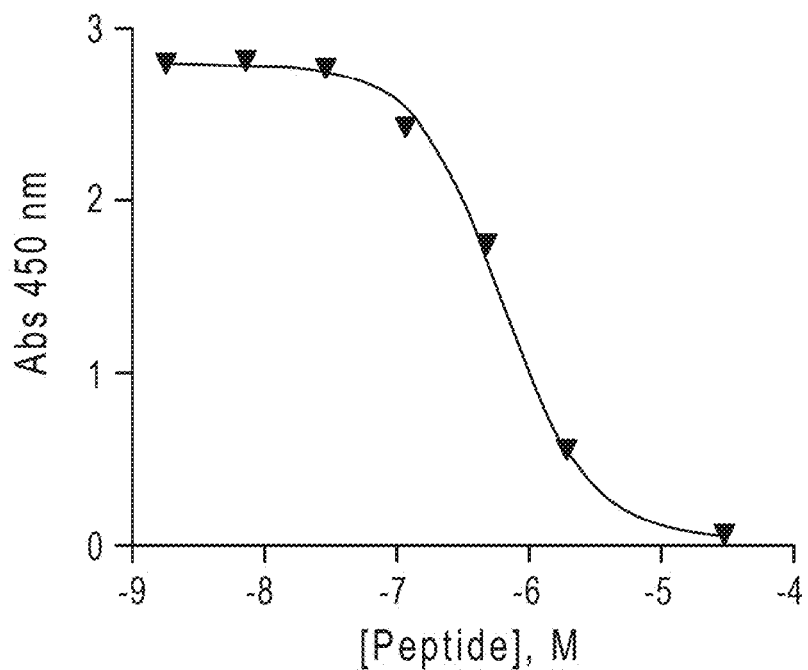
FIG. 1 shows competitive binding of an IL-7Rαγc ligand having SEQ ID NO: 30 to the hu-IL-7Rα subunit.

"Agonist" refers to a biologically active ligand that binds to its complementary biologically active receptor or subunit(s) and activates the receptor to cause a biological response mediated by the receptor, or to enhance a preexisting biological activity mediated by the receptor.

Amino acid residues are abbreviated as follows: alanine is Ala or A; arginine is Arg or R; asparagine is Asn or N; aspartic acid is Asp or D; cysteine is Cys or C; glutamic acid is Glu or E; glutamine is Gln or Q; glycine is Gly or G; histidine is His or H; isoleucine is Ile or I; leucine is Leu or L; lysine is Lys or K; methionine is Met or M; phenylalanine is Phe or F; proline is Pro or P; serine is Ser or S; threonine is Thr or T; tryptophan is Trp or W; tyrosine is Tyr or Y; and valine is Val or V.

"Conservative amino acid substitution" means that amino acids within each of the following groups can be substituted with another amino acid within the group: amino acids having a small hydrophobic side chain comprising alanine (A), glycine (G), proline (P), serine (S), and threonine (T); amino acids having a hydroxyl-containing side chain comprising serine (S), threonine (T), and tyrosine (Y); amino acids having an acidic side chain comprising aspartate (D) and glutamate (E); amino acids comprising a polar-neutral side chain comprising histidine (H), asparagine (N), glutamine (Q), serine (S), threonine (T), and tyrosine (Y); amino acids having a basic side chain comprising arginine (R), lysine (K), and histidine (H); amino acids having a large hydrophobic side chain comprising isoleucine (I), leucine (L), methionine (M), valine (V), phenylalanine (F), tyrosine (Y), and tryptophan (W)); and amino acids having an aromatic side chain comprising phenylalanine (F), histidine (H), tryptophan (W), and tyrosine (Y).

An "IL-7Rα ligand" refers to a peptide capable of binding to the IL-7Rα subunit of a mammalian IL-7 receptor, such as the IL-7Rα subunit (hu-IL-7Rα subunit) of the human IL-7 receptor (hu-IL-7 receptor), with an $IC_{50}$ of less than 100 μM as determined using an enzyme linked immunosorbant assay (ELISA) binding assay.

An "Rγc ligand" refers to a peptide capable of binding to the Rγc subunit of a mammalian IL-7 receptor, such the IL-7Rγc subunit (hu-IL-7Rγc subunit) of the human IL-7 receptor, with an $IC_{50}$ of less than 100 μM, as determined using ELISA binding assay.

An "IL-7Rαγc ligand" refers to a ligand consisting of or comprising one or more IL-7Rα ligands and one or more Rγc ligands. The one or more IL-7Rα ligands and one or more Rγc ligands can be bound together with an IL-7Rαγc ligand linker. An IL-7Rαγc ligand can comprise an IL-7Rαγc ligand comprising two or more IL-7Rαγc ligands, or an IL-7Rαγc ligand can comprise a single ligand that simultaneously binds to both the IL-7Rα subunit and to the IL-7Rγc subunit. An IL-7Rαγc ligand is capable of binding to a mammalian IL-7Rα subunit and to the IL-7Rγc subunit such as the hu-IL-7Rα subunit and to the hu-IL-7Rγc subunit of IL-7R with an $IC_{50}$ of less than 100 μM.

The "hu-IL-7Rα subunit" refers to the human (*Homo sapiens*) interleukin-7 receptor subunit α precursor NCBI Reference Sequence NP_002176.2.

The "hu-Rγc subunit" refers to the human (*Homo sapiens*) interleukin-7 receptor subunit γc precursor NCBI Reference Sequence NP_000197.1.

"Hu-IL-7R" refers to the human IL-7R receptor, which is a heterodimer, and consists of two subunits, interleukin-7 receptor-α (CD127) and common-γ chain receptor (CD132).

A recombinant "ligand fusion protein" refers to a protein made by recombinant DNA technology in which the translational reading frame of a ligand of a mammalian IL-7 receptor is fused to that of another protein, i.e., the IL-7R ligand fusion partner, to produce a single recombinant polypeptide. A ligand fusion protein can comprise an IL-7Rα ligand and a Rγc ligand and/or an IL-7Rαγc ligand. A fusion partner can be the Fc domain of an IgG molecule where the IL-7Rαγc ligand is bonded to one or to both of the two N-termini of the IgG CH3 domain. A ligand fusion protein can include a peptidyl fusion linker binding the IL-7Rαγc ligand to the IgG molecule, such that the peptidyl linker amino acid sequence is not derived from either the IL-7Rαγc ligand or from the IgG molecule. Peptidyl fusion linkers can be incorporated into fusion proteins as spacers to promote suitable protein folding and stability of the component protein moieties, to improve protein expression, and/or to impart bioactivity of the two fusion partners. Peptidyl linkers can include, for example, a flexible peptide or a rigid peptide.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a composition comprising an IL-7Rαγc ligand provided by the present disclosure and/or an IL-7Rαγc IgG-Fc fusion protein and at least one pharmaceutically acceptable vehicle with which the IL-7Rαγc ligand and/or an IL-7Rαγc IgG-Fc fusion protein is administered to a patient.

"Preventing" or "prevention" refers to a reduction in risk of acquiring a disease or disorder such as, for example, causing at least one of the clinical symptoms of the disease not to develop in a patient that may be exposed to or predisposed to the disease but does not yet experience or display symptoms of the disease. In some embodiments, "preventing" or "prevention" refers to reducing symptoms of the disease by taking the compound in a preventative fashion.

"Therapeutically effective amount" refers to the amount of a compound that, when administered to a patient for treating a disease, or at least one of the clinical symptoms of a disease, is sufficient to treat the disease or symptom thereof. A "therapeutically effective amount" may vary depending, for example, on the compound, the disease and/or symptoms of the disease, severity of the disease and/or symptoms of the disease or disorder, the age, weight, and/or health of the patient to be treated, and the judgment of a prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. In certain embodiments, "treating" or "treatment" refers to delaying the onset of the disease or at least one or more symptoms thereof in a patient who may be exposed to or predisposed to a disease or disorder even though that patient does not yet experience or display symptoms of the disease.

"Fc", "Fc region" or "Fc chain" refers to polypeptide comprising the constant region of an antibody, in some instances, excluding all or a portion of the first constant region immunoglobulin domain (e.g., CHI) or a portion thereof, and in some cases, further excluding all or a portion of the hinge. An Fc can refer to the last two constant region immunoglobulin domains (e.g., CH2 and CH3) of IgA, IgD, and IgG, the last three constant region immunoglobulin domains of IgE and IgM, and optionally, all or a portion of the flexible hinge N-terminal to these domains. For IgA and IgM, Fc may include the J chain. For IgG, the Fc chain comprises immunoglobulin domains CH2 and CH3 (Cγ2 and Cγ3), and optionally all or a portion of the hinge region between CHI (Cγ1) and CH2 (Cγ2). Although the boundaries of the Fc region may vary, the human IgG heavy chain Fc region is usually defined to include from residues E216, C226, or A231 to its carboxyl-terminus. An amino acid modification can be made to the Fc region, for example, to alter binding to one or more FcγR or to the FcRn. In EU numbering for human IgG1, the CH2-CH3 domain comprises amino acids 231 to 447, and the hinge comprises amino acids 216 to 230. Thus, the definition of Fc chain can include both amino acids 231-447 (CH2-CH3) or 216-447 (hinge-CH2-CH3), or fragments thereof. An Fc fragment can contain fewer amino acids from either or both of the N- and C-termini that retains the ability to form a dimer with another Fc chain or Fc fragment as can be detected using standard methods, generally based on size (e.g., non-denaturing chromatography, size exclusion chromatography, etc.). Human IgG-Fc fragments can be, for example, the Fc chain from human IgG1, human IgG2 or human IgG4.

"Heavy constant region" refers to the CH1-hinge-CH2-CH3 portion of an antibody or fragments thereof, excluding the variable heavy domain; in EU numbering of human IgG1, such as amino acids 118-447.

"Heavy chain constant region fragment" refers to a heavy chain constant region that contains fewer amino acids from either or both of the N- and C-termini that retains the ability to form a dimer with another heavy chain constant region.

"Immunoglobulin" refers to a protein having the structure of a naturally occurring antibody. For example, immunoglobulins of the IgG class are heterotetrameric glycoproteins of about 150,000 Da, having two light chains and two heavy chains that are bonded together through disulfide bonds. From N-to C-terminus, each heavy chain has a variable region (VH), also referred to as a variable heavy domain or a heavy chain variable domain, followed by three constant domains (CHI, CH2, and CH3), also called a heavy chain constant region. Similarly, from N- to C-terminus, each light chain has a variable region (VL), also referred to as a variable light domain or a light chain variable domain, followed by a constant light (CL) domain, also referred to as a light chain constant region. The heavy chain of an immunoglobulin may be assigned to one of five classes, called a (IgA), Ii (IgD), E (IgE), y (IgG), or μ (IgM), some of which may be further divided into subclasses, e.g., γ1 (IgG1), γ2 (IgG2), γ3 (IgG3), γ4(Gg4), α1 (IgA1) and α2 (IgA2). The light chain of an immunoglobulin may be assigned to one of two types, kappa (κ) or lambda (λ), based on the amino acid sequence of its constant domain. An immunoglobulin essentially consists of two Fab molecules and an Fc chain, linked via the immunoglobulin hinge region.

"Percent (%) sequence similarity" is determined by comparing the number of amino acids that are the same with respect to a reference peptide such as, for example, an IL-7Rα ligand, a Rγc ligand, an IL-7Rαγc ligand, or an IL-7Rαγc ligand IgG-Fc fusion protein. A peptide provided by the present disclosure can comprise, for example, greater than 70%, greater than 75%, greater than 80%, greater than 85%, greater than 90%, or greater than 95% sequence similarity to a reference peptide. For example, based on a reference peptide having SEQ ID NO: 201, peptides having SEQ ID NO: 202-207, have either 1, 2, 3, 4, or 5 amino acids in which an amino acid of the reference peptide has been substituted or replaced with the amino acid, alanine. Peptides having SEQ ID NO: 202-207 are characterized by a 95%, 90%, 85%, 80%, 75%, or 70% sequence similarity, respectively, to the reference peptide having SEQ ID NO: 201.

```
                                            SEQ ID NO: 201
    Y P C W L A R V G E L C D L D S G D V H

SEQ ID NO: 202
    A P C W L A R V G E L C D L D S G D V H

SEQ ID NO: 203
    A P C A L A R V G E L C D L D S G D V H

SEQ ID NO: 204
    A P C A L A A V G E L C D L D S G D V H

SEQ ID NO: 205
    A P C A L A A V G A L C D L D S G D V H

SEQ ID NO: 206
    A P C A L A A V G A L C D L A S G D V H

SEQ ID NO: 207
    A P C A L A A V G A L C D L A A G D V H
```

An IL-7Rα ligand, a Rγc ligand, an IL-7Rαγc ligand, or an IL-7Rαγc IgG-Fc fusion protein provided by the present disclosure can have an amino acid sequence in which, for example, from 1 to 10 amino acids such as from 1 to 5 amino acids of a reference amino acid sequence are substituted with another amino acid.

For example, a reference ligand or reference IgG-Fc fusion protein can have from 1 to 10 amino acid substitutions, from 1 to 5 amino acid substitutions, from 1 to 4, from 1 to 3, or from 1 to 2 amino acid substitutions. For example, a reference ligand or reference IgG-Fc fusion protein can have 1 amino acid substitution, 2 amino acid substitutions, 3 amino acid substitutions, 4 amino acid substitutions, or 5 amino acid substitutions.

Each amino acid substitution can be independent each of the other amino acid substitutions.

Each amino acid substitution can independently be a conservative amino acid substitution or a non-conservative amino acid substitution.

For example, a reference peptide can have the amino acid sequence of SEQ ID NO: 211. Peptides having SEQ ID NO: 212-216 represent substituted peptides in which the reference peptide having SEQ ID NO: 211 has been substituted with from 1 to 5 amino acid substitutions, respectively.

```
                                SEQ ID NO: 211
    Y W C W M A Q V G E L C D L

SEQ ID NO: 212
    Y H C W M A Q V G E L C D L

SEQ ID NO: 213
    Y H C W M G Q V G E L C D L

SEQ ID NO: 214
    Y H C W M G Q M G E L C D L

SEQ ID NO: 215
    Y H C W M G Q M G E L C E L

SEQ ID NO: 216
    Y H C W M G Q M G E L C E M
```

A peptide provided by the present disclosure can comprise an amino acid sequence in which from 1 to 3 glycines are independently bonded to the N-terminus, to the C-terminus, or to both the N-terminus and to the C-terminus of a reference peptide.

For example, a reference peptide can have SEQ ID NO: 220. Peptides having SEQ ID NO: 221-223 have from 1 to 3 glycines bonded to the N-terminus of the reference peptide, respectively; peptides having SEQ ID NO: 224-226 have from 1 to 3 glycines bonded to the C-terminus of the reference peptide, respectively; and peptides having SEQ ID NO: 227-228 independently have 1 or 2 glycines bonded to both the N-terminus and to the C-terminus of the reference peptide having SEQ ID NO: 220.

```
                                            SEQ ID NO: 220
    K Y C G F A Q L G E L C V L

SEQ ID NO: 221
    G K Y C G F A Q L G E L C V L

SEQ ID NO: 222
    G G K Y C G F A Q L G E L C V L

SEQ ID NO: 223
    G G G K Y C G F A Q L G E L C V L

SEQ ID NO: 224
    K Y C G F A Q L G E L C V L G

SEQ ID NO: 225
    K Y C G F A Q L G E L C V L G G

SEQ ID NO: 226
    K Y C G F A Q L G E L C V L G G G

SEQ ID NO: 227
    G K Y C G F A Q L G E L C V L G

SEQ ID NO: 228
    G G K Y C G F A Q L G E L C V L G
```

Reference is now made in detail to certain embodiments of compounds, compositions, and methods. The disclosed embodiments are not intended to be limiting of the claims. To the contrary, the claims are intended to cover all alternatives, modifications, and equivalents.

IL-7Rαγc ligands provided by the present disclosure are hu-IL-7R agonists and cyno-IL-7Rα agonists. IL-7Rαγc IgG-Fc fusion proteins comprise an IL-7Rαγc ligand bonded to the CH3 domain of the IgG-Fc fragments. The IL-7Rαγc Fc fusion proteins are hu-IL-7R agonists and cyno-IL-7R agonists.

An IL-7Rαγc ligand provided by the present disclosure comprises an IL-7Rα ligand and an Rγc ligand.

An IL-7Rα ligand provided by the present disclosure can comprise, for example, an amino acid sequence having SEQ ID NO: 1, an amino acid sequence having greater than 70% sequence similarity to an amino acid sequence having SEQ ID NO: 1, an amino acid sequence derived from SEQ ID NO: 1 having from 1 to 5 amino acid substitutions, or a combination of any of the foregoing.

```
                                            SEQ ID NO: 1
    W G I P W C T L D P G S L Q C A W L G K H
```

An IL-7Rα ligand provided by the present disclosure can comprise an amino acid sequence having SEQ ID NO: 1.

An IL-7Rα ligand provided by the present disclosure can comprise, for example, an amino acid sequence having greater than 70% sequence similarity to an amino acid sequence having SEQ ID NO: 1, greater than 75%, greater than 80%, greater than 85%, or greater than 90% sequence similarity to an amino acid sequence having SEQ ID NO: 1.

An IL-7Rα ligand provided by the present disclosure can comprise, for example, an amino acid sequence derived from SEQ ID NO: 1 having from 1 to 5 amino acid substitutions, such as 1, 2, 3, 4 or 5 amino acid substitutions. Each of the from 1 to 5 amino acid substitutions can independently be selected from a conservative amino acid substitution and a non-conservative amino acid substitution.

An IL-7Rα ligand provided by the present disclosure can comprise, for example, from 0 to 5 glycines (G) on the C-terminus, on the N-terminus, or on both the C-terminus and the N-terminus. An IL-7Rα ligand provided by the present disclosure can comprise, for example, 0, 1, 2, 3, 4, or 5 glycines (G) on the C-terminus, the N-terminus, or both the C-terminus and the N-terminus. The number of glycines (G) on the C-terminus and the N-terminus can be the same or can be different.

An IL-7Rα ligand provided by the present disclosure can bind to the hu-IL-7Rα subunit with an IC50, for example, of less than 10 μM, less than 1 μM, less than 100 nM, less than 10 nM, or less than 1 nM as determined using an ELISA binding assay.

An IL-7Rα ligand provided by the present disclosure can competitively bind to a unique binding site of the hu-IL-7Rα subunit with an IC50 less than 10 μM, less than 1 μM, less than 100 nM, less than 10 nM, or less than 1 nM as determined using an ELISA binding assay.

An IL-7Rα ligand provided by the present disclosure can bind to the cyno-IL-7Rα subunit with an IC50, for example, of less than 10 μM, less than 1 μM, less than 100 nM, less than 10 nM, or less than 1 nM as determined using an ELISA binding assay.

An Rγc ligand provided by the present disclosure can comprise an amino acid sequence having SEQ ID NO: 11, an amino acid sequence having greater than 70% sequence similarity to an amino acid sequence having SEQ ID NO: 11, greater than 75%, greater than 80%, greater than 85%, or greater than 90% sequence similarity to an amino acid sequence having SEQ ID NO: 11, an amino acid sequence derived from SEQ ID NO: 11 having from 1 to 5 amino acid substitutions, or a combination of any of the foregoing.

```
                                            SEQ ID NO: 11
    V V C Q D W E G V E L C W Q
```

An Rγc ligand provided by the present disclosure can comprise an amino acid sequence having SEQ ID NO: 11.

A Rγc ligand provided by the present disclosure can comprise, for example, an amino acid sequence having greater than 70% sequence similarity to an amino acid sequence having SEQ ID NO: 11, greater than 75%, greater than 80%, greater than 85%, or greater than 90% sequence similarity to an amino acid sequence having SEQ ID NO: 11.

An Rγc ligand provided by the present disclosure can comprise, for example, an amino acid sequence derived from SEQ ID NO: 11 having from 1 to 5 amino acid substitutions, such as 1, 2, 3, 4 or 5 amino acid substitutions. Each of the from 1 to 5 amino acid substitutions can independently selected be selected from a conservative amino acid substitution and a non-conservative amino acid substitution.

An Rγc ligand provided by the present disclosure can comprise, for example, from 0 to 5 glycines (G) on the C-terminus, the N-terminus, or both the C-terminus and the N-terminus. An Rγc ligand provided by the present disclosure can comprise, for example, 0, 1, 2, 3, 4, or 5 glycines (G) on the C-terminus, the N-terminus, or both the C-terminus and the N-terminus. The number of glycines (G) on the C-terminus and the N-terminus can be the same or different.

An Rγc ligand provided by the present disclosure can bind to the hu-IL-7Rγc subunit with an IC50, for example, less than 10 µM, less than 1 µM, less than 100 nM, less than 10 nM, or less than 1 nM as determined using an ELISA binding assay.

An Rγc ligand provided by the present disclosure can competitively bind to a unique binding site on the hu-IL-7Rγc subunit with an IC50 less than 10 µM, less than 1 µM, less than 100 nM, less than 10 nM, or less than 1 nM as determined using an ELISA binding assay.

An Rγc ligand provided by the present disclosure can bind to the cyno-IL-7Rγc subunit with an IC50, for example, less than 10 µM, less than 1 µM, less than 100 nM, less than 10 nM, or less than 1 nM as determined using an ELISA binding assay.

An IL-7Rαγc ligand provided by the present disclosure can comprise an IL-7Rα ligand provided by the present disclosure and a Rγc ligand provided by the present disclosure.

For example, an IL-7Rαγc ligand provided by the present disclosure can comprise an IL-7Rα ligand of SEQ ID NO: 1 or an IL-7Rα ligand having greater than 70% sequence similarity to SEQ ID NO: 1; and an Rγc ligand of SEQ ID NO: 11 or an Rγc ligand having greater than 70% sequence similarity to SEQ ID NO: 11.

In an IL-7Rαγc ligand provided by the present disclosure, the IL-7Rα ligand and the Rγc ligand can be bound together through a ligand linker.

For example, the C-terminus of the IL-7Rα ligand can be bound to the N-terminus of the Rγc ligand through a ligand linker.

The ligand linker can be a rigid ligand linker or a flexible ligand linker.

Examples of suitable rigid ligand linkers include $(P)_n$ where n is an integer from 1 to 20 (SEQ ID NO: 101) such as from 5 to 15 (SEQ ID NO: 102); $(PA)_n$ where n is an integer from 1 to 20 (SEQ ID NO: 103) such as from 5 to 15 (SEQ ID NO: 104); $(P)_nG$ where n is an integer from 1 to 20 (SEQ ID NO: 105) such as from 5 to 15 (SEQ ID NO: 106); $(PA)_nG$ where n is an integer from 1 to 20 (SEQ ID NO: 107) such as from 5 to 15 (SEQ ID NO: 108); $(P)_nGG$ where n is an integer from 1 to 20 (SEQ ID NO: 109) such as from 5 to 15 (SEQ ID NO: 110); and $(PA)_nGG$ where n is an integer from 1 to 20 (SEQ ID NO: 111) such as from 5 to 15 (SEQ ID NO: 112).

Examples of suitable flexible ligand linkers include $(G)_n$ where n is an integer from 1 to 20 (SEQ ID NO: 113) such as from 1 to 15 (SEQ ID NO: 114); $(GS)_n$ where n is an integer from 1 to 20 (SEQ ID NO: 115) such as from 1 to 15 (SEQ ID NO: 116); $(GGS)_n$ where n is an integer from 1 to 20 (SEQ ID NO: 117) such as from 1 to 15 (SEQ ID NO: 118); $(GGGS)_n$ where n is an integer from 1 to 20 (SEQ ID NO: 119) such as from 1 to 15 (SEQ ID NO: 120); and $(GGGGS)_n$ where n is an integer from 1 to 20 (SEQ ID NO: 121) such as from 1 to 8 (SEQ ID NO: 122).

A flexible ligand linker can comprise $(GGGGS)_n$ where n is an integer from 1 to 10 (SEQ ID NO: 123), $(GGGGS)_n$ where n is an integer from 1 to 5 (SEQ ID NO: 124), $(GGGGS)_1$ (SEQ ID NO: 125), $(GGGGS)_2$ (SEQ ID NO: 126), $(GGGGS)_3$ (SEQ ID NO: 127), $(GGGGS)_4$ (SEQ ID NO: 128), or $(GGGGS)_5$ (SEQ ID NO: 129).

A flexible ligand linker can comprise $(GGGGS)_nG$ where n is an integer from 1 to 10 (SEQ ID NO: 130), $(GGGGS)_nG$ where n is an integer from 1 to 5 (SEQ ID NO: 131), $(GGGGS)_1G$ (SEQ ID NO: 132), $(GGGGS)_2G$ (SEQ ID NO: 133), $(GGGGS)_3G$ (SEQ ID NO: 134), $(GGGGS)_4G$ (SEQ ID NO: 135), or $(GGGGS)_5G$ (SEQ ID NO: 136).

A flexible ligand linker can comprise $(GGGGS)_nGG$ where n is an integer from 1 to 10 (SEQ ID NO: 137), $(GGGGS)_nGG$ where n is an integer from 1 to 5 (SEQ ID NO: 138), $(GGGGS)_1GG$ (SEQ ID NO: 139), $(GGGGS)_2GG$ (SEQ ID NO: 140), $(GGGGS)_3GG$ (SEQ ID NO: 141), $(GGGGS)_4GG$ (SEQ ID NO: 142), or $(GGGGS)_5GG$ (SEQ ID NO: 143).

A ligand linker can have an amino acid sequence selected from any one of SEQ ID NO: 113-136. A ligand linker can have an amino acid sequence of SEQ ID NO: 132.

An IL-7Rαγc ligand provided by the present disclosure can comprise an amino acid sequence of any one of SEQ ID NO: 21-32, where $X^1$ comprises a ligand linker, including, for example, any of the ligand linkers disclosed herein.

```
                                          SEQ ID NO: 21
WGIPWCTLDPGSLQCAWLGKH-X¹-VVCQDWEGVELCWQ

SEQ ID NO: 22
GWGIPWCTLDPGSLQCAWLGKH-X¹-VVCQDWEGVELCWQ

SEQ ID NO: 23
WGIPWCTLDPGSLQCAWLGKH-X¹-VVCQDWEGVELCWQGG

SEQ ID NO: 24
GWGIPWCTLDPGSLQCAWLGKH-.X¹-VVCQDWEGVELCWQGG

SEQ ID NO: 25
GGWGIPWCTLDPGSLQCAWLGKH-X¹-VVCQDWEGVELCWQGG

SEQ ID NO: 26
GGGWGIPWCTLDPGSLQCAWLGKH-X¹-VVCQDWEGVELCWQGG

SEQ ID NO: 27
WGIPWCTLDPGSLQCAWLGKHGGGGSGGVVCQDWEGVELCWQ

SEQ ID NO: 28
GWGIPWCTLDPGSLQCAWLGKHGGGGSGGVVCQDWEGVELCWQ

SEQ ID NO: 29
WGIPWCTLDPGSLQCAWLGKHGGGGSGGVVCQDWEGVELCWQGG

SEQ ID NO: 30
GWGIPWCTLDPGSLQCAWLGKHGGGGSGGVVCQDWEGVELCWQGG

SEQ ID NO: 31
GGWGIPWCTLDPGSLQCAWLGKHGGGGSGGVVCQDWEGVELCWQGG

SEQ ID NO: 32
GGGWGIPWCTLDPGSLQCAWLGKHGGGGSGGVVCQDWEGVELCWQGG
```

An IL-7Rαγc ligand provided by the present disclosure can comprise an amino acid sequence having greater than 70% sequence similarity to any one of SEQ ID NO: 21-26, such as greater than 75%, greater than 80%, greater than 85%, greater than 90%, or greater than 95% sequence similarity to any one of SEQ ID NO: 21-26, where $X^1$ comprises a ligand linker, such as any of the ligand linkers disclosed herein.

An IL-7Rαγc ligand provided by the present disclosure can comprise, for example, an amino acid sequence derived from any one of SEQ ID NO: 21-26 having from 1 to 5 amino acid substitutions, such as 1, 2, 3, 4 or 5 amino acid substitutions. Each of the from 1 to 5 amino acid substitutions can independently be selected from a conservative amino acid substitution and a non-conservative amino acid substitution. Each of the one or more of the amino acid substitutions can be a conservative amino acid substitution, and $X^1$ comprises a ligand linker, such as any of the ligand linkers disclosed herein.

An IL-7Rαγc ligand provided by the present disclosure can comprise an amino acid sequence of any one of SEQ ID NO: 27-32.

An IL-7Rαγc ligand provided by the present disclosure can comprise an amino acid sequence having greater than 70% sequence similarity to any one of SEQ ID NO: 27-32, such as greater than 75%, greater than 80%, greater than 85%, greater than 90%, or greater than 95% sequence similarity to any one of SEQ ID NO: 27-32.

An IL-7Rαγc ligand provided by the present disclosure can comprise, for example, an amino acid sequence derived from any one of SEQ ID NO: 27-32 having from 1 to 5 amino acid substitutions, such as 1, 2, 3, 4 or 5 amino acid substitutions. Each of the from 1 to 5 amino acid substitutions can independently be selected from a conservative amino acid substitution and a non-conservative amino acid substitution. Each of the one or more of the amino acid substitutions can be a conservative amino acid substitution.

An IL-7Rαγc ligand provided by the present disclosure can comprise an amino acid sequence of SEQ ID NO: 32.

An IL-7Rαγc ligand provided by the present disclosure can comprise an amino acid sequence having greater than 70% sequence similarity to SEQ ID NO: 32, such as greater than 75%, greater than 80%, greater than 85%, greater than 90%, or greater than 95% sequence similarity to SEQ ID NO: 32.

An IL-7Rαγc ligand provided by the present disclosure can comprise, for example, an amino acid sequence derived from SEQ ID NO: 32 having from 1 to 5 amino acid substitutions, such as 1, 2, 3, 4 or 5 amino acid substitutions. Each of the from 1 to 5 amino acid substitutions can independently be selected from a conservative amino acid substitution and a non-conservative amino acid substitution. Each of the one or more of the amino acid substitutions can be a conservative amino acid substitution.

An IL-7Rαγc ligand provided by the present disclosure can comprise, for example, from 0 to 5 glycines (G) on the C-terminus, on the N-terminus, or on both the C-terminus and the N-terminus. An IL-7Rαγc ligand provided by the present disclosure can comprise, for example, 0, 1, 2, 3, 4, or 5 glycines (G) on the C-terminus, on the N-terminus, or on both the C-terminus and the N-terminus. The number of glycines (G) on the C-terminus and the N-terminus of the IL-7Rαγc ligand can be the same or different.

An IL-7Rαγc ligand provided by the present disclosure can bind to the hu-IL-7Rα subunit with an IC50 less than 10 μM, less than 1 μM, less than 100 nM, less than 10 nM, or less than 1 nM, as determined using an ELISA binding assay.

An IL-7Rαγc ligand provided by the present disclosure can bind to the hu-IL-7Rγc subunit with an IC50 less than 10 μM, less than 1 μM, less than 100 nM, less than 10 nM, or less than 1 nM, as determined using an ELISA binding assay.

For an IL-7Rαγc ligand provided by the present disclosure the ratio of the IC50 for binding to the hu-IL-7Rα subunit to the hu-IL-7Rγc subunit can be, for example, from 100 to 1, from 50 to 2, or from 30 to 3.

For example, in an IL-7Rαγc ligand provided by the present disclosure, the IL-7Rαγc ligand can bind to the hu-IL-7Rα subunit with an IC50 from 1 μM to 10 μM and can bind to the hu-IL-7Rγc subunit with an IC50 from 10 nM to 100 nM as determined using an ELISA binding assay.

An IL-7Rαγc ligand provided by the present disclosure can activate STAT5 phosphorylation in TF-1-7Rα cells with an EC50, for example, of less than 1 μM, less than 100 nM, less than 10 nM, or less than 1 nM.

An IL-7Rαγc ligand provided by the present disclosure can be a hu-IL-7R agonist.

An IL-7Rαγc ligand provided by the present disclosure can bind to the cyno-IL-7Rα subunit with an IC50 less than 10 μM, less than 1 μM, less than 100 nM, less than 10 nM, or less than 1 nM as determined using an ELISA binding assay.

An IL-7Rαγc ligand provided by the present disclosure can bind to the cyno-IL-7Rγc subunit with an IC50 less than 10 μM, less than 1 μM, less than 100 nM, less than 10 nM, or less than 1 nM, as determined using an ELISA binding assay.

An IL-7Rαγc ligand provided by the present disclosure can be a cyno-IL-7R agonist.

An IL-7Rαγc ligand provided by the present disclosure can be a hu-IL-7R agonist and a cyno-IL-7R agonist.

An IL-7Rαγc IgG-Fc fusion protein provided by the present disclosure can comprise an IL-7Rαγc ligand provided by the present disclosure bound to an IgG-Fc fragment.

An IgG-Fc fragment can comprise, for example, a hu-IgG1 Fc fragment, a hu-IgG2-Fc fragment, or a hu-IgG4-Fc fragment. The hu-hIgG-Fc-fragment refers to the Fc region consisting of the CH2 and CH3 domains of the human hu-IgG heavy chain and the hinge region. The first and second cysteines of the hinge region can be replaced with serine to prevent detrimental disulfide bridges. The last amino acid of the Fc region such as the lysine of the hu-IgG2-Fc region can be replaced with an alanine for stability of the fusion protein.

An IL-7Rαγc ligand provided by the present disclosure can be bound to an IgG1 Fc fragment through a fusion linker such as an IgG-Fc linker.

An IgG-Fc linker can comprise a rigid IgG-Fc linker, a flexible IgG-Fc linker, or a combination of rigid and flexible IgG-Fc linker segments.

Examples of suitable rigid IgG-Fc linkers include linkers having SEQ ID NO: 113-136.

Examples of suitable flexible IgG-Fc linkers include linkers having SEQ ID NO: 101-112.

Examples of suitable flexible IgG-Fc linkers include $(GS)_nGG$ where n is an integer from 1 to 20 (SEQ ID NO: 150) such as from 1 to 15 (SEQ ID NO: 151); $(GGS)_nGG$ where n is an integer from 1 to 20 (SEQ ID NO: 152) such as from 1 to 15 (SEQ ID NO: 153); $(GGGS)_nGG$ where n is an integer from 1 to 20 (SEQ ID NO: 154) such as from 1 to 15 (SEQ ID NO: 155); and $(GGGGS)_nGG$ where n is an integer from 1 to 20 (SEQ ID NO: 156) such as from 1 to 15 (SEQ ID NO: 157).

An IgG-Fc linker can comprise $(GS)_n$ where n is an integer from 1 to 20 (SEQ ID NO: 115), such as from 5 to 15 (SEQ ID NO: 301). An IgG-Fc linker can comprise, for example, $(GS)_5$ (SEQ ID NO: 158), $(GS)_6$ (SEQ ID NO: 159), $(GS)_7$ (SEQ ID NO: 160), $(GS)_8$ (SEQ ID NO: 161), $(GS)_9$ (SEQ ID NO: 162), $(GS)_{10}$ (SEQ ID NO: 163), $(GS)_{11}$ (SEQ ID NO: 164), $(GS)_{12}$ (SEQ ID NO: 165), $(GS)_{13}$ (SEQ ID NO: 166), $(GS)_{14}$ (SEQ ID NO: 167), or $(GS)_{15}$ (SEQ ID NO: 168).

An IgG-Fc linker can comprise $(GS)_nGG$ where n is an integer from 1 to 20 (SEQ ID NO: 150), such as from 1 to 15 (SEQ ID NO: 151). An IgG-Fc linker can comprise, for example, $(GS)_5GG$ (SEQ ID NO: 169), $(GS)_6GG$ (SEQ ID NO: 170), $(GS)_7GG$ (SEQ ID NO: 171), $(GS)_8GG$ (SEQ ID NO: 172), $(GS)_9GG$ (SEQ ID NO: 173), $(GS)_{10}GG$ (SEQ ID NO: 174), $(GS)_{11}GG$ (SEQ ID NO: 175), $(GS)_{12}GG$ (SEQ ID NO: 176), $(GS)_{13}GG$ (SEQ ID NO: 177), $(GS)_{14}GG$ (SEQ ID NO: 178), or $(GS)_{15}GG$ (SEQ ID NO: 179).

An IgG-Fc linker can have an amino acid sequence of SEQ ID NO: 163.

The N-terminus of the IL-7Rαγc ligand can be bound to the IgG-Fc linker such as a linker having and amino acid sequence of any one of SEQ ID NO: 150-179. The N-terminus of the IgG-Fc linker can be bound to the CH3 domain of the IgG-Fc fragment. An IL-7Rαγc ligand can be bound to the C-terminus of one CH3 domain of the IgG-Fc fragment. An IL-7Rαγc ligand can be bound to the C-terminus of each CH3 domain of the IgG-Fc fragment.

An IL-7Rαγc ligand provided by the present disclosure can be bound to the CH3 domain of an IgG-Fc fragment through the IgG-Fc linker. For example, the N-terminus of the IL-7Rαγc ligand can be bound to the C-terminus of a CH3 domain of an IgG-Fc fragment.

An IL-7Rαγc IgG-Fc fusion protein provided by the present disclosure can comprise an IL-7Rαγc ligand bound to a single CH3 domain of an IgG-Fc fragment, or an IL-7Rαγc ligand can be bound to each CH3 domain of an IgG-Fc fragment.

The terminal amino acid of the IgG-Fc region such as the lysine of the IgG2-Fc region or a terminal replacement amino acid can be bound to the IL-7Rαγc ligand through an IgG-Fc linker.

An IL-7Rγc ligand provided by the present disclosure can be bound to an IgG-Fc fragment through an IgG-Fc linker.

Figure 4:
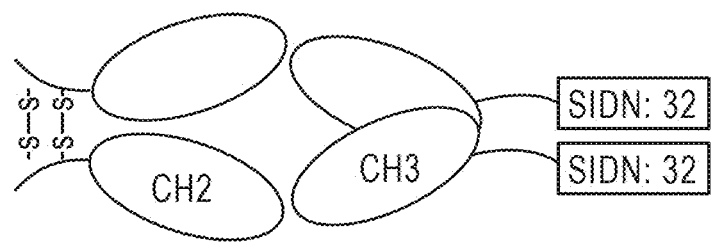
FIG. 4 shows a schematic structure of an IL-7Rαγc IgG-Fc fusion protein provided by the present disclosure.

A schematic of an IL-7Rαγc ligand IgG-Fc fusion protein provided by the present disclosure is shown in FIG. 4. As shown in FIG. 4 an IL-7Rαγc ligand is bound to each CH3 domain of an IgG-Fc fragment. The IL-7Rαγc ligand IgG-Fc fusion protein shown in FIG. 4 consists of two heavy chains comprising a CH2 domain and a CH3 domain where the hinge regions of the CH2 domains are bound by disulfide bonds and each IL-7Rαγc ligand is bound to the C-terminus of a respective CH3 domain through an IgG-Fc linker.

An IgG-Fc fragment can comprise an amino acid sequence of any one of SEQ ID NO: 41-43, an amino acid sequence having greater than 70% sequence similarity to an amino acid sequence having any one of SEQ ID NO: 41-43, an amino acid sequence derived from any one of SEQ ID NO: 41-43 having from 1 to 10 amino acid substitutions, or a combination of any of the foregoing.

An IL-7Rαγc IgG-Fc fusion fragment provided by the present disclosure can comprise an IL-7Rαγc IgG-Fc fragment having any one of SEQ ID NO: 44-55, an amino acid sequence having greater than 70% sequence similarity to an amino acid sequence having any one of SEQ ID NO: 44-55, an amino acid sequence derived from any one of SEQ ID NO: 44-55 having from 1 to 10 amino acid substitutions, or a combination of any of the foregoing.

hu-IgG1-Fc (N297A mutant)
SEQ ID NO: 41
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGA hu-IgG2-F
SEQ ID NO: 42
ERKSSVECPPCPAPPVAGPSVFLFPPKPKDTLMISRTPEVTCVVVDVSHE

DPEVQFNWYVDGVEVHNAKTKPREEQFNSTFRVVSVLTVVHQDWLN

GKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVD

KSRWQQGNVFSCSVMHEALHNHYTQKSLSLSPGA hu-IgG4-Fc
SEQ ID NO: 43
APPCPPCPAPEFEGGPSVFLFPPKPKDTLMISRTPEVTCVVVDVSQEDPE

VQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTC

LVKGFYPSDIAVEWESNGQPENNYKTTPPVLDSDGSFFLYSRLTVDKSR

WQEGNVFSCSVMHEALHNHYTQKSLSLSLGART hu-IgG1-Fc-(GS)$_{10}$GG-IL-7Rαγc
SEQ ID NO: 44
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGAGSGSGSGSGSGSG

SGSGSGGGWGIPWCTLDPGSLQCAWLGKHGGGGSGGVVCQDWEGVE

LCWQGG hu-IgG2-Fc-(GS)$_{10}$GG-IL-7Rαγc
SEQ ID NO: 45
ERKSSVECPPCPAPPVAGPSVFLFPPKPKDTLMISRTPEVTCVVVDVSHE

DPEVQFNWYVDGVEVHNAKTKPREEQFNSTFRVVSVLTVVHQDWLN

GKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVD

KSRWQQGNVFSCSVMHEALHNHYTQKSLSLSPGAGSGSGSGSGSGSGS

GSGSGSGGGWGIPWCTLDPGSLQCAWLGKHGGGGSGGVVCQDWEGV

ELCWQGG hu-IgG4-Fc-(GS)$_{10}$GG-IL-7Rαγc
SEQ ID NO: 46
APPCPPCPAPEFEGGPSVFLFPPKPKDTLMISRTPEVTCVVVDVSQEDPE

VQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTC

LVKGFYPSDIAVEWESNGQPENNYKTTPPVLDSDGSFFLYSRLTVDKSR

WQEGNVFSCSVMHEALHNHYTQKSLSLSLGARTGSGSGSGSGSGSGSG

SGSGSGGGWGIPWCTLDPGSLQCAWLGKHGGGGSGGVVCQDWEGVE

LCWQGG hu-IgG1-Fc-X$^2$-IL-7Rαγc
SEQ ID NO: 47
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGA-X$^2$-

GGGWGIPWCTLDPGSLQCAWLGKHGGGGSGGVVCQDWEGVELCWQ

GG hu-IgG2-Fc-X²-IL-7Rαγc
SEQ ID NO: 48
ERKSSVECPPCPAPPVAGPSVFLFPPKPKDTLMISRTPEVTCVVVDVSHE

DPEVQFNWYVDGVEVHNAKTKPREEQFNSTFRVVSVLTVVHQDWLN

GKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVD

KSRWQQGNVFSCSVMHEALHNHYTQKSLSLSPGA-X²-

GGGWGIPWCTLDPGSLQCAWLGKHGGGGSGGVVCQDWEGVELCWQ

GG hu-IgG4-Fc-X²-IL-7Rαγc
SEQ ID NO: 49
APPCPPCPAPEFEGGPSVFLFPPKPKDTLMISRTPEVTCVVVDVSQEDPE

VQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTC

LVKGFYPSDIAVEWESNGQPENNYKTTPPVLDSDGSFFLYSRLTVDKSR

WQEGNVFSCSVMHEALHNHYTQKSLSLSLGART-X²-

GGGWGIPWCTLDPGSLQCAWLGKHGGGGSGGVVCQDWEGVELCWQ

GG hu-IgG1-Fc-(GS)₁₀GG-IL-7Rαγc
SEQ ID NO: 50
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGAGSGSGSGSGSGSG

SGSGSGGGWGIPWCTLDPGSLQCAWLGKH-X¹-

VVCQDWEGVELCWQGG hu-IgG2-Fc-(GS)₁₀GG-IL-7Rαγc
SEQ ID NO: 51
ERKSSVECPPCPAPPVAGPSVFLFPPKPKDTLMISRTPEVTCVVVDVSHE

DPEVQFNWYVDGVEVHNAKTKPREEQFNSTFRVVSVLTVVHQDWLN

GKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVD

KSRWQQGNVFSCSVMHEALHNHYTQKSLSLSPGAGSGSGSGSGSGS

GSGSGSGGGWGIPWCTLDPGSLQCAWLGKH-X¹-

VVCQDWEGVELCWQGG hu-IgG1-Fc-(GS)₁₀GG-IL-7Rαγc
SEQ ID NO: 52
APPCPPCPAPEFEGGPSVFLFPPKPKDTLMISRTPEVTCVVVDVSQEDPE

VQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTC

LVKGFYPSDIAVEWESNGQPENNYKTTPPVLDSDGSFFLYSRLTVDKSR

WQEGNVFSCSVMHEALHNHYTQKSLSLSLGARTGSGSGSGSGSGSG

SGSGSGGGWGIPWCTLDPGSLQCAWLGKH-X¹-

VVCQDWEGVELCWQGG hu-IgG1-Fc-X²-IL-7Rαγc
SEQ ID NO: 53
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGA-X²-

GGGWGIPWCTLDPGSLQCAWLGKH-X¹-VVCQDWEGVELCWQGG hu-IgG2-Fc-X²-IL-7Rαγc
SEQ ID NO: 54
ERKSSVECPPCPAPPVAGPSVFLFPPKPKDTLMISRTPEVTCVVVDVSHE

DPEVQFNWYVDGVEVHNAKTKPREEQFNSTFRVVSVLTVVHQDWLN

GKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVD

KSRWQQGNVFSCSVMHEALHNHYTQKSLSLSPAGA-X²-

GGGWGIPWCTLDPGSLQCAWLGKH-X¹-VVCQDWEGVELCWQGG hu-IgG4-Fc-X²-IL-7Rαγc
SEQ ID NO: 55
APPCPPCPAPEFEGGPSVFLFPPKPKDTLMISRTPEVTCVVVDVSQEDPE

VQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTC

LVKGFYPSDIAVEWESNGQPENNYKTTPPVLDSDGSFFLYSRLTVDKSR

WQEGNVFSCSVMHEALHNHYTQKSLSLSLGART-X²-

GGGWGIPWCTLDPGSLQCAWLGKH-X¹-VVCQDWEGVELCWQGG

In an IL-7Rαγc IgG-Fc fusion fragment having SEQ ID NO: 47-55, $X^1$ can be a ligand linker as disclosed herein and $X^2$ can be an IgG-Fc linker as disclosed herein.

An IL-7Rαγc IgG-Fc fusion fragment provided by the present disclosure can comprise an amino acid sequence having any one of SEQ ID NO: 44-55.

An IL-7Rαγc IgG-Fc fusion fragment provided by the present disclosure can comprise, for example, an amino acid sequence having greater than 70% sequence similarity to an amino acid sequence having any one of SEQ ID NO: 44-55, greater than 75%, greater than 80%, greater than 85%, greater than 90%, or greater than 95% sequence similarity to an amino acid sequence having any one of SEQ ID NO: 44-55.

An IL-7Rαγc IgG-Fc fusion fragment provided by the present disclosure can comprise, for example, an amino acid sequence derived from any one of SEQ ID NO: 44-55 having from 1 to 10 amino acid substitutions, such as from 1 to 5 amino acid substitutions, such as 1, 2, 3, 4 or 5 amino acid substitutions. Each of the from 1 to 10 amino acid substitutions can independently be selected from a conservative amino acid substitution and a non-non-conservative amino acid substitution. Each of the one or more of the amino acid substitutions can be a conservative amino acid substitution.

An IL-7Rαγc IgG-Fc fusion fragment provided by the present disclosure can bind to the hu-IL-7Rα subunit with an IC50 less than 10 μM, less than 1 μM, less than 100 nM, less than 10 nM, or less than 1 nM, as determined using an ELISA binding assay.

An IL-7Rαγc IgG-Fc fusion fragment provided by the present disclosure can bind to the hu-Rγc subunit with an IC50 less than 10 µM, less than 1 µM, less than 100 nM, less than 10 nM, or less than 1 nM, as determined using an ELISA binding assay.

An IL-7Rαγc IgG-Fc fusion fragment provided by the present disclosure can bind to a unique binding site on hu-IL-7R with an IC50 less than 10 µM, less than 1 µM, less than 100 nM, less than 10 nM, or less than 1 nM, as determined using an ELISA binding assay.

For an IL-7Rαγc IgG-Fc fusion fragment provided by the present disclosure the ratio of the IC50 for binding to the hu-IL-7Rα subunit to the hu-IL-7Rγc subunit can be, for example, from 100 to 1, or from 30 to 3, where binding is determined using an ELISA binding assay.

For an IL-7Rαγc IgG-Fc fusion fragment provided by the present disclosure the ratio of the IC50 for binding to the hu-IL-7Rα subunit to the hu-IL-7Rγc subunit can be, for example, greater than 1, greater than 3, greater than 10, greater than 30, greater than 100, or greater than 300, where binding is determined using an ELISA binding assay.

For example, in an IL-7Rαγc IgG-Fc fusion fragment provided by the present disclosure, the IL-7Rαγc ligand can bind to the hu-IL-7Rα subunit with and IC50 from 1 µM to 10 µM and can bind to the hu-IL-7Rγc subunit with an IC50 from 10 nM to 100 nM, as determined using an ELISA binding assay.

An IL-7Rαγc IgG-Fc fusion fragment provided by the present disclosure can activate STAT5 phosphorylation in TF-1-7Rα cells with an EC50 less than 1 µM, less than 100 nM, less than 10 nM, or less than 1 nM.

An IL-7Rαγc IgG-Fc fusion fragment provided by the present disclosure can be a hu-IL-7R agonist.

An IL-7Rαγc IgG-Fc fusion fragment provided by the present disclosure can be a hu-IL-7R agonist and a cyno-IL-7R agonist.

An IL-7Rαγc IgG-Fc fusion protein provided by the present disclosure can comprise two IL-7Rαγc IgG-Fc fusion fragments provided by the present disclosure such as an IL-7Rαγc IgG-Fc fragment having any one of SEQ ID NO: 44-55, an amino acid sequence having greater than 70% sequence similarity to an amino acid sequence having any one of SEQ ID NO: 44-55, an amino acid sequence derived from any one of SEQ ID NO: 44-55 having from 1 to 10 amino acid substitutions, or a combination of any of the foregoing.

An IL-7Rαγc IgG-Fc fusion protein provided by the present disclosure can comprise two IL-7Rαγc IgG-Fc fragments provided by the present disclosure such as any of the IL-7Rαγc IgG-Fc fragments having SEQ ID NO: 44-55 bound together at the hinge region through one or more disulfide bonds.

Each of the IL-7Rαγc IgG-Fc fragments of an IL-7Rαγc IgG-Fc fusion protein can be the same IL-7Rαγc IgG-Fc fragment provided by the present disclosure.

Each of the IL-7Rαγc IgG-Fc fragments of an IL-7Rαγc IgG-Fc fusion protein can comprise a different IL-7Rα ligand, a different Rγc ligand, a different IL-7Rαγc ligand linker, a different IL-7Rαγc ligand, a different IgG-Fc fragment, a different IgG-Fc linker, or a combination of any of the foregoing.

An IL-7Rαγc IgG-Fc fusion protein provided by the present disclosure can bind to the hu-IL-7Rα subunit with an IC50 less than 10 µM, less than 1 µM, less than 100 nM, less than 10 nM, or less than 1 nM, as determined using an ELISA binding assay.

An IL-7Rαγc IgG-Fc fusion protein provided by the present disclosure can bind to the hu-Rγc subunit with an IC50 less than 10 µM, less than 1 µM, less than 100 nM, less than 10 nM, or less than 1 nM, as determined using an ELISA binding assay.

An IL-7Rαγc IgG-Fc fusion protein provided by the present disclosure can bind to a unique binding site on hu-IL-7R with an IC50 less than 10 µM, less than 1 µM, less than 100 nM, less than 10 nM, or less than 1 nM, as determined using an ELISA binding assay.

For an IL-7Rαγc IgG-Fc fusion protein provided by the present disclosure the ratio of the IC50 for binding to the hu-IL-7Rα subunit to the hu-IL-7Rγc subunit can be, for example, from 100 to 1, or from 30 to 3, where binding is determined using an ELISA binding assay.

For an IL-7Rαγc IgG-Fc fusion protein provided by the present disclosure the ratio of the IC50 for binding to the hu-IL-7Rα subunit to the hu-IL-7Rγc subunit can be, for example, greater than 1, greater than 3, greater than 10, greater than 30, greater than 100, or greater than 300, where binding is determined using an ELISA binding assay.

For example, in an IL-7Rαγc IgG-Fc fusion protein provided by the present disclosure, the IL-7Rαγc ligand can bind to the hu-IL-7Rα subunit with and IC50 from 1 µM to 10 µM and can bind to the hu-IL-7Rγc subunit with an IC50 from 10 nM to 100 nM, as determined using an ELISA binding assay.

An IL-7Rαγc IgG-Fc fusion protein provided by the present disclosure can activate STAT5 phosphorylation in TF-1-7Rα cells with an EC50 less than 1 µM, less than 100 nM, less than 10 nM, or less than 1 nM.

An IL-7Rαγc IgG-Fc fusion protein provided by the present disclosure can be a hu-IL-7R agonist.

An IL-7Rαγc IgG-Fc fusion protein provided by the present disclosure can competitively bind to the cyno-IL-7Rα subunit with an IC50 less than 10 µM, less than 1 µM, less than 100 nM, less than 10 nM, or less than 1 nM, as determined using an ELISA binding assay.

An IL-7Rαγc IgG-Fc fusion protein provided by the present disclosure can competitively bind to the cyno-IL-7Rγc subunit with an IC50 less than 10 less than 1 µM, less than 100 nM, less than 10 nM, or less than 1 nM, as determined using an ELISA binding assay.

An IL-7Rαγc IgG-Fc fusion protein provided by the present disclosure can be a cyno-IL-7R agonist.

An IL-7Rαγc IgG-Fc fusion protein provided by the present disclosure can be a hu-IL-7R agonist and a cyno-IL-7R agonist.

A pharmaceutical composition provided by the present disclosure can comprise an IL-7Rαγc ligand provided by the present disclosure, an IL-7Rαγc IgG-Fc fusion protein provided by the present disclosure, or a combination thereof.

An IL-7Rαγc ligand and/or IL-7Rαγc IgG-Fc fusion protein provided by the present disclosure, can be incorporated into a pharmaceutical composition to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. A pharmaceutical composition provided by the present disclosure can be an injectable intravenous formulation. A pharmaceutical composition provided by the present disclosure can be an oral formulation. Oral formulations may be oral dosage forms. A pharmaceutical composition can be formulated for intravenous administration or for subcutaneous administration.

A pharmaceutical composition provided by the present disclosure can comprise a therapeutically effective amount of an IL-7Rαγc ligand and/or IL-7Rαγc IgG-Fc fusion protein together with a suitable amount of one or more pharmaceutically acceptable vehicles so as to provide a composition for administration to a patient. Suitable pharmaceutical vehicles and methods of preparing pharmaceutical compositions are described in the art.

An IL-7Rαγc ligand and/or IL-7Rαγc IgG-Fc fusion protein and pharmaceutical composition thereof can be used in an amount effective to achieve an intended purpose such as to treat a disease such as cancer, an autoimmune disease, an inflammatory disease, or a viral disease. For use to treat a disease such as cancer, an autoimmune disease, an inflammatory disease, or a viral disease, an IL-7Rαγc ligand and/or IL-7Rαγc IgG-Fc fusion or pharmaceutical composition thereof, can be administered or applied in a therapeutically effective amount.

The amount of an IL-7Rαγc ligand and/or IL-7Rαγc IgG-Fc fusion protein or pharmaceutical composition thereof that will be effective in the treatment of a particular disease, disorder or condition can depend in part on the nature of the disease, disorder or condition, and can be determined by standard clinical techniques known in the art. In addition, in vitro or in vivo assays can be employed to help identify optimal dosage ranges. The amount of an IL-7Rαγc ligand and/or IL-7Rαγc IgG-Fc fusion protein or pharmaceutical composition administered can depend, for example, on the patient being treated, the weight of the patient, the severity of the disease, the manner of administration and the judgment of the prescribing physician.

An IL-7Rαγc ligand and/or IL-7Rαγc IgG-Fc fusion protein can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

A therapeutically effective dose of an IL-7Rαγc ligand and/or IL-7Rαγc IgG-Fc fusion protein or pharmaceutical composition thereof can provide therapeutic benefit without causing substantial toxicity. Toxicity of an IL-7Rαγc ligand and/or IL-7Rαγc IgG-Fc fusion protein or pharmaceutical compositions thereof can be determined using standard pharmaceutical procedures. The dose ratio between toxic and therapeutic effect is the therapeutic index. An IL-7Rαγc ligand and/or IL-7Rαγc IgG-Fc fusion protein or pharmaceutical composition thereof can exhibit a high therapeutic index in treating certain diseases and disorders. A dose of an IL-7Rαγc ligand and/or IL-7Rαγc IgG-Fc fusion protein or pharmaceutical composition thereof can be within a range of circulating plasma concentrations that reflect a therapeutically effective dose with minimal toxicity.

An IL-7Rαγc ligand and/or IL-7Rαγc IgG-Fc fusion protein provided by the present disclosure, or a pharmaceutical composition thereof may be included in a kit that can be used to administer the peptide to a patient for therapeutic purposes. A kit can include a pharmaceutical composition comprising an IL-7Rαγc ligand and/or IL-7Rαγc IgG-Fc fusion protein provided by the present disclosure suitable for administration to a patient and instructions for administering the pharmaceutical composition to the patient. The kit can be a kit for treating cancer, for treating an autoimmune disease, for treating an inflammatory disease, or for treating a viral disease. For example, a kit for use in treating cancer, an autoimmune disease, an inflammatory disease, an immunodeficiency disease, or a viral disease in a patient can comprise an IL-7Rαγc ligand and/or IL-7Rαγc IgG-Fc fusion protein provided by the present disclosure, a pharmaceutically acceptable vehicle for administering the compound, and instructions for administering the compound to a patient.

A pharmaceutical composition can be included in a container, pack, or dispenser together with instructions for administration to a patient.

Instructions supplied with a kit can be provided in a written or electronic format.

An IL-7Rαγc ligand or IL-7Rαγc IgG-Fc fusion protein provided by the present disclosure can be used, for example, to treat diseases such as cancer, an inflammatory disease, an autoimmune disease, an immunodeficiency disease, or a viral disease such as COVID-19.

A method provided by the present disclosure can comprise treating a disease in a patient such as cancer, an inflammatory disease, an autoimmune disease, an immunodeficiency disease, or a viral disease comprising administering to a patient in need of such treatment a therapeutically effective amount of an IL-7Rαγc ligand or IL-7Rαγc IgG-Fc fusion protein provided by the present disclosure or pharmaceutical composition thereof.

An IL-7Rαγc ligand or IL-7Rαγc IgG-Fc fusion protein provided by the present disclosure can be used for treating cancer in a patient. The cancer can be, for example, a solid tumor or a metastasis.

An IL-7Rαγc ligand or IL-7Rαγc IgG-Fc fusion protein provided by the present disclosure or pharmaceutical compositions thereof can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

An IL-7Rαγc ligand or IL-7Rαγc IgG-Fc fusion protein provided by the present disclosure, or a pharmaceutical composition thereof can be used to treat solid tumors.

An IL-7Rαγc ligand or IL-7Rαγc IgG-Fc fusion protein provided by the present disclosure, or a pharmaceutical composition thereof can be used to treat tumor metastases. An IL-7Rαγc ligand or IL-7Rαγc IgG-Fc fusion protein provided by the present disclosure, or a pharmaceutical composition thereof can be used to treat circulating tumor cells.

An IL-7Rαγc ligand or IL-7Rαγc IgG-Fc fusion protein provided by the present disclosure or pharmaceutical compositions thereof can be used to treat, for example, a cancer selected from primary adult and childhood brain and CNS cancers including glioblastoma (GBM) and astrocytoma, skin cancers including melanoma, lung cancers including small cell lung cancers, non-small cell lung cancers (NSCLC), and large cell lung cancers, breast cancers including triple negative breast cancer (TNBC), blood cancers including myelodysplastic syndrome (MDS), multiple myeloma (MM), and acute myeloid leukemia (AML), prostate cancer including castrate resistant prostate cancer (CRPC), liver cancers including hepatocellular carcinoma (HCC), esophageal and gastric cancers, and any systemic and central metastases of any of the foregoing.

An IL-7Rαγc ligand or IL-7Rαγc IgG-Fc fusion protein provided by the present disclosure can be used, for example, in combination with temozolomide to treat glioblastoma, with atezolizumab to treat skin cancers such as MCC, C5CC and melanoma, with pembrolizumab to treat triple-negative breast cancer, and in combination with CAR-T therapy to treat pediatric acute lymphoblastic leukemia.

An IL-7Rαγc ligand or IL-7Rαγc IgG-Fc fusion protein provided by the present disclosure, or a pharmaceutical composition thereof can be administered to a patient in need of such treatment to treat an inflammatory disease.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

An IL-7Rαγc ligand or IL-7Rαγc IgG-Fc fusion protein provided by the present disclosure, or a pharmaceutical composition thereof can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases*, Rose and Mackay, 2014, Academic Press.

An IL-7Rαγc ligand or IL-7Rαγc IgG-Fc fusion protein provided by the present disclosure, or a pharmaceutical composition thereof can be administered to a patient to treat an autoimmune disease.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo's disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan's syndrome, cold agglutinin disease, congenital heart block, Coxsackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, post-myocardial infarction syndrome, post-pericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vasculitis, vitiligo, and Wegener's granulomatosis.

An IL-7Rαγc ligand or IL-7Rαγc IgG-Fc fusion protein provided by the present disclosure or a pharmaceutical composition thereof can be used to treat autoimmune disorders such as, for example, lupus, graft-versus-host disease, hepatitis C-induced vasculitis, Type I diabetes, multiple sclerosis, spontaneous loss of pregnancy, atopic diseases, and inflammatory bowel disease.

An IL-7Rαγc ligand or IL-7Rαγc IgG-Fc fusion protein provided by the present disclosure can be administered with one or more additional therapeutic agents for treating an autoimmune disease. For example, an IL-7Rαγc ligand or IL-7Rαγc IgG-Fc fusion protein or a pharmaceutical composition thereof can be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

An IL-7Rαγc ligand or IL-7Rαγc IgG-Fc fusion protein provided by the present disclosure or a pharmaceutical composition thereof can be administered to a patient to treat a disease associated with the activation, proliferation, metabolism, and/or differentiation of T-cells.

An IL-7Rαγc ligand or IL-7Rαγc IgG-Fc fusion protein provided by the present disclosure, or a pharmaceutical composition thereof can be administered to a patient to treat an infectious disease such as a viral disease.

Examples of infectious diseases include *Acinetobacter* infections, actinomycosis, African sleeping sickness (African trypanosomiasis), AIDS (acquired immunodeficiency syndrome), amoebiasis, anaplasmosis, angiostrongyliasis, anisakiasis, anthrax, *Arcanobacterium haemolyticum* infection, Argentine hemorrhagic fever, ascariasis, aspergillosis, astrovirus infection, babesiosis, *Bacillus cereus* infection, bacterial meningitis, bacterial pneumonia, bacterial vaginosis, *Bacteroides* infection, balantidiasis, bartonellosis, *Baylisascaris* infection, Bejel, syphilis, yaws, BK virus infection, black piedra, blastocystosis, blastomycosis, Bolivian hemorrhagic fever, botulism (and Infant botulism), Brazilian hemorrhagic fever, brucellosis, bubonic plague, *Burkholderia* infection, buruli ulcer, calicivirus infection (Norovirus and Sapovirus), campylobacteriosis, candidiasis (Moniliasis; Thrush), capillariasis, carrion's disease, cat-scratch disease, cellulitis, Chagas disease (American trypanosomiasis), chancroid, chickenpox, chikungunya, chlamydia, *Chlamydophila pneumoniae* infection (Taiwan acute respiratory agent or TWAR), cholera, chromoblastomycosis, *Chytridiomycosis*, clonorchiasis, *Clostridium difficile colitis*, coccidioidomycosis, Colorado tick fever (CTF), common cold (acute viral rhinopharyngitis; Acute coryza, Coronavirus disease 2019 (COVID-19), Creutzfeldt-Jakob disease (CJD), Crimean-Congo hemorrhagic fever (CCHF), cryptococcosis, cryptosporidiosis, cysticercosis, cytomegalovirus infection, Dengue fever, desmodesmus infection, dientamoebiasis, diphtheria, diphyllobothriasis, dracunculiasis, Ebola hemorrhagic fever, echinococcosis, Ehrlichiosis, enterobiasis (pinworm infection), *Enterococcus* infection, enterovirus infection, epidemic typhus, Epstein-Barr virus infectious mononucleosis (Mono), erythema infectiosum (Fifth disease), fxanthem subitum (Sixth disease), fasciolosis, fasciolopsiasis, fatal familial insomnia (FFI), filariasis, food poisoning by *Clostridium perfringens*, free-living amebic infection, *Fusobacterium* infection, gas gangrene (Clostridial myonecrosis), geotrichosis, Gerstmann-Sträussler-Scheinker syndrome (GSS), giardiasis, glanders, gnathostomiasis, gonorrhea, granuloma inguinale (Donovanosis), Group A streptococcal infection, Group B streptococcal infection, *Haemophilus influenzae* infection, hand, foot and mouth disease (HFMD), Hantavirus Pulmonary Syndrome (HPS), Heartland virus disease, *Helicobacter pylori* infection, hemolytic-uremic syndrome (HUS), hemorrhagic fever with renal syndrome (HFRS), Hendra virus infection, Hepatitis A, Hepatitis B, Hepatitis C, Hepatitis D, Hepatitis E, Herpes simplex, histoplasmosis, hookworm infection, human bocavirus infection, human ewingii ehrlichiosis, human granulocytic anaplasmosis (HGA), human metapneumovirus infection, human monocytic ehrlichiosis, human papillomavirus (HPV) infection, human parainfluenza virus infection, hymenolepiasis, influenza (flu), isosporiasis, Kawasaki disease, keratitis, *Kingella kingae* infection, Kuru, Lassa fever, Legionellosis (Legionnaires' disease), leishmaniasis, leprosy, leptospirosis, listeriosis, Lyme disease (Lyme borreliosis), lymphatic filariasis (elephantiasis), lymphocytic choriomeningitis, malaria, Marburg hemorrhagic fever (MHF), measles, melioidosis (Whitmore's disease), meningitis, meningococcal disease, metagonimiasis, microsporidiosis, Middle East respiratory syndrome (MERS), molluscum contagiosum (MC), monkeypox, mumps, murine typhus (Endemic typhus), mycetoma, *Mycoplasma genitalium* infection, mycoplasma pneumonia, myiasis, neonatal conjunctivitis (Ophthalmia neonatorum), Nipah virus infection, nocardiosis, Norovirus (children and babies), onchocerciasis (River blindness), opisthorchiasis, paracoccidioidomycosis (South American blastomycosis), paragonimiasis, pasteurellosis, pediculosis capitis (Head lice), pediculosis corporis (Body lice), pediculosis pubis (pubic lice, crab lice), pelvic inflammatory disease (PID), pertussis (whooping cough), plague, pneumococcal infection, pneumocystis pneumonia (PCP), pneumonia, poliomyelitis, Pontiac fever, *Prevotella* infection, primary amoebic meningoencephalitis (PAM), progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley fever (RVF), Rocky Mountain spotted fever (RMSF), rotavirus infection, rubella, salmonellosis, SARS (severe acute respiratory syndrome), scabies, scarlet fever, schistosomiasis, sepsis, shigellosis (bacillary dysentery), shingles (Herpes zoster), smallpox (variola), sporotrichosis, staphylococcal food poisoning, staphylococcal infection, strongyloidiasis, subacute sclerosing panencephalitis, taeniasis, tetanus (lockjaw), tinea barbae (barber's itch), tinea capitis (ringworm of the scalp), tinea corporis (ringworm of the body), tinea cruris (Jock itch), tinea manuum (ringworm of the hand), tinea nigra, tinea pedis (athlete's foot), tinea unguium (onychomycosis), tinea versicolor (Pityriasis versicolor), toxocariasis (ocular larva migrans (OLM), toxocariasis (visceral larva migrans (VLM), toxoplasmosis, trachoma, trichinosis, trichomoniasis, trichuriasis (whipworm infection), tuberculosis, tularemia, typhoid fever, typhus fever, *Ureaplasma urealyticum* infection, valley fever, Venezuelan equine encephalitis, Venezuelan hemorrhagic fever, vibrio parahaemolyticus enteritis, vibrio vulnificus infection, viral pneumonia, West Nile fever, white piedra (tinea blanca), yellow fever, *Yersinia pseudotuberculosis* infection, yersiniosis, zeaspora, Zika fever, and zygomycosis.

Examples of viral diseases include respiratory viral diseases such as influenza, respiratory syncytial virus infection, adenovirus infection, parainfluenza virus infection, and severe acute respiratory syndrome; gastrointestinal viral diseases such as nonovirus infection, rotovirus infection, and astrovirus infection; exanthematous viral disease such as measles, rubella, chickenpox and shingles, roseola, smallpox, fifth disease, and chikungunya virus infection; hepatic viral diseases such as hepatitis A, B, C, D, and E; cutaneous viral diseases such as warts, oral herpes, viral herpes, and molluscum contagiosum; hemorrhagic diseases such as Ebola, Lassa fever, dengue fever, yellow fever, Marburg hemorrhagic fever, and Crimean-Congo hemorrhagic fever; neurological diseases such as polio, viral meningitis, viral encephalitis, and rabies.

An IL-7Rαγc ligand or IL-7Rαγc IgG-Fc fusion protein provided by the present disclosure, or a pharmaceutical composition thereof can be administered to a patient to treat an organ transplant.

An IL-7Rαγc ligand or IL-7Rαγc IgG-Fc fusion protein provided by the present disclosure, or a pharmaceutical composition thereof can be administered in conjunction with an agent known or believed to interfere with proliferation, to interfere with mitosis, to interfere with DNA replication, or to interfere with DNA repair.

An IL-7Rαγc ligand or IL-7Rαγc IgG-Fc fusion protein provided by the present disclosure, or a pharmaceutical composition thereof can be administered to a patient to treat an immune deficiency disease.

Examples of primary immune deficiency diseases include autoimmune lymphoproliferative syndrome, autoimmune polyglandular syndrome type 1, BENTA disease, caspase eight deficiency state, CARDS deficiency, chronic granulomatous disease, common variable immunodeficiency, congenital neutropenia syndromes, CTLA4 deficiency, DOCK8 deficiency, GATA2 deficiency, glycosylation disorders, hyper-immunoglobulin E syndromes, hyper-immunoglobulin M syndromes, interferon β, interleukin 12 and interleukin 23 deficiency, leukocyte adhesion deficiency, LRBA deficiency, PI2 kinase disease, PLCG2-associated antibody deficiency and immune dysregulation, severe combined immunodeficiency, STAT3 dominant-negative disease, STAT3 gain-of-function disease, warts, hypogammaglobulinemia, infections, and myelokathexis syndrome, Wiskott-Aldrich syndrome, X-linked agammaglobulinemia, X-linked lymphoproliferative disease, and XMEN disease.

Secondary immune deficiency disease occurs when the immune system is compromised due to environmental factors such as infection, chemotherapy, severe burns, or malnutrition. Examples of secondary immune deficiency diseases include newborn immunodeficiencies such as immature lymphoid organs, absent memory immunity, low maternal IgG levels, decreased neutrophil storage pool, decreased neutrophil function, and decreased natural killer cell activity; advanced age related immunodeficiencies such as decreased antigen-specific cellular immunity, T-cell oligoconality, and restricted B-cell repertoire; malnutrition related immunodeficiencies such as decreased cellular immune response and weakened mucosal barriers; diabetes mellitus related immunodeficiencies such as decreased mitogen-induced lymphoproliferation, defective phagocytosis, and decreased chemotaxis; chronic uremia related immunodeficiencies such as decreased cellular immune response, decreased generation of memory antibody responses, and decreased chemotaxis; genetic syndromes such as defective phagocytosis, defective chemotaxis, and variable defects of antigen-specific immune responses; and anti-inflammatory, immunomodulatory, and immuno-suppressive drug therapy related immune deficiencies such as lymphopenia, decreased cellular immune response and anergy, decreased proinflammatory cytokines, decreased phagocytosis, decreased chemotaxis, neutropenia, and weakened mucosal barriers; environmental conditions such as increased lymphocyte apoptosis, increased secretion of tolerogenic cytokines, cytopenia, decreased cellular immunity and anergy, and stress-induced nonspecific immune activation; and infectious diseases such as T-cell lymphopenia, decreased cellular immune response and anergy, and defective antigen-specific antibody responses.

An IL-7Rαγc ligand or IL-7Rαγc IgG-Fc fusion protein provided by the present disclosure, or a pharmaceutical composition thereof can be administered to a patient to increase the immune response in an immuno-compromised patient.

An IL-7Rαγc ligand or IL-7Rαγc IgG-Fc fusion protein provided by the present disclosure, or a pharmaceutical composition thereof can be administered to a patient to increase the immune response in an elderly patient.

An IL-7Rαγc ligand or IL-7Rαγc IgG-Fc fusion protein provided by the present disclosure can be used to treat, for example, an umbilical cord blood transplant, human immunodeficiency virus (HIV), idiopathic CD4+ T-lymphocytopenia, chronic hepatitis B virus infection, severe sepsis with septic shock, hepatitis C virus infection, cancer including breast cancer, lymphogenic metastatic breast cancer, colon cancer, and bladder cancer, kidney cancer, prostate cancer, sarcoma, glioblastoma, and melanoma, which can be a solid tumor or metastatic tumor, Coronavirus (COVID-19), human papillomavirus (HPV), peripheral blood stem cell transplant, and incurable non-hematologic malignancy.

An IL-7Rαγc ligand or IL-7Rαγc IgG-Fc fusion protein provided by the present disclosure provided by the present disclosure can be used to treat, for example, newly diagnosed high grade glioma treated with radiation and temozolomide, metastatic breast cancer, post-allogeneic stem cell transplant, and solid tumors where improved outcomes are associated with increased tumor-infiltrating lymphocyte density.

An IL-7Rαγc ligand or IL-7Rαγc IgG-Fc fusion protein provided by the present disclosure can be used as a pretreatment to chemotherapy with a known risk of neutropenic fever or as a pre-treatment prior to apheresis in patients being administered CAR-T therapy.

An IL-7Rαγc ligand or IL-7Rαγc IgG-Fc fusion protein provided by the present disclosure can be used, either alone or in combination, to treat diseases including acute myeloid leukemia, B-cell lymphoma, chronic myelogenous leukemia, depression, gingival recession, hepatitis C, HIV infections, human papillomavirus, idiopathic CD4 lymphopenia, immunodeficiency secondary to organ transplantation, lipodystrophy, Kaposi sarcoma lymphoma, lymphopenia, mantle cell lymphoma, multiple sclerosis, myelodysplastic syndrome, non-Hodgkin lymphoma, recurrent adult diffuse large cell lymphoma, recurrent follicular lymphoma, rheumatoid arthritis, sepsis, and Type 2 diabetes.

An IL-7Rαγc ligand or IL-7Rαγc IgG-Fc fusion protein provided by the present disclosure can be used to treat newly diagnosed high grade glioma, metastatic breast cancer, postallogenic stem cell transplant engraftment, solid tumors, pre-treatment prior to initiation of dose dense chemotherapy with a known risk of neutropenic fever, or pre-treatment prior to apheresis in patient receiving CAR-T therapy.

An IL-7Rαγc ligand or IL-7Rαγc IgG-Fc fusion protein provided by the present disclosure can be used to treat severe sepsis with septic shock, peripheral blood stem cell transplant, prostate cancer, HIV, HCV, lymphopenic metastatic breast cancer, chronically infected HIV, solid tumors, metastatic melanoma, metastatic sarcoma, incurable nonhematologic malignancy, metastatic or recurrent tumors, HPV, locally advanced or metastatic solid tumors, or newly diagnosed glioblastoma.

An IL-7Rαγc ligand or IL-7Rαγc IgG-Fc fusion protein provided by the present disclosure can be used to treat lymphopenic patients with COVID-19 infection, urothelial carcinoma, non-tuberculous mycobacteria lung disease, cord blood transplant, COVID-19, refractory or relapsed triple negative breast cancer, Kaposi sarcoma, squamous cell carcinoma, lymphopenia in progressive multifocal leukoencephalopathy (PML), Merkel cell carcinoma, cutaneous squamous cell carcinoma, vaccine response, high grade gliomas, or gastric or gastro-esophageal junction or esophageal adenocarcinoma.

An IL-7Rαγc ligand or IL-7Rαγc IgG-Fc fusion protein provided by the present disclosure and pharmaceutical compositions of any of the foregoing can be administered to a patient together with another compound for treating an inflammatory disease, an autoimmune disease, an immunodeficiency disease, or a viral disease in a patient. The at least one other therapeutic agent can be an IL-7Rαγc ligand or IL-7Rαγc IgG-Fc fusion protein provided by the present disclosure. An IL-7Rαγc ligand or IL-7Rαγc IgG-Fc fusion protein and the at least one other therapeutic agent can act additively or synergistically. The at least one additional therapeutic agent can be included in the same pharmaceutical composition or vehicle comprising the IL-7Rαγc ligand or IL-7Rαγc IgG-Fc fusion protein or can be in a separate pharmaceutical composition or vehicle. Accordingly, methods provided by the present disclosure further include, in addition to administering an IL-7Rαγc ligand or IL-7Rαγc IgG-Fc fusion protein, administering one or more therapeutic agents effective for treating an inflammatory disease or an autoimmune disease or a different disease, disorder or condition than an inflammatory disease or an autoimmune disease. Methods provided by the present disclosure include administration of an IL-7Rαγc ligand or IL-7Rαγc IgG-Fc fusion protein and one or more other therapeutic agents provided that the combined administration does not inhibit the therapeutic efficacy of an IL-7Rαγc ligand or IL-7Rαγc IgG-Fc fusion protein and/or does not produce adverse combination effects.

An IL-7Rαγc ligand or IL-7Rαγc IgG-Fc fusion protein provided by the present disclosure can be used in combination with at least one other therapeutic agent. An IL-7Rαγc ligand or IL-7Rαγc IgG-Fc fusion protein can be administered to a patient together with another compound for treating cancer in the patient. The at least one other therapeutic agent can be a second, different IL-7Rαγc ligand or IL-7Rαγc IgG-Fc fusion protein. An IL-7Rαγc ligand or IL-7Rαγc IgG-Fc fusion protein and the at least one other therapeutic agent can act additively or, and in certain embodiments, synergistically with another IL-7Rαγc ligand or IL-7Rαγc IgG-Fc. The at least one additional therapeutic agent can be included in the same pharmaceutical composition or vehicle comprising the IL-7Rαγc ligand or IL-7Rαγc IgG-Fc fusion protein or can be in a separate pharmaceutical composition or vehicle. Accordingly, methods provided by the present disclosure further include, in addition to administering an IL-7Rαγc ligand or IL-7Rαγc IgG-Fc fusion protein, administering one or more therapeutic agents effective for treating cancer or a different disease, disorder or condition than cancer. Methods provided by the present disclosure include administration of an IL-7Rαγc ligand or IL-7Rαγc IgG-Fc fusion protein and one or more other therapeutic agents provided that the combined administration does not inhibit the therapeutic efficacy of an IL-7Rαγc ligand or IL-7Rαγc IgG-Fc fusion protein and/or does not produce adverse combination effects.

A pharmaceutical composition comprising an IL-7Rαγc ligand or IL-7Rαγc IgG-Fc fusion protein can be administered concurrently with the administration of another therapeutic agent, which can be part of the same pharmaceutical composition as, or in a different pharmaceutical composition than that comprising an IL-7Rαγc ligand or IL-7Rαγc IgG-Fc fusion protein. An IL-7Rαγc ligand or IL-7Rαγc IgG-Fc fusion protein can be administered prior or after administration of another therapeutic agent. In certain combination therapies, the combination therapy can comprise alternating between administering an IL-7Rαγc ligand or IL-7Rαγc IgG-Fc fusion protein and a composition comprising another therapeutic agent, e.g., to minimize adverse drug effects associated with a particular drug. When an IL-7Rαγc ligand or IL-7Rαγc IgG-Fc fusion protein is administered concurrently with another therapeutic agent that potentially can produce an adverse drug effect including, for example, toxicity, the other therapeutic agent can be administered at a dose that falls below the threshold at which the adverse drug reaction is elicited.

A pharmaceutical composition comprising an IL-7Rαγc ligand or IL-7Rαγc IgG-Fc fusion protein provided by the present disclosure can be administered with one or more substances, for example, to enhance, modulate and/or control release, bioavailability, therapeutic efficacy, therapeutic potency, and/or stability, of the IL-7Rαγc ligand or IL-7Rαγc IgG-Fc fusion protein. For example, a pharmaceutical composition comprising an IL-7Rαγc ligand or IL-7Rαγc IgG-Fc fusion protein can be co-administered with an active agent having pharmacological effects that enhance the therapeutic efficacy of the IL-7Rαγc ligand or IL-7Rαγc IgG-Fc fusion protein.

An IL-7Rαγc ligand or IL-7Rαγc IgG-Fc fusion protein, or a pharmaceutical composition thereof can be administered in conjunction with an agent known or believed to be effective in treating a disease such as cancer, an autoimmune disease, an inflammatory disease in a patient, an immunodeficiency disease, or a viral disease in a patient, such as the same disease being treated with the IL-7Rαγc ligand or IL-7Rαγc IgG-Fc fusion protein.

Pharmaceutical compositions comprising an IL-7Rαγc ligand or IL-7Rαγc IgG-Fc fusion protein be administered concurrently with the administration of another therapeutic agent, which can be part of the same pharmaceutical composition as, or in a different pharmaceutical composition than that comprising an IL-7Rαγc ligand or IL-7Rαγc IgG-Fc fusion protein. An IL-7Rαγc ligand or IL-7Rαγc IgG-Fc fusion protein can be administered prior or subsequent to administration of another therapeutic agent. In combination therapy, the combination therapy can comprise alternating between administering an IL-7Rαγc ligand or IL-7Rαγc IgG-Fc fusion protein and a composition comprising another therapeutic agent, e.g., to minimize adverse drug effects associated with a particular drug. When an IL-7Rαγc ligand or IL-7Rαγc IgG-Fc fusion protein is administered concurrently with another therapeutic agent that potentially can produce an adverse drug effect including, for example, toxicity, the other therapeutic agent can be administered at a dose that falls below the threshold at which the adverse drug reaction is elicited.

An IL-7Rαγc ligand or IL-7Rαγc IgG-Fc fusion protein, or a pharmaceutical composition thereof can be administered in conjunction with an agent known or believed to interfere with cell proliferation.

An IL-7Rαγc ligand or IL-7Rαγc IgG-Fc fusion protein, or a pharmaceutical composition thereof can be administered in conjunction with an agent known or believed to interfere with cellular metabolism, to be an anti-metabolite, to interfere with RNA transcription, to interfere with RNA translation, to interfere with cellular protein synthesis, to interfere with synthesis of precursors for DNA synthesis and replication, to interfere with purine synthesis, to interfere with nucleoside synthesis, to interact with mTOR, to be an mTOR inhibitor, to interfere with cell cycle checkpoints.

An IL-7Rαγc ligand or IL-7Rαγc IgG-Fc fusion protein or a pharmaceutical composition thereof can be administered in conjunction with a checkpoint inhibitor including a CTLA-4 inhibitor such as ipilimumab, a PD-1 inhibitor such as pembrolizumab and nivolumab, and/or a PD-LI inhibitor such as atezolizumab, avelumab, and durvalumab. An IL-7Rαγc ligand or IL-7Rαγc IgG-Fc fusion protein or a pharmaceutical composition thereof can be administered in conjunction with an immunomodulator such as CD137/4-1BB, CD27, GIYR, and/or OC40.

An IL-7Rαγc ligand or IL-7Rαγc IgG-Fc fusion protein or a pharmaceutical composition thereof can be administered in conjunction with an agent known or believed to be cytotoxic, to cause DNA damage, to cause cell cycle arrest, or to cause mitotic catastrophe.

An IL-7Rαγc ligand or IL-7Rαγc IgG-Fc fusion protein or a pharmaceutical composition thereof can be administered in conjunction with an agent known or believed to modulate glutathione concentration, to modulate glutathione concentration within cells, to decrease glutathione concentration within cells, to reduce glutathione uptake into cells, to reduce glutathione synthesis, or to reduce glutathione synthesis within cells.

An IL-7Rαγc ligand or IL-7Rαγc IgG-Fc fusion protein provided by the present disclosure, or a pharmaceutical composition thereof can be administered in conjunction with an agent known or believed to interfere with neovascularization, to reduce neovascularization, or to promote neovascularization.

An IL-7Rαγc ligand or IL-7Rαγc IgG-Fc fusion protein provided by the present disclosure, or a pharmaceutical composition thereof can be administered in conjunction with an agent known or believed to interfere with hormone homeostasis, to interfere with hormone synthesis, to interfere with hormone receptor binding, or to interfere with hormone signal transduction.

An IL-7Rαγc ligand or IL-7Rαγc IgG-Fc fusion protein provided by the present disclosure, or a pharmaceutical composition thereof can be administered in conjunction with an agent known or believed to interfere with growth factor homeostasis, to interfere with growth factor receptor expression, to interfere with growth factor binding to growth factor receptors, to interfere with growth factor receptor signal transduction, to interfere with the Hedgehog (Hh) signaling, to inhibit the Hedgehog pathway signaling, to inhibit ALK (anaplastic lymphoma kinase) pathway signaling, or to inhibit the non-homologous end joining (NHEJ) pathway.

An IL-7Rαγc ligand or IL-7Rαγc IgG-Fc fusion protein provided by the present disclosure, or a pharmaceutical composition thereof can be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhancer of zeste homolog 2) inhibitor, a BET (bromodomain and extraterminal domain motif) inhibitor, a SYK (spleen tyrosine kinase) inhibitor, JAK (janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selective RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (casein kinase) inhibitor, a CK2 inhibitor, a Bcr-Abl (breakpoint cluster region-Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl peptidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

An IL-7Rαγc ligand or IL-7Rαγc IgG-Fc fusion protein provided by the present disclosure, or a pharmaceutical composition thereof can be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; a nuclear translocation factor such as JSH-23; a PORCn inhibitor such as Wnt-C59; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tsl-sporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

For example, an IL-7Rαγc ligand or IL-7Rαγc IgG-Fc fusion protein provided by the present disclosure, or a pharmaceutical composition thereof can be administered in conjunction with another chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

An IL-7Rαγc ligand or IL-7Rαγc IgG-Fc fusion protein provided by the present disclosure, or a pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

An IL-7Rαγc ligand or IL-7Rαγc IgG-Fc fusion protein or a pharmaceutical composition thereof can be co-administered with a compound that inhibits DNA repair such as, for example, O6-benzylguanine (O6-BG).

An IL-7Rαγc ligand or IL-7Rαγc IgG-Fc fusion protein provided by the present disclosure or a pharmaceutical composition thereof can be administered in conjunction with one or more chemotherapeutic agents, such as, for example, abarelix, abiraterone, abiraterone acetate, n-acetyl cysteine, aclarubicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, 1-asparaginase, azacitidine, azathioprine sodium, bazedoxifene (serm), belinostat, bendamustine hcl, 06-benzylguanine, bevacizumab, bexarotene, bicalutamide, biricodar, bleomycin sulfate, bortezomib, bosutinib, brivudine, buserelin, busulfan, buthionine sulfoxime, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defribrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idarubicin HCl, idelalisib, idoxuridine, ifosfamide, interferon alpha, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, revlimide, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

An IL-7Rαγc ligand or IL-7Rαγc IgG-Fc fusion protein provided by the present disclosure, or a pharmaceutical composition thereof can be administered in conjunction with one or more chemotherapeutic agents such as, for example, abemaciclib, abiraterone acetate, ABVD, ABVE, ABVE-PC, AC, acalabrutinib, AC-T, ADE, ado-trastuzumab emtansine, afatinib dimaleate, aldesleukin, alectinib, alemtuzumab, alpelisib, amifostine, aminolevulinic acid hydrochloride, anastrozole, apalutamide, aprepitant, arsenic trioxide, asparaginase Erwinia chrysanthemi, atezolizumab, avelumab, axicabtagene ciloleucel, axitinib, azacitidine, BEACOPP, belinostat, bendamustine hydrochloride, BEP, bevacizumab, bexarotene, bicalutamide, binimetinib, bleomycin sulfate, blinatumomab, bortezomib, bosutinib, brentuximab vedotin, brigatinib, BuMel, busulfan, cabazitaxel, cabozantinib-s-malate, CAF, calaspargase pegol-mknl, capecitabine, caplacizumab-yhdp, CAPDX, carboplatin, carboplatin-taxol, carfilzomib, carmustine, carmustine implant, CEM, cemiplimab-rwlc, ceritinib, cetuximab, CEV, chlorambucil, chlorambucil-prednisone, CHOP, cisplatin, cladribine, clofarabine, CMF, cobimetinib, copanlisib hydrochloride, COPDAC, COPP, COPP-ABV, crizotinib, CVP, cyclophosphamide, cytarabine, cytarabine liposome, dabrafenib mesylate, dacarbazine, dacomitinib, dactinomycin, daratumumab, darbepoetin α, dasatinib, daunorubicin hydrochloride, daunorubicin hydrochloride and cytarabine liposome, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, durvalumab, duvelisib, elotuzumab, eltrombopag olamine, emapalumab-lzsg, enasidenib mesylate, encorafenib, enzalutamide, epirubicin hydrochloride, EPOCH, epoetin alfa, erdafitinib, eribulin mesylate, erlotinib hydrochloride, etoposide, etoposide phosphate, everolimus, exemestane, fec, filgrastim, fludarabine phosphate, fluorouracil injection, fluorouracil-topical, flutamide, folfiri, folfiri-bevacizumab, folfiri-cetuximab, folfirinox, folfox, fostamatinib disodium, FU-LV, fulvestrant, gefitinib, gemcitabine hydrochloride, gemcitabine-cisplatin, gemcitabine-oxaliplatin, gemtuzumab ozogamicin, gilteritinib fumarate, glasdegib maleate, glucarpidase, goserelin acetate, granisetron, HPV bivalent vaccine, HPV bivalent vaccine, recombinant HPV nonavalent vaccine, HPV nonavalent vaccine, recombinant, HPV quadrivalent vaccine, HPV uadrivalent vaccine recombinant, hydroxyurea, hyper-CVAD, ibritumomab tiuxetan, ibrutinib, ICE, idarubicin hydrochloride, idelalisib, ifosfamide, imatinib mesylate, imiquimod, inotuzumab ozogamicin, interferon α-2b recombinant, iobenguane I$^{131}$, ipilimumab, irinotecan hydrochloride, irinotecan hydrochloride liposome, ivosidenib, ixabepilone, ixazomib citrate, JEB, lanreotide acetate, lapatinib ditosylate, larotrectinib sulfate, lenalidomide, lenvatinib mesylate, letrozole, leucovorin calcium, leuprolide acetate, lomustine, lorlatinib, lutetium Lu 177-dotatate, mechlorethamine hydrochloride, megestrol acetate, melphalan, melphalan hydrochloride, mercaptopurine, mesna, methotrexate, methylnaltrexone bromide, midostaurin, mitomycin c, mitoxantrone hydrochloride, mogamulizumab-kpkc, moxetumomab pasudotox-tdfk, MVAC, necitumumab, nelarabine, neratinib maleate, netupitant and palonosetron hydrochloride, nilotinib, nilutamide, niraparib tosylate monohydrate, nivolumab, obinutuzumab, OEPA, ofatumumab, OFF, olaparib, olaratumab, omacetaxine mepesuccinate, ondansetron hydrochloride, OPPA, osimertinib mesylate, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, pegfilgrastim, peginterferon α-2b, pembrolizumab, pemetrexed disodium, pertuzumab, plerixafor, polatuzumab vedotin-piiq, pomalidomide, ponatinib hydrochloride, pralatrexate, prednisone, procarbazine hydrochloride, propranolol hydrochloride, radium 223 dichloride, raloxifene hydrochloride, ramucirumab, rasburicase, ravulizumab-cwvz, R-CHOP, R-CVP, recombinant HPV bivalent vaccine, recombinant HPV nonavalent vaccine, recombinant HPV quadrivalent vaccine, recombinant interferon α-2b, regorafenib, R-EPOCH, ribociclib, R-ICE, rituximab, rituximab and hyaluronidase human, rolapitant hydrochloride, romidepsin, romiplostim, rucaparib camsylate, ruxolitinib phosphate, siltuximab, sipuleucel-t, sonidegib, sorafenib tosylate, STANFORD V, sunitinib malate, TAC, tagraxofusp-erzs, talazoparib tosylate, talc, talimogene laherparepvec, tamoxifen citrate, temozolomide, temsirolimus, thalidomide, thioguanine, thiotepa, tisagenlecleucel, tocilizumab, topotecan hydrochloride, toremifene, TPF, trabectedin, trametinib, trastuzumab, trastuzumab and hyaluronidase-oysk, trifluridine and tipiracil hydrochloride, uridine triacetate, VAC, Valrubicin, VAMP, vandetanib, VeIP, vemurafenib, venetoclax, vinblastine sulfate, vincristine sulfate liposome, vinorelbine tartrate, vip, vismodegib, vorinostat, XELIRI, XELOX, Ziv-aflibercept, zoledronic acid, and combinations of any of the foregoing.

The efficacy of administering an IL-7Rαγc ligand or IL-7Rαγc IgG-Fc fusion protein provided by the present disclosure or a pharmaceutical composition thereof for treating cancer can be assessed using in vitro and animal studies and in clinical trials.

The suitability of an IL-7Rαγc ligand or IL-7Rαγc IgG-Fc fusion protein provided by the present disclosure or a pharmaceutical composition thereof in treating cancer can be determined by methods described in the art.

An IL-7Rαγc ligand or IL-7Rαγc IgG-Fc fusion protein provided by the present disclosure, or a pharmaceutical composition thereof can be used to treat a disease in combination with an immune-oncology agent.

Examples of suitable immune-oncology agents include anti-PD1, PDL1, CTLA4, TIGIT, LAG3, and combinations of any of the foregoing.

Examples of suitable immune-oncology agents include cytokine derivatives of IL-2, IL-15, IL-12, IL-18, and IL-21; and interferons, and combinations of any of the foregoing.

Immune-oncology agents include immune checkpoint inhibitors such as pembrolizumab, nivolumab, atezolizumab, atezolizumab, durvalumab, avelumab, cemiplimab, ipilimumab, toripalimab, sintilimab, camrelizumab, and tislelizumab; T-cell transfer therapy such as tumor-infiltrating lymphocyte therapy and CAR T-cell therapy; monoclonal antibody therapy; cancer treatment vaccines, and immune system modulators such as interferons, interleukins, BCG, and immunomodulatory drugs such as thalidomide, lenalidomide, pomalidomide, and imiquimod.

Examples of CAR-T cell therapies include axicabtagene ciloleucel, brexucabtagene autoleucel, ciltacabtagene autoleucel, idecabtagene vicleucel, lisocabtagene maraleucel, and tisagenlecleucel.

Examples of interferons include interferon β-1a, peginterferon β-1a, interferon β-1b, interferon alfacon-1, interferon α-n3, and interferon γ-1b.

An IL-7Rαγc ligand or IL-7Rαγc IgG-Fc fusion protein provided by the present disclosure, or a pharmaceutical composition thereof can be used in combination with radiation therapy to treat cancer. Radiation therapy includes ionizing radiation such as X-rays, gamma-rays, and particle radiation beams. The radiation can be ionizing radiation such as a beam of protons, alpha particles, or beta particles. The radiation can be indirectly ionizing radiation such as electromagnetic waves and neutron beams. Radiation therapy includes external beam radiation therapy and internal radiation therapy such as brachytherapy.

Pharmaceutical compositions comprising an IL-7Rαγc ligand or IL-7Rαγc IgG-Fc fusion protein provided by the present disclosure can be administered with one or more substances to enhance, modulate and/or control release, bioavailability, therapeutic efficacy, therapeutic potency, and stability, of an IL-7Rαγc ligand or IL-7Rαγc IgG-Fc fusion protein. For example, to enhance the therapeutic efficacy of an IL-7Rαγc ligand or IL-7Rαγc IgG-Fc fusion protein, metabolite thereof, or a pharmaceutical composition of any of the foregoing can be co-administered with one or more active agents to increase the absorption or diffusion of the IL-7Rαγc ligand or IL-7Rαγc IgG-Fc fusion protein from the gastrointestinal tract to the systemic circulation, or to inhibit degradation of the IL-7Rαγc ligand or IL-7Rαγc IgG-Fc fusion protein in the blood of a subject. A pharmaceutical composition comprising an s IL-7Rαγc ligand or IL-7Rαγc IgG-Fc fusion protein can be co-administered with an active agent having pharmacological effects that enhance the therapeutic efficacy of the IL-7Rαγc ligand or IL-7Rαγc IgG-Fc fusion protein.

The amount of an IL-7Rαγc ligand or IL-7Rαγc IgG-Fc fusion protein provided by the present disclosure, or pharmaceutical composition thereof that will be effective in the treatment of a cancer, an inflammatory disease, an autoimmune disease, or a viral disease can depend, at least in part, on the nature of the disease, and can be determined by standard clinical techniques known in the art. In addition, in vitro or in vivo assays can be employed to help identify optimal dosing ranges. Dosing regimens and dosing intervals can also be determined by methods known to those skilled in the art. The amount of an IL-7Rαγc ligand or IL-7Rαγc IgG-Fc fusion protein provided by the present disclosure administered can depend on, among other factors, the patient being treated, the weight of the patient, the severity of the disease, the route of administration, and the judgment of the prescribing physician.

For systemic administration, a therapeutically effective dose can be estimated initially from in vitro assays. Initial doses can also be estimated from in vivo data, e.g., animal models, using techniques that are known in the art. Such information can be used to more accurately determine useful doses in humans. One having ordinary skill in the art can optimize administration to humans based on animal data.

A dose of an IL-7Rαγc ligand or IL-7Rαγc IgG-Fc fusion protein provided by the present disclosure and appropriate dosing intervals can be selected to maintain a sustained therapeutically effective concentration of the IL-7Rαγc ligand or IL-7Rαγc IgG-Fc fusion protein provided by the present disclosure in the blood of a patient, and in certain embodiments, without exceeding a minimum adverse concentration.

A pharmaceutical composition comprising an IL-7Rαγc ligand or IL-7Rαγc IgG-Fc fusion protein provided by the present disclosure can be administered, for example, once per week, every 2 weeks, every 3 weeks, every 4 weeks, every 5 weeks, or every 6 weeks. Dosing can be provided alone or in combination with other drugs and can continue as required for effective treatment of the disease. Dosing can also be undertaken using continuous or semi-continuous administration over a duration. Dosing includes administering a pharmaceutical composition to a mammal, such as a human, in a fed or fasted state.

A pharmaceutical composition can be administered in a single dosage form or in multiple dosage forms or as a continuous or an accumulated dose over a duration. When multiple dosage forms are used the amount of an IL-7Rαγc ligand or IL-7Rαγc IgG-Fc fusion protein provided by the present disclosure contained within each of the multiple dosage forms can be the same or different.

Suitable daily dosage ranges for administration can range, for example, from about 2 μg to about 200 mg of an IL-7Rαγc ligand or IL-7Rαγc IgG-Fc fusion protein provided by the present disclosure per kilogram body weight.

Suitable daily dosage ranges for administration can range, for example, from about 1 μg to about 50 mg of an IL-7Rαγc ligand or IL-7Rαγc IgG-Fc fusion protein provided by the present disclosure per square me ter ($m^2$) of body surface.

An IL-7Rαγc ligand or IL-7Rαγc IgG-Fc fusion protein provided by the present disclosure can be administered to treat cancer in a patient in an amount, for example, from 0.001 mg/day to 100 mg/day, or in any other appropriate daily dose. A dose can be, for example, from 0.01 μg/kg body weight/week to 100 μg/kg body weight/week or any other suitable dose.

A pharmaceutical composition comprising an IL-7Rαγc ligand or IL-7Rαγc IgG-Fc fusion protein provided by the present disclosure can be administered to treat cancer in a patient so as to provide a therapeutically effective concentration of an IL-7Rαγc ligand or IL-7Rαγc IgG-Fc fusion protein provided by the present disclosure in the blood or plasma of the patient. A therapeutically effective concentration of a compound of an IL-7Rαγc ligand or IL-7Rαγc IgG-Fc fusion protein provided by the present disclosure in the plasma of a patient can be, for example, from 0.01 μg/L to 1,000 μg/L, from 0.1 μg/L to 500 μg/L, from 1 μg/L to 250 μg/L, or from about 10 μg/L to about 100 μg/L. A therapeutically effective concentration of an IL-7Rαγc ligand or IL-7Rαγc IgG-Fc fusion protein provided by the present disclosure in the plasma of a patient can be, for example, at least 0.01 μg/L, at least 0.1 μg/L, at least 1 μg/L, at least about 10 μg/L, or at least 100 μg/L. A therapeutically effective concentration of an IL-7Rαγc ligand or IL-7Rαγc IgG-Fc fusion protein in the plasma of a patient can be, for example, less than an amount that causes unacceptable adverse effects including adverse effects to homeostasis. A therapeutically effective concentration of an IL-7Rαγc ligand or IL-7Rαγc IgG-Fc fusion protein in the plasma of a patient can be an amount sufficient to restore and/or maintain homeostasis in the patient.

Pharmaceutical compositions comprising an IL-7Rαγc ligand or IL-7Rαγc IgG-Fc fusion protein can be administered to treat a disease in a patient so as to provide a therapeutically effective concentration of the IL-7Rαγc ligand or IL-7Rαγc IgG-Fc fusion protein in the blood or plasma of a patient for an extended period of time such as, for example, for at least 1 day, for at least 1 week, at least 2 weeks, at least 4 weeks, at least 5 weeks, or at least 6 weeks.

The amount of an IL-7Rαγc ligand or IL-7Rαγc IgG-Fc fusion protein administered can vary during a treatment regimen.

Pharmaceutical compositions provided by the present disclosure can further comprise one or more pharmaceutically active compounds in addition to an IL-7Rαγc ligand or IL-7Rαγc IgG-Fc fusion protein provided by the present disclosure. Such compounds can be provided, for example, to treat the cancer being treated with the IL-7Rαγc ligand or IL-7Rαγc IgG-Fc fusion protein or to treat a disease, disorder, or condition other than the cancer being treated with the IL-7Rαγc ligand or IL-7Rαγc IgG-Fc fusion protein, to treat a side-effect caused by administering the IL-7Rαγc ligand or IL-7Rαγc IgG-Fc fusion protein, to augment the efficacy of the IL-7Rαγc ligand or IL-7Rαγc IgG-Fc fusion protein, and/or to modulate the activity of the an IL-7Rαγc ligand or IL-7Rαγc IgG-Fc fusion protein.

IL-7Rαγc ligands and IL-7Rαγc IgG-Fc fusion proteins provided by the present disclosure can be useful in vitro as tools for understanding the biological role of IL-7, including the evaluation of the many factors thought to influence, and be influenced by, the production of IL-7 and the receptor binding process. The present compounds are also useful in the development of other compounds that bind to and activate IL-7R, because the present compounds provide useful information concerning the relationship between structure and activity that should facilitate such development.

The IL-7Rαγc ligands and IL-7Rαγc IgG-Fc fusion proteins are also useful as competitive binders in assays to screen for new IL-7 receptor agonists and antagonists. In such assays, an IL-7Rαγc ligand or IL-7Rαγc IgG-Fc fusion protein can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I, enzymes such as peroxidase and alkaline phosphatase, and fluorescent labels capable of monitoring the change in fluorescence intensity, wavelength shift, or fluorescence polarization. Possibilities for indirect labeling include biotinylation of one constituent followed by binding to avidin coupled to one of the above label groups. The compounds can also include spacers or linkers in cases where the compounds are to be attached to a solid support.

Based on the ability to bind to IL-7R, an IL-7Rαγc ligand or IL-7Rαγc IgG-Fc fusion protein provided by the present disclosure can be used as reagents for detecting IL-7R, for example, on living cells, fixed cells, in biological fluids, in tissue homogenates, in purified, and natural biological materials. For example, by labeling such peptides, one can identify cells expressing the IL-7Rα and Rγc subunits. In addition, based on the ability to bind to IL-7R, the IL-7Rαγc ligand and IL-7Rαγc IgG-Fc fusion protein provided by the present disclosure can be used, for example, in in situ staining, FACS (fluorescence-activated cell sorting), Western Blotting, and ELISA. In addition, based on the ability to bind to IL-7R, the IL-7Rαγc ligand and IL-7Rαγc IgG-Fc fusion proteins provided by the present disclosure can be used in receptor purification, or in purifying cells expressing IL-7R on the cell surface (or inside permeabilized cells).

IL-7Rαγc ligands and IL-7Rαγc IgG-Fc fusion proteins provided by the present disclosure can also be utilized as commercial reagents for various medical research and diagnostic uses. Such uses include, for example, (1) use as a calibration standard for quantitating the activities of candidate IL-7 agonists in a variety of functional assays; (2) use to maintain the proliferation and growth of IL-7-dependent cell lines; (3) use in structural analysis of IL-7R through co-crystallization; (4) use to investigate the mechanism of IL-7 signal transduction/receptor activation; and (5) other research and diagnostic applications wherein the IL-7 receptor is implicated.

An IL-7Rαγc ligand or IL-7Rαγc IgG-Fc fusion protein includes diagnostic reagents. As a diagnostic agent, an IL-7Rαγc ligand or IL-7Rαγc IgG-Fc fusion protein can be used to detect and/or to measure cells expressing the IL-7R subunit. The compounds can be used to determine the level of IL-7R expression of a cell, of a population of cells, or of a tissue. The compounds can be used to assess the binding affinity to IL-7R in a cell or population of cells. The compounds can be used to determine a particular type of cell, for example, based on IL-7R expression levels.

The IL-7Rαγc ligands and IL-7Rαγc IgG-Fc fusion proteins can be useful for in vitro and in vivo diagnostics.

A diagnostic IL-7Rαγc ligand or IL-7Rαγc IgG-Fc fusion protein can comprise a detectable marker. The detectable marker can be cleavable or non-cleavable.

A detectable marker can comprise, for example, a radiolabel, a fluorescent label, and/or an enzymatic label.

A diagnostic IL-7Rαγc ligand or IL-7Rαγc IgG-Fc fusion protein can be used to measure cells expressing the IL-7Rα subunit and/or the level of expression of cells expressing the IL-7Rα subunit in a biological sample such as a sample of blood of a patient. Measurements can be made, for example, using flow cytometry. The number of cells expressing the IL-7Rα subunit and/or the expression level of the IL-7Rα subunit, when correlated with a disease in a patient or a pharmacologically significant parameter of the disease in a patient can be used to inform treatment of the disease. For example, if a level of expression of the IL-7Rα subunit is above or below a therapeutically meaningful threshold for a particular disease, a compound comprising an IL-7Rα ligand provided by the present disclosure can be administered to the patient to treat the disease.

An IL-7Rαγc ligand or IL-7Rαγc IgG-Fc fusion protein can be attached to a solid support. Based on the ability of the compounds to bind to IL-7R, the compounds can be used as reagents for detecting IL-7R, for example, on living cells, fixed cells, in biological fluids, in tissue homogenates, in purified, and natural in biological materials. In addition, based on the ability to bind to IL-7R and/or to an IL-7R subunit, the peptides provided by the present disclosure can be used, for example, in in situ staining, FACS (fluorescence-activated cell sorting), Western Blotting, and ELISA. In addition, compounds provided by the present disclosure can be used in receptor purification, or to purify cells expressing IL-7R on the cell surface.

An IL-7Rαγc ligand or IL-7Rαγc IgG-Fc fusion protein provided by the present disclosure can be therapeutically useful when combined with certain vaccines, including cancer neo-antigen vaccines. Mutations in tumor DNA produces new protein sequences that are foreign to the body.

Vaccines can be designed to specifically activate a patient's immune system with respect to tumor-specific neo-antigens. When administered in combination with a neo-antigen vaccine and IL-7Rαγc ligand or IL-7Rαγc IgG-Fc fusion protein provided by the present disclosure can expand and proliferate neo-antigen-specific T-cells in the tumor microenvironment and thereby drive maximal expansion of vaccine-induced neo-antigen-specific T-cells for the treatment of cancer.

An IL-7Rαγc ligand or IL-7Rαγc IgG-Fc fusion protein provided by the present disclosure can be used as an adjuvant. An adjuvant refers to a compound that enhances the efficacy of a vaccine without directly participating in the protective immunity. For example, an IL-7Rαγc ligand or IL-7Rαγc IgG-Fc fusion protein provided by the present disclosure can be used in conjunction with a cancer vaccine or a viral vaccine.

Recent research suggests that IL-7 can serve as an effective vaccine adjuvant. For example, IL-7Rα is expressed on the majority of resting, naive CD8+ T cells; IL-7 signaling recruits T cells specific for low-affinity antigens into the proliferative pool in lymphopenic hosts; and, as with other Rγc cytokines, IL-7 prevents programmed cell death. Because IL-7 is important during the expansion and development of effector T-cells into memory T-cells, it is reasonable that IL-7 could be used to stimulate the development and expansion of effector T-cells during vaccination.

Administration of IL-7 has been shown therapeutic potential for augmenting the immune response and can enhance the effectiveness of vaccine-induced T cell responses.

For example, co-delivery of hu-IL-7 DNA augmented multigenic HCV DNA vaccine-induced T-cell responses in a non-human primate model.

In bacterial infections, therapeutic potential of IL-7 in the setting of sepsis mouse model was proven by increasing the number of recruited neutrophils.

Therapies involving administration of IL-7 showed enhanced virus-specific T-cell responses which led to viral clearance in a chronic lymphocytic choriomeningitis (LCMV) mouse infection model. Administration of recombinant IL-7 during the contraction phase of CD8+ T cell responses elicited in response to DNA vaccines increased the number of LCMV-specific memory T-cells.

In a murine model of influenza, A virus (IAV) it was demonstrated that a single intranasal pretreatment with Fc-fused IL-7 (IL-7-mFc), but not a native form of IL-7, protected mice from IAV-induced mortality for an extended period of time, even without preexisting IAV-specific immunity. IL-7-mFc treatment induced altered immune environments in the lung, with prolonged occupancy of lung-retentive effector/memory phenotype T (TRM-like) cells, which play an essential role in protection from IAVs by limiting viral replication and immunopathology, while helping IAV-specific cytotoxic T lymphocytes (CTLs) to propagate.

In another study, in which a recombinant RABV (rRABV) expressing mouse IL-7 was administered to mice, it was found that overexpressing IL-7 improved the production of long-lasting primary and secondary antibody responses to RABV infection.

It has been reported that recombinant IL-7 protein enhances the survival of Mycobacterium tuberculosis-infected mice by the activation of antigen-specific effector CD8+ T cells.

Furthermore, IL-7-expressing plasmids can enhance vaccine-induced CTL and/or Th2-type immune responses in mice injected with HSV-2 gD DNA vaccine.

In another study a DNA vaccine encoding the VP1 capsid protein of foot and mouth disease virus was co-delivered to mice with an IL-6 expressing plasmid as an initial adjuvant and boosted with an IL-7 expressing plasmid as a secondary adjuvant. Mice immunized with pVAX-IL-6 and boosted with pVAX-IL-7 produced the highest expression of CD44high CD62Llow in activated CD4+ T cells.

An IL-7Rαγc ligand or IL-7Rαγc IgG-Fc fusion protein provided by the present disclosure can be therapeutically useful for cell therapy when engineered to be expressed on the membrane surface of cells that also express the IL-7Rαγc subunits. Adoptive immunotherapy using NK cells or using re-targeted chimeric antigen receptor (CAR) T-cells is currently being studied as a treatment for neoplasms and viral infections. One challenge with these cell therapies is the suboptimal sustained survival of the infused cells.

DNA encoding an IL-7Rαγc ligand fused to a membrane protein in such a way that the IL-7Rαγc ligand is expressed on the extracellular surface of a cell can be constructed using standard techniques. When the fusion protein comprising the IL-7Rαγc ligand is expressed, IL-7 receptors on the cell become activated leading to long-term persistence of the cell.

DNA encoding an IL-7Rαγc ligand can be incorporated into a cell and can be configured to produce an IL-7Rαγc ligand provided by the present disclosure. An IL-7Rαγc ligand can be secreted from the cell and can interact with the secreting cells (i.e., autocrine signaling) and/or cells in the vicinity of the secreting cell (i.e., paracrine signaling). A secreted IL-7Rαγc ligand or IL-7Rαγc IgG-Fc fusion protein provided by the present disclosure can be an IL-7R agonist and can be designed to localize near the secreting cell.

An IL-7Rαγc ligand or IL-7Rαγc IgG-Fc fusion protein provided by the present disclosure can be used to expand T-cells within a patient or within a biological sample. Methods of increasing the ratio of non-regulatory T-cells to Treg cells can comprise contacting a population of T-cells with an effective amount of an IL-7Rαγc ligand or IL-7Rαγc IgG-Fc fusion protein provided by the present disclosure. The ratio can be measured by determining the ratio of CD3+FOXP3+ cells to CD3+FOXP3-cells within the population of T-cells. A typical Treg frequency in human blood is 5% to 10% of the total CD4+CD3+ T-cells, however, in certain diseases this percentage may be lower or higher.

An IL-7Rαγc ligand or IL-7Rαγc IgG-Fc fusion protein can be used to expand T-cells. T-cells modified with chimeric antigen receptors (CARs), which redirect immune cell activity to target cancer cells have been demonstrated to exhibit improved antitumor responses. CARs can comprise an antibody-derived extracellular domain, which binds to the desired tumor-associated antigen (TAA) and triggers an intracellular signaling cascade to activate the immune cell against the target cells.

An IL-7Rαγc ligand or IL-7Rαγc IgG-Fc fusion protein that is immobilized to a surface such as a bead can be exposed to populations of T-cells in vitro or ex vivo to induce expansion of the cell population prior to transferring to a patient. CAR-T cells can be expanded by exposure to an immobilized form of an IL-7Rαγc ligand or IL-7Rαγc IgG-Fc fusion protein. An immobilized IL-7Rαγc ligand or IL-7Rαγc IgG-Fc fusion protein can be separated from the CAR-T cells prior to transferring the CAR-T cells to a patient.

CAR T-cells can be genetically engineered to co-express a tethered form of an IL-7Rαγc ligand provided by the present disclosure to support in vivo persistence and maintenance of an immature state of differentiation and to exhibit in vivo antitumor activity.

An IL-7Rαγc ligand or IL-7Rαγc IgG-Fc fusion protein provided by the present disclosure can be used to mobilize and/or increase the number of T-cells and/or CD34+ stem cells in peripheral blood for increased yield from leukapheresis. The T cells and/or CD34+ stem cells can be manipulated ex vivo and used for cell therapy to treat cancer.

Assessing single patient response to therapy and qualifying a patient for optimal therapy are among the greatest challenges of modern healthcare and relate to trends in personalized medicine. An IL-7Rαγc ligand or IL-7Rαγc IgG-Fc fusion protein can have target selectivity, for example, for certain cancers and immune cells. An IL-7Rαγc ligand or IL-7Rαγc IgG-Fc fusion protein radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using IL-7Rαγc ligands or IL-7Rαγc IgG-Fc fusion proteins, once correlated to the concentration can provide a three-dimensional distribution map, which can then be used for macroscopic dose calculations.

An IL-7Rαγc ligand or IL-7Rαγc IgG-Fc fusion protein can comprise one or more imaging agents. An IL-7Rαγc ligand or IL-7Rαγc IgG-Fc fusion protein can direct and localize the compound to cells, populations of cells, and tissue expressing IL-7R. The imaging compounds can comprise one or more imaging agents such as radiolabels, fluorescent labels, enzymatic labels, or PET imaging agents.

The imaging agents can be used to determine the number of cells expressing IL-7R, the expression level of cells expressing IL-7R, or properties of IL-7R such as the binding affinity of IL-7R to a particular IL-7Rαγc ligand or IL-7Rαγc IgG-Fc fusion protein. The imaging agents can be used, for example, to evaluate cancer cells expressing IL-7Rα subunit, or to evaluate Treg and/or Teff cells.

The label can be detected to determine a biodistribution of the compound in a patient or to assess the potential for therapeutic efficacy. For example, tumors expressing high levels of IL-7R can be attractive targets for a therapeutic IL-7Rαγc ligand or IL-7Rαγc IgG-Fc fusion protein provided by the present disclosure.

The imaging agents can be used to evaluate cells expressing IL-7R before therapy, during therapy, and/or following therapy.

Imaging agents comprising an IL-7Rαγc ligand or IL-7Rαγc IgG-Fc fusion protein can further comprise a moiety capable of binding to a cell surface and in particular to a protein expressed on the cell surface. The protein can be indicative of a certain cell type and is referred to as a cell surface marker. Imaging agents comprising both an IL-7Rαγc ligand or IL-7Rαγc IgG-Fc fusion protein and a cell surface marker can be used to assess cells, a population of cells, and/or a tissue expressing both IL-7R and the cell surface marker. Assessment can include determining the number of cells expressing both IL-7R and the cell surface marker, the expression levels of IL-7R and the cell surface marker, and/or the binding affinity of the imaging agent to IL-7R and/or the cell surface marker.

The imaging agents can be used to evaluate cells expressing IL-7R and the cell surface marker before therapy, during therapy, and/or following therapy.

An IL-7Rαγc ligand or IL-7Rαγc IgG-Fc fusion protein provided by the present disclosure can be labeled. Labeled compounds can be useful in diagnostics.

An IL-7Rαγc ligand or IL-7Rαγc IgG-Fc fusion protein provided by the present disclosure can be labeled with a detectable marker. The label can be used to determine a biodistribution of the compound in a patient or to assess the potential for therapeutic efficacy. For example, tumors expressing high levels of IL-7R can be attractive targets for selective IL-7R agonists and compounds comprising an IL-7Rαγc ligand provided by the present disclosure.

An IL-7Rαγc ligand or IL-7Rαγc IgG-Fc fusion protein provided by the present disclosure include labeled compounds. A labeled compound can be a detectable marker, for example, a radiolabeled amino acid or an attachment of biotinyl moieties to a polypeptide, where the attached biotinyl moieties can be detected by marked avidin (e.g., streptavidin containing a fluorescent marker or enzymatic activity that can be detected by optical or colorimetric methods). Various methods of labeling polypeptides and glycoproteins are known in the art and can be used. Examples of labels for polypeptides include, for example, radioisotopes such as $^3$H, $^{14}$C, $^{35}$S, $^{125}$I, and $^{131}$I, fluorescent labels such as FITC, rhodamine, and lanthanide phosphors, enzymatic labels such as horseradish peroxidase, β-galactosidase, luciferase, and alkaline phosphatase, biotinyl groups, predetermined polypeptide epitopes recognized by a secondary reporter such as leucine zipper pair sequences, binding sites for secondary antibodies, metal ligands, and epitope tags. A label can be attached by spacer arms of various lengths to reduce potential steric hindrance.

A nucleic acid provided by the present disclosure can encode for an IL-7Rαγc ligand provided by the present disclosure.

A nucleic acid provided by the present disclosure can encode for an IL-7Rαγc IgG-Fc fusion protein provided by the present disclosure.

A nucleic acid can be, for example, a deoxyribonucleic acid (DNA) or a ribonucleic acid (RNA) such as a messenger RNA (mRNA), a ribosomal RNA (rRNA), or an antisense RNA.

Nucleic acids/isolated polynucleotides encoding for an IL-7Rαγc or IL-7Rαγc IgG-Fc fusion protein provided by the present disclosure can be incorporated into expression vectors depending in part on the host cells used to produce the IL-7Rαγc or IL-7Rαγc IgG-Fc fusion protein. Generally, the nucleic acids can be operably linked to any number of regulatory elements such as, for example, promoters, origin of replication, selectable markers, ribosomal binding sites, and/or inducers. The expression vectors can be extra-chromosomal or integrating vectors.

The nucleic acids and/or expression vectors can be transformed into any number of different types of host cells including mammalian, bacterial, yeast, insect and/or fungal cells, with mammalian cells such as CHO cells.

A nucleic acid encoding an IL-7Rαγc ligand can comprise a first nucleic acid sequence encoding an IL-7Rα ligand; a second nucleic acid sequence encoding a peptidyl ligand linker; and a third nucleic acid sequence encoding an Rγc ligand.

A nucleic acid encoding an IL-7Rαγc IgG-Fc fusion protein can comprise a first nucleic acid sequence encoding the IL-7Rαγc ligand provided by the present disclosure; and a second nucleic acid sequence encoding a fusion partner such as an IgG-Fc fragment. A nucleic acid encoding an IL-7Rαγc fusion protein can comprise a nucleic acid encoding an IL-7Rαγc ligand and the fusion partner such as an IgG-Fc fragment. A nucleic acid encoding an IL-7Rαγc ligand fusion protein can further comprise a nucleic acid segment encoding a construct linker and a nucleic acid encoding an IL-7Rαγc ligand fusion protein can comprise a nucleic acid encoding an IL-7Rαγc ligand, the IgG-Fc fragment, or the IL-7Rαγc IgG-Fc fusion protein.

The fusion partner can comprise, for example, an IgG-Fc fragment, such as an IgG1-Fc fragment, an IgG2-Fc fragment, or an IgG4-Fc fragment.

A nucleic acid encoding an IL-7Rαγc IgG-Fc fusion protein can further comprise a nucleic acid encoding a peptidyl linker, where the peptidyl linker is configured to bind the IL-7Rαγc ligand to the IgG-Fc fragment.

A nucleic acid provided by the present disclosure can encode a fusion protein comprising a dimeric Fc-Fragment of IgG1, IgG2, or IgG4, an IL-7Rαγc ligand, and a linker binding the N-terminus of an IL-7Rαγc ligand to the C-terminus of one CH3 domain of the dimeric Fc-fragment.

A nucleic acid provided by the present disclosure can encode a fusion protein comprising a dimeric Fc-Fragment of IgG1, IgG2, or IgG4, two IL-7Rαγc ligands, and a linker binding the N-terminus of each of the two IL-7Rαγc ligands to the C-terminus of each CH3 domain of the dimeric Fc-fragment.

A nucleic acid provided by the present disclosure can encode a fusion protein comprising a heavy chain of an immunoglobulin molecule such as IgG1, IgG2, or IgG4, an IL-7Rαγc ligand, and an Fc linker bonding the N-terminus of the IL-7Rαγc ligand to the C-terminus of the Fc region.

A nucleic acid provided by the present disclosure can comprise a nucleic acid encoding for an IL-7Rαγc ligand or an IL-7Rαγc IgG-Fc fusion protein such as an IL-7Rαγc IgG-Fc fusion protein provided by the present disclosure and an RNA and/or DNA vaccine.

A nucleic acid provided by the present disclosure can comprise a nucleic acid encoding for an IL-7Rαγc IgG-Fc fusion protein vaccine construct. The vaccine can comprise, for example, a cancer vaccine or a viral vaccine.

A nucleic acid provided by the present disclosure can comprise a nucleic acid encoding for an IL-7Rαγc IgG-Fc fusion protein comprising a viral surface antigen.

A nucleic acid provided by the present disclosure can comprise a nucleic acid encoding for an IL-7Rαγc IgG-Fc fusion protein comprising a virus-like particle.

A nucleic acid provided by the present disclosure can encode for an IL-7Rα ligand comprising an amino acid sequence of any one of SEQ ID NO: 1, a substituted amino acid sequence of any one of SEQ ID NO: 1, and/or can encode for an amino acid sequence comprising an amino acid sequence having greater than 60%, greater than 70%, greater than 80%, greater than 85%, greater than 90%, or greater than 95% sequence similarity to any one of: SEQ ID NO: 1.

A nucleic acid provided by the present disclosure can encode for an Rγc ligand comprising an amino acid sequence of any one of SEQ ID NO: 11, a substituted amino acid sequence of any one of SEQ ID NO: 11, and/or can encode for an amino acid sequence comprising an amino acid sequence having greater than 60%, greater than 70%, greater than 80%, greater than 85%, greater than 90%, or greater than 95% sequence similarity to any one of SEQ ID NO: 11.

A nucleic acid provided by the present disclosure can encode for an IL-7Rαγc ligand comprising an amino acid sequence of any one of SEQ ID NOS: 21-32, or can encode for an amino acid sequence comprising an amino acid sequence having greater than 60%, greater than 70%, greater than 80%, greater than 85%, greater than 90%, or greater than 95% sequence similarity to any one of SEQ ID NOS: 21-32; and an IL-7Rαγc ligand comprising an amino acid sequence of any one of SEQ ID NOS: 21-32, or can encode for an amino acid sequence comprising an amino acid sequence having greater than 60%, greater than 70%, greater than 80%, greater than 85%, greater than 90%, or greater than 95% sequence similarity to any one of SEQ ID NOS: 21-32.

A nucleic acid provided by the present disclosure can encode for an IL-7Rαγc ligand comprising an amino acid sequence of any one of SEQ ID NOS: 27-32 or can encode for an amino acid sequence comprising an amino acid sequence having greater than 60%, greater than 70%, greater than 80%, greater than 85%, greater than 90%, or greater than 95% sequence similarity to any one of SEQ ID NOS: 27-32.

A nucleic acid provided by the present disclosure can encode for an IL-7Rαγc IgG-Fc fusion protein comprising an amino acid sequence of any one of SEQ ID NOS: 44-55 or can encode for an amino acid sequence comprising an amino acid sequence having greater than 60%, greater than 70%, greater than 80%, greater than 85%, greater than 90%, or greater than 95% sequence similarity to any one of SEQ ID NOS: 44-55.

A nucleic acid provided by the present disclosure can encode for an IL-7Rαγc IgG-Fc fusion protein comprising an IL-7Rα ligand comprising an amino acid sequence of any one of SEQ ID NO: 1 or an amino acid sequence comprising an amino acid sequence having greater than 60%, greater than 70%, greater than 80%, greater than 85%, greater than 90%, or greater than 95% sequence similarity to SEQ ID NO: 1; and an Rγc ligand comprising an amino acid sequence of SEQ ID NO: 11 or an amino acid sequence comprising an amino acid sequence having greater than 60%, greater than 70%, greater than 80%, greater than 85%, greater than 90%, or greater than 95% sequence similarity to any one of SEQ ID NO: 11.

A nucleic acid provided by the present disclosure can encode for an IL-7Rαγc IgG-Fc fusion protein having an amino acid sequence of any one of SEQ ID NO: 45 or an amino acid sequence comprising an amino acid sequence having greater than 60%, greater than 70%, greater than 80%, greater than 85%, greater than 90%, or greater than 95% sequence similarity to SEQ ID NO: 45.

Aspects of the invention further include a host cell comprising an expression vector comprising a nucleic acid encoding an IL-7Rα ligand, an Rγc ligand, an IL-7Rαγc ligand, or an IL-7Rαγc fusion protein such as an IL-7Rαγc IgG-Fc fusion protein provided by the present disclosure.

Methods provided by the present disclosure include methods of making an IL-7Rα ligand, an Rγc ligand, an IL-7Rαγc ligand, or an IL-7Rαγc fusion protein such as an IL-7Rαγc IgG-Fc fusion protein provided by the present disclosure, comprising culturing a host cell, wherein the host cell comprises an expression vector comprising a nucleic acid encoding an IL-7Rα ligand, an Rγc ligand, an IL-7Rαγc ligand, or an IL-7Rαγc fusion protein such as an IL-7Rαγc IgG-Fc fusion protein provided by the present disclosure, under conditions where the IL-7Rαγc fusion protein such as an IL-7Rαγc IgG-Fc fusion protein is expressed, and recovering the expressed IL-7Rαγc fusion protein such as an IL-7Rαγc IgG-Fc fusion protein.

ASPECTS

The invention is further defined by one or more of the following aspects:

Aspect 1. An IL-7Rαγc ligand comprising: an IL-7Rα ligand comprising an amino acid sequence of SEQ ID NO: 1 or an amino acid sequence having greater than 70% sequence similarity to SEQ ID NO: 1; and an Rγc ligand comprising an amino acid sequence of SEQ ID NO: 11 or an amino acid sequence having greater than 70% sequence similarity to SEQ ID NO: 11.

Aspect 2. The IL-7Rαγc ligand of aspect 1, wherein the IL-7Rαγc ligand comprises: an IL-7Rα ligand comprising an amino acid sequence of SEQ ID NO: 1 and an Rγc ligand comprising an amino acid sequence of SEQ ID NO: 11.

Aspect 3. The IL-7Rαγc ligand of aspect 1, wherein the IL-7Rαγc ligand comprises: an IL-7Rα ligand comprising an amino acid sequence having greater than 70% sequence similarity to SEQ ID NO: 1; and an Rγc ligand comprising an amino acid sequence having greater than 70% sequence similarity to SEQ ID NO: 11.

Aspect 4. The IL-7Rαγc ligand of aspect 1, wherein the IL-7Rαγc ligand comprises: an IL-7Rα ligand comprising an amino acid sequence based on SEQ ID NO: 1 and having from 1 to 10, such as from 1 to 5 amino acid substitutions; and an Rγc ligand comprising an amino acid sequence based on SEQ ID NO: 11 and having from 1 to 10, such as from 1 to 5 amino acid substitutions.

Aspect 5. The IL-7Rαγc ligand of any one of aspects 1 to 4, wherein each of the IL-7Rα ligand and the Rγc ligand independently comprises from 1 to 6 glycines (G) on the N-terminus, on the C-terminus, or on both the N-terminus and the C-terminus.

Aspect 6. The IL-7Rαγc ligand of any one of aspects 1 to 5, wherein the IL-7Rα ligand and the Rγc ligand are bound together through a ligand linker.

Aspect 7. The IL-7Rαγc ligand of aspect 6, wherein the C-terminus of the IL-7Rα ligand is bound to the N-terminus of the Rγc ligand through the ligand linker.

Aspect 8. The IL-7Rαγc ligand of any one of aspects 6 to 7, wherein the ligand linker is a flexible ligand linker.

Aspect 9. The IL-7Rαγc ligand of any one of aspects 6 to 8, wherein the ligand linker comprises an amino acid sequence selected from any one of SEQ ID NO: 113-136.

Aspect 10. The IL-7Rαγc ligand of any one of aspects 6 to 8, wherein the ligand linker comprises an amino acid sequence having SEQ ID NO: 132.

Aspect 11. The IL-7Rαγc ligand of any one of aspects 1 to 10, wherein the IL-7Rαγc ligand comprises: an amino acid sequence of any one of SEQ ID NO: 21-26 or an amino acid sequence having greater than 70% sequence similarity to any one of SEQ ID NO: 21-26; and $X^1$ is selected from an amino acid sequence of any one of SEQ ID NO: 101-148.

Aspect 12. The IL-7Rαγc ligand of aspect 11, wherein $X^1$ is selected from of any one of SEQ ID NO: 137-143.

Aspect 13. The IL-7Rαγc ligand of aspect 11, wherein $X^1$ has an amino acid sequence of SEQ ID NO: 139.

Aspect 14. The IL-7Rαγc ligand of any one of aspects 1 to 13, wherein the IL-7Rαγc ligand comprises an amino acid sequence of any one of SEQ ID NO: 27-32, or an amino acid sequence having greater than 70% sequence similarity to any one of SEQ ID NO: 27-32.

Aspect 15. The IL-7Rαγc ligand of any one of aspects 1 to 13, wherein the IL-7Rαγc ligand comprises an amino acid sequence of SEQ ID NO: 32 or an amino acid sequence having greater than 70% sequence similarity to SEQ ID NO: 32.

Aspect 16. The IL-7Rαγc ligand of any one of aspects 1 to 15, wherein the IL-7Rαγc ligand binds to the hu-IL-7Rα subunit with an IC50 of less than 1 μM.

Aspect 17. The IL-7Rαγc ligand of any one of aspects 1 to 16, wherein the IL-7Rαγc ligand binds to the hu-Rγc subunit with an IC50 of less than 1 μM.

Aspect 18. The IL-7Rαγc ligand of any one of aspects 1 to 17, wherein the IL-7Rαγc ligand activates STAT5 phosphorylation in TF-1-7Rα cells with an EC50 of less than 1 μM.

Aspect 19. The IL-7Rαγc ligand of any one of aspects 1 to 18, wherein the IL-7Rαγc ligand is a hu-IL-7R agonist.

Aspect 20. The IL-7Rαγc ligand of any one of aspects 1 to 19, wherein the IL-7Rαγc ligand binds to the cyno-IL-7Rα subunit with an IC50 of less than 1 μM.

Aspect 21. The IL-7Rαγc ligand of any one of aspects 1 to 20, wherein the IL-7Rαγc ligand binds to the cyno-Rγc subunit with an IC50 of less than 1 μM.

Aspect 22. The IL-7Rαγc ligand of any one of aspects 1 to 21, wherein the IL-7Rαγc ligand is a cyno-IL-7R agonist.

Aspect 23. An IL-7Rαγc IgG-Fc fusion fragment comprising the IL-7Rαγc ligand of any one of aspects 1 to 22 bound to an IgG-Fc fragment.

Aspect 24. The IL-7Rαγc IgG-Fc fusion fragment of aspect 23, wherein the IgG-Fc fragment is selected from an IgG1-Fc fragment, an IgG2-Fc fragment, and an IgG4-Fc fragment.

Aspect 25. The IL-7Rαγc IgG-Fc fusion fragment of aspect 23, wherein the IgG-Fc fragment is an IgG2-Fc fragment.

Aspect 26. The IL-7Rαγc IgG-Fc fusion fragment of any one of aspects 23 to 25, wherein the IL-7Rαγc ligand is bound to the IgG-Fc fragment through an IgG-Fc linker.

Aspect 27. The IL-7Rαγc IgG-Fc fusion fragment of aspect 26, wherein the IgG-Fc linker comprises a flexible IgG-Fc linker.

Aspect 28. The IL-7Rαγc IgG-Fc fusion fragment of any one of aspects 26 to 27, wherein the IgG-Fc linker comprises an amino acid sequence of any one of SEQ ID NO: 150-179.

Aspect 29. The IL-7Rαγc IgG-Fc fusion fragment of any one of aspects 26 to 27, wherein the IgG-Fc linker comprises an amino acid sequence of SEQ ID NO: 163.

Aspect 30. The IL-7Rαγc IgG-Fc fusion fragment of any one of aspects 26 to 29, wherein the N-terminus of the IL-7Rαγc ligand is bound to the IgG-Fc linker.

Aspect 31. The IL-7Rαγc IgG-Fc fusion fragment of any one of aspects 26 to 30, wherein the N-terminus of the IgG-Fc linker is bound to the CH3 domain of the IgG-Fc fragment.

Aspect 32. The IL-7Rαγc IgG-Fc fusion fragment of any one of aspects 23 to 31, wherein the IL-7Rαγc ligand is bound to the C-terminus of each CH3 domain of the IgG-Fc fragment.

Aspect 33. The IL-7Rαγc IgG-Fc fusion fragment of aspect 23, wherein the IL-7Rαγc IgG-Fc fusion fragment comprises an amino acid sequence having greater than 70% sequence similarity to any one of SEQ ID NO: 44-55.

Aspect 34. The IL-7Rαγc IgG-Fc fusion fragment of aspect 23, wherein the IL-7Rαγc IgG-Fc fusion fragment comprises an amino acid sequence of any one of SEQ ID NO: 44-55.

Aspect 35. The IL-7Rαγc IgG-Fc fusion p fragment of aspect 23, wherein the IL-7Rαγc IgG-Fc fusion fragment comprises an amino acid sequence having greater than 70% sequence similarity to SEQ ID NO: 45.

Aspect 36. The IL-7Rαγc IgG-Fc fusion fragment of aspect 23, wherein the IL-7Rαγc IgG-Fc fusion fragment comprises an amino acid sequence having SEQ ID NO: 45.

Aspect 37. The IL-7Rαγc IgG-Fc fusion fragment of aspect 23, wherein the IL-7Rαγc IgG-Fc fusion fragment is derived from an amino acid sequence of SEQ ID NO: 45 and having from 1 to 10 amino acid substitutions.

Aspect 38. The IL-7Rαγc IgG-Fc fusion fragment of any one of aspects 23 to 37, wherein the IL-7Rαγc IgG-Fc fusion fragment binds to the hu-IL-7Rα subunit with an IC50 of less than 1 μM.

Aspect 39. The IL-7Rαγc IgG-Fc fusion fragment of any one of aspects 23 to 38, wherein the IL-7Rαγc IgG-Fc fusion protein binds to the hu-IL-7Rγc subunit with an IC50 of less than 1 μM.

Aspect 40. The IL-7Rαγc IgG-Fc fusion fragment of any one of aspects 23 to 39, wherein the IL-7Rαγc IgG-Fc fusion fragment activates STAT5 phosphorylation in TF-1-7Rα cells with an EC50 of less than 1 μM.

Aspect 41. The IL-7Rαγc IgG-Fc fusion fragment of any one of aspects 23 to 40, wherein the IL-7Rαγc IgG-Fc fusion fragment is a hu-IL-7R agonist.

Aspect 42. The IL-7Rαγc IgG-Fc fusion fragment of any one of aspects 23 to 41, wherein the IL-7Rαγc IgG-Fc fusion protein binds to the cyno-IL-7Rα subunit with an IC50 of less than 1 μM.

Aspect 43. The IL-7Rαγc IgG-Fc fusion fragment of any one of aspects 23 to 42, wherein the IL-7Rαγc IgG-Fc fusion fragment binds to the cyno-IL-7Rγc subunit with an IC50 of less than 1 μM.

Aspect 44. The IL-7Rαγc IgG-Fc fusion fragment of any one of aspects 23 to 42, wherein the IL-7Rαγc IgG-Fc fusion fragment activates STAT5 phosphorylation in TF-1-7Rα cells with an EC50 of less than 1 μM.

Aspect 45. The IL-7Rαγc IgG-Fc fusion fragment of any one of aspects 22 to 44, wherein the IL-7Rαγc IgG-Fc fragment is a cyno-IL-7R agonist.

Aspect 46. An IL-7Rαγc IgG-Fc fusion protein comprising: a first IL-7Rαγc IgG-Fc fusion fragment of any one of aspects 23 to 45; and a second IL-7Rαγc IgG-Fc fusion fragment of any one of aspects 23 to 45, wherein the first IL-7Rαγc IgG-Fc fusion fragment and the second first IL-7Rαγc IgG-Fc fusion fragment are bound at the hinge region through disulfide bonds.

Aspect 47. The IL-7Rαγc IgG-Fc fusion protein of aspect 46, wherein the first IL-7Rαγc IgG-Fc fusion fragment and the second IL-7Rαγc IgG-Fc fusion fragment have the same amino acid sequence.

Aspect 48. The IL-7Rαγc IgG-Fc fusion protein of aspect 46, wherein the first IL-7Rαγc IgG-Fc fusion fragment and the second IL-7Rαγc IgG-Fc fusion fragment comprise a different amino acid sequence.

Aspect 49. The IL-7Rαγc IgG-Fc fusion protein of aspect 46, wherein the first IL-7Rαγc IgG-Fc fusion fragment and the second IL-7Rαγc IgG-Fc fusion fragment comprise a different IL-7Rα ligand.

Aspect 50. The IL-7Rαγc IgG-Fc fusion protein of aspect 46, wherein the first IL-7Rαγc IgG-Fc fusion fragment and the second IL-7Rαγc IgG-Fc fusion fragment comprise a different Rγc ligand.

Aspect 51. The IL-7Rαγc IgG-Fc fusion protein of aspect 46, wherein the first IL-7Rαγc IgG-Fc fusion fragment and the second IL-7Rαγc IgG-Fc fusion fragment comprise a different ligand linker.

Aspect 52. The IL-7Rαγc IgG-Fc fusion protein of aspect 46, wherein the first IL-7Rαγc IgG-Fc fusion fragment and the second IL-7Rαγc IgG-Fc fusion fragment comprise a different IL-7Rαγc ligand.

Aspect 53. The IL-7Rαγc IgG-Fc fusion protein of aspect 46, wherein the first IL-7Rαγc IgG-Fc fusion fragment and the second IL-7Rαγc IgG-Fc fusion fragment comprise a different IgG-Fc linker. Aspect 54. The IL-7Rαγc IgG-Fc fusion protein of aspect 46, wherein the first IL-7Rαγc IgG-Fc fusion fragment and the second IL-7Rαγc IgG-Fc fusion fragment comprise a different IgG-Fc fragment.

Aspect 55. A pharmaceutical composition comprising the IL-7Rαγc ligand of any one of aspects 1 to 22.

Aspect 56. A pharmaceutical composition comprising the IL-7Rαγc IgG-Fc fusion protein of any one of aspects 23 to 55.

Aspect 57. A method of treating a cancer, an inflammatory disease, an autoimmune disease, an immunodeficiency disease, or a viral disease in a patient comprising administering to a patient in need of such treatment a therapeutically effective amount of the IL-7Rαγc ligand of any one of aspects 1 to 22, or the IL-7Rαγc IgG-Fc fusion protein of any one of aspects 23 to 55.

Aspect 58. A method of treating a cancer, an inflammatory disease, an autoimmune disease, an immunodeficiency disease, or a viral disease in a patient comprising administering to a patient in need of such treatment a therapeutically effective amount of the IL-7Rαγc ligand of any one of aspects 1 to 22, or the IL-7Rαγc IgG-Fc fusion protein of any one of aspects 23 to 55.

Aspect 59. A nucleic acid encoding for the IL-7Rαγc ligand of any one of aspects 1 to 22.

Aspect 60. A nucleic acid encoding for the IL-7Rαγc IgG-Fc fusion protein of any one of aspects 23 to 55.

Aspect 61. The nucleic acid of aspect 60, wherein the IL-7Rαγc ligand has an amino acid sequence of any one of SEQ ID NO: 27-32 or has greater that 70% sequence similarity to an amino acid sequence of any one of SEQ ID NO: 27-32.

Aspect 62. The nucleic acid of aspect 60, wherein the IL-7Rαγc ligand has an amino acid sequence of SEQ ID NO: 32 or has greater that 70% sequence similarity to an amino acid sequence of SEQ ID NO: 32.

Aspect 63. A nucleic acid encoding for the IL-7Rαγc IgG-Fc fusion protein of any one of aspects 23 to 55.

Aspect 64. The nucleic acid of aspect 63, wherein the IL-7Rαγc IgG-Fc fusion protein has an amino acid sequence of any one of SEQ ID NO: 44-55 or has greater than 70% sequence similarity an amino acid sequence of any one of SEQ ID NO: 44-55.

Aspect 65. The nucleic acid of aspect 63, wherein the IL-7Rαγc IgG-Fc fusion protein has an amino acid sequence of SEQ ID NO: 45 or having greater than 70% sequence similarity to an amino acid sequence of SEQ ID NO: 45.

EXAMPLES

The following examples describe in detail methods of synthesizing IL-7Rαγc ligands, methods of synthesizing IL-7Rαγc IgG-Fc fusions, and methods of determining the activity of IL-7Rαγc ligands and IL-7Rαγc IgG-Fc fusions provided by the present disclosure and the experimental results. The following examples also describe in detail methods for determining properties of the IL-7Rαγc ligands and IL-7Rαγc IgG-Fc fusions provided by the present disclosure. It will be apparent to those skilled in the art that many modifications, both to materials and methods, may be practiced without departing from the scope of the invention.

Example 1

Chemical Synthesis of IL-7Rα Ligands and Rγc Ligands

2-Cholorotrityl resin (1 g, 1.5 mmole/g, from Anaspec) was washed with DMF (2×), and then allowed to stand in 50 mL DMF for 10 min. The swollen resin was treated with an activated solution of Fmoc-glycine prepared from 5 eq. of amino acid and 5 eq. of HATU dissolved at 0.5 M in DMF, followed by the addition of 10 eq. of DIEA, and the mixture was gently stirred for 30 min at 25° C. The resin was washed (DMF, THF, DCM, and MeOH) and dried to yield the Fmoc-protected resin. Fmoc groups were then removed by gently shaking the resin with 30% piperidine in DMF for 20 min, followed by washing (DMF, THF, DCM, and MeOH), and drying. The resin was then subjected to repeated cycles of Fmoc-amino acid couplings with HATU activation and Fmoc removal with piperidine to build a desired amino acid sequence. Except for examples with four cysteine residues in the sequence, standard 95% TFA-labile amino acid side-chain protecting groups were used. With compounds with four cysteines, for the two cysteine residues proximal to the resin, Trt protection was used, and for the two cysteine residues distal to the resin, Acm protection was used. After Fmoc removal from the final amino acid of the dimer sequence, in some cases, the terminal amine groups were acylated with acetic anhydride (10 eq.) and DIEA (20 eq.) in DMF for 20 min, followed by washing as described above.

The completed peptide was cleaved from the resin by suspension in a solution of TFA (95 vol %), water (2.5 vol %), and trisopropylsilane (2.5 vol %) for 3 h at 25° C. The TFA solution was cooled to 5° C. and poured into $Et_2O$ to precipitate the peptide. Filtration and drying under reduced pressure gave the desired peptide. Purification via preparative HPLC with a C18 column afforded the pure peptide with the two C-terminal thiol groups in a reduced state. This peptide was dissolved in 20% DMSO/water (1 mg dry weight peptide/mL) and allowed to stand at 25° C. for 36 h, and then purified by reverse phase HPLC to provide the peptide with the two C-terminal thiols linked by a disulfide bridge. In compounds containing four cysteines, the two N-terminal Acm-protected cysteine residues were then deprotected by dissolving 0.1 mmole of peptide in 25 mL of 50% acetic acid/$H_2O$ and 2.5 mL of 1 M HCl and adding 5 mL of 0.1 M iodine (in glacial acetic acid; 5 eq.) dropwise with stirring under a nitrogen atmosphere. The deprotection/oxidation reaction was allowed to proceed for 2 h at 25° C. with frequent monitoring (analytical HPLC) to ensure complete reaction. The reaction was stopped by addition of ice-cooled diethyl ether (9 volume eq.). The resulting solution was cooled on dry ice (3 min), the ether solution carefully decanted, and the resulting light-yellow solid purified by preparative reverse phase HPLC (95%) to yield the final peptide dimer having an IL-7Rα ligand and an Rγc ligand.

Example 2

Competitive Binding to the IL-7Rα Subunit, to the IL-7Rγc Subunit, and to IL-7R

Binding of the synthetic IL-7Rα ligands to IL-7Rα was evaluated using a competition binding ELISA. Microtiter plate wells were coated with IL-7Rα-Fc (CD127 protein, Fc tag; ECD 21-236; ACRObiosystems, Inc, Cat. #ILA-H5258) at 1 μg/mL; 50 μL per well in PBS for at least 1 h. The plate was washed once with wash buffer (200 μL, PBS containing 0.05% Tween®-20 (Sigma). Wells were blocked with blocking buffer (PBS containing 1% BSA (BSA Fraction V; VWR Cat. No. 97061-416) for 1 h. A serial dilution of the peptides was prepared, at twice the final concentration, in assay buffer (PBS containing 0.5% BSA and 0.05% Tween®-20) in a 96-well polypropylene plate. A terminal biotinylated form of the reference IL-7Rα peptide ligand having SEQ ID NO: 300 (VHRIPWCTLDPGGLQCAWLRQMGG) was used to make a precomplex with NeutrAvidin-HRP (NA-HRP; ThermoFisher Cat. No. 31030) (Precomplex referred to as bnPeptide::NA-HRP). The bnPeptide::NA-HRP precomplex was prepared by mixing 1.5 μL 100 μM biotinylated peptide, 2 μL NA-HRP and 11.5 PBS and incubated at 4° C. for at least 45 min. After blocking the wells, the plate was washed with a plate washer and serial dilutions of the peptides were added (50 μL/well) and the plate was incubated at 4° C. for 1 h on a plate shaker. The bnPeptide:NA-HRP precomplex was diluted to 40 nM and, without washing, 50 μL was added to each assay well. The plate was returned to a temperature of 4° C. and incubated for 45 min. The plate was washed using the plate washer and cold wash buffer. Fifty (50) μL of TMB One Component HRP Microwell substrate (TMB; Surmodics Cat. #TMBW-1000-01) was then added to each well, and the wells were incubated for 1-10 min at 25° C. Fifty (50) μL of a solution (Surmodics Cat. #LSTP-0100-0) was then added and the plate read at 450 nm.

A similar method was used to assess the binding of Rγc ligands to the IL-7Rγc subunit; and a similar method was used to assess the binding of IL-7Rαγc ligands to the IL-7Rα subunit, to the IL-7Rγc subunit, and to IL-7R.

Figure 2:
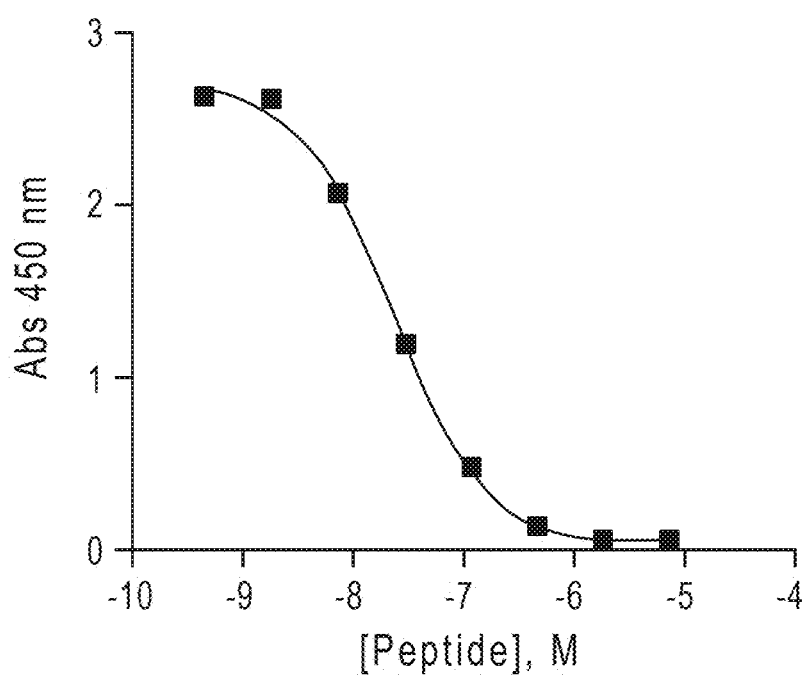
FIG. 2 shows competitive binding of an IL-7Rαγc ligand having SEQ ID NO: 30 to the hu-Rγc subunit.

For example, competitive binding of the IL-7Rαγc ligand having SEQ ID NO: 30 to the hu-IL-7Rα subunit and to the hu-IL-7Rγc subunit is shown in FIGS. 1 and 2, respectively.

Example 3

STAT5 Phosphorylation in TF-1-7α Cells Induced by IL-7Rαγc Ligands

IL-7Rαγc ligands were evaluated for induction of STAT5 phosphorylation in TF-1-7α cells. TF-1-7α cells were derived from the growth factor-dependent human erythroleukemia cell line TF-1 (ATCC No. CRL-2003), which naturally express common γc receptors (Rγc) but not IL-7Rα. The cells were engineered to be IL-7 responsive by transfection with human full-length IL-7Rα. A cell line expressing higher levels of IL-7Rα was selected by growth in IL-7, and both IL-7Rα and Rγc subunit expression levels were verified by qPCR analysis.

To test compounds for induction of STAT5 phosphorylation, TF-1-7α cells were starved overnight at $5\times10^5$ cells/mL in starvation medium (RPMI 1640+2.5 g/L glucose+5% FBS+2 mM L-glutamine+1 mM NaPyr+ 10 mM HEPES with no GM-CSF or rhIL-7 supplement) in T75 flasks. The following day, cells were plated in 96-well V-bottom plates at $2\times10^5$ cells/well. Three-fold serial dilutions of IL-7Rαγc ligands or IL-7 in starvation media were added to the cells and incubated for 30 min at 37° C. Cell extracts were prepared by adding a mixture of 10× Cell Lysis Buffer (Cell Signaling Technology #9803) and 1×HALT Phosphatase and Protease Inhibitor Cocktail (Thermo Fisher #78442) directly to the wells. The plates were agitated at 25° C. for 5 min to prepare cell extracts for immediate use or stored at −80° C.

Detection of pSTAT5 was performed using a PathScan® Phospho-Stat5 (Tyr694) Sandwich ELISA Kit (Cell Signaling Technology #7113). Cell extracts were added to microwells that were pre-coated with a mouse anti-phospho-STAT5 antibody and incubated overnight at 4° C. Wells were then washed with PBS and bound phospho-STAT5 (Tyr694) was detected by adding a rabbit anti-STAT5 detection antibody and incubating for 1 h at 37° C. Wells were washed with PBS and an anti-rabbit IgG HRP-linked antibody was added to each well. After a final wash TMB substrate solution was added to measure the amount of HRP in each well. Absorbance at 450 nm was read in a microplate reader. The signal that was produced is proportional to the quantity of phosphorylated STAT5 in each cell extract.

Figure 3:
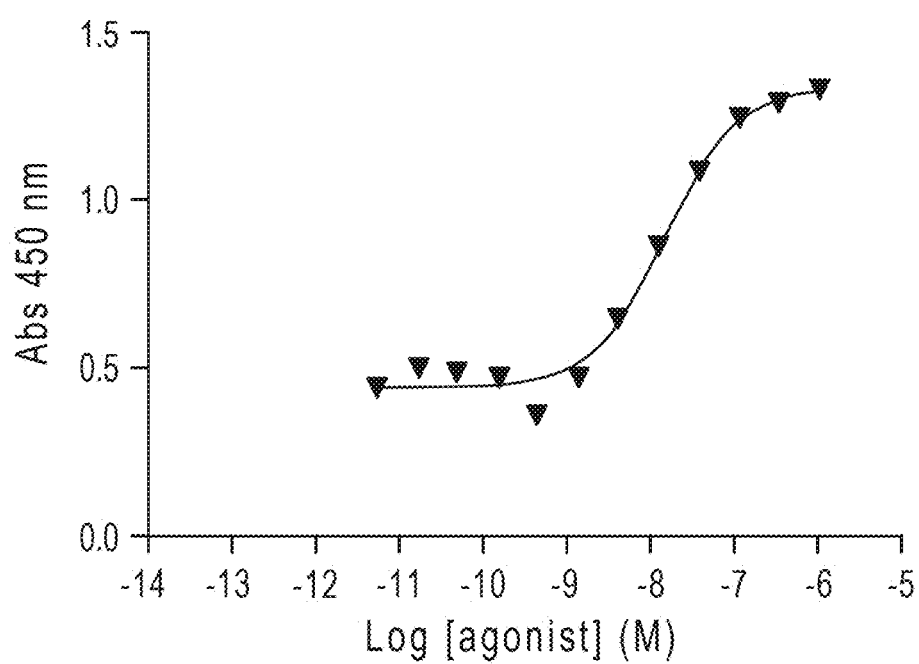
FIG. 3 shows STAT5 phosphorylation in TF-1-7Rα cells following exposure to an IL-7Rαγc ligand SEQ ID NO: 30.

STAT5 phosphorylation of TF-1-7Rα cells induced by the IL-7Rαγc ligand having SEQ ID NO: 30 is shown in FIG. 3.

Example 4

Recombinant Fusion Proteins Incorporating an IL-7Rαγc Ligand

Mammalian expression vectors were constructed to express IL-7Rαγc ligands linked to full-length human IgG, or to Fc-fragments consisting of the CH2 and CH3 domains of the heavy chain and hinge regions of human IgG2. Each vector included strong constitutive promoter (CMV or hEF1-HTLV) and an IL-7 signal peptide sequence for secretion of the fusion protein into the culture media. Vectors were designed to enable peptide ligands to be fused to either the N- or C-terminus of the immunoglobulin proteins and to incorporate construct linkers of varying lengths between the IL-7Rαγc ligands and IgG. Fusion proteins were transiently expressed in 293 human embryonic kidney cells (FreeStyle® 293-F) by transfecting plasmid DNA into the cells using polyethyleneimine reagent PEI MAX (Polysciences, Inc.). Transfected cells were grown in FreeStyle® 293 Expression Medium (ThermoFisher) in shaker flasks in a 37° C. humidified $CO_2$ incubator on an orbital shaker rotating at 125 rpm. Cultures were harvested 96 h post-transfection by centrifugation and the secreted fusion proteins were purified from the supernatants using Protein A affinity chromatography.

Protein A agarose resin was mixed with culture supernatant and incubated at room temperature for several hours. The resin was then washed three times with PBS and bound IL-7Rαγc IgG-Fc fusion was eluted with 0.1 M glycine buffer (pH 2.8). Eluates were neutralized with 1 M Tris buffer and quantified by measuring absorbance at 280 nm using a NanoDrop® spectrophotometer. Protein concentrations were determined using calculated extinction coefficients derived from the primary sequence of the protein. Size exclusion chromatography was used to remove high molecular weight impurities prior to measuring the activities of the fusion proteins in bioassays.

The amino acid sequences of the IL-7Rαγc IgG2-Fc fusion proteins used in the experimental examples has the amino acid sequence of SEQ ID NO: 45. The hu-IgG2-Fc-fragment refers to the Fc region consisting of the CH2 and CH3 domains of the IgG2 heavy chain and the hinge region. The first and second cysteines of the hinge region were replaced with serine to prevent detrimental disulfide bridges. The last amino acid (lysine) of the Fc region was replaced with an alanine for fusion stability. The N-terminus of IgG2-Fc fusion constructs may include Ala-Pro-Leu (derived from InvivoGen vector).

A schematic of the structure is shown in FIG. 4.

Example 5

IL-7Rαγc IgG-Fc Fusion Protein Pharmacokinetics in Non-Human Primates

A pharmacokinetic study of an IL-7Rαγc IgG2-Fc fusion protein was performed in non-human primates. The IL-7Rαγc IgG2-Fc fusion having SEQ ID NO: 45 was administered intravenously (IV), subcutaneously (SC), or intramuscularly (IM) with a single dose of 1 mg/kg into each non-human primate (n=10). Blood samples were collected at times post-dose into serum separator vials. Samples were centrifuged at 10,000× g for 5 min at 4° C. followed by transferring the serum to a new tube. Samples were frozen and stored at −80° C. prior to testing.

Figure 5:
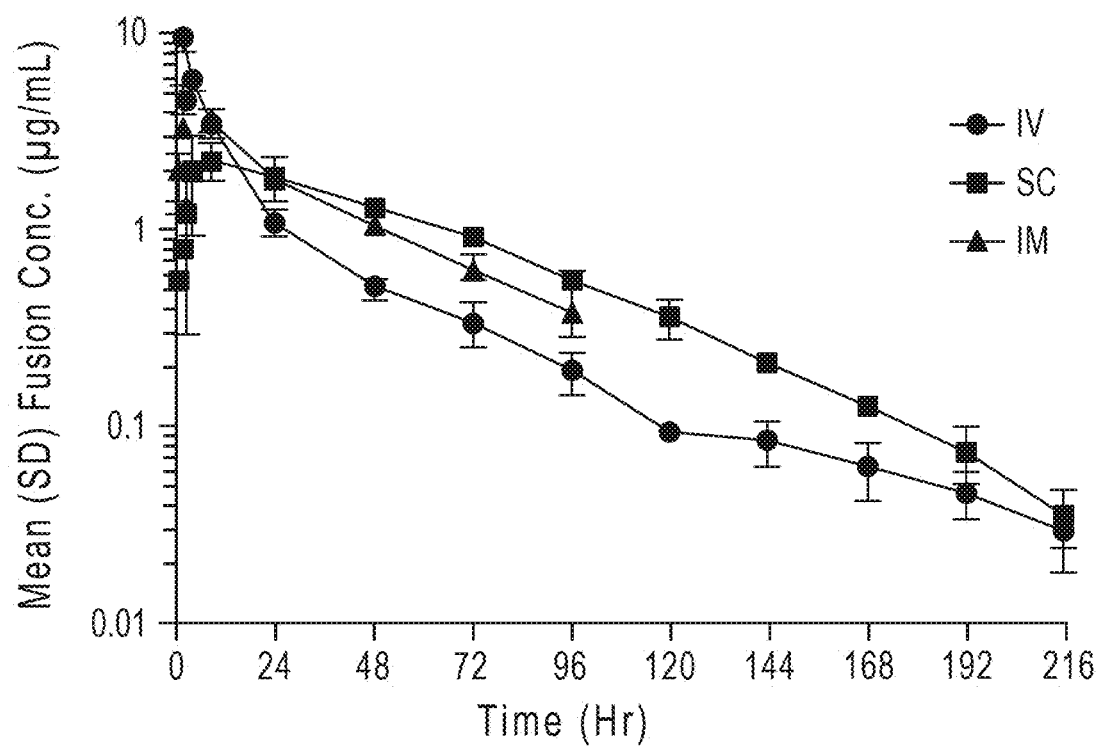
FIG. 5 shows the mean plasma concentration of an IL-7Rαγc IgG2-Fc fusion protein having SEQ ID NO: 45 following intravenous (IV), subcutaneous (SC), and intramuscular (IM) administration at a dose of 1 mg/kg to non-human primates.

The TF-1-7Rα STAT5 phosphorylation bioassay was used to quantity the amount of the IL-7Rαγc IgG2-Fc fusion in each of the serum samples. Three-fold serial dilutions of each serum sample or a compound reference standard in starvation media were added to the cells and incubated for 30 mins with the cells. Cells extracts were prepared and the quantity of phosphorylated STAT5 was determined as described in Example 3. The IL-7Rαγc IgG2-Fc fusion protein concentration in each serum sample was calculated using a standard curve generated from the reference standard. The results are presented in FIG. 5. The bioavailability % F for IM administration was 117 and the bioavailability % F for SC administration was 112.

Figure 6:
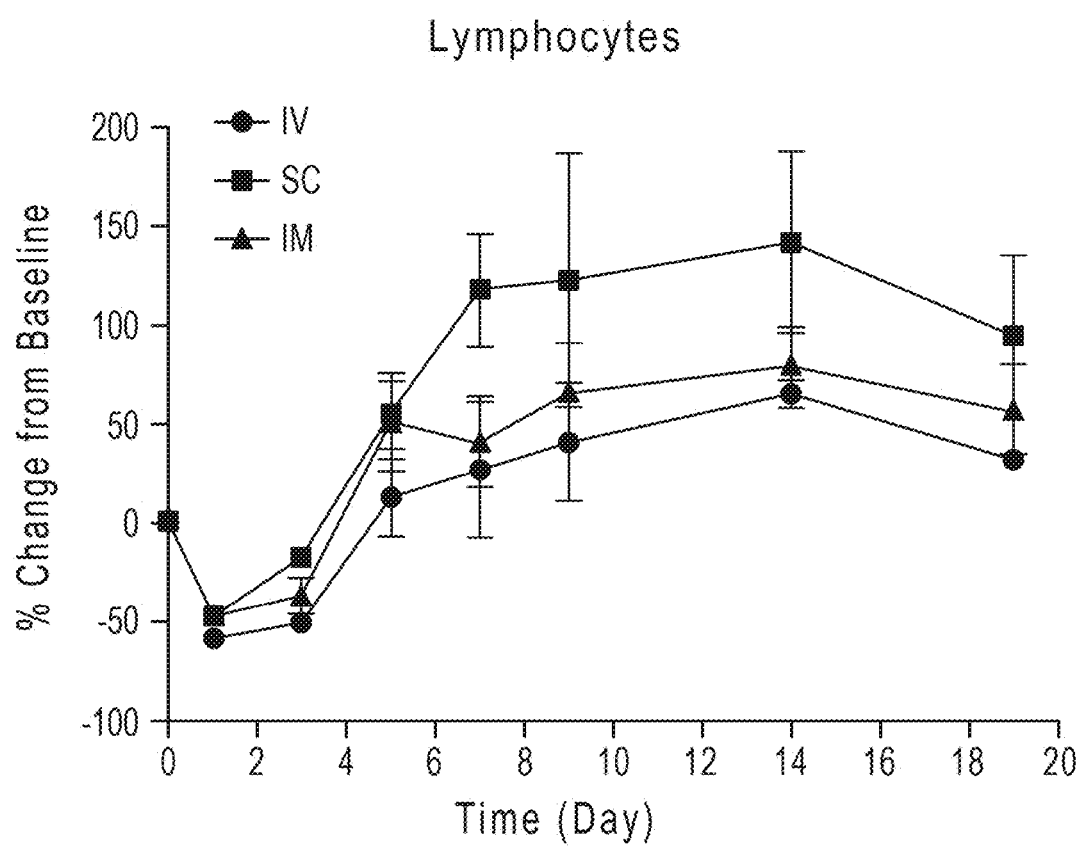
FIG. 6 shows the percent change in blood lymphocyte counts following intravenous (IV), subcutaneous (SC), and intramuscular (IM) administration of a 1 mg/kg dose of an IL-7Rαγc IgG2-Fc fusion protein having SEQ ID NO: 45 to non-human primates.

The absolute lymphocyte counts of each blood sample was determined using a hematology analyzer. The results are presented in FIG. 6.

Figure 7A:
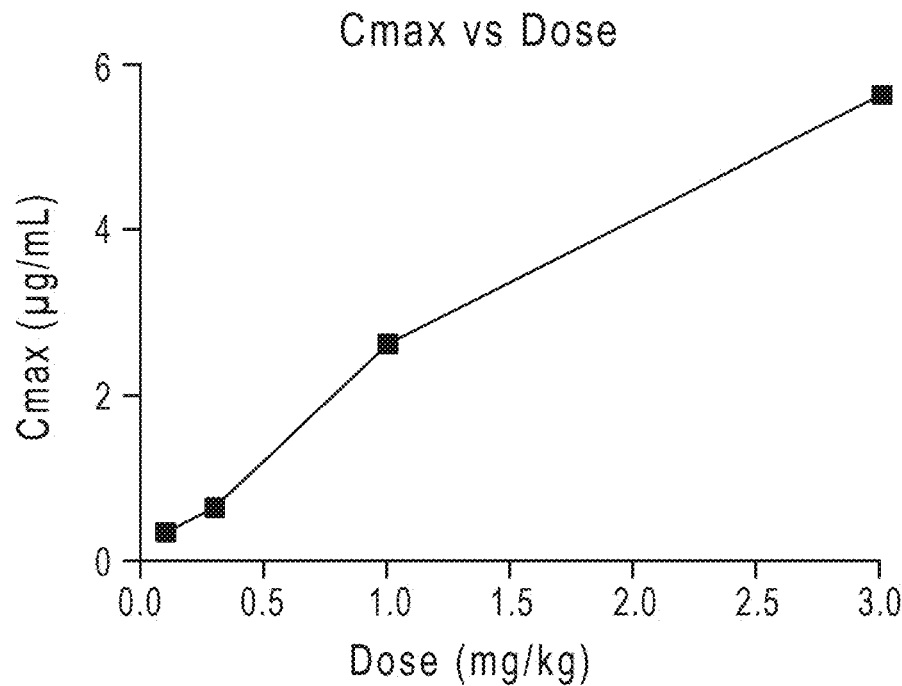
FIGS. 7A and 7B show the plasma IL-7Rαγc IgG2-Fc fusion protein (SEQ ID NO: 45) $C_{max}$ and $AUC_{inf}$, respectively, following subcutaneous administration at doses of from 0.1 mg/kg to 3.0 mg/kg to non-human primates.
Figure 7B:
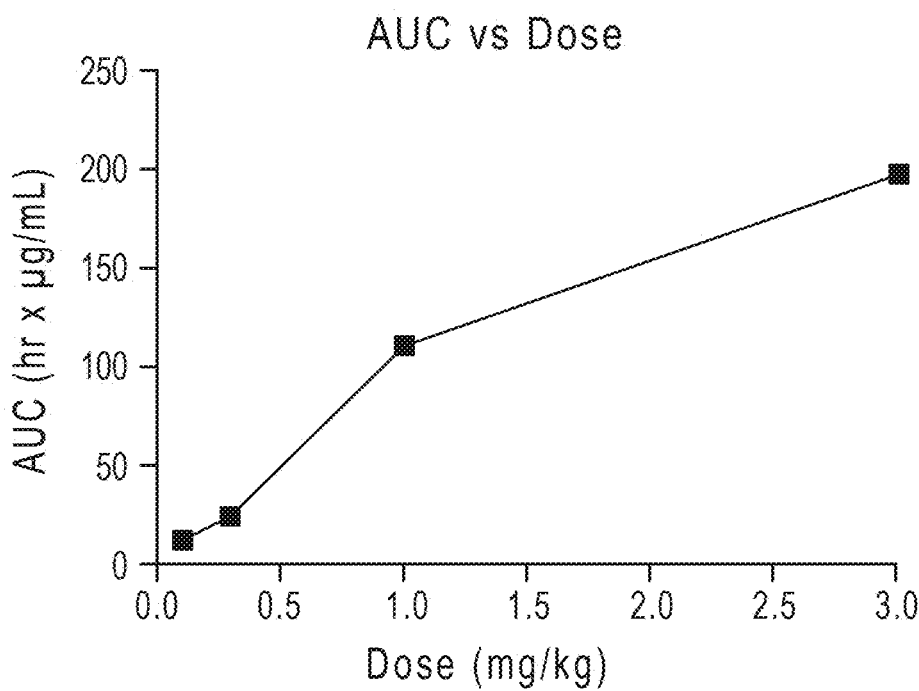
Figure 8A:
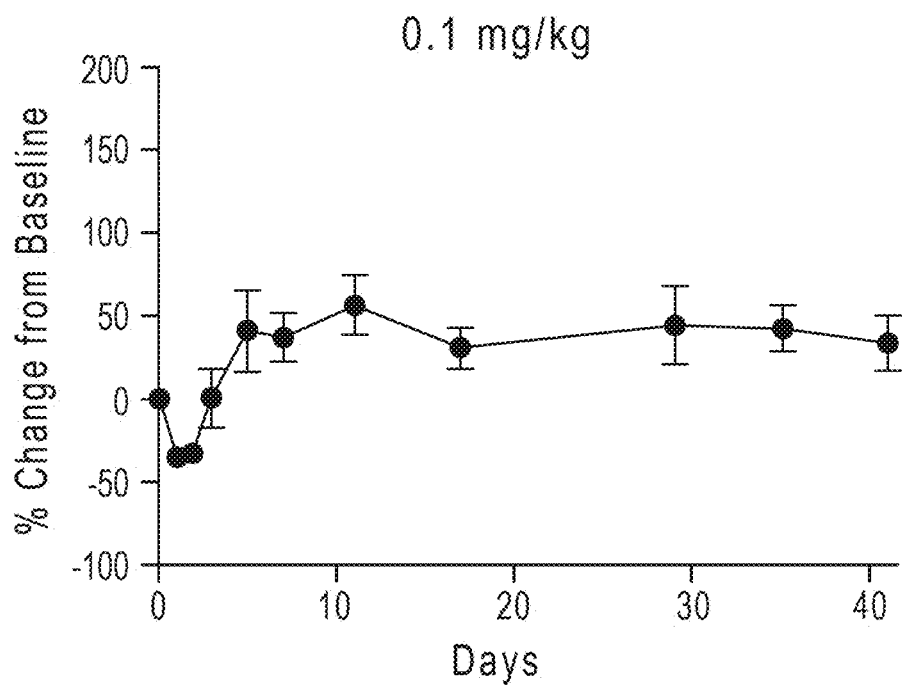
FIGS. 8A-8D show the percent change in blood lymphocyte counts following subcutaneous administration of from 0.1 mg/kg to 3.0 mg/kg of an IL-7Rαγc IgG2-Fc fusion protein (SEQ ID NO: 45) to non-human primates.
Figure 8B:
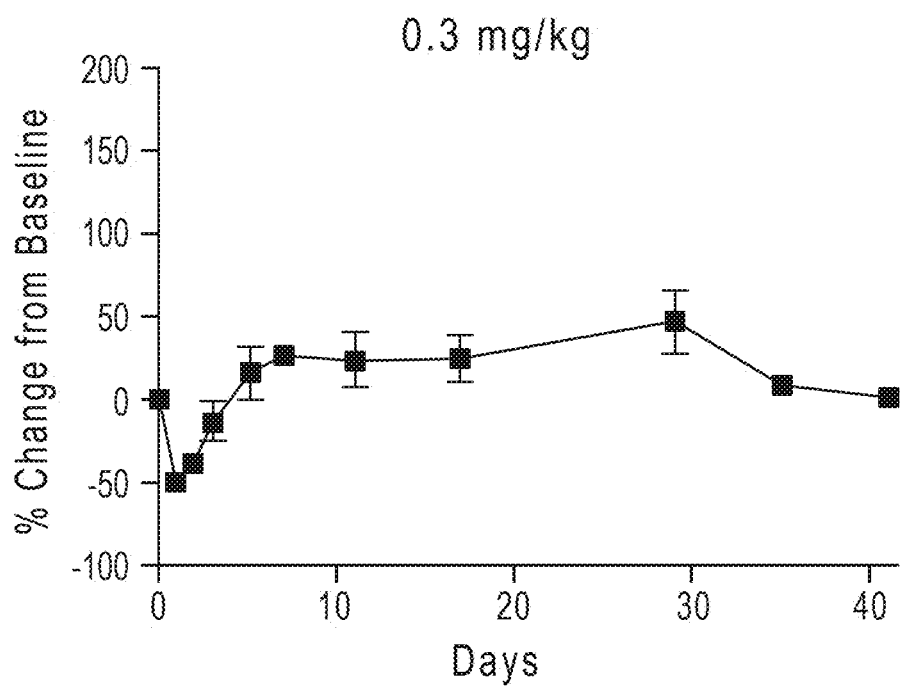
Figure 8C:
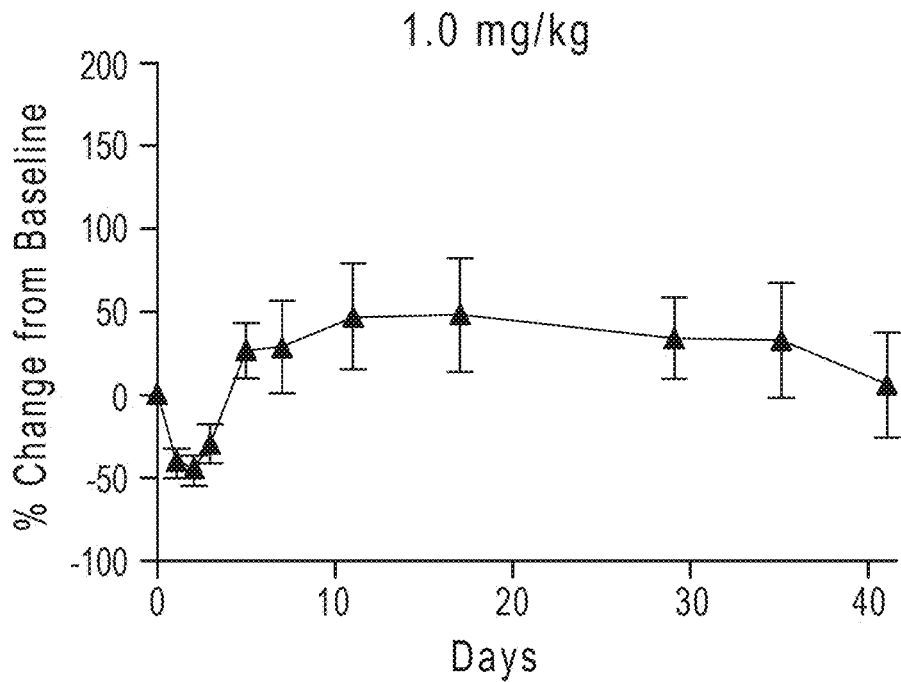
Figure 8D:
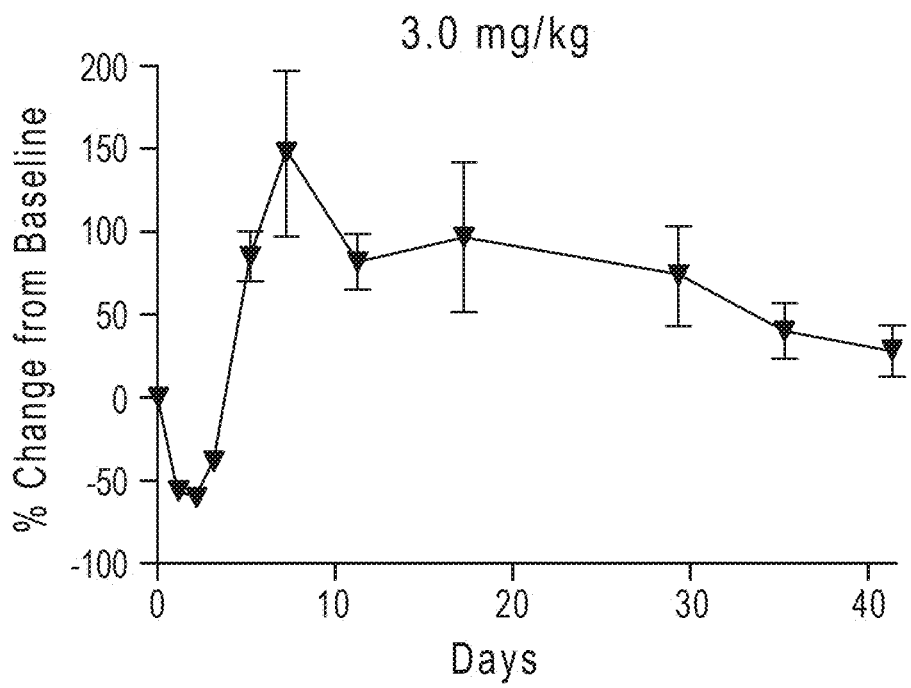
Figure 9A:
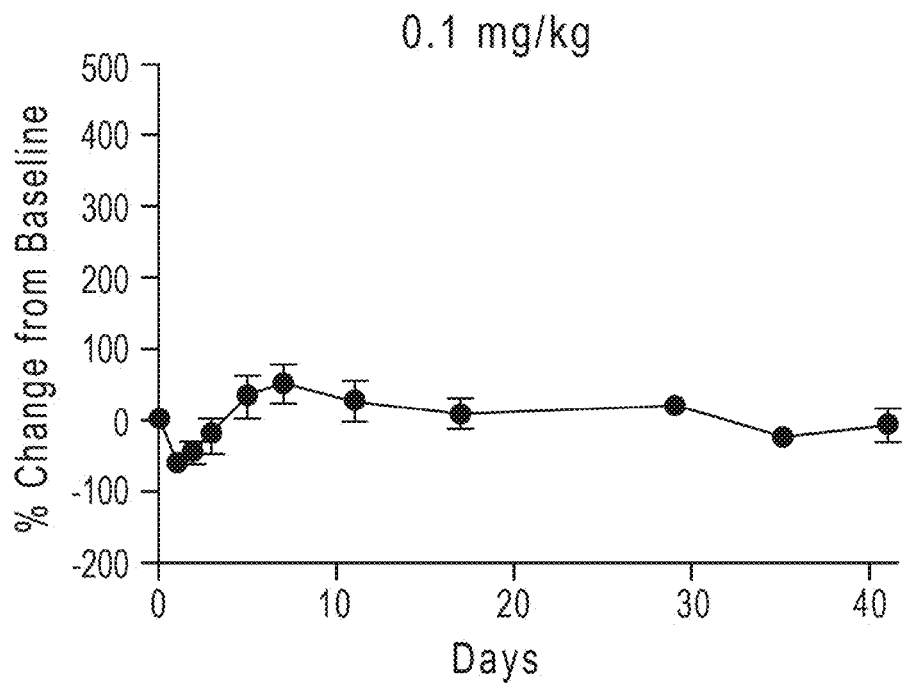
FIGS. 9A-9D show the percent change in CD8+ T cell counts in peripheral blood following subcutaneous administration of from 0.1 mg/kg to 3.0 mg/kg of an IL-7Rαγc IgG2-Fc fusion protein (SEQ ID NO: 45) to non-human primates.
Figure 9B:
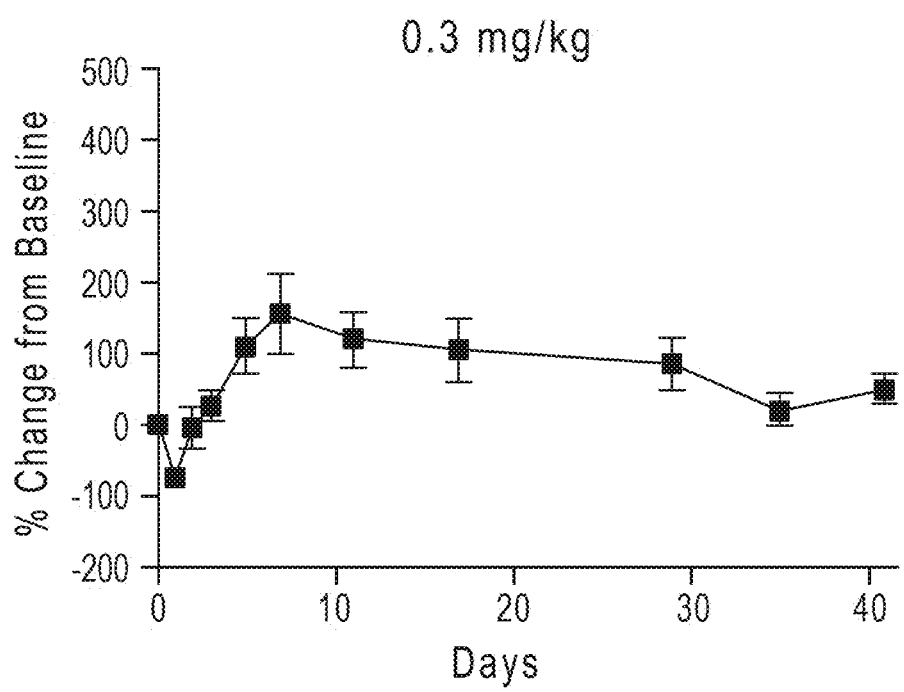
Figure 9C:
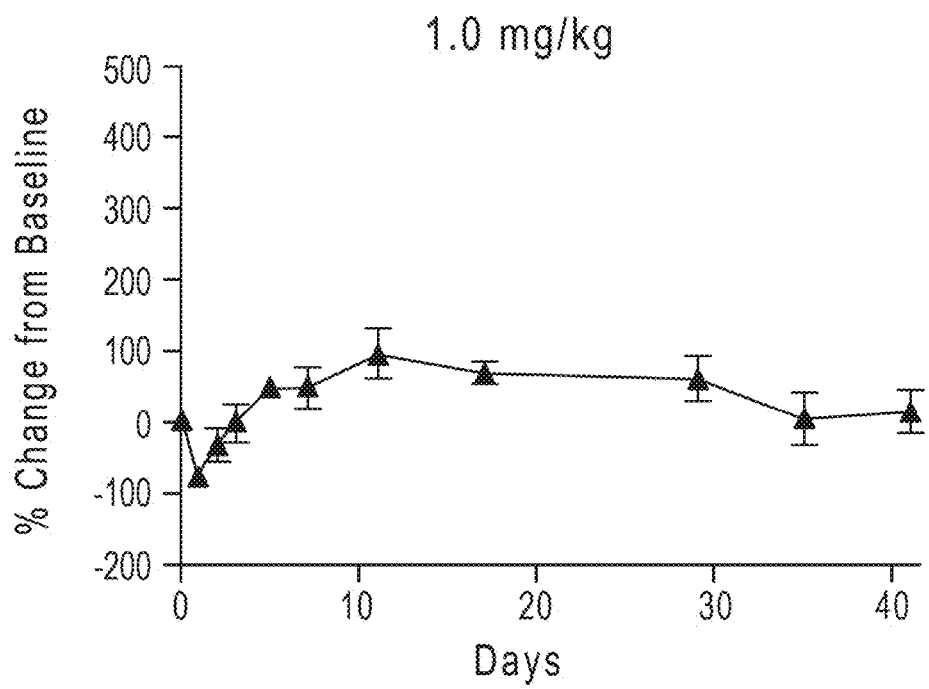
Figure 9D:
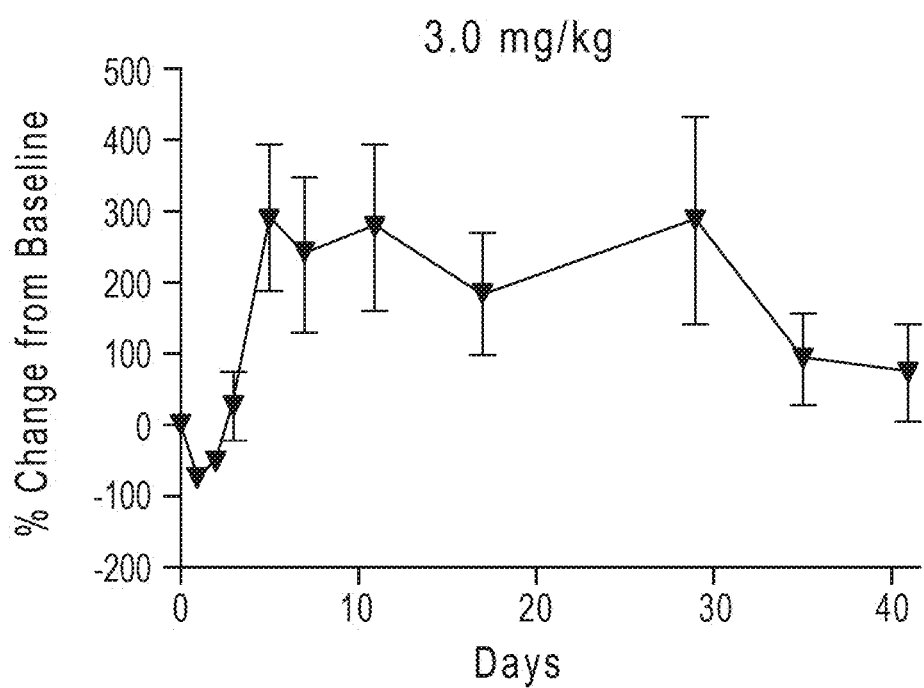
Figure 10A:
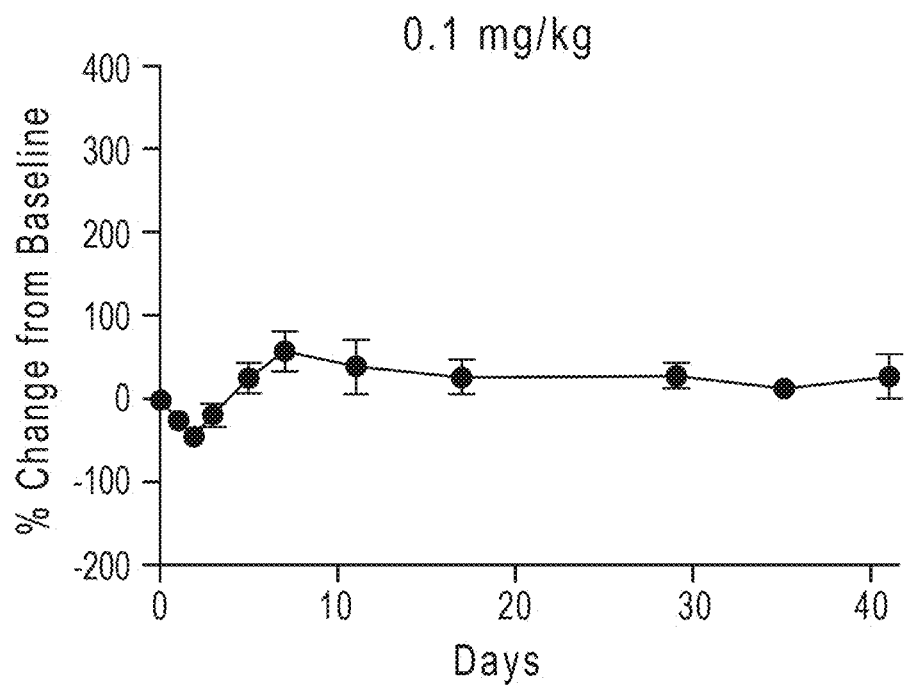
FIGS. 10A-10D show the percent change in CD4+ T cell counts in peripheral blood following subcutaneous administration of from 0.1 mg/kg to 3.0 mg/kg of an IL-7Rαγc IgG2-Fc fusion protein (SEQ ID NO: 45) to non-human primates.
Figure 10B:
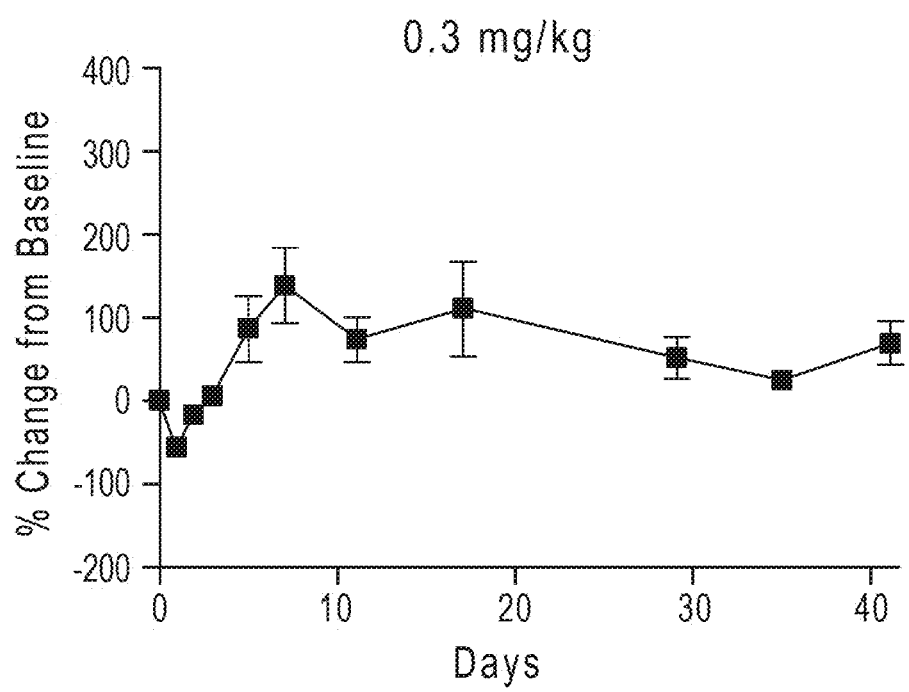
Figure 10C:
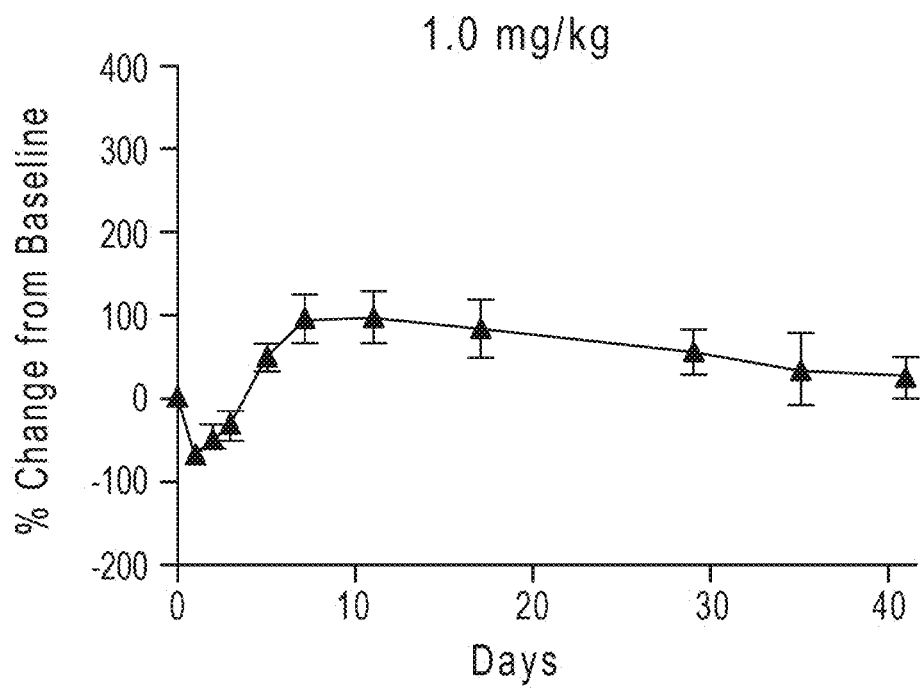
Figure 10D:
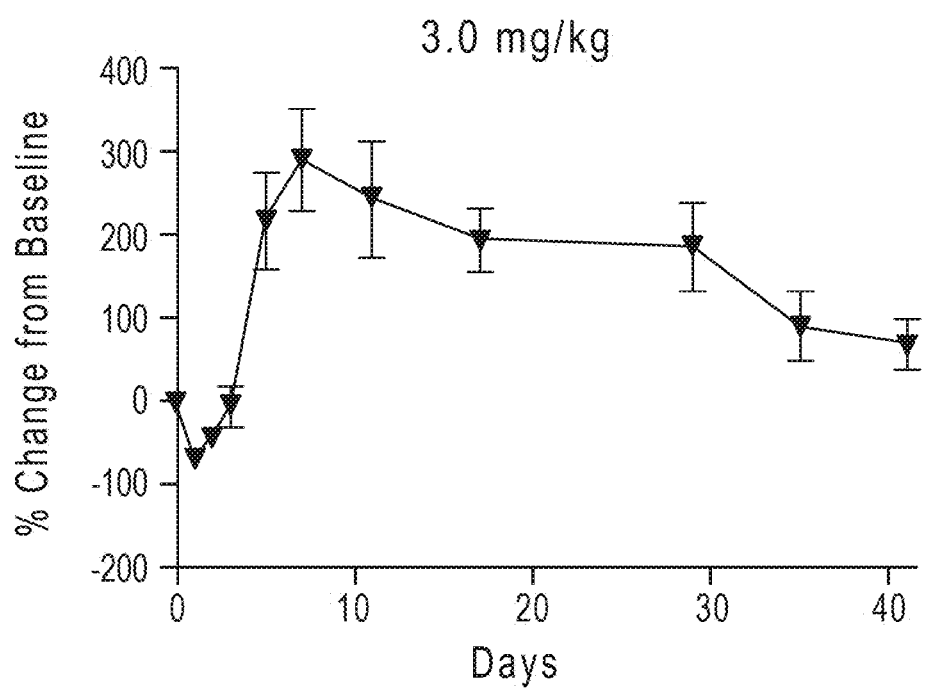
Figure 11A:
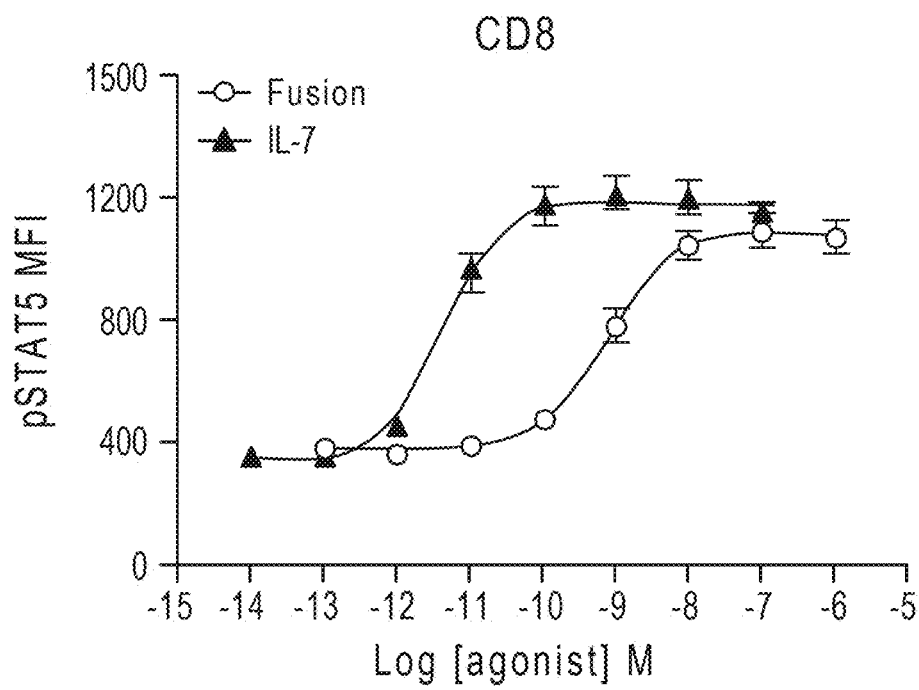
FIGS. 11A-11D show STAT5 phosphorylation in CD8+ T, CD4+ T, Treg, and NK cells in human PBMCs, respectively, following exposure to the IL-7Rαγc IgG2-Fc fusion protein having SEQ ID NO: 45 or to IL-7.
Figure 11B:
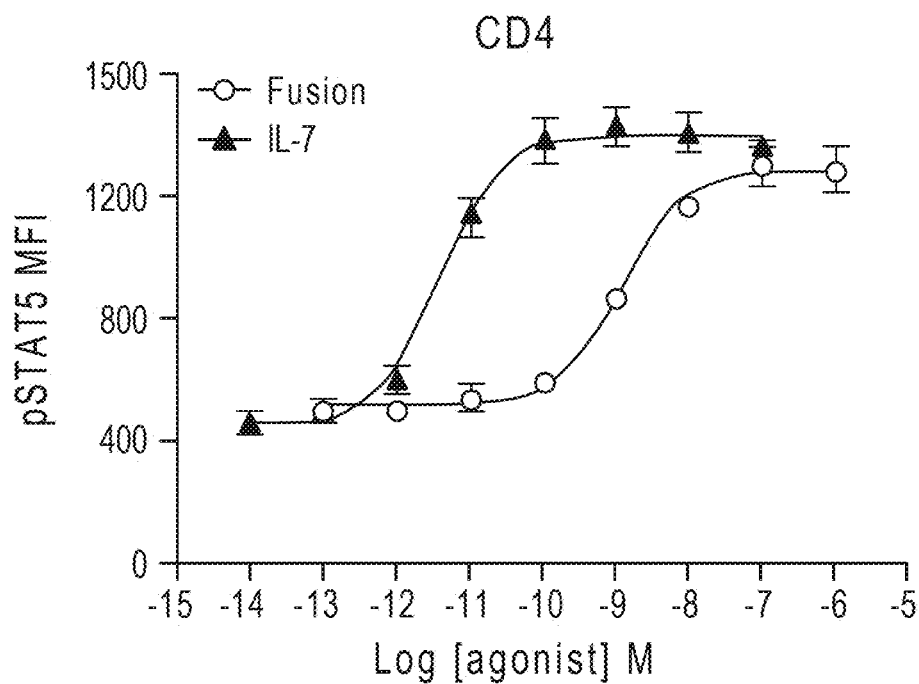
Figure 11C:
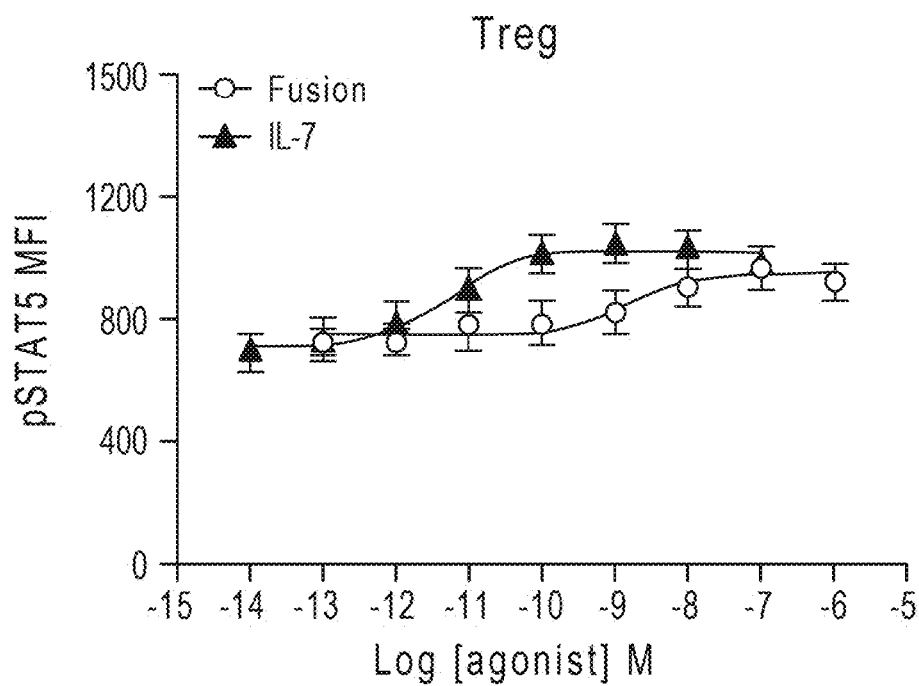
Figure 11D:
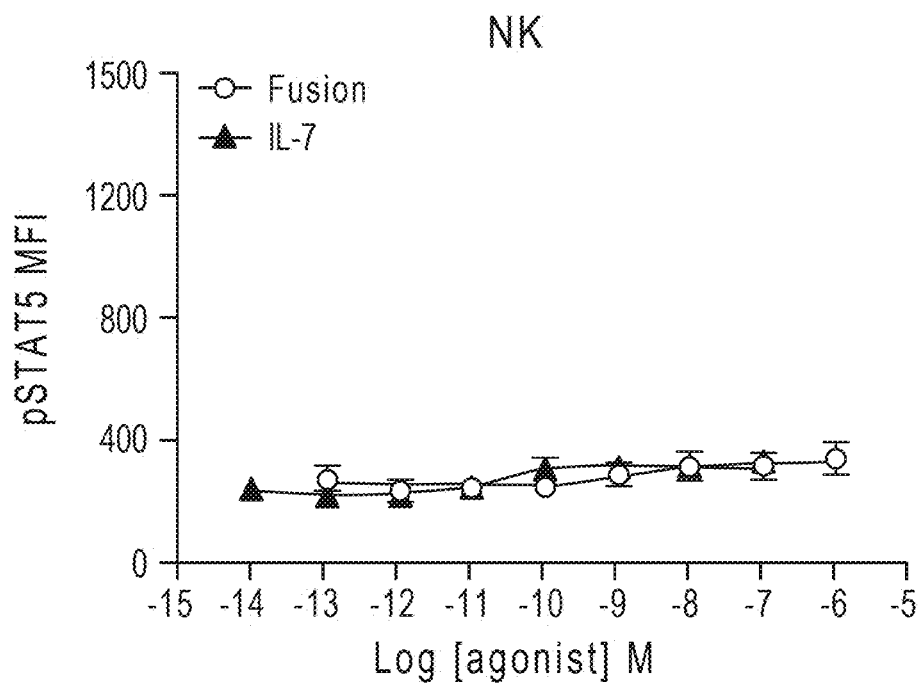
Figure 11E:
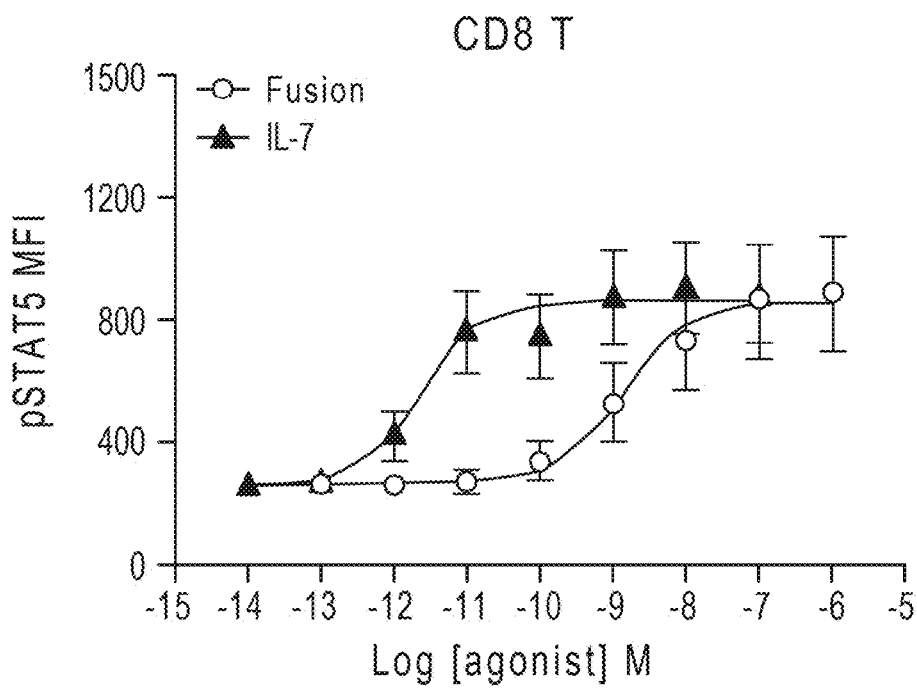
FIGS. 11E-11H show STAT5 phosphorylation in CD8+ T, CD4+ T, Treg, and NK cells in resting Cynomolgus monkey peripheral blood mononuclear cells (PBMCs), respectively, following exposure to the IL-7Rαγc IgG2-Fc fusion protein having SEQ ID NO: 45 or to IL-7.
Figure 11F:
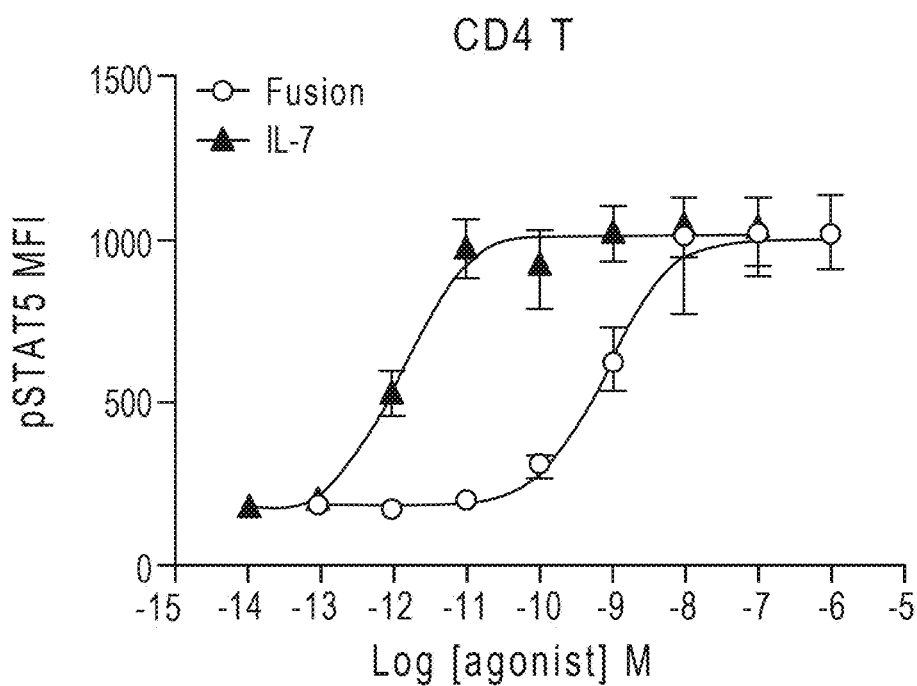
Figure 11G:
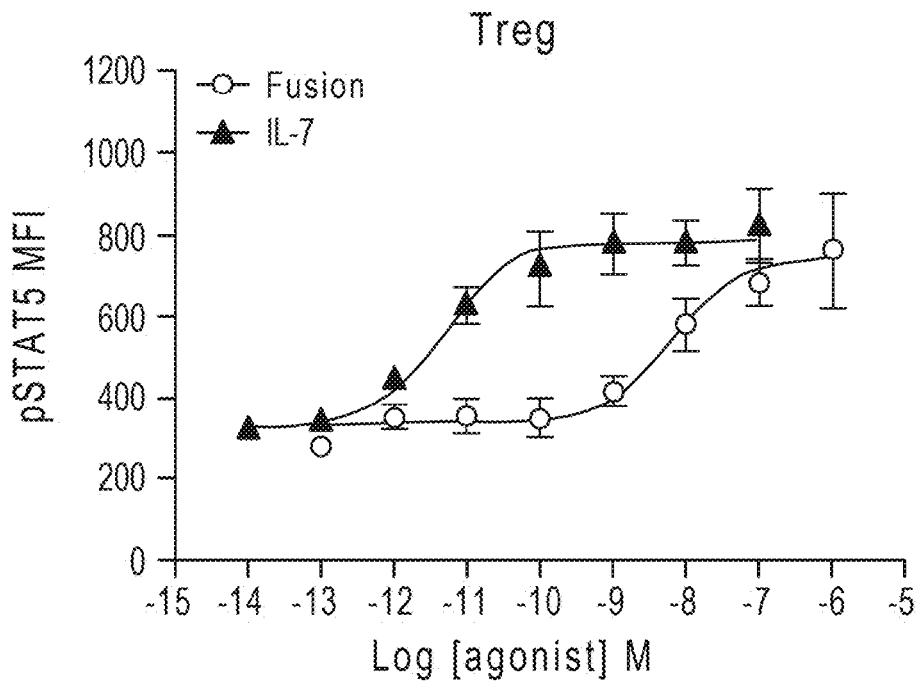
Figure 11H:
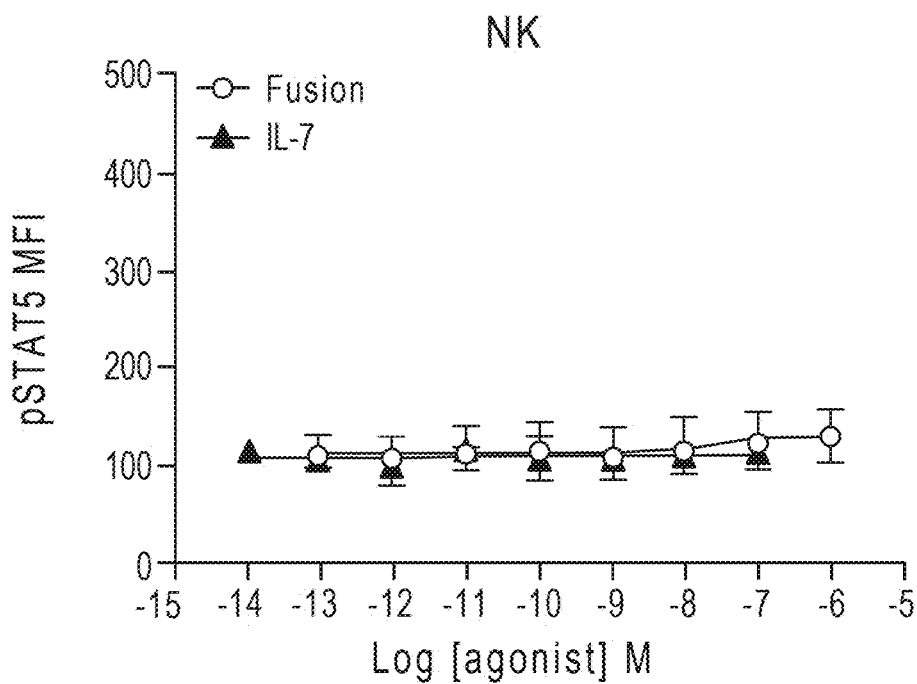
Figure 12A:
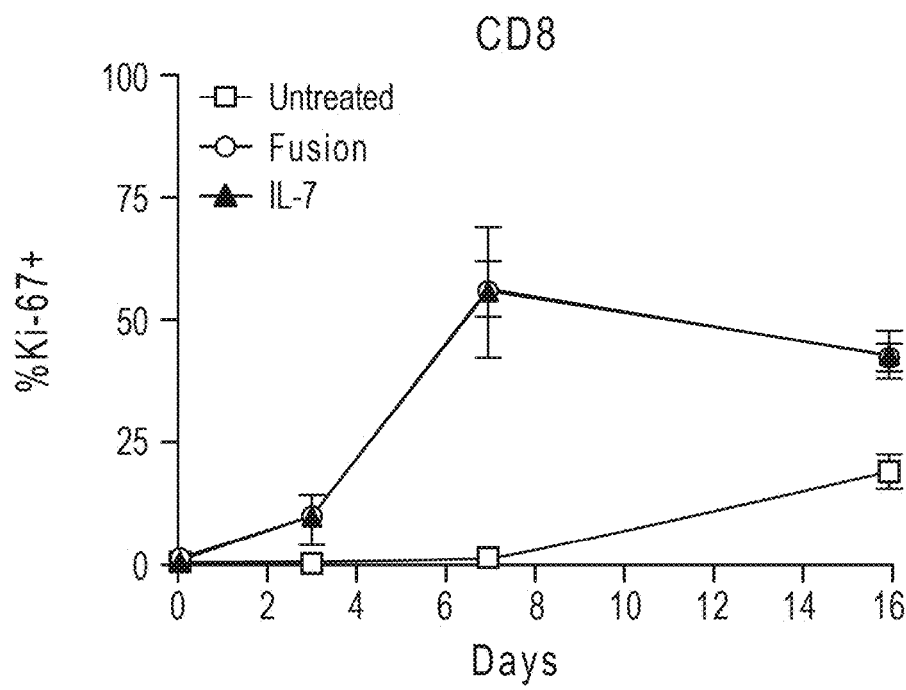
FIGS. 12A-12D show Ki-67 frequency in untreated CD8+ T, CD4+ T, Treg, and NK cells, respectively, and in CD8+ T, CD4+ T, Treg, and NK cells from resting PBMCs following exposure to the IL-7Rαγc IgG2-Fc fusion protein having SEQ ID NO: 45 or to IL-7.
Figure 12B:
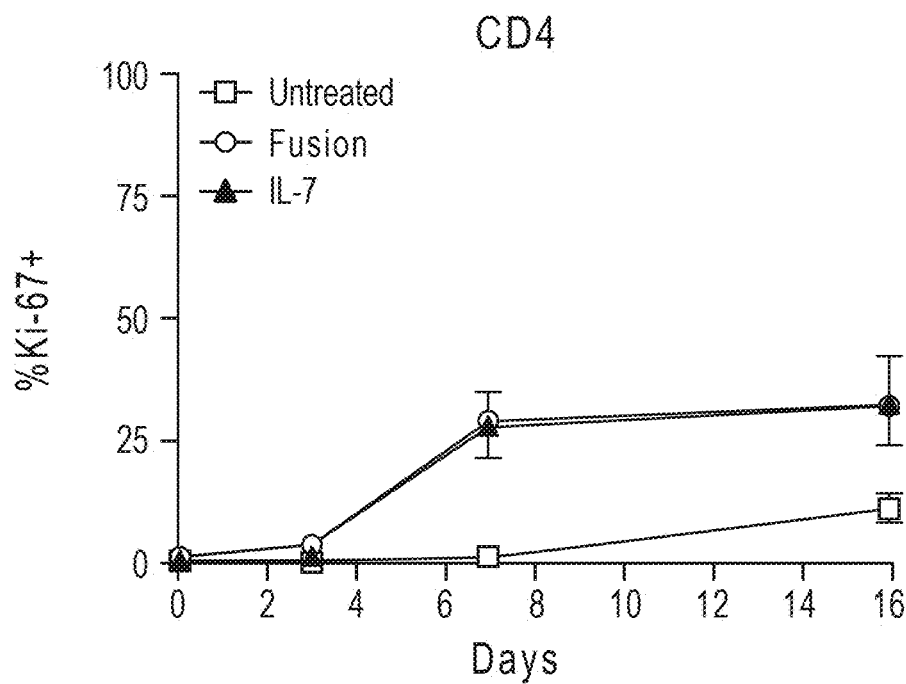
Figure 12C:
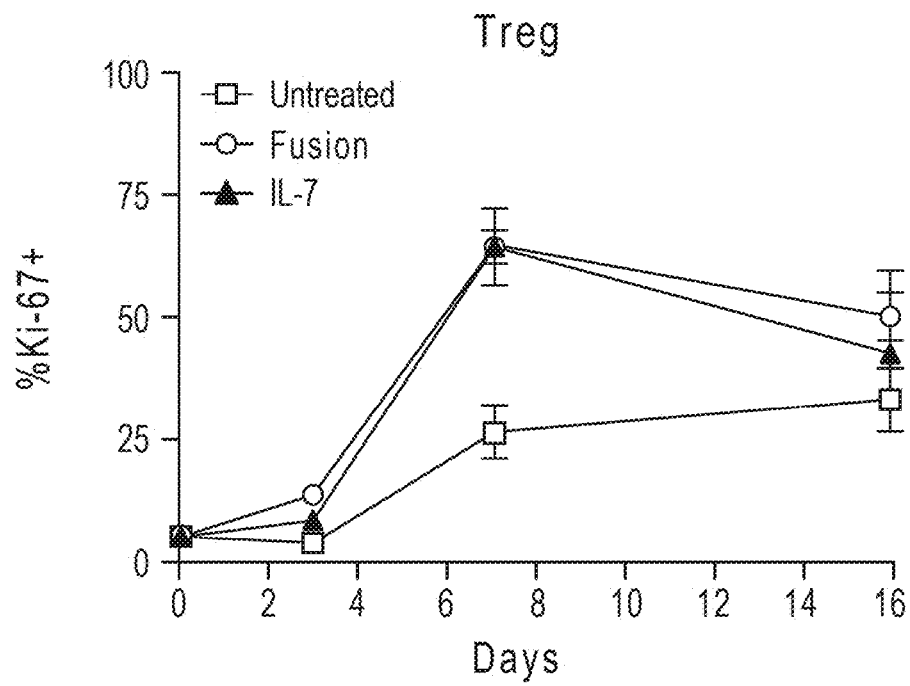
Figure 12D:
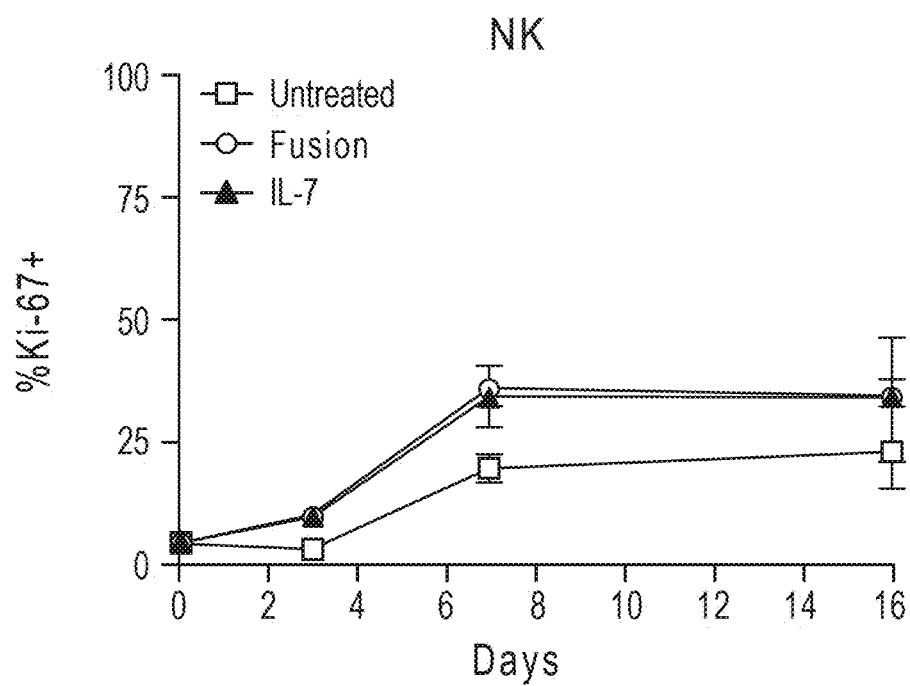
Figure 13A:
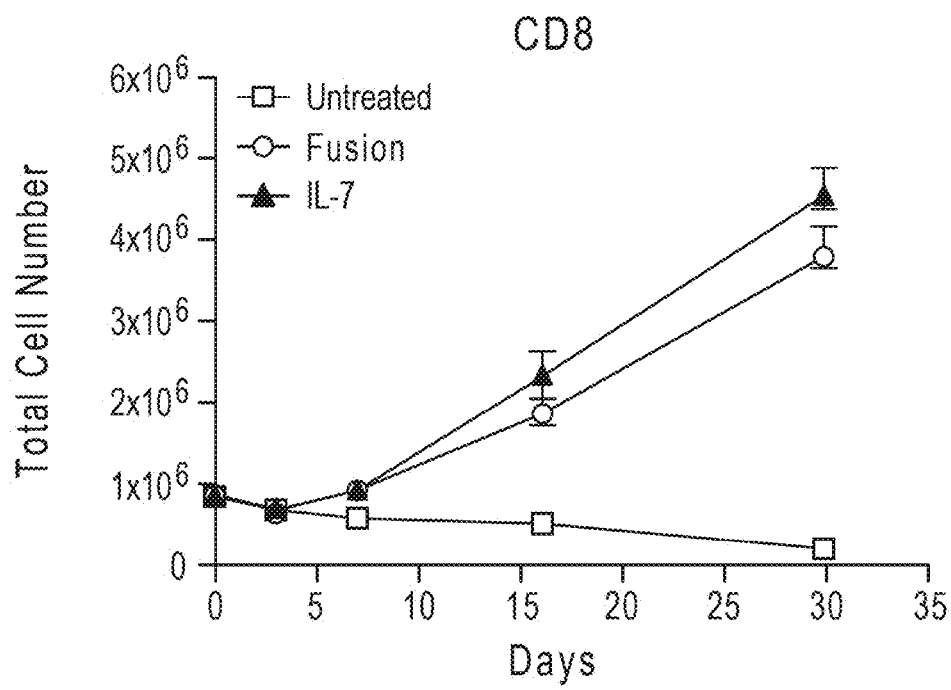
FIGS. 13A-13D show the total cell number in untreated CD8+ T, CD4+ T, Treg, and NK cells, respectively, and in CD8+ T, CD4+ T, Treg, and NK cells in PMBCs following exposure to the IL-7Rαγc IgG2-Fc fusion protein having SEQ ID NO: 45 or to IL-7.
Figure 13B:
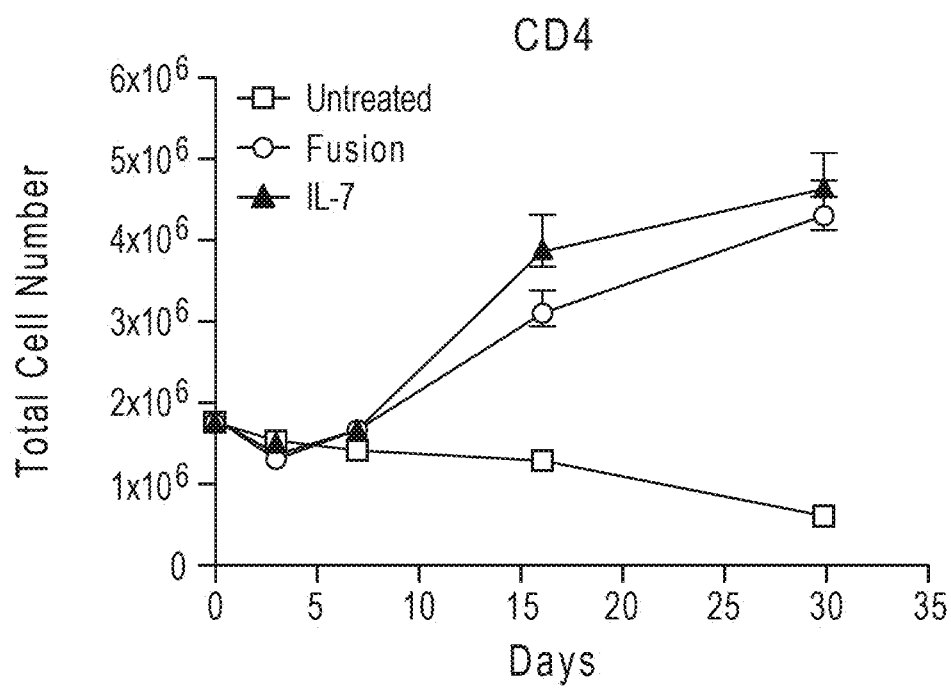
Figure 13C:
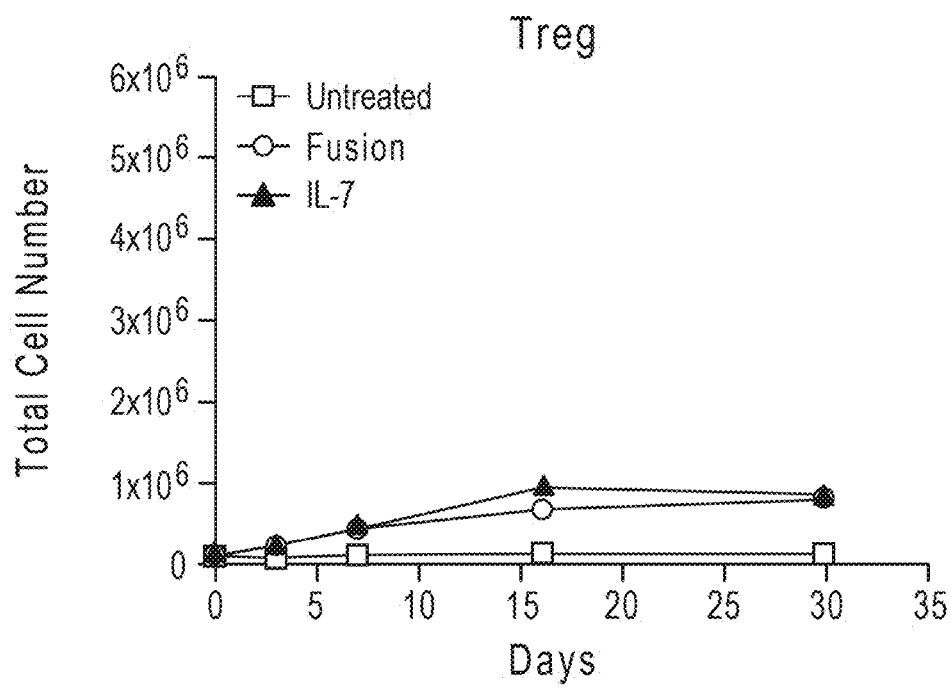
Figure 13D:
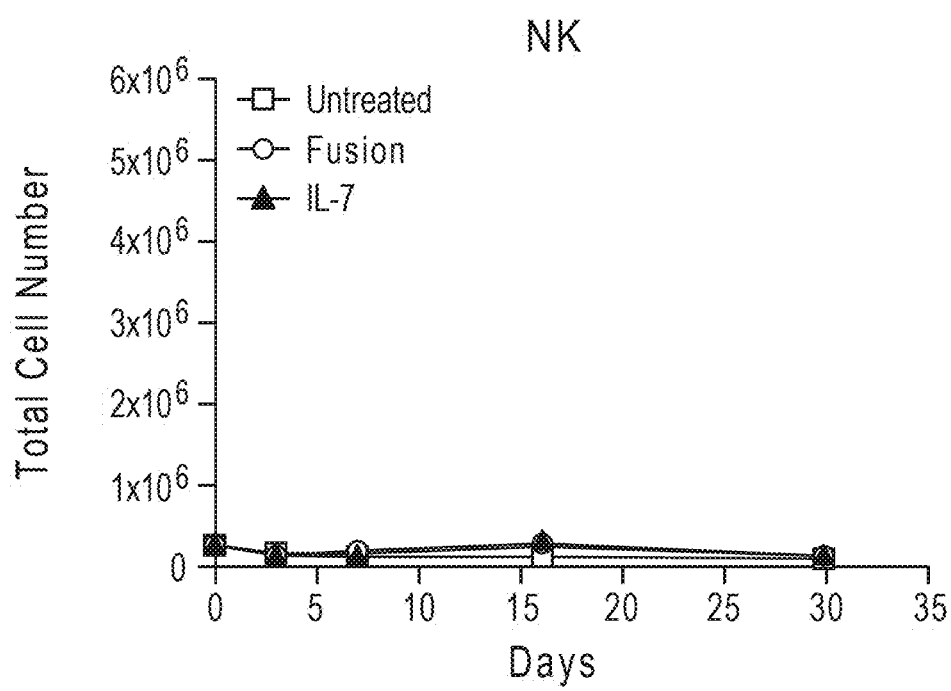
Figure 14A:
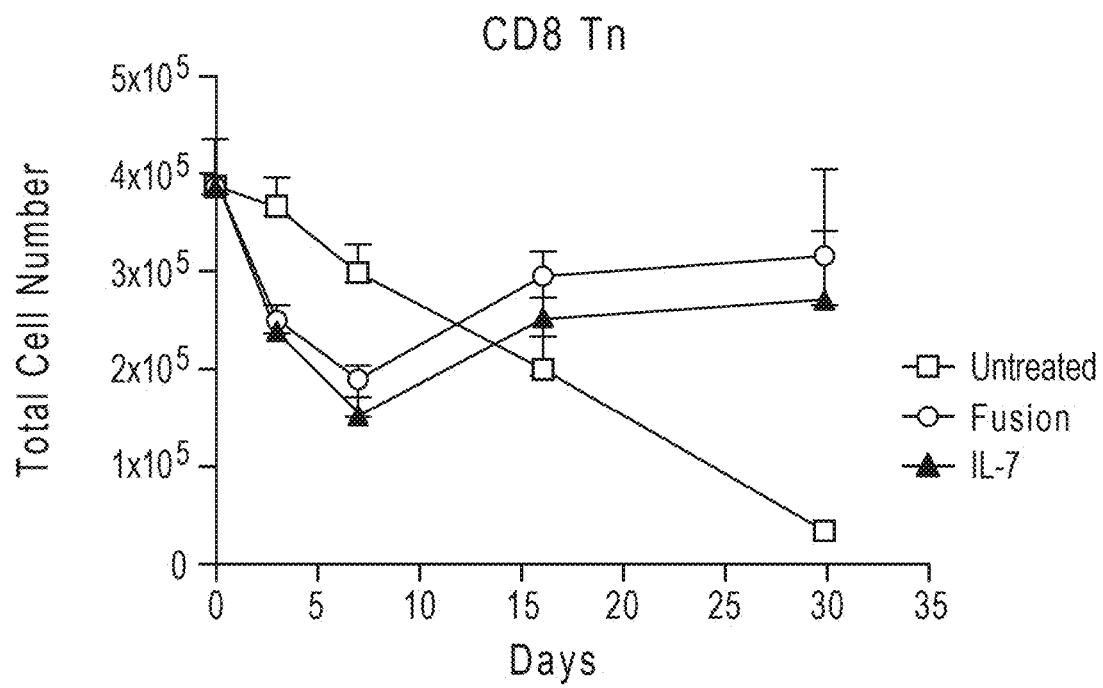
FIGS. 14A-14E show total cell number of CD8+ Tn (naïve T), CD8+ Tscm (stem memory T), CD8+ Tcm (central memory T), CD8+ Tem (effector memory T), and CD8+ Temra (terminally differentiated effector memory T) cells, respectively, without treatment or following exposure to the IL-7Rαγc IgG2-Fc fusion protein having SEQ ID NO: 45 or to IL-7.
Figure 14B:
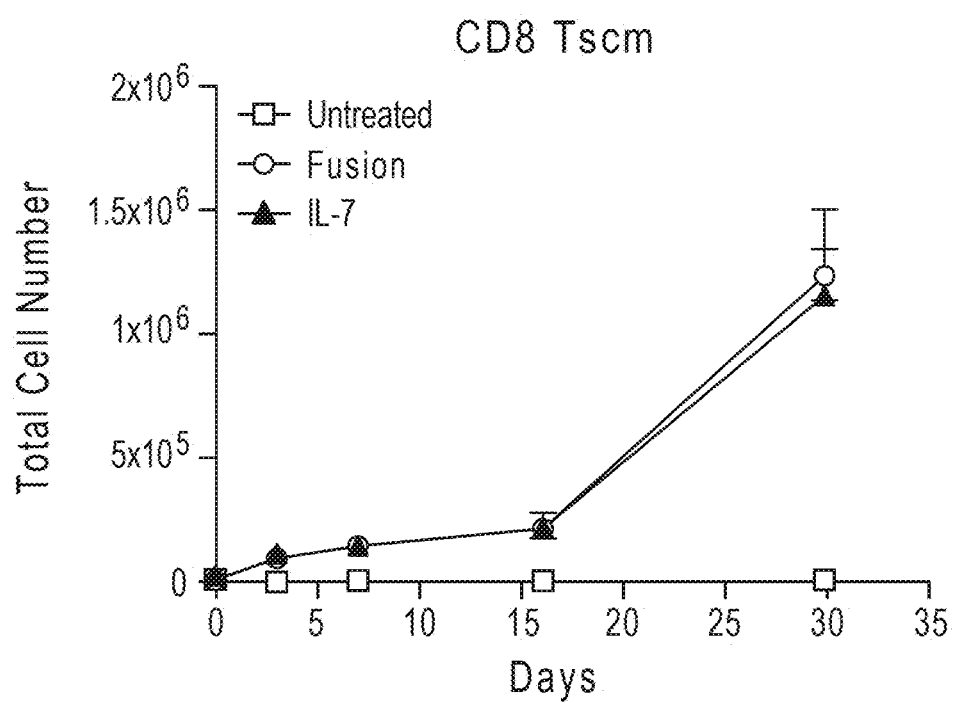
Figure 14C:
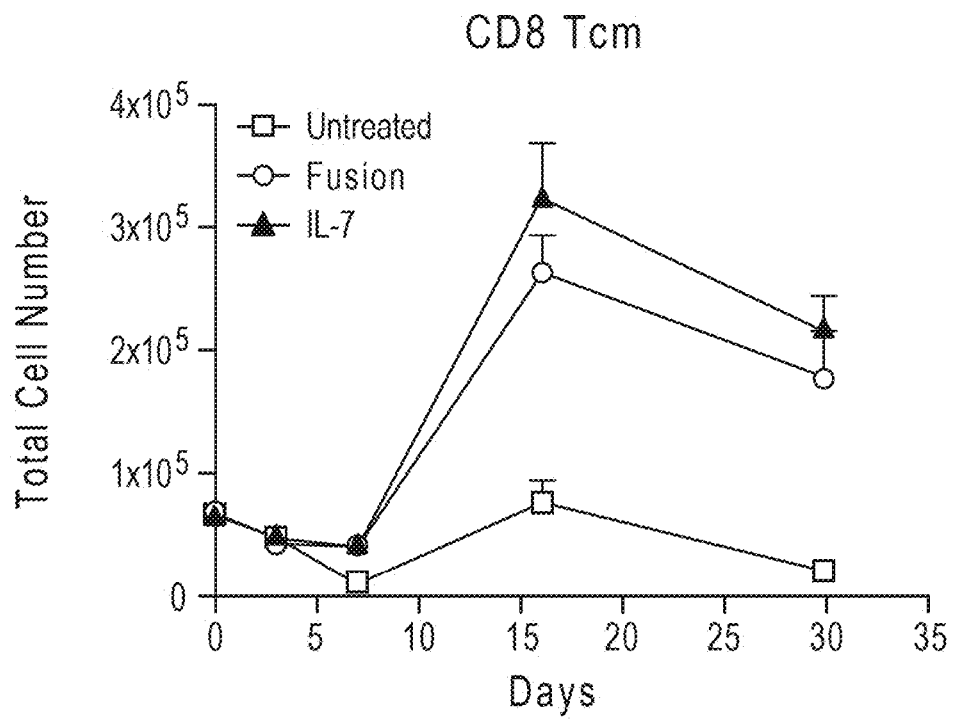
Figure 14D:
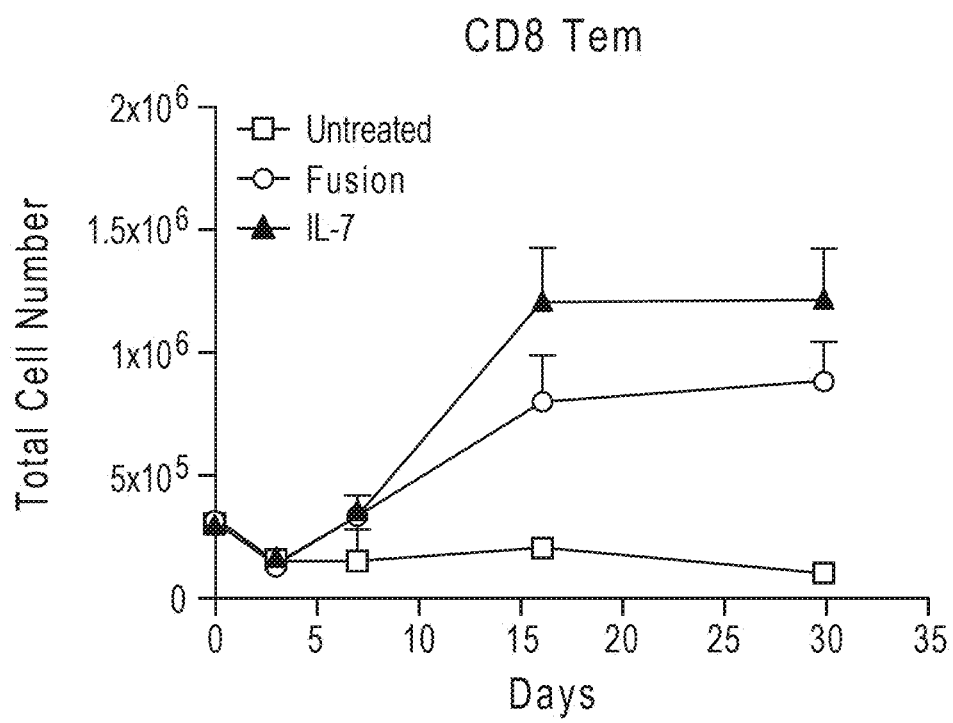
Figure 14E:
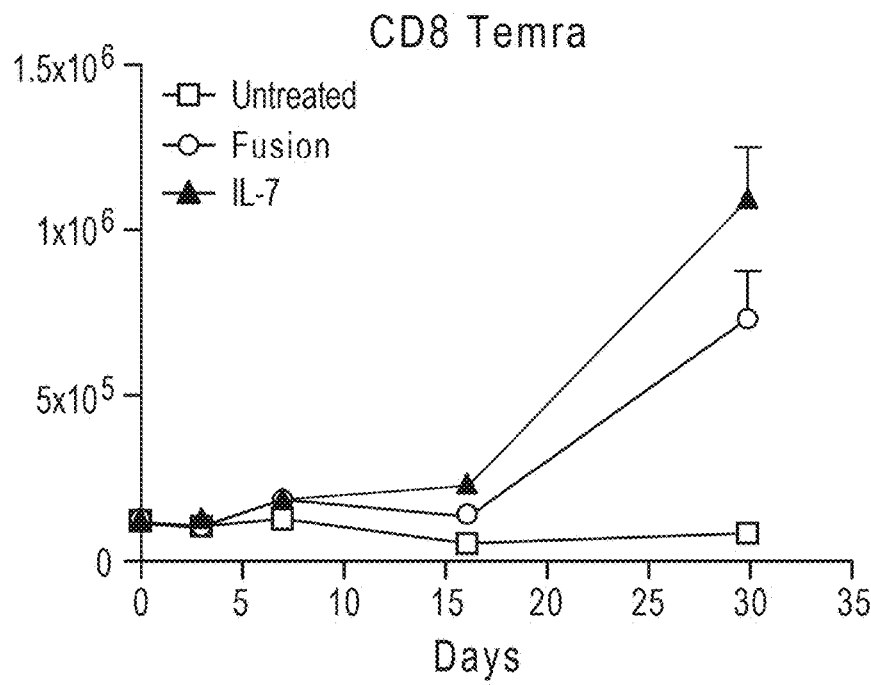

The pharmacokinetics of IL-7Rαγc IgG2-Fc fusion protein administered at doses from 0.1 mg/kg to 3.0 mg/kg was determined using a similar method. The $C_{max}$ and $AUC_{0-inf}$ of the plasma IL-7Rαγc IgG2-Fc fusion protein concentration following SC administration of from 0.1 mg/kg to 3.0 mg/kg of the IL-7Rαγc IgG2-Fc fusion protein having SEQ ID NO: 45 to non-human primates is shown in FIGS. 7A and 7B, respectively.

The CD8+ T cell and CD4+ T cell populations in the peripheral blood were determined by flow cytometry at the indicated time point following a single subcutaneous injection of various doses of the IL-7Rαγc IgG2-Fc fusion protein having SEQ ID NO: 45 to non-human primates. The data for the total lymphocyte population, CD8+ T cell population, and CD4+ T cell population, are shown in FIGS. 8A-8D, FIGS. 9A-9D, and FIGS. 10A-10D, respectively.

Example 6

In Vitro STAT5 Phosphorylation in Human and Cynomolgus Monkey PBMCs

Frozen PBMCs from 5 healthy human donors or Cynomolgus monkeys were rested overnight and stained for viability, followed by cell surface antibody staining on ice. Cells were washed and incubated with the IL-7Rαγc IgG2-Fc fusion protein having SEQ ID NO: 45 or IL-7 for 30 min at 37° C. After washing, the cells were fixed, permeabilized, stained with anti-pSTAT5 antibody and FoxP3 antibody, and analyzed by flow cytometry. Antibody-stained cells were analyzed immediately by flow cytometry using a Novocyte® Advanteon™ Instrument (Agilent) and the data analyzed using FlowJo™ software.

Induction of pSTAT5 in resting human PBMCs treated with either the IL-7Rαγc IgG2-Fc fusion protein having SEQ ID NO: 45 or IL-7 is shown for CD8+ T, CD4+ T, Treg, and NK cells in FIGS. 11A-11D, respectively.

Induction of pSTAT5 in resting Cynomolgus monkey PBMCs treated with either the IL-7Rαγc IgG2-Fc fusion protein having SEQ ID NO: 45 or IL-7 is shown for CD8+ T, CD4+ T, Treg, and NK cells in FIGS. 11E-11H, respectively.

Example 7

Proliferation of Human CD4+ T, CD8+ T, Treg and NK Cells

Frozen PBMCs from 5 healthy donors were rested overnight or activated with CD3 antibody and left untreated or treated with 100 nM of the IL-7Rαγc IgG2-Fc fusion protein having SEQ ID NO: 45 or with 1 nM IL-7 in culture. On days 3, 7, 16, and 30, cell aliquots were taken to determine Ki-67 expression in immune cells and total cell counts in the culture.

PBMCs and cell culture: Frozen human PBMCs from 5 healthy donors (Stem Cell Technologies, cat no. 70025.2) were thawed and rested overnight at 37° C., 5% $CO_2$ in CTS™ OpTmizer™ T Cell Expansion SFM (ThermoFisher Scientific No. A1048501). Four million cells were cultured in the plate coated with or without 10 ng/mL of CD3 antibody (Clone SP34-2) and in the presence or absence of 100 nM of the IL-7Rαγc IgG2-Fc fusion protein having SEQ ID NO: 45 or 1 nM IL-7. Fresh media containing the IL-7Rαγc IgG2-Fc fusion protein having SEQ ID NO: 45 and IL-7 were provided every 4-5 days.

Flow cytometry: On day 3, day 7, day 16, and day 30, cell aliquots were taken, and cell surface staining was performed using antibodies, followed by fixable viability dye staining. For Ki-67 and FoxP3 staining, surfaced stained cells were fixed and permeabilized according to the manufacturer's instruction and analyzed immediately using a Novocyte® Advanteon™ instrument (Agilent). The data were analyzed using FlowJo™ software. Fluorescent Minus One (FMO) controls were used to draw gates. Percentages of Ki67+ cell populations were expressed as average ±SEM.

Cell counting: Cultures were initially plated at $4\times10^6$ cells in 2 mL per well. At each assay time point, 50 μL/well of cells were taken from each culture and incubated with 200 μL of the viability dye solution. The Novocyte® Advanteon™ flow cytometer was set up to analyze precisely 50 μL (12.5 μL original culture volume), which allowed the calculation of the absolute live cell counts. Because the culture volumes change over time due to splitting and removal, dilution factors were considered when calculating the total number of cells.

FIGS. 12A-12D show Ki-67 expression in resting CD8+ T, CD4+ T, Treg and NK cells, respectively.

FIGS. 13A-13D show total cell counts in resting CD8+ T, CD4+ T, Treg and NK cells, respectively.

Example 8

Expansion of Tscm in PBMCs

Frozen PBMCs from 5 healthy donors were rested overnight or activated with CD3 antibody and treated with vehicle, 100 nM of the IL-7Rαγc IgG2-Fc fusion protein having SEQ ID NO: 45, or with 1 nM IL-7 in a serum-free culture medium. On days 3, 7, 16, and 30, cell aliquots were analyzed by flow cytometry for memory T cell populations and cell counts.

PBMCs and cell culture: Frozen human PBMCs from 5 healthy donors (Stem Cell Technologies, cat no. 70025.2) were thawed and rested overnight at 37° C., 5% $CO_2$ in CTS™ OpTmizer™ T Cell Expansion SFM (ThermoFisher Scientific No. A1048501). Four million cells were cultured in the plate coated with or without 10 ng/mL of CD3 antibody (Clone SP34-2) and in the presence or absence of 100 nM of the IL-7Rαγc IgG2-Fc fusion protein or 1 nM IL-7. Fresh media containing the IL-7Rαγc IgG2-Fc fusion protein and IL-7 were provided every 4-5 days.

Flow cytometry: On day 3, day 7, day 16, and day 30, cell aliquots were taken, and cell surface staining was performed using antibodies, followed by fixable viability dye staining. For Ki-67 and FoxP3 staining, surfaced stained cells were fixed and permeabilized according to the manufacturer's instruction and analyzed immediately using the Novocyte® Advanteon™ instrument (Agilent). The data were analyzed using FlowJo™ software. Fluorescent Minus One (FMO) controls were used to draw gates. Percentages of Ki67+ cell populations were expressed average ±SEM.

Cell counting: Cultures were initially plated at $4\times10^6$ cells in 2 mL per well. At each assay time point, 50 μL/well of cells were taken from each culture and incubated with 200 μL of the viability dye solution. A Novocyte® Advanteon™ flow cytometer was set up to analyze precisely 50 μL (12.5 μL original culture volume), which allowed the calculation of the absolute live cell counts. Because the culture volumes change over time due to splitting and removal, dilution factors were considered when calculating the total number of cells.

Figure 15A:
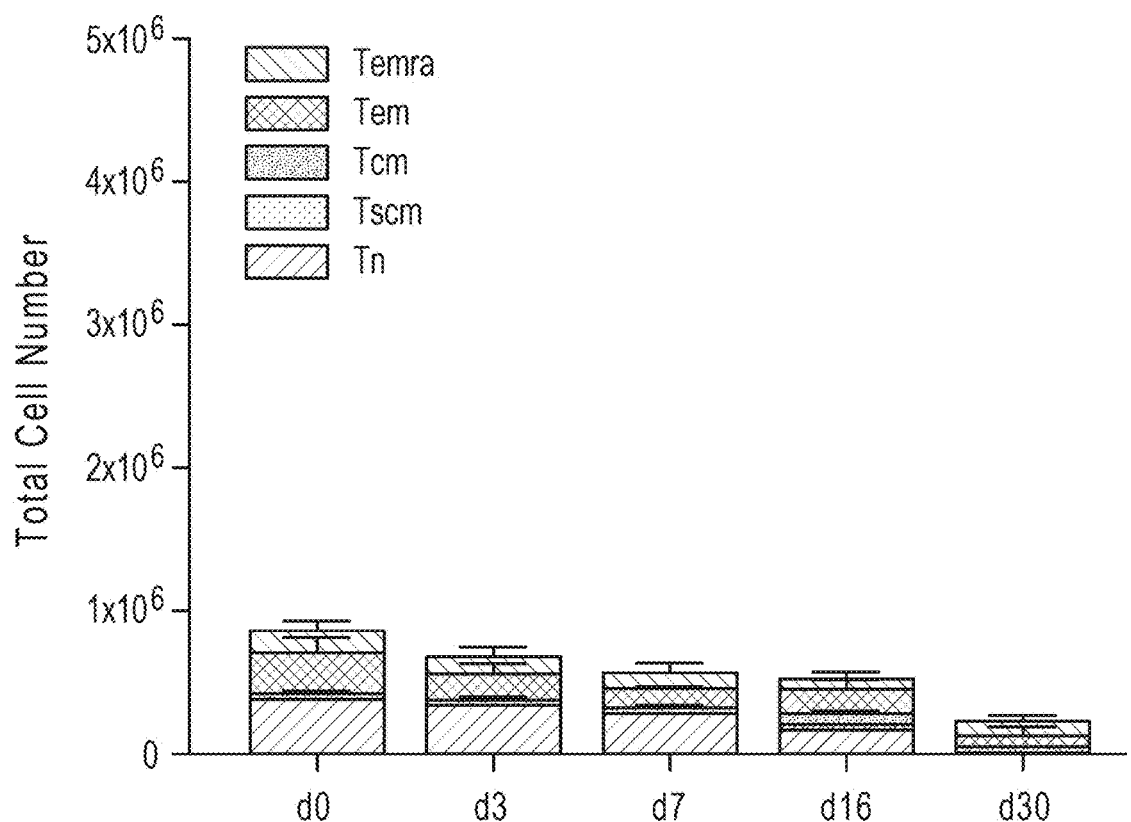
FIGS. 15A-15C show the sum of cell numbers of CD8+ Tn, CD8+ Tscm, CD8+ Tcm, CD8+ Tem, and CD8+ Temra cells, without treatment (FIG. 15A) or following exposure to the IL-7Rαγc IgG2-Fc fusion protein having SEQ ID NO: 45 (FIG. 15B) or following exposure to IL-7 (FIG. 15C).
Figure 15B:
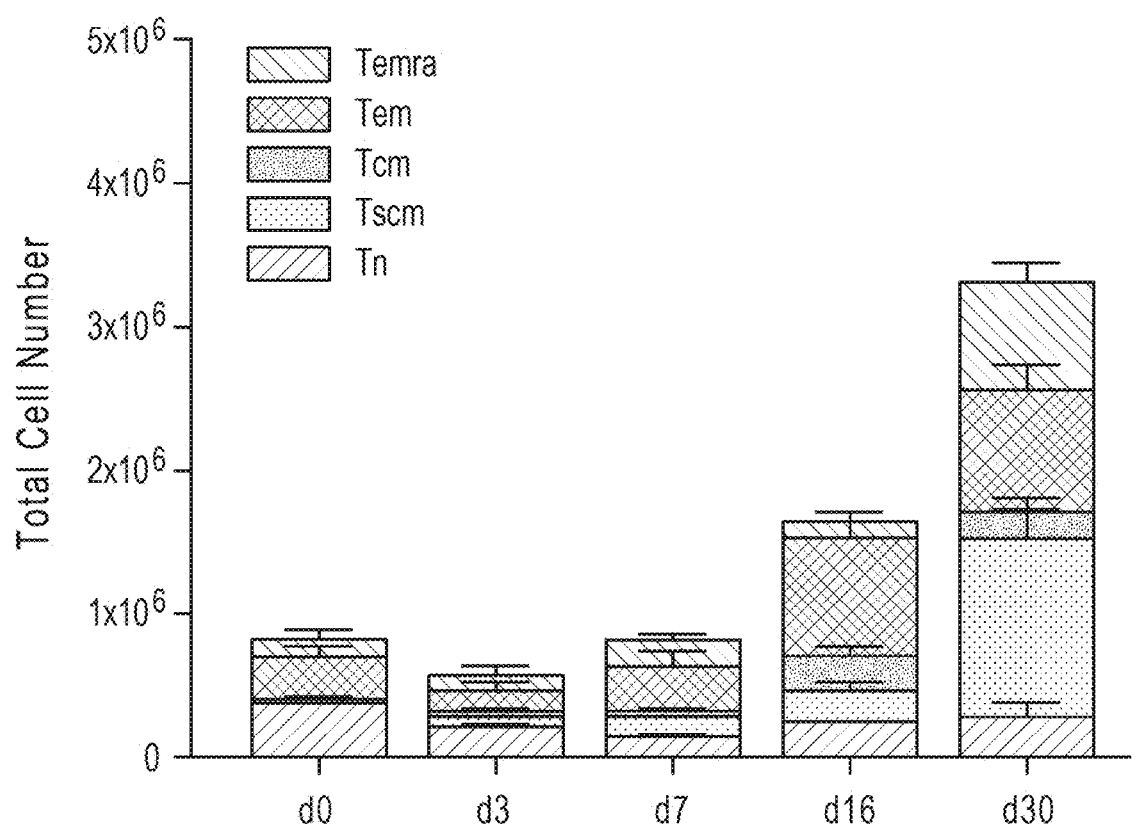
Figure 15C:
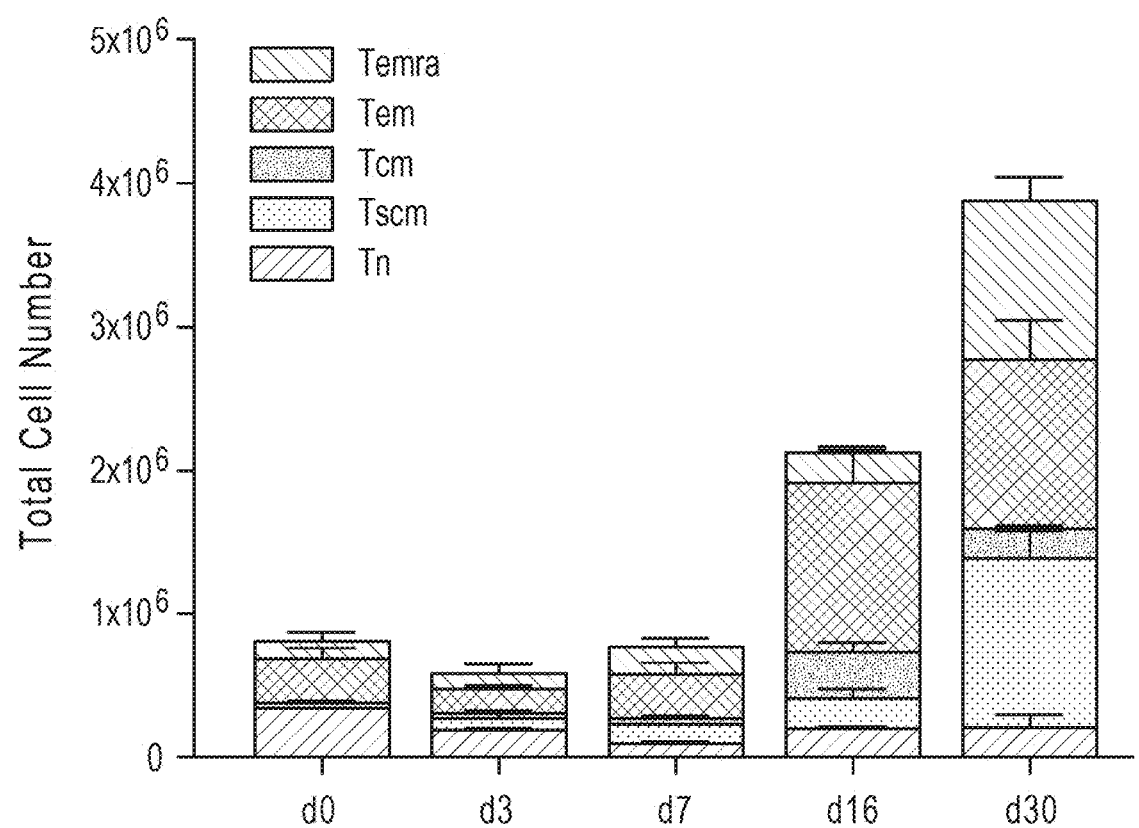

Changes in memory T-cell populations mediated by the IL-7Rαγc IgG2-Fc fusion protein having SEQ ID NO: 45 or by IL-7 in PBMCs is shown in FIGS. 14A-14E and in FIGS. 15A-15C.

FIGS. 14A-14E show the total cell number of CD8+ Tn, CD8+ Tscm, CD8+ Tcm, CD8+ Tem, and CD8+ Temra cells, respectively, without treatment (FIG. 14A) or following exposure to either the IL-7Rαγc IgG2-Fc fusion protein or to IL-7 with time.

FIGS. 15A-15C show the total cell number of CD8+ Tn, CD8+ Tscm, CD8+ Tcm, CD8+ Tem, and CD8+ Temra cells, without treatment (FIG. 15A) or following exposure to the IL-7Rαγc IgG2-Fc fusion protein having SEQ ID NO: 45 (FIG. 15B) or to IL-7 (FIG. 15C).

Figure 16A:
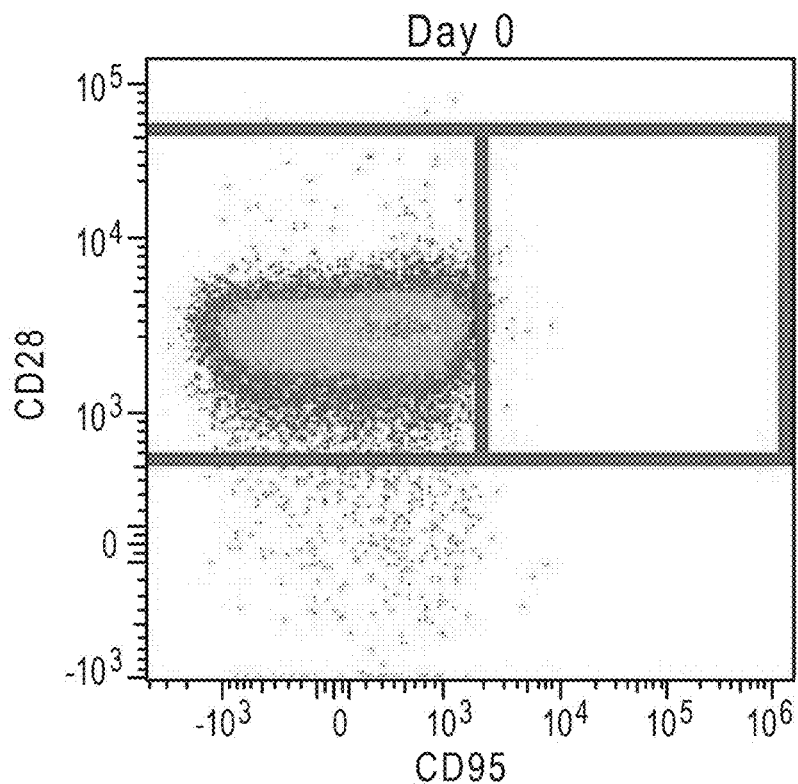
FIGS. 16A and 16B show the relative populations of CD28+CD95−CD8+ Tn cells and CD28+CD95+CD8+ Tscm cells in resting PBMCs before treatment (FIG. 16A), and at 30 days following exposure (FIG. 16B) to the IL-7Rαγc IgG2-Fc fusion protein having SEQ ID NO: 45.
Figure 16B:
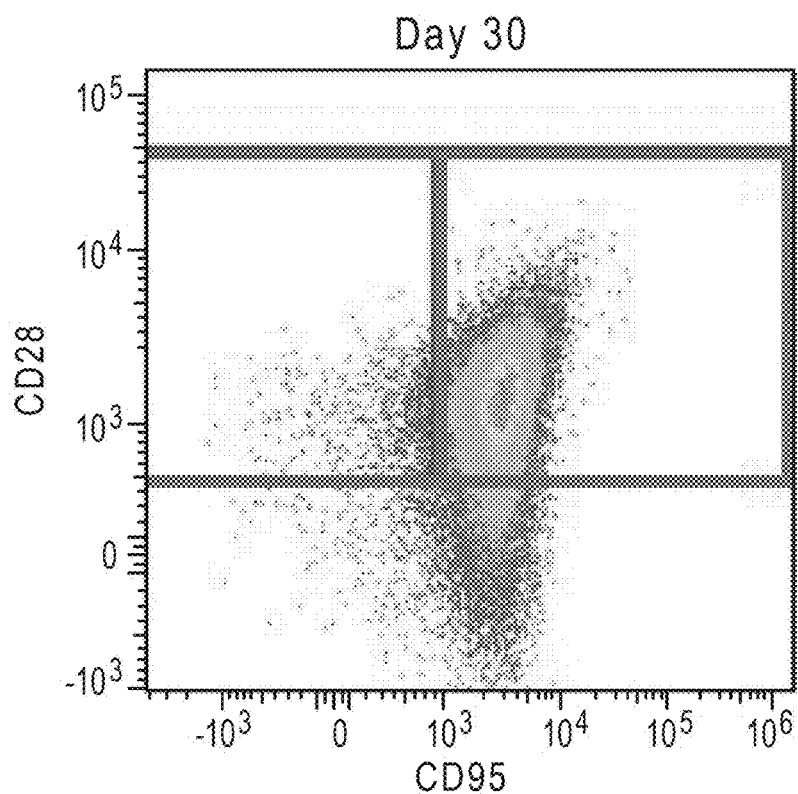

FIGS. 16A and 16B show the relative cell populations at day 0 and at day 30, respectively.

Figure 17A:
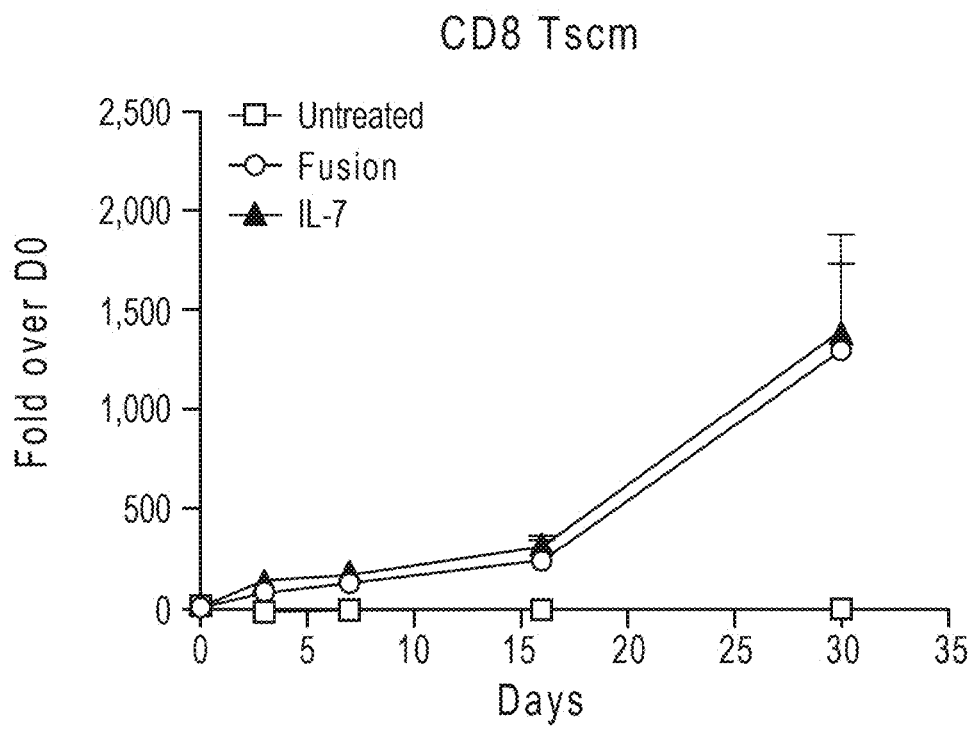
FIG. 17A-17D show the expansion of Tscm cells (stem memory T cells) in resting PBMCs (FIGS. 17A-17B) and in CD3-activated PBMCs FIGS. 17C-17D).
Figure 17B:
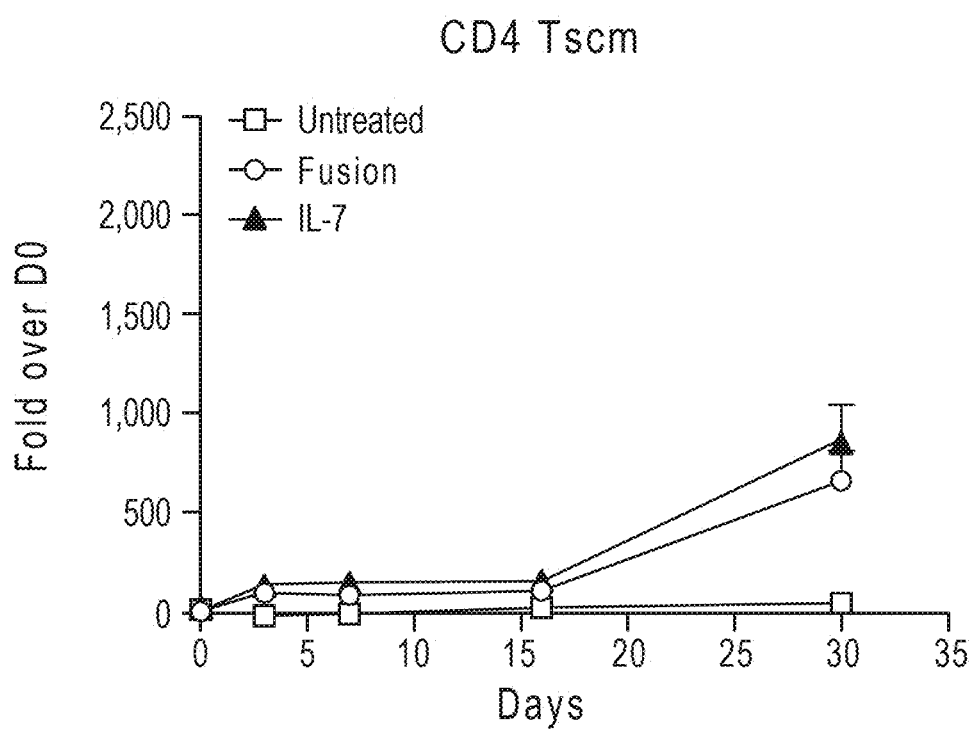
Figure 17C:
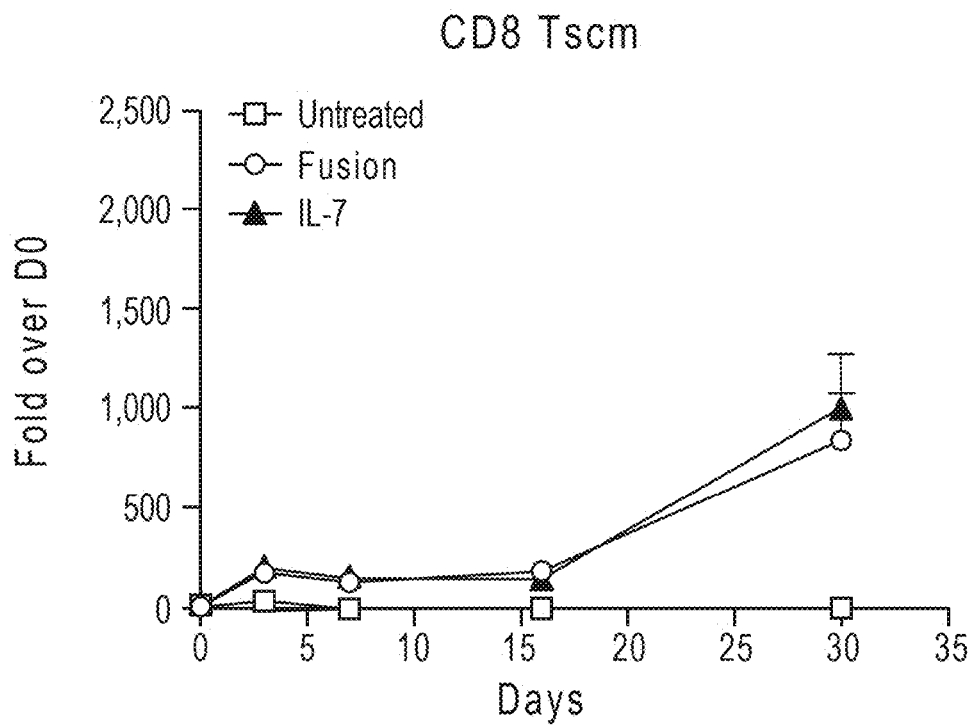
Figure 17D:
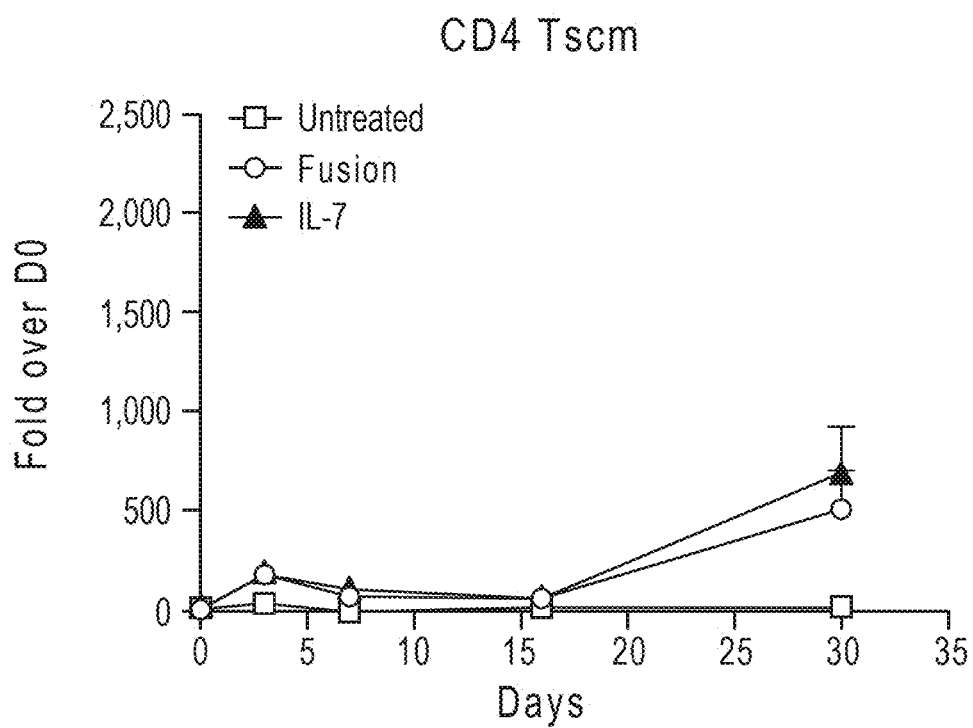

FIG. 17A-17D show the expansion of Tscm cells in resting PBMCs (FIGS. 17A-17B) and in CD3-activated PBMCs (FIGS. 17C-17D).

Example 9

Figures 18D, 18E:
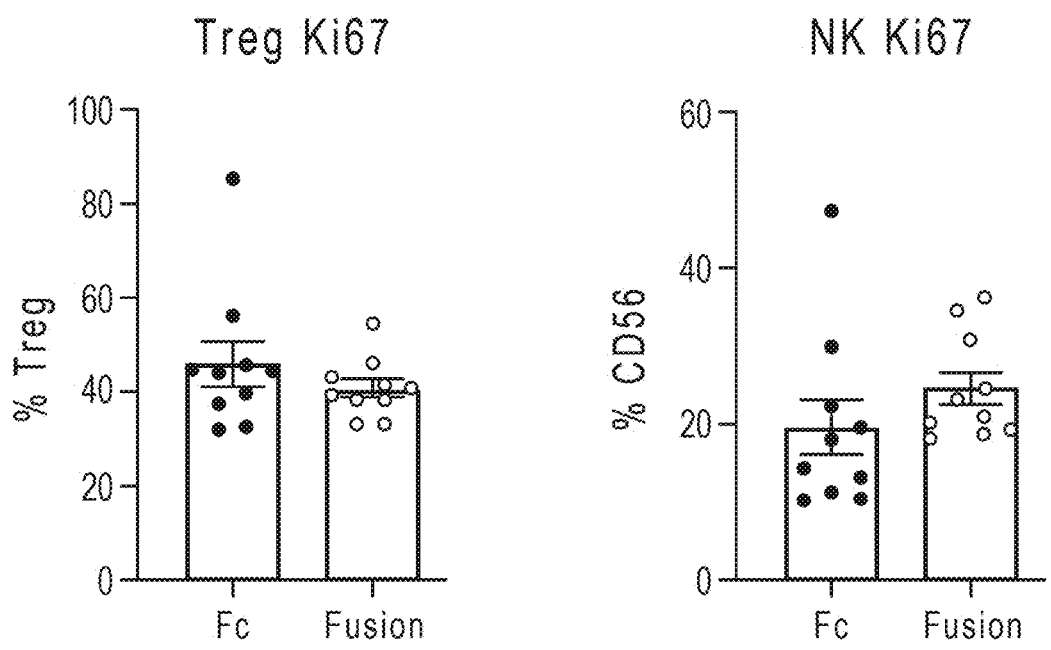
Figure 19A:
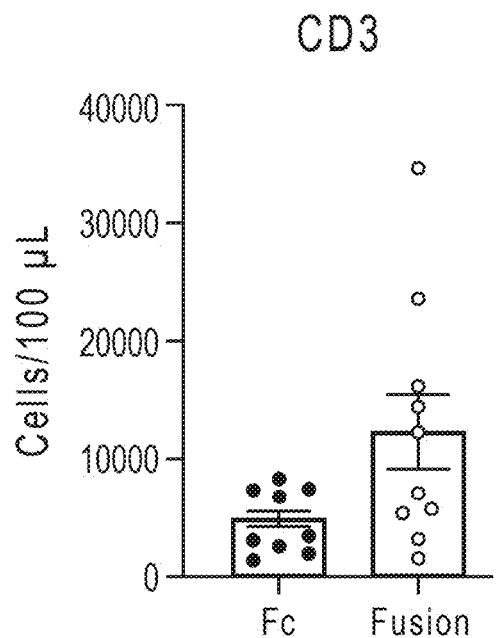
FIGS. 19A-19E show T-cell and NK cell counts in peripheral blood from humanized mice treated with either a control Fc fragment or the IL-7Rαγc IgG2-Fc fusion protein having SEQ ID NO: 45.
Figure 19B:
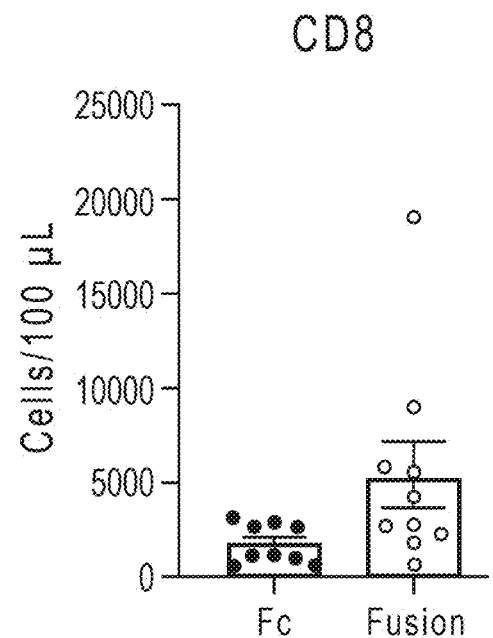
Figure 19C:
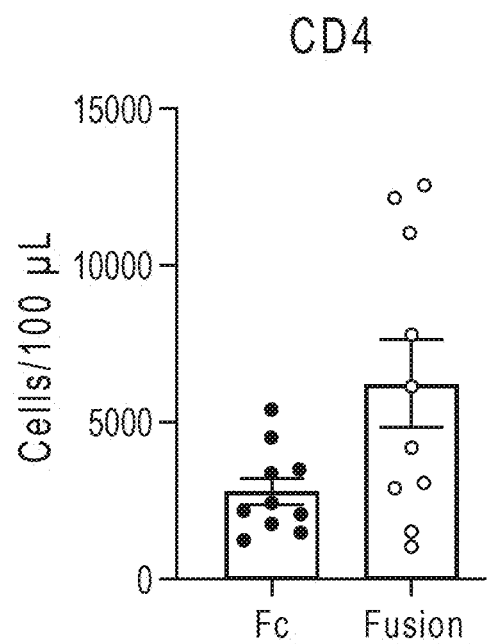
Figure 19D:
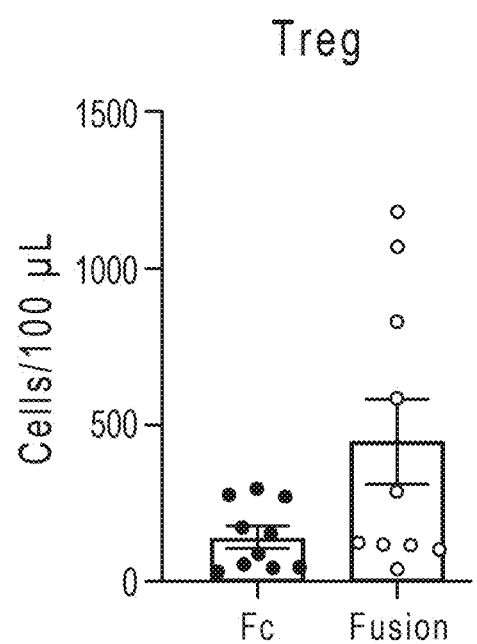
Figure 19E:
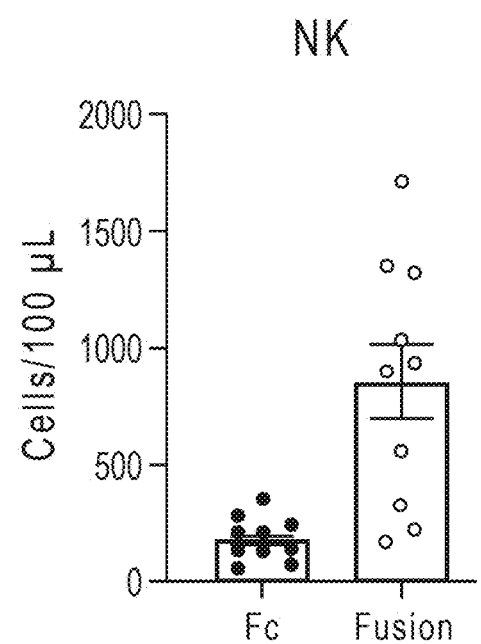
Figure 20A:
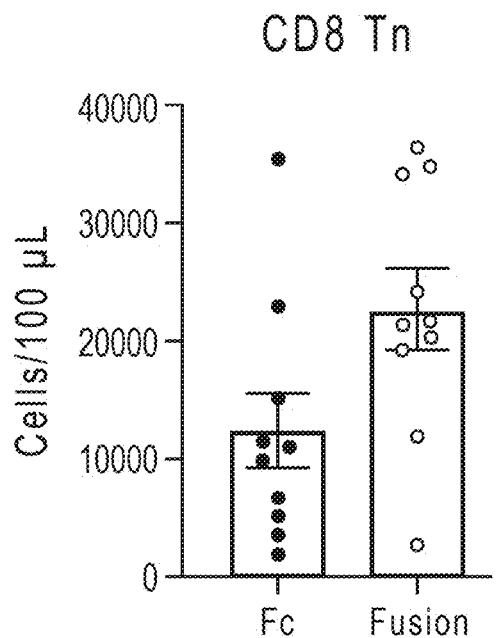
FIGS. 20A-20F show memory T-cell subpopulations in blood from humanized mice treated with either control a Fc fragment or the IL-7Rαγc IgG2-Fc fusion protein having SEQ ID NO: 45.
Figure 20B:
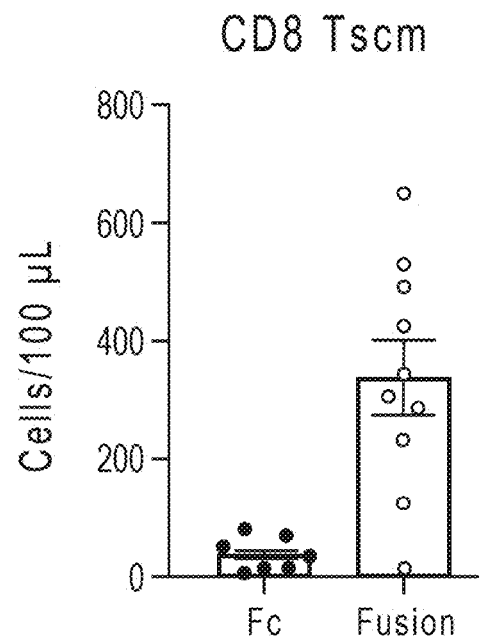
Figure 20C:
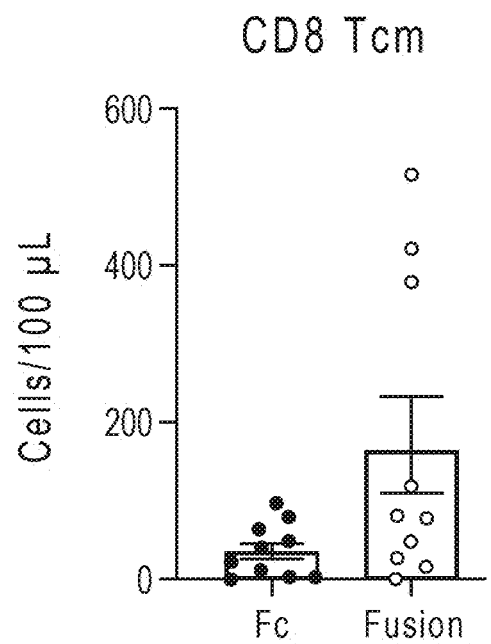
Figure 20D:
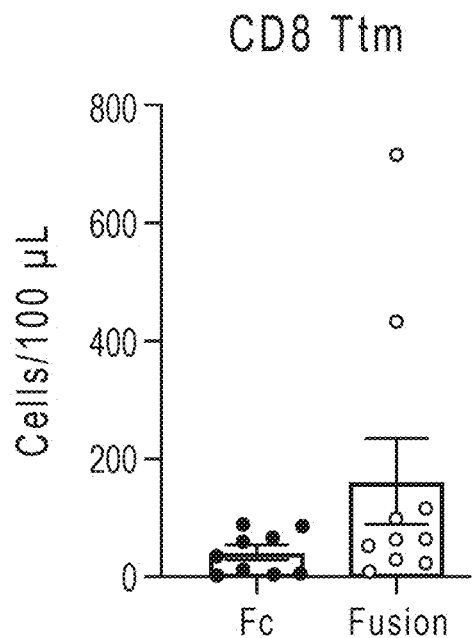
Figure 20E:
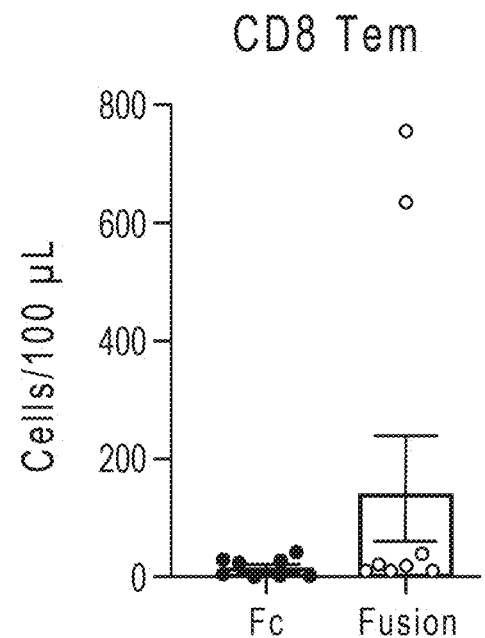
Figure 20F:
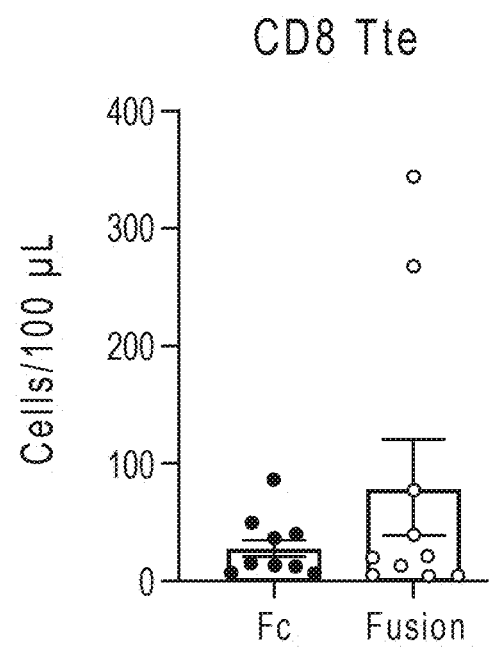
Figure 21A:
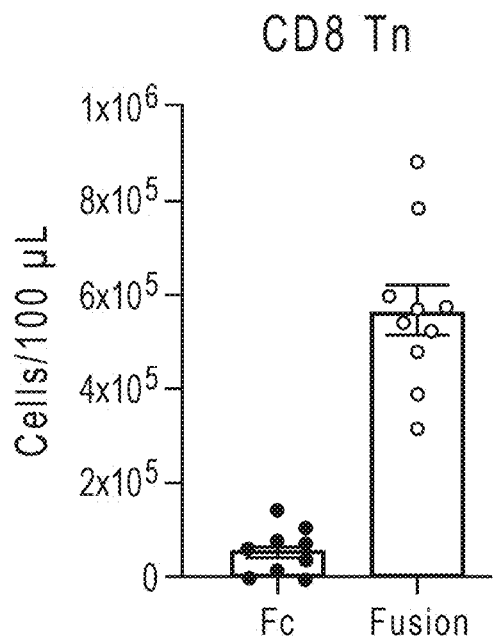
FIGS. 21A-21F show memory T-cell populations in the spleen from humanized mice treated with either a control Fc fragment or the IL-7Rαγc IgG2-Fc fusion protein having SEQ ID NO: 45.
Figure 21B:
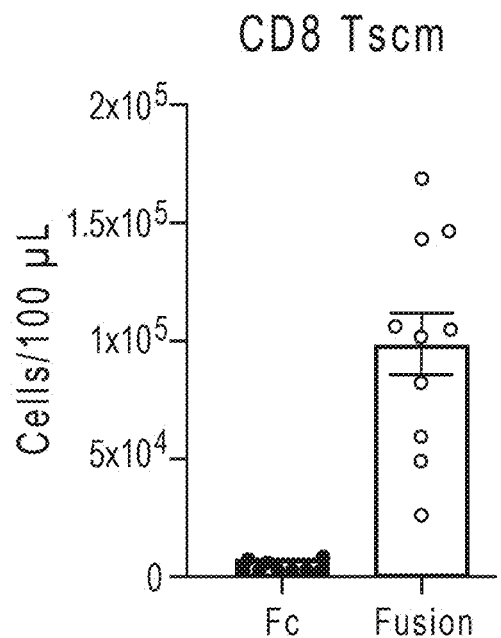
Figure 21C:
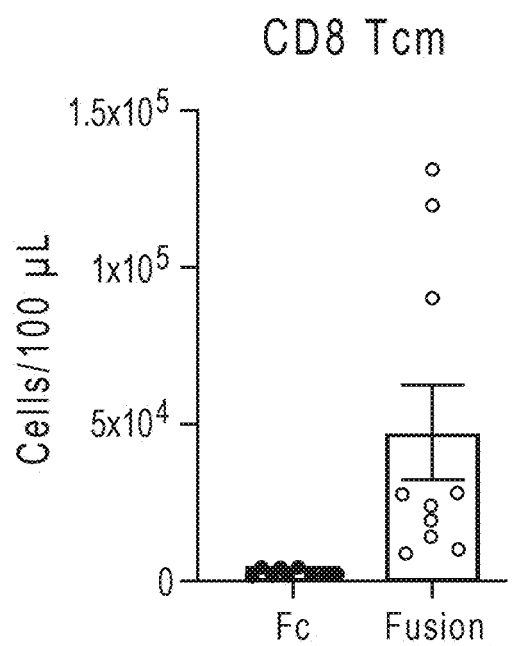
Figure 21D:
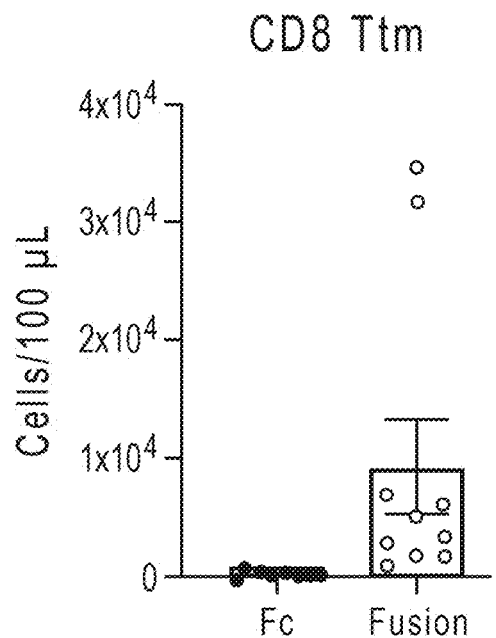
Figure 21E:
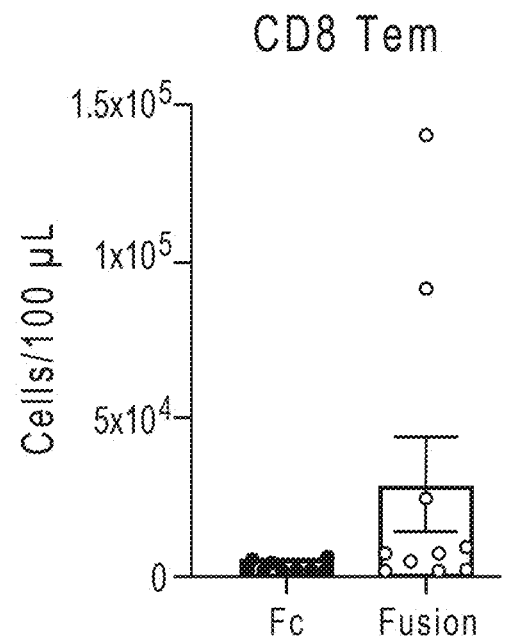
Figure 21F:
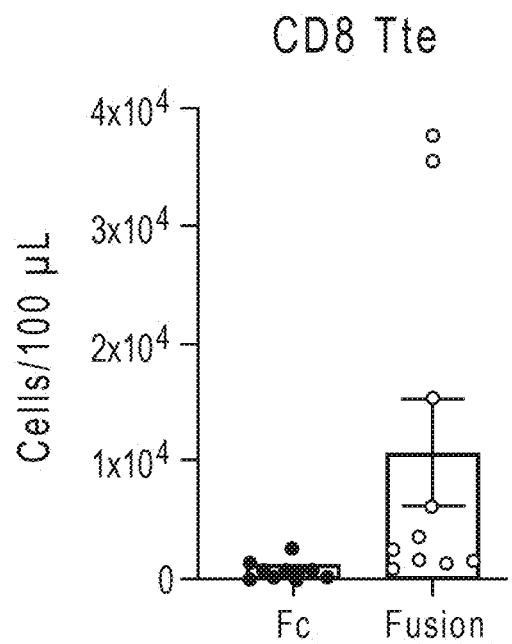
Figure 22A:
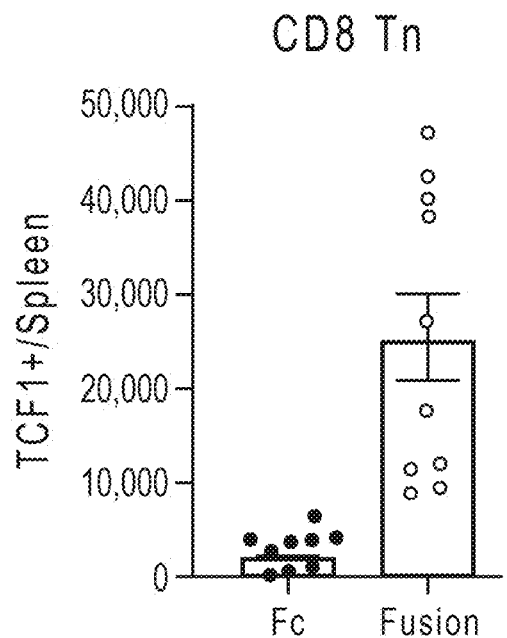
FIGS. 22A-22F show TCF1+ expression in memory cells in the spleen from humanized mice treated with either a control Fc fragment or the IL-7Rαγc IgG2-Fc fusion protein having SEQ ID NO: 45.
Figure 22B:
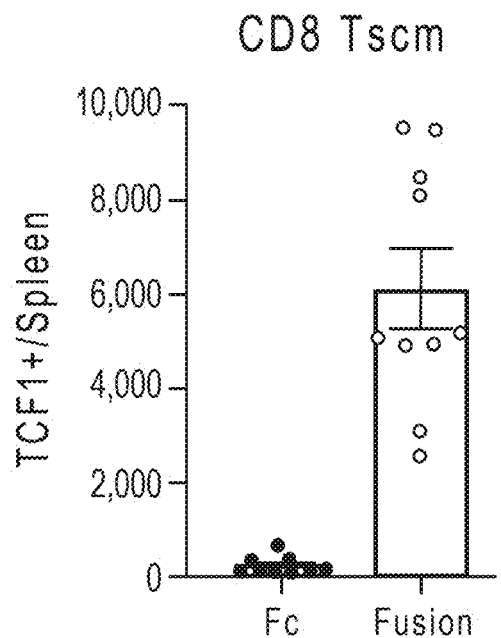
Figure 22C:
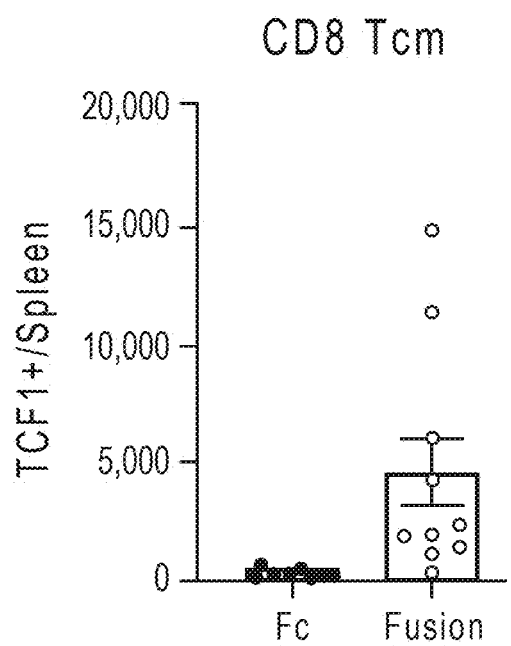
Figure 22D:
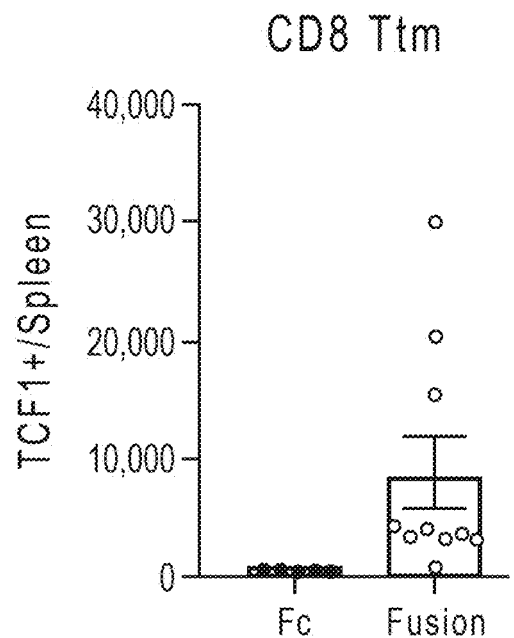
Figure 22E:
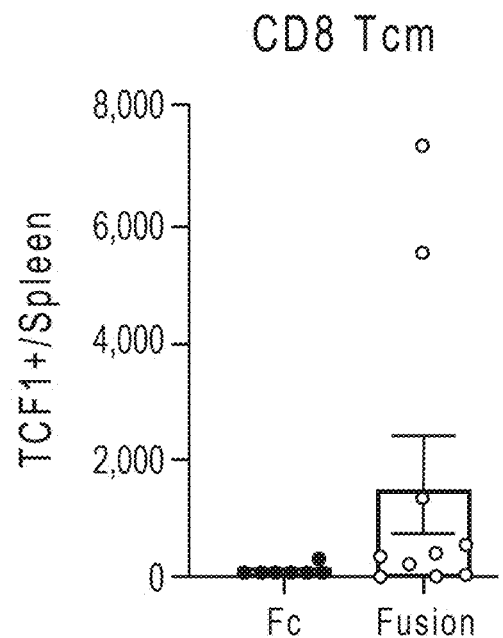
Figure 22F:
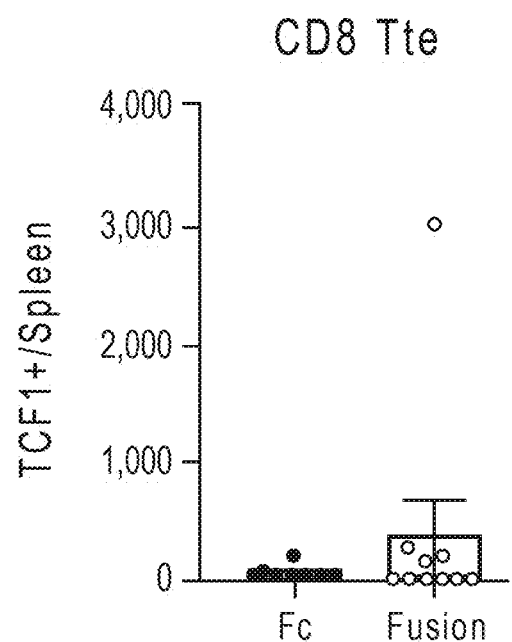

T-Cell Populations in Humanized Mice Treated with an IL-7Rαγc IgG2-Fc Fusion Protein NSG (NOD scid gamma) mice separately engrafted with human CD34+ cells from two donors were dosed once intravenously with 1 mg/kg hu-Fc or with 1 mg/kg of the IL-7Rαγc IgG2-Fc fusion protein having SEQ ID NO: 45. On day 7, peripheral blood was collected, processed and stained for the flow cytometry using a 12-color panel, followed by flow cytometry data acquisition and analysis to determine Ki-67+ cells in immune populations (FIGS. 18A-

18E). On day 12, terminal blood samples and spleens were collected for immune profiling (FIGS. 19A-19E). Markers used for memory T cell populations (FIGS. 20A-20E and FIGS. 21A-21E) are shown in Table 5. TCF1+ expression (FIGS. 22A-22E) of memory cells in spleen was also determined. Population gates were drawn based on FMO controls. Statistical analysis was done using Student's T-Test.

TABLE 5

Markers for memory T cell populations.

| Tn | CD45RA+ | CCR7+ | CD28+ | CD95− |
|---|---|---|---|---|
| Tscm | CD45RA+ | CCR7+ | CD28+ | CD95+ |
| Tcm | CD45RA− | CCR7+ | CD28+ | CD95+ |
| Ttm | CD45RA− | CCR7− | CD28+ | CD95+ |
| Tem | CD45RA− | CCR7− | CD28− | CD95+ |
| Tte | CD45RA+ | CCR7− | CD28− | CD95+ |

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

```
SEQUENCE LISTING

Sequence total quantity: 302
SEQ ID NO: 1             moltype = AA   length = 21
FEATURE                  Location/Qualifiers
source                   1..21
                         mol_type = protein
                         organism = synthetic construct
SEQUENCE: 1
WGIPWCTLDP GSLQCAWLGK H                                           21

SEQ ID NO: 2             moltype =      length =
SEQUENCE: 2
000

SEQ ID NO: 3             moltype =      length =
SEQUENCE: 3
000

SEQ ID NO: 4             moltype =      length =
SEQUENCE: 4
000

SEQ ID NO: 5             moltype =      length =
SEQUENCE: 5
000

SEQ ID NO: 6             moltype =      length =
SEQUENCE: 6
000

SEQ ID NO: 7             moltype =      length =
SEQUENCE: 7
000

SEQ ID NO: 8             moltype =      length =
SEQUENCE: 8
000

SEQ ID NO: 9             moltype =      length =
SEQUENCE: 9
000

SEQ ID NO: 10            moltype =      length =
SEQUENCE: 10
000

SEQ ID NO: 11            moltype = AA   length = 14
FEATURE                  Location/Qualifiers
source                   1..14
                         mol_type = protein
                         organism = synthetic construct
SEQUENCE: 11
VVCQDWEGVE LCWQ                                                   14

SEQ ID NO: 12            moltype =      length =
SEQUENCE: 12
000

SEQ ID NO: 13            moltype =      length =
SEQUENCE: 13
```

```
SEQ ID NO: 14            moltype =    length =
SEQUENCE: 14
000

SEQ ID NO: 15            moltype =    length =
SEQUENCE: 15
000

SEQ ID NO: 16            moltype =    length =
SEQUENCE: 16
000

SEQ ID NO: 17            moltype =    length =
SEQUENCE: 17
000

SEQ ID NO: 18            moltype =    length =
SEQUENCE: 18
000

SEQ ID NO: 19            moltype =    length =
SEQUENCE: 19
000

SEQ ID NO: 20            moltype =    length =
SEQUENCE: 20
000

SEQ ID NO: 21            moltype = AA   length = 135
FEATURE                  Location/Qualifiers
source                   1..135
                         mol_type = protein
                         organism = synthetic construct
VARIANT                  22..121
                         note = This region may encompass one of the following
                           sequences: (P)n where n is an integer from 1 to 20, (P)n
                           where n is an integer from 5 to 15, (PA)n where n is an
                           integer from 1 to 20, (PA)n where n is an integer from 5
                           to 15, (P)nG where n is an integer from 1 to 20, (P)nG
                           where n is an integer from 5 to 15, (PA)nG where n is an
                           integer from 1 to 20, (PA)nG where n is an integer from 5
                           to 15, (P)nGG where n is an integer from 1 to 20, (P)nGG
                           where n is an integer from 5 to 15, (PA)nGG where n is an
                           integer from 1 to 20, (PA)nGG where n is an integer from 5
                           to 15, (G)n where n is an integer from 1 to 20, (G)n where
                           n is an integer from 1 to 15, (GS)n where n is an integer
                           from 1 to 20, (GS)n where n is an integer from 1 to 15,
                           (GGS)n where n is an integer from 1 to 20, (GGS)n where n
                           is an integer from 1 to 15, (GGGS)n where n is an integer
                           from 1 to 20, (GGGS)n where n is an integer from 1 to 15,
VARIANT                  22..121
                         note = CONT. FROM ABOVE: (GGGGS)n where n is an integer
                           from 1 to 20,(GGGGS)n where n is an integer from 1 to
                           8,(GGGGS)n where n is an integer from 1 to 10, (GGGGS)n
                           where n is an integer from 1 to 5, GGGGS, GGGGSGGGGS,
                           GGGGSGGGGSGGGGS, GGGGSGGGGSGGGGSGGGGS,
                           GGGGSGGGGSGGGGSGGGGSGGGGS, (GGGGS)nG where n is an integer
                           from 1 to 10, (GGGGS)nG where n is an integer from 1 to 5,
                           GGGGSG, GGGGSGGGGSG, GGGGSGGGGSGGGGSG,
                           GGGGSGGGGSGGGGSGGGGSG, GGGGSGGGGSGGGGSGGGGSGGGGSG,
                           (GGGGS)nGG where n is an integer from 1 to 10, (GGGGS)nGG
                           where n is an integer from 1 to 5, GGGGSGG, GGGGSGGGGSGG,
                           GGGGSGGGGSGGGGSGG, GGGGSGGGGSGGGGSGGGGSGG, or
                           GGGGSGGGGSGGGGSGGGGSGGGGSGG
SEQUENCE: 21
WGIPWCTLDP GSLQCAWLGK HXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XVVCQDWEGV ELCWQ                                                    135

SEQ ID NO: 22            moltype = AA   length = 136
FEATURE                  Location/Qualifiers
source                   1..136
                         mol_type = protein
                         organism = synthetic construct
VARIANT                  23..122
                         note = This region may encompass one of the following
                           sequences: (P)n where n is an integer from 1 to 20, (P)n
```

|   | | |
|---|---|---|
| | | where n is an integer from 5 to 15, (PA)n where n is an integer from 1 to 20, (PA)n where n is an integer from 5 to 15, (P)nG where n is an integer from 1 to 20, (P)nG where n is an integer from 5 to 15, (PA)nG where n is an integer from 1 to 20, (PA)nG where n is an integer from 5 to 15, (P)nGG where n is an integer from 1 to 20, (P)nGG where n is an integer from 5 to 15, (PA)nGG where n is an integer from 1 to 20, (PA)nGG where n is an integer from 5 to 15, (G)n where n is an integer from 1 to 20, (G)n where n is an integer from 1 to 15, (GS)n where n is an integer from 1 to 20, (GS)n where n is an integer from 1 to 15, (GGS)n where n is an integer from 1 to 20, (GGS)n where n is an integer from 1 to 15, (GGGS)n where n is an integer from 1 to 20, (GGGS)n where n is an integer from 1 to 15, |
| VARIANT | 23..122 | |
| | note = CONT. FROM ABOVE: (GGGGS)n where n is an integer from 1 to 20,(GGGGS)n where n is an integer from 1 to 8,(GGGGS)n where n is an integer from 1 to 10, (GGGGS)n where n is an integer from 1 to 5, GGGGS, GGGGSGGGGS, GGGGSGGGGSGGGGS, GGGGSGGGGSGGGGSGGGGS, GGGGSGGGGSGGGGSGGGGSGGGGS, (GGGGS)nG where n is an integer from 1 to 10, (GGGGS)nG where n is an integer from 1 to 5, GGGGSG, GGGGSGGGGSG, GGGGSGGGGSGGGGSG, GGGGSGGGGSGGGGSGGGGSG, GGGGSGGGGSGGGGSGGGGSGGGGSG, (GGGGS)nGG where n is an integer from 1 to 10, (GGGGS)nGG where n is an integer from 1 to 5, GGGGSGG, GGGGSGGGGSGG, GGGGSGGGGSGGGGSGG, GGGGSGGGGSGGGGSGGGGSGG, or GGGGSGGGGSGGGGSGGGGSGGGGSGG | |

SEQUENCE: 22
GWGIPWCTLD PGSLQCAWLG KHXXXXXXXX XXXXXXXXXX XXXXXXXXXX XXXXXXXXXX 60
XXXXXXXXXX XXXXXXXXXX XXXXXXXXXX XXXXXXXXXX XXXXXXXXXX XXXXXXXXXX 120
XXVVCQDWEG VELCWQ 136

| SEQ ID NO: 23 | moltype = AA length = 137 |
|---|---|
| FEATURE | Location/Qualifiers |
| source | 1..137 |
| | mol_type = protein |
| | organism = synthetic construct |
| VARIANT | 22..121 |
| | note = This region may encompass one of the following sequences: (P)n where n is an integer from 1 to 20, (P)n where n is an integer from 5 to 15, (PA)n where n is an integer from 1 to 20, (PA)n where n is an integer from 5 to 15, (P)nG where n is an integer from 1 to 20, (P)nG where n is an integer from 5 to 15, (PA)nG where n is an integer from 1 to 20, (PA)nG where n is an integer from 5 to 15, (P)nGG where n is an integer from 1 to 20, (P)nGG where n is an integer from 5 to 15, (PA)nGG where n is an integer from 1 to 20, (PA)nGG where n is an integer from 5 to 15, (G)n where n is an integer from 1 to 20, (G)n where n is an integer from 1 to 15, (GS)n where n is an integer from 1 to 20, (GS)n where n is an integer from 1 to 15, (GGS)n where n is an integer from 1 to 20, (GGS)n where n is an integer from 1 to 15, (GGGS)n where n is an integer from 1 to 20, (GGGS)n where n is an integer from 1 to 15, |
| VARIANT | 22..121 |
| | note = CONT. FROM ABOVE: (GGGGS)n where n is an integer from 1 to 20,(GGGGS)n where n is an integer from 1 to 8,(GGGGS)n where n is an integer from 1 to 10, (GGGGS)n where n is an integer from 1 to 5, GGGGS, GGGGSGGGGS, GGGGSGGGGSGGGGS, GGGGSGGGGSGGGGSGGGGS, GGGGSGGGGSGGGGSGGGGSGGGGS, (GGGGS)nG where n is an integer from 1 to 10, (GGGGS)nG where n is an integer from 1 to 5, GGGGSG, GGGGSGGGGSG, GGGGSGGGGSGGGGSG, GGGGSGGGGSGGGGSGGGGSG, GGGGSGGGGSGGGGSGGGGSGGGGSG, (GGGGS)nGG where n is an integer from 1 to 10, (GGGGS)nGG where n is an integer from 1 to 5, GGGGSGG, GGGGSGGGGSGG, GGGGSGGGGSGGGGSGG, GGGGSGGGGSGGGGSGGGGSGG, or GGGGSGGGGSGGGGSGGGGSGGGGSGG |

SEQUENCE: 23
WGIPWCTLDP GSLQCAWLGK HXXXXXXXXX XXXXXXXXXX XXXXXXXXXX XXXXXXXXXX 60
XXXXXXXXXX XXXXXXXXXX XXXXXXXXXX XXXXXXXXXX XXXXXXXXXX XXXXXXXXXX 120
XVVCQDWEGV ELCWQGG 137

| SEQ ID NO: 24 | moltype = AA length = 138 |
|---|---|
| FEATURE | Location/Qualifiers |
| source | 1..138 |
| | mol_type = protein |
| | organism = synthetic construct |

| | |
|---|---|
| VARIANT | 23..122 |
| | note = This region may encompass one of the following sequences: (P)n where n is an integer from 1 to 20, (P)n where n is an integer from 5 to 15, (PA)n where n is an integer from 1 to 20, (PA)n where n is an integer from 5 to 15, (P)nG where n is an integer from 1 to 20, (P)nG where n is an integer from 5 to 15, (PA)nG where n is an integer from 1 to 20, (PA)nG where n is an integer from 5 to 15, (P)nGG where n is an integer from 1 to 20, (P)nGG where n is an integer from 5 to 15, (PA)nGG where n is an integer from 1 to 20, (PA)nGG where n is an integer from 5 to 15, (G)n where n is an integer from 1 to 20, (G)n where n is an integer from 1 to 15, (GS)n where n is an integer from 1 to 20, (GS)n where n is an integer from 1 to 15, (GGS)n where n is an integer from 1 to 20, (GGS)n where n is an integer from 1 to 15, (GGGS)n where n is an integer from 1 to 20, (GGGS)n where n is an integer from 1 to 15, |
| VARIANT | 23..122 |
| | note = CONT. FROM ABOVE: (GGGGS)n where n is an integer from 1 to 20,(GGGGS)n where n is an integer from 1 to 8,(GGGGS)n where n is an integer from 1 to 10, (GGGGS)n where n is an integer from 1 to 5, GGGGS, GGGGSGGGGS, GGGGSGGGGSGGGGS, GGGGSGGGGSGGGGSGGGGS, GGGGSGGGGSGGGGSGGGGSGGGGS, (GGGGS)nG where n is an integer from 1 to 10, (GGGGS)nG where n is an integer from 1 to 5, GGGGSG, GGGGSGGGGSG, GGGGSGGGGSGGGGSG, GGGGSGGGGSGGGGSGGGGSG, GGGGSGGGGSGGGGSGGGGSGGGGSG, (GGGGS)nGG where n is an integer from 1 to 10, (GGGGS)nGG where n is an integer from 1 to 5, GGGGSGG, GGGGSGGGGSGG, GGGGSGGGGSGGGGSGG, GGGGSGGGGSGGGGSGGGGSGG, or GGGGSGGGGSGGGGSGGGGSGGGGSGG |
| SEQUENCE: 24 | |

```
GWGIPWCTLD PGSLQCAWLG KHXXXXXXXX XXXXXXXXXX XXXXXXXXXX XXXXXXXXXX   60
XXXXXXXXXX XXXXXXXXXX XXXXXXXXXX XXXXXXXXXX XXXXXXXXXX XXXXXXXXXX  120
XXVVCQDWEG VELCWQGG                                                138
```

| | |
|---|---|
| SEQ ID NO: 25 | moltype = AA  length = 139 |
| FEATURE | Location/Qualifiers |
| source | 1..139 |
| | mol_type = protein |
| | organism = synthetic construct |
| VARIANT | 24..123 |
| | note = This region may encompass one of the following sequences: (P)n where n is an integer from 1 to 20, (P)n where n is an integer from 5 to 15, (PA)n where n is an integer from 1 to 20, (PA)n where n is an integer from 5 to 15, (P)nG where n is an integer from 1 to 20, (P)nG where n is an integer from 5 to 15, (PA)nG where n is an integer from 1 to 20, (PA)nG where n is an integer from 5 to 15, (P)nGG where n is an integer from 1 to 20, (P)nGG where n is an integer from 5 to 15, (PA)nGG where n is an integer from 1 to 20, (PA)nGG where n is an integer from 5 to 15, (G)n where n is an integer from 1 to 20, (G)n where n is an integer from 1 to 15, (GS)n where n is an integer from 1 to 20, (GS)n where n is an integer from 1 to 15, (GGS)n where n is an integer from 1 to 20, (GGS)n where n is an integer from 1 to 15, (GGGS)n where n is an integer from 1 to 20, (GGGS)n where n is an integer from 1 to 15, |
| VARIANT | 24..123 |
| | note = CONT. FROM ABOVE: (GGGGS)n where n is an integer from 1 to 20,(GGGGS)n where n is an integer from 1 to 8,(GGGGS)n where n is an integer from 1 to 10, (GGGGS)n where n is an integer from 1 to 5, GGGGS, GGGGSGGGGS, GGGGSGGGGSGGGGS, GGGGSGGGGSGGGGSGGGGS, GGGGSGGGGSGGGGSGGGGSGGGGS, (GGGGS)nG where n is an integer from 1 to 10, (GGGGS)nG where n is an integer from 1 to 5, GGGGSG, GGGGSGGGGSG, GGGGSGGGGSGGGGSG, GGGGSGGGGSGGGGSGGGGSG, GGGGSGGGGSGGGGSGGGGSGGGGSG, (GGGGS)nGG where n is an integer from 1 to 10, (GGGGS)nGG where n is an integer from 1 to 5, GGGGSGG, GGGGSGGGGSGG, GGGGSGGGGSGGGGSGG, GGGGSGGGGSGGGGSGGGGSGG, or GGGGSGGGGSGGGGSGGGGSGGGGSGG |
| SEQUENCE: 25 | |

```
GGWGIPWCTL DPGSLQCAWL GKHXXXXXXX XXXXXXXXXX XXXXXXXXXX XXXXXXXXXX   60
XXXXXXXXXX XXXXXXXXXX XXXXXXXXXX XXXXXXXXXX XXXXXXXXXX XXXXXXXXXX  120
XXXVVCQDWE GVELCWQGG                                               139
```

| | |
|---|---|
| SEQ ID NO: 26 | moltype = AA  length = 140 |
| FEATURE | Location/Qualifiers |

```
source                  1..140
                        mol_type = protein
                        organism = synthetic construct
VARIANT                 25..124
                        note = This region may encompass one of the following
                         sequences: (P)n where n is an integer from 1 to 20, (P)n
                         where n is an integer from 5 to 15, (PA)n where n is an
                         integer from 1 to 20, (PA)n where n is an integer from 5
                         to 15, (P)nG where n is an integer from 1 to 20, (P)nG
                         where n is an integer from 5 to 15, (PA)nG where n is an
                         integer from 1 to 20, (PA)nG where n is an integer from 5
                         to 15, (P)nGG where n is an integer from 1 to 20, (P)nGG
                         where n is an integer from 5 to 15, (PA)nGG where n is an
                         integer from 1 to 20, (PA)nGG where n is an integer from 5
                         to 15, (G)n where n is an integer from 1 to 20, (G)n where
                         n is an integer from 1 to 15, (GS)n where n is an integer
                         from 1 to 20, (GS)n where n is an integer from 1 to 15,
                         (GGS)n where n is an integer from 1 to 20, (GGS)n where
                         is an integer from 1 to 15, (GGGS)n where n is an integer
                         from 1 to 20, (GGGS)n where n is an integer from 1 to 15,
VARIANT                 25..124
                        note = CONT. FROM ABOVE: (GGGGS)n where n is an integer
                         from 1 to 20,(GGGGS)n where n is an integer from 1 to
                         8,(GGGGS)n where n is an integer from 1 to 10, (GGGGS)n
                         where n is an integer from 1 to 5, GGGGS, GGGGSGGGGS,
                         GGGGSGGGGSGGGGS, GGGGSGGGGSGGGGSGGGGS,
                         GGGGSGGGGSGGGGSGGGGSGGGGS, (GGGGS)nG where n is an integer
                         from 1 to 10, (GGGGS)nG where n is an integer from 1 to 5,
                         GGGGSG, GGGGSGGGGSG, GGGGSGGGGSGGGGSG,
                         GGGGSGGGGSGGGGSGGGGSG, GGGGSGGGGSGGGGSGGGGSGGGGSG,
                         (GGGGS)nGG where n is an integer from 1 to 10, (GGGGS)nGG
                         where n is an integer from 1 to 5, GGGGSGG, GGGGSGGGGSGG,
                         GGGGSGGGGSGGGGSGG, GGGGSGGGGSGGGGSGGGGSGG, or
                         GGGGSGGGGSGGGGSGGGGSGGGGSGG
SEQUENCE: 26
GGGWGIPWCT LDPGSLQCAW LGKHXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXVVCQDW EGVELCWQGG                                               140

SEQ ID NO: 27           moltype = AA  length = 42
FEATURE                 Location/Qualifiers
source                  1..42
                        mol_type = protein
                        organism = synthetic construct
SEQUENCE: 27
WGIPWCTLDP GSLQCAWLGK HGGGGSGGVV CQDWEGVELC WQ                        42

SEQ ID NO: 28           moltype = AA  length = 43
FEATURE                 Location/Qualifiers
source                  1..43
                        mol_type = protein
                        organism = synthetic construct
SEQUENCE: 28
GWGIPWCTLD PGSLQCAWLG KHGGGGSGGV VCQDWEGVEL CWQ                       43

SEQ ID NO: 29           moltype = AA  length = 44
FEATURE                 Location/Qualifiers
source                  1..44
                        mol_type = protein
                        organism = synthetic construct
SEQUENCE: 29
WGIPWCTLDP GSLQCAWLGK HGGGGSGGVV CQDWEGVELC WQGG                      44

SEQ ID NO: 30           moltype = AA  length = 45
FEATURE                 Location/Qualifiers
source                  1..45
                        mol_type = protein
                        organism = synthetic construct
SEQUENCE: 30
GWGIPWCTLD PGSLQCAWLG KHGGGGSGGV VCQDWEGVEL CWQGG                     45

SEQ ID NO: 31           moltype = AA  length = 46
FEATURE                 Location/Qualifiers
source                  1..46
                        mol_type = protein
                        organism = synthetic construct
SEQUENCE: 31
GGWGIPWCTL DPGSLQCAWL GKHGGGGSGG VVCQDWEGVE LCWQGG                    46
```

-continued

```
SEQ ID NO: 32             moltype = AA  length = 47
FEATURE                   Location/Qualifiers
source                    1..47
                          mol_type = protein
                          organism = synthetic construct
SEQUENCE: 32
GGGWGIPWCT LDPGSLQCAW LGKHGGGGSG GVVCQDWEGV ELCWQGG             47

SEQ ID NO: 33             moltype =   length =
SEQUENCE: 33
000

SEQ ID NO: 34             moltype =   length =
SEQUENCE: 34
000

SEQ ID NO: 35             moltype =   length =
SEQUENCE: 35
000

SEQ ID NO: 36             moltype =   length =
SEQUENCE: 36
000

SEQ ID NO: 37             moltype =   length =
SEQUENCE: 37
000

SEQ ID NO: 38             moltype =   length =
SEQUENCE: 38
000

SEQ ID NO: 39             moltype =   length =
SEQUENCE: 39
000

SEQ ID NO: 40             moltype =   length =
SEQUENCE: 40
000

SEQ ID NO: 41             moltype = AA  length = 227
FEATURE                   Location/Qualifiers
source                    1..227
                          mol_type = protein
                          organism = Homo sapiens
SEQUENCE: 41
DKTHTCPPCP APELLGGPSV FLFPPKPKDT LMISRTPEVT CVVVDVSHED PEVKFNWYVD   60
GVEVHNAKTK PREEQYASTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGA               227

SEQ ID NO: 42             moltype = AA  length = 228
FEATURE                   Location/Qualifiers
source                    1..228
                          mol_type = protein
                          organism = Homo sapiens
SEQUENCE: 42
ERKSSVECPP CPAPPVAGPS VFLFPPKPKD TLMISRTPEV TCVVVDVSHE DPEVQFNWYV   60
DGVEVHNAKT KPREEQFNST FRVVSVLTVV HQDWLNGKEY KCCKVSNKGLP APIEKTISKT  120
KGQPREPQVY TLPPSREEMT KNQVSLTCLV KGFYPSDIAV EWESNGQPEN NYKTTPPMLD  180
SDGSFFLYSK LTVDKSRWQQ GNVFSCSVMH EALHNHYTQK SLSLSPGA              228

SEQ ID NO: 43             moltype = AA  length = 227
FEATURE                   Location/Qualifiers
source                    1..227
                          mol_type = protein
                          organism = Homo sapiens
SEQUENCE: 43
APPCPPCPAP EFEGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLGSSI EKTISKAKGQ  120
PREPQVYTLP PSQEEMTKNQ VSLTCLVKGF YPSDIAVEWE SNGQPENNYK TTPPVLDSDG  180
SFFLYSRLTV DKSRWQEGNV FSCSVMHEAL HNHYTQKSLS LSLGART              227

SEQ ID NO: 44             moltype = AA  length = 294
FEATURE                   Location/Qualifiers
source                    1..294
                          mol_type = protein
                          organism = synthetic construct
SEQUENCE: 44
```

```
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGAGSG SGSGSGSGSG   240
SGSGSGSGGG WGIPWCTLDP GSLQCAWLGK HGGGGSGGVV CQDWEGVELC WQGG         294

SEQ ID NO: 45             moltype = AA  length = 295
FEATURE                   Location/Qualifiers
source                    1..295
                          mol_type = protein
                          organism = synthetic construct
SEQUENCE: 45
ERKSSVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP APIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGAGS GSGSGSGSGS   240
GSGSGSGSGG GWGIPWCTLD PGSLQCAWLG KHGGGGSGGV VCQDWEGVEL CWQGG         295

SEQ ID NO: 46             moltype = AA  length = 294
FEATURE                   Location/Qualifiers
source                    1..294
                          mol_type = protein
                          organism = synthetic construct
SEQUENCE: 46
APPCPPCPAP EFEGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLGSSI EKTISKAKGQ   120
PREPQVYTLP PSQEEMTKNQ VSLTCLVKGF YPSDIAVEWE SNGQPENNYK TTPPVLDSDG   180
SFFLYSRLTV DKSRWQEGNV FSCSVMHEAL HNHYTQKSLS LSLGARTGSG SGSGSGSGSG   240
SGSGSGSGGG WGIPWCTLDP GSLQCAWLGK HGGGGSGGVV CQDWEGVELC WQGG         294

SEQ ID NO: 47             moltype = AA  length = 376
FEATURE                   Location/Qualifiers
source                    1..376
                          mol_type = protein
                          organism = synthetic construct
VARIANT                   228..329
                          note = This region may encompass one of the following
                            sequences: (GS)n where n is an integer from 1 to 20,
                            (GS)nGG where n is an integer from 1 to 20, (GS)nGG where
                            n is an integer from 1 to 15, (GGS)nGG where n is an
                            integer from 1 to 20, (GGS)nGG where n is an integer from
                            1 to 15, (GGGS)nGG where n is an integer from 1 to 20,
                            (GGGS)nGG where n is an integer from 1 to 15, (GGGGS)nGG
                            where n is an integer from 1 to 20, (GGGGS)nGG where n is
                            an integer from 1 to 15, GSGSGSGSGS, GSGSGSGSGSGS,
                            GSGSGSGSGSGSGSGS, GSGSGSGSGSGSGSGS, GSGSGSGSGSGSGSGSGS,
                            GSGSGSGSGSGSGSGSGSGS, GSGSGSGSGSGSGSGSGSGSGS,
                            GSGSGSGSGSGSGSGSGSGSGSGS, GSGSGSGSGSGSGSGSGSGSGSGSGS,
                            GSGSGSGSGSGSGSGSGSGSGSGSGSGS,
                            GSGSGSGSGSGSGSGSGSGSGSGSGSGSGS, GSGSGSGSGSGGG,
                            GSGSGSGSGSGSGSGGG, GSGSGSGSGSGSGSGSGSGGG,
                            GSGSGSGSGSGSGSGSGSGSGGG, GSGSGSGSGSGSGSGSGSGSGSGGG,
                            GSGSGSGSGSGSGSGSGSGSGSGSGGG, GSGSGSGSGSGSGSGSGSGSGSGSGSGGG,
                            GSGSGSGSGSGSGSGSGSGSGSGSGSGSGGG,
VARIANT                   228..329
                          note = CONT. FROM ABOVE: GSGSGSGSGSGSGSGSGSGSGSGSGSGSGSGGG,
                            GSGSGSGSGSGSGSGSGSGSGSGSGSGSGSGSGGG, or (GS)n where n is an
                            integer from 5 to 15
SEQUENCE: 47
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGAXXX XXXXXXXXX    240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXG GGWGIPWCTL DPGSLQCAWL GKHGGGGSGG   360
VVCQDWEGVE LCWQGG                                                   376

SEQ ID NO: 48             moltype = AA  length = 377
FEATURE                   Location/Qualifiers
source                    1..377
                          mol_type = protein
                          organism = synthetic construct
VARIANT                   229..330
                          note = This region may encompass one of the following
                            sequences: (GS)n where n is an integer from 1 to 20,
                            (GS)nGG where n is an integer from 1 to 20, (GS)nGG where
                            n is an integer from 1 to 15, (GGS)nGG where n is an
                            integer from 1 to 20, (GGS)nGG where n is an integer from
                            1 to 15, (GGGS)nGG where n is an integer from 1 to 20,
```

|  |  |
|---|---|
| | (GGGS)nGG where n is an integer from 1 to 15, (GGGGS)nGG where n is an integer from 1 to 20, (GGGGS)nGG where n is an integer from 1 to 15, GSGSGSGSGS, GSGSGSGSGSGS, GSGSGSGSGSGSGS, GSGSGSGSGSGSGSGS, GSGSGSGSGSGSGSGSGS, GSGSGSGSGSGSGSGSGSGS, GSGSGSGSGSGSGSGSGSGSGS, GSGSGSGSGSGSGSGSGSGSGSGS, GSGSGSGSGSGSGSGSGSGSGSGSGS, GSGSGSGSGSGSGSGSGSGSGSGSGSGS, GSGSGSGSGSGSGSGSGSGSGSGSGSGSGS, GSGSGSGSGG, GSGSGSGSGSGSGG, GSGSGSGSGSGSGSGSGG, GSGSGSGSGSGSGSGSGSGSGG, GSGSGSGSGSGSGSGSGSGSGSGSGG, GSGSGSGSGSGSGSGSGSGSGSGSGSGSGG, GSGSGSGSGSGSGSGSGSGSGSGSGSGSGSGSGG, |
| VARIANT | 229..330<br>note = CONT. FROM ABOVE: GSGSGSGSGSGSGSGSGSGSGSGSGSGSGSGSGSGG, GSGSGSGSGSGSGSGSGSGSGSGSGSGSGSGSGSGSGG, or (GS)n where n is an integer from 5 to 15 |

SEQUENCE: 48

```
ERKSSVECPP CPAPPVAGPS VFLFPPKPKD TLMISRTPEV TCVVVDVSHE DPEVQFNWYV   60
DGVEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDIAV EWESNGQPEN NYKTTPPMLD  180
SDGSFFLYSK LTVDKSRWQQ GNVFSCSVMH EALHNHYTQK SLSLSPGAXX XXXXXXXXXX  240
XXXXXXXXXX XXXXXXXXXX XXXXXXXXXX XXXXXXXXXX XXXXXXXXXX XXXXXXXXXX  300
XXXXXXXXXX XXXXXXXXXX XXXXXXXXXX GGGWGIPWCT LDPGSLQCAW LGKHGGGGSG  360
GVVCQDWEGV ELCWQGG                                                377
```

| | |
|---|---|
| SEQ ID NO: 49 | moltype = AA  length = 376 |
| FEATURE | Location/Qualifiers |
| source | 1..376<br>mol_type = protein<br>organism = synthetic construct |
| VARIANT | 228..329<br>note = This region may encompass one of the following sequences: (GS)n where n is an integer from 1 to 20, (GS)nG where n is an integer from 1 to 20, (GS)nGG where n is an integer from 1 to 15, (GGS)nGG where n is an integer from 1 to 20, (GGS)nGG where n is an integer from 1 to 15, (GGGS)nGG where n is an integer from 1 to 20, (GGGS)nGG where n is an integer from 1 to 15, (GGGGS)nGG where n is an integer from 1 to 20, (GGGGS)nGG where n is an integer from 1 to 15, GSGSGSGSGS, GSGSGSGSGSGS, GSGSGSGSGSGSGS, GSGSGSGSGSGSGSGS, GSGSGSGSGSGSGSGSGS, GSGSGSGSGSGSGSGSGSGS, GSGSGSGSGSGSGSGSGSGSGS, GSGSGSGSGSGSGSGSGSGSGSGS, GSGSGSGSGSGSGSGSGSGSGSGSGS, GSGSGSGSGSGSGSGSGSGSGSGSGSGS, GSGSGSGSGSGSGSGSGSGSGSGSGSGSGS, GSGSGSGSGG, GSGSGSGSGSGSGG, GSGSGSGSGSGSGSGSGG, GSGSGSGSGSGSGSGSGSGSGG, GSGSGSGSGSGSGSGSGSGSGSGSGG, GSGSGSGSGSGSGSGSGSGSGSGSGSGSGG, GSGSGSGSGSGSGSGSGSGSGSGSGSGSGSGSGG, |
| VARIANT | 228..329<br>note = CONT. FROM ABOVE: GSGSGSGSGSGSGSGSGSGSGSGSGSGSGSGSGSGG, GSGSGSGSGSGSGSGSGSGSGSGSGSGSGSGSGSGSGG, or (GS)n where n is an integer from 5 to 15 |

SEQUENCE: 49

```
APPCPPCPAP EFEGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLGSSI EKTISKAKGQ  120
PREPQVYTLP PSQEEMTKNQ VSLTCLVKGF YPSDIAVEWE SNGQPENNYK TTPPVLDSDG  180
SFFLYSRLTV DKSRWQEGNV FSCSVMHEAL HNHYTQKSLS LSLGARTXXX XXXXXXXXXX  240
XXXXXXXXXX XXXXXXXXXX XXXXXXXXXX XXXXXXXXXX XXXXXXXXXX XXXXXXXXXX  300
XXXXXXXXXX XXXXXXXXXG GGWGIPWCTL DPGSLQCAWL GKHGGGGSGG             360
VVCQDWEGVE LCWQGG                                                 376
```

| | |
|---|---|
| SEQ ID NO: 50 | moltype = AA  length = 387 |
| FEATURE | Location/Qualifiers |
| source | 1..387<br>mol_type = protein<br>organism = synthetic construct |
| VARIANT | 272..371<br>note = This region may encompass one of the following sequences: (P)n where n is an integer from 1 to 20, (P)n where n is an integer from 5 to 15, (PA)n where n is an integer from 1 to 20, (PA)n where n is an integer from 5 to 15, (P)nG where n is an integer from 1 to 20, (P)nG where n is an integer from 5 to 15, (PA)nG where n is an integer from 1 to 20, (PA)nG where n is an integer from 5 to 15, (P)nGG where n is an integer from 1 to 20, (P)nGG where n is an integer from 5 to 15, (PA)nGG where n is an integer from 1 to 20, (PA)nGG where n is an integer from 5 to 15, (G)n where n is an integer from 1 to 20, (G)n where |

```
                              n is an integer from 1 to 15, (GS)n where n is an integer
                              from 1 to 20, (GS)n where n is an integer from 1 to 15,
                              (GGS)n where n is an integer from 1 to 20, (GGS)n where n
                              is an integer from 1 to 15, (GGGS)n where n is an integer
                              from 1 to 20, (GGGS)n where n is an integer from 1 to 15,
VARIANT                       272..371
                              note = CONT. FROM ABOVE: (GGGGS)n where n is an integer
                              from 1 to 20,(GGGGS)n where n is an integer from 1 to
                              8,(GGGGS)n where n is an integer from 1 to 10, (GGGGS)n
                              where n is an integer from 1 to 5, GGGGS, GGGGSGGGGS,
                              GGGGSGGGGSGGGGS, GGGGSGGGGSGGGGSGGGGS,
                              GGGGSGGGGSGGGGSGGGGSGGGGS, (GGGGS)nG where n is an integer
                              from 1 to 10, (GGGGS)nG where n is an integer from 1 to 5,
                              GGGGSG, GGGGSGGGGSG, GGGGSGGGGSGGGGSG,
                              GGGGSGGGGSGGGGSGGGGSG, GGGGSGGGGSGGGGSGGGGSGGGGSG,
                              (GGGGS)nGG where n is an integer from 1 to 10, (GGGGS)nGG
                              where n is an integer from 1 to 5, GGGGSGG, GGGGSGGGGSGG,
                              GGGGSGGGGSGGGGSGG, GGGGSGGGGSGGGGSGGGGSGG, or
                              GGGGSGGGGSGGGGSGGGGSGGGGSGG
SEQUENCE: 50
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGAGSG SGSGSGSGSG   240
SGSGSGSGGG WGIPWCTLDP GSLQCAWLGK HXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XVVCQDWEGV ELCWQGG                                       387

SEQ ID NO: 51             moltype = AA  length = 388
FEATURE                   Location/Qualifiers
source                    1..388
                          mol_type = protein
                          organism = synthetic construct
VARIANT                   273..372
                          note = This region may encompass one of the following
                          sequences: (P)n where n is an integer from 1 to 20, (P)n
                          where n is an integer from 5 to 15, (PA)n where n is an
                          integer from 1 to 20, (PA)n where n is an integer from 5
                          to 15, (P)nG where n is an integer from 1 to 20, (P)nG
                          where n is an integer from 5 to 15, (PA)nG where n is an
                          integer from 1 to 20, (PA)nG where n is an integer from 5
                          to 15, (P)nGG where n is an integer from 1 to 20, (P)nGG
                          where n is an integer from 5 to 15, (PA)nGG where n is an
                          integer from 1 to 20, (PA)nGG where n is an integer from 5
                          to 15, (G)n where n is an integer from 1 to 20, (G)n where
                          n is an integer from 1 to 15, (GS)n where n is an integer
                          from 1 to 20, (GS)n where n is an integer from 1 to 15,
                          (GGS)n where n is an integer from 1 to 20, (GGS)n where n
                          is an integer from 1 to 15, (GGGS)n where n is an integer
                          from 1 to 20, (GGGS)n where n is an integer from 1 to 15,
VARIANT                   273..372
                          note = CONT. FROM ABOVE: (GGGGS)n where n is an integer
                          from 1 to 20,(GGGGS)n where n is an integer from 1 to
                          8,(GGGGS)n where n is an integer from 1 to 10, (GGGGS)n
                          where n is an integer from 1 to 5, GGGGS, GGGGSGGGGS,
                          GGGGSGGGGSGGGGS, GGGGSGGGGSGGGGSGGGGS,
                          GGGGSGGGGSGGGGSGGGGSGGGGS, (GGGGS)nG where n is an integer
                          from 1 to 10, (GGGGS)nG where n is an integer from 1 to 5,
                          GGGGSG, GGGGSGGGGSG, GGGGSGGGGSGGGGSG,
                          GGGGSGGGGSGGGGSGGGGSG, GGGGSGGGGSGGGGSGGGGSGGGGSG,
                          (GGGGS)nGG where n is an integer from 1 to 10, (GGGGS)nGG
                          where n is an integer from 1 to 5, GGGGSGG, GGGGSGGGGSGG,
                          GGGGSGGGGSGGGGSGG, GGGGSGGGGSGGGGSGGGGSGG, or
                          GGGGSGGGGSGGGGSGGGGSGGGGSGG
SEQUENCE: 51
ERKSSVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP APIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGAGS GSGSGSGSGS   240
GSGSGSGSGG GWGIPWCTLD PGSLQCAWLG KHXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXVVCQDWEG VELCWQGG                                      388

SEQ ID NO: 52             moltype = AA  length = 387
FEATURE                   Location/Qualifiers
source                    1..387
                          mol_type = protein
                          organism = synthetic construct
VARIANT                   272..371
```

|  | |
|---|---|
| | note = This region may encompass one of the following<br>sequences: (P)n where n is an integer from 1 to 20, (P)n<br>where n is an integer from 5 to 15, (PA)n where n is an<br>integer from 1 to 20, (PA)n where n is an integer from 5<br>to 15, (P)nG where n is an integer from 1 to 20, (P)nG<br>where n is an integer from 5 to 15, (PA)nG where n is an<br>integer from 1 to 20, (PA)nG where n is an integer from 5<br>to 15, (P)nGG where n is an integer from 1 to 20, (P)nGG<br>where n is an integer from 5 to 15, (PA)nGG where n is an<br>integer from 1 to 20, (PA)nGG where n is an integer from 5<br>to 15, (G)n where n is an integer from 1 to 20, (G)n where<br>n is an integer from 1 to 15, (GS)n where n is an integer<br>from 1 to 20, (GS)n where n is an integer from 1 to 15,<br>(GGS)n where n is an integer from 1 to 20, (GGS)n where n<br>is an integer from 1 to 15, (GGGS)n where n is an integer<br>from 1 to 20, (GGGS)n where n is an integer from 1 to 15, |
| VARIANT | 272..371<br>note = CONT. FROM ABOVE: (GGGGS)n where n is an integer<br>from 1 to 20,(GGGGS)n where n is an integer from 1 to<br>8,(GGGGS)n where n is an integer from 1 to 10, (GGGGS)n<br>where n is an integer from 1 to 5, GGGGS, GGGGSGGGGS,<br>GGGGSGGGGSGGGGS, GGGGSGGGGSGGGGSGGGGS,<br>GGGGSGGGGSGGGGSGGGGSGGGGS, (GGGGS)nG where n is an integer<br>from 1 to 10, (GGGGS)nG where n is an integer from 1 to 5,<br>GGGGSG, GGGGSGGGGSG, GGGGSGGGGSGGGGSG,<br>GGGGSGGGGSGGGGSGGGGSG, GGGGSGGGGSGGGGSGGGGSGGGGSG,<br>(GGGGS)nGG where n is an integer from 1 to 10, (GGGGS)nGG<br>where n is an integer from 1 to 5, GGGGSGG, GGGGSGGGGSGG,<br>GGGGSGGGGSGGGGSGG, GGGGSGGGGSGGGGSGGGGSGG, or<br>GGGGSGGGGSGGGGSGGGGSGGGGSGG |

```
SEQUENCE: 52
APPCPPCPAP EFEGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLGSSI EKTISKAKGQ 120
PREPQVYTLP PSQEEMTKNQ VSLTCLVKGF YPSDIAVEWE SNGQPENNYK TTPPVLDSDG 180
SFFLYSRLTV DKSRWQEGNV FSCSVMHEAL HNHYTQKSLS LSLGARTGSG SGSGSGSGSG 240
SGSGSGSGGG WGIPWCTLDP GSLQCAWLGK HXXXXXXXXX XXXXXXXXXX XXXXXXXXXX 300
XXXXXXXXXX XXXXXXXXXX XXXXXXXXXX XXXXXXXXXX XXXXXXXXXX XXXXXXXXXX 360
XXXXXXXXXX XVVCQDWEGV ELCWQGG                                   387
```

|  | |
|---|---|
| SEQ ID NO: 53<br>FEATURE<br>source | moltype = AA length = 469<br>Location/Qualifiers<br>1..469<br>mol_type = protein<br>organism = synthetic construct |
| VARIANT | 228..329<br>note = This region may encompass one of the following<br>sequences: (GS)n where n is an integer from 1 to 20,<br>(GS)nGG where n is an integer from 1 to 20, (GS)nGG where<br>n is an integer from 1 to 15, (GGS)nGG where n is an<br>integer from 1 to 20, (GGS)nGG where n is an integer from<br>1 to 15, (GGGS)nGG where n is an integer from 1 to 20,<br>(GGGS)nGG where n is an integer from 1 to 15, (GGGGS)nGG<br>where n is an integer from 1 to 20, (GGGGS)nGG where n is<br>an integer from 1 to 15, GSGSGSGSGS, GSGSGSGSGSGSGS,<br>GSGSGSGSGSGSGSGS, GSGSGSGSGSGSGSGSGS,<br>GSGSGSGSGSGSGSGSGSGS, GSGSGSGSGSGSGSGSGSGSGS,<br>GSGSGSGSGSGSGSGSGSGSGSGS, GSGSGSGSGSGSGSGSGSGSGSGSGS,<br>GSGSGSGSGSGSGSGSGSGSGSGSGSGS,<br>GSGSGSGSGSGSGSGSGSGSGSGSGSGSGS, GSGSGSGSGSGG,<br>GSGSGSGSGSGSGG, GSGSGSGSGSGSGSGG, GSGSGSGSGSGSGSGSGG,<br>GSGSGSGSGSGSGSGSGSGG, GSGSGSGSGSGSGSGSGSGSGG,<br>GSGSGSGSGSGSGSGSGSGSGSGG, GSGSGSGSGSGSGSGSGSGSGSGSGG,<br>GSGSGSGSGSGSGSGSGSGSGSGSGSGG, |
| VARIANT | 228..329<br>note = CONT. FROM ABOVE: GSGSGSGSGSGSGSGSGSGSGSGSGSGSGG,<br>GSGSGSGSGSGSGSGSGSGSGSGSGSGSGSGG, or (GS)n where n is an<br>integer from 5 to 15 |
| VARIANT | 354..453<br>note = This region may encompass one of the following<br>sequences: (P)n where n is an integer from 1 to 20, (P)n<br>where n is an integer from 5 to 15, (PA)n where n is an<br>integer from 1 to 20, (PA)n where n is an integer from 5<br>to 15, (P)nG where n is an integer from 1 to 20, (P)nG<br>where n is an integer from 5 to 15, (PA)nG where n is an<br>integer from 1 to 20, (PA)nG where n is an integer from 5<br>to 15, (P)nGG where n is an integer from 1 to 20, (P)nGG<br>where n is an integer from 5 to 15, (PA)nGG where n is an<br>integer from 1 to 20, (PA)nGG where n is an integer from 5<br>to 15, (G)n where n is an integer from 1 to 20, (G)n where |

| | |
|---|---|
| VARIANT | 354..453<br>note = CONT. FROM ABOVE: (GGGGS)n where n is an integer from 1 to 20,(GGGGS)n where n is an integer from 1 to 8,(GGGGS)n where n is an integer from 1 to 10, (GGGGS)n where n is an integer from 1 to 5, GGGGS, GGGGSGGGGS, GGGGSGGGGSGGGGS, GGGGSGGGGSGGGGSGGGGS, GGGGSGGGGSGGGGSGGGGSGGGGS, (GGGGS)nG where n is an integer from 1 to 10, (GGGGS)nG where n is an integer from 1 to 5, GGGGSG, GGGGSGGGGSG, GGGGSGGGGSGGGGSG, GGGGSGGGGSGGGGSGGGGSG, GGGGSGGGGSGGGGSGGGGSGGGGSG, (GGGGS)nGG where n is an integer from 1 to 10, (GGGGS)nGG where n is an integer from 1 to 5, GGGGSGG, GGGGSGGGGSGG, GGGGSGGGGSGGGGSGG, GGGGSGGGGSGGGGSGGGGSGG, or GGGGSGGGGSGGGGSGGGGSGGGGSGG |

```
SEQUENCE: 53
DKTHTCPPCP APELLGGPSV FLFPPKPKDT LMISRTPEVT CVVVDVSHED PEVKFNWYVD   60
GVEVHNAKTK PREEQYASTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGAXXX XXXXXXXXXX  240
XXXXXXXXXX XXXXXXXXXX XXXXXXXXXX XXXXXXXXXX XXXXXXXXXX XXXXXXXXXX  300
XXXXXXXXXX XXXXXXXXXX XXXXXXXXG GGWGIPWCTL DPGSLQCAWL GKHXXXXXXX  360
XXXXXXXXXX XXXXXXXXXX XXXXXXXXXX XXXXXXXXXX XXXXXXXXXX XXXXXXXXXX  420
XXXXXXXXXX XXXXXXXXXX XXXXXXXXXX XXXVVCQDWE GVELCWQGG             469
```

| | |
|---|---|
| SEQ ID NO: 54<br>FEATURE<br>source<br><br><br>VARIANT | moltype = AA  length = 471<br>Location/Qualifiers<br>1..471<br>mol_type = protein<br>organism = synthetic construct<br>230..331<br>note = This region may encompass one of the following sequences: (GS)n where n is an integer from 1 to 20, (GS)nGG where n is an integer from 1 to 20, (GS)nGG where n is an integer from 1 to 15, (GGS)nGG where n is an integer from 1 to 20, (GGS)nGG where n is an integer from 1 to 15, (GGGS)nGG where n is an integer from 1 to 20, (GGGS)nGG where n is an integer from 1 to 15, (GGGGS)nGG where n is an integer from 1 to 20, (GGGGS)nGG where n is an integer from 1 to 15, GSGSGSGSGS, GSGSGSGSGSGS, GSGSGSGSGSGSGS, GSGSGSGSGSGSGSGS, GSGSGSGSGSGSGSGSGS, GSGSGSGSGSGSGSGSGSGS, GSGSGSGSGSGSGSGSGSGSGS, GSGSGSGSGSGSGSGSGSGSGSGS, GSGSGSGSGSGSGSGSGSGSGSGSGS, GSGSGSGSGSGSGSGSGSGSGSGSGSGS, GSGSGSGSGSGSGSGSGSGSGSGSGSGSGS, GSGSGSGSGSGSGG, GSGSGSGSGSGSGSGG, GSGSGSGSGSGSGSGSGG, GSGSGSGSGSGSGSGSGSGG, GSGSGSGSGSGSGSGSGSGSGG, GSGSGSGSGSGSGSGSGSGSGSGG, GSGSGSGSGSGSGSGSGSGSGSGSGG, GSGSGSGSGSGSGSGSGSGSGSGSGSGG, |
| VARIANT | 230..331<br>note = CONT. FROM ABOVE: GSGSGSGSGSGSGSGSGSGSGSGSGSGSGG, GSGSGSGSGSGSGSGSGSGSGSGSGSGSGSGG, or (GS)n where n is an integer from 5 to 15 |
| VARIANT | 356..455<br>note = This region may encompass one of the following sequences: (P)n where n is an integer from 1 to 20, (P)n where n is an integer from 5 to 15, (PA)n where n is an integer from 1 to 20, (PA)n where n is an integer from 5 to 15, (P)nG where n is an integer from 1 to 20, (P)nG where n is an integer from 5 to 15, (PA)nG where n is an integer from 1 to 20, (PA)nG where n is an integer from 5 to 15, (P)nGG where n is an integer from 1 to 20, (P)nGG where n is an integer from 5 to 15, (PA)nGG where n is an integer from 1 to 20, (PA)nGG where n is an integer from 5 to 15, (G)n where n is an integer from 1 to 20, (G)n where n is an integer from 1 to 15, (GS)n where n is an integer from 1 to 20, (GS)n where n is an integer from 1 to 15, (GGS)n where n is an integer from 1 to 20, (GGS)n where n is an integer from 1 to 15, (GGGS)n where n is an integer from 1 to 20, (GGGS)n where n is an integer from 1 to 15, |
| VARIANT | 356..455<br>note = CONT. FROM ABOVE: (GGGGS)n where n is an integer from 1 to 20,(GGGGS)n where n is an integer from 1 to 8,(GGGGS)n where n is an integer from 1 to 10, (GGGGS)n where n is an integer from 1 to 5, GGGGS, GGGGSGGGGS, |

```
                        GGGGSGGGGSGGGGS, GGGGSGGGGSGGGGSGGGGS,
                        GGGGSGGGGSGGGGSGGGGSGGGGS, (GGGGS)nG where n is an integer
                        from 1 to 10, (GGGGS)nG where n is an integer from 1 to 5,
                        GGGGSG, GGGGSGGGGSG, GGGGSGGGGSGGGGSG,
                        GGGGSGGGGSGGGGSGGGGSG, GGGGSGGGGSGGGGSGGGGSGGGGSG,
                        (GGGGS)nGG where n is an integer from 1 to 10, (GGGGS)nGG
                        where n is an integer from 1 to 5, GGGGSGG, GGGGSGGGGSGG,
                        GGGGSGGGGSGGGGSGG, GGGGSGGGGSGGGGSGGGGSGG, or
                        GGGGSGGGGSGGGGSGGGGSGGGGSGG
SEQUENCE: 54
ERKSSVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP APIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPAGAX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XGGGWGIPWC TLDPGSLQCA WLGKHXXXXX   360
XXXXXXXXXX XXXXXXXXXX XXXXXXXXXX XXXXXXXXXX XXXXXXXXXX XXXXXXXXX   420
XXXXXXXXXX XXXXXXXXXX XXXXXXXXXX XXXXXVVCQD WEGVELCWQG G           471

SEQ ID NO: 55           moltype = AA  length = 469
FEATURE                 Location/Qualifiers
source                  1..469
                        mol_type = protein
                        organism = synthetic construct
VARIANT                 228..329
                        note = This region may encompass one of the following
                        sequences: (GS)n where n is an integer from 1 to 20,
                        (GS)nGG where n is an integer from 1 to 20, (GS)nGG where
                        n is an integer from 1 to 15, (GGS)nGG where n is an
                        integer from 1 to 20, (GGS)nGG where n is an integer from
                        1 to 15, (GGGS)nGG where n is an integer from 1 to 20,
                        (GGGS)nGG where n is an integer from 1 to 15, (GGGGS)nGG
                        where n is an integer from 1 to 20, (GGGGS)nGG where n is
                        an integer from 1 to 15, GSGSGSGSGS, GSGSGSGSGSGS,
                        GSGSGSGSGSGSGS, GSGSGSGSGSGSGSGS, GSGSGSGSGSGSGSGSGS,
                        GSGSGSGSGSGSGSGSGSGS, GSGSGSGSGSGSGSGSGSGSGS,
                        GSGSGSGSGSGSGSGSGSGSGSGS, GSGSGSGSGSGSGSGSGSGSGSGSGS,
                        GSGSGSGSGSGSGSGSGSGSGSGSGSGS,
                        GSGSGSGSGSGSGSGSGSGSGSGSGSGSGS, GSGSGSGSGSGG,
                        GSGSGSGSGSGSGG, GSGSGSGSGSGSGSGG, GSGSGSGSGSGSGSGSGG,
                        GSGSGSGSGSGSGSGSGSGG, GSGSGSGSGSGSGSGSGSGSGG,
                        GSGSGSGSGSGSGSGSGSGSGSGG, GSGSGSGSGSGSGSGSGSGSGSGSGG,
                        GSGSGSGSGSGSGSGSGSGSGSGSGSGG,
VARIANT                 228..329
                        note = CONT. FROM ABOVE: GSGSGSGSGSGSGSGSGSGSGSGSGSGSGG,
                        GSGSGSGSGSGSGSGSGSGSGSGSGSGSGSGG, or (GS)n where n is an
                        integer from 5 to 15
VARIANT                 354..453
                        note = This region may encompass one of the following
                        sequences: (P)n where n is an integer from 1 to 20, (P)n
                        where n is an integer from 5 to 15, (PA)n where n is an
                        integer from 1 to 20, (PA)n where n is an integer from 5
                        to 15, (P)nG where n is an integer from 1 to 20, (P)nG
                        where n is an integer from 5 to 15, (PA)nG where n is an
                        integer from 1 to 20, (PA)nG where n is an integer from 5
                        to 15, (P)nGG where n is an integer from 1 to 20, (P)nGG
                        where n is an integer from 5 to 15, (PA)nGG where n is an
                        integer from 1 to 20, (PA)nGG where n is an integer from 5
                        to 15, (G)n where n is an integer from 1 to 20, (G)n where
                        n is an integer from 1 to 15, (GS)n where n is an integer
                        from 1 to 20, (GS)n where n is an integer from 1 to 15,
                        (GGS)n where n is an integer from 1 to 20, (GGS)n where n
                        is an integer from 1 to 15, (GGGS)n where n is an integer
                        from 1 to 20, (GGGS)n where n is an integer from 1 to 15,
VARIANT                 354..453
                        note = CONT. FROM ABOVE: (GGGGS)n where n is an integer
                        from 1 to 20,(GGGGS)n where n is an integer from 1 to
                        8,(GGGGS)n where n is an integer from 1 to 10, (GGGGS)n
                        where n is an integer from 1 to 5, GGGGS, GGGGSGGGGS,
                        GGGGSGGGGSGGGGS, GGGGSGGGGSGGGGSGGGGS,
                        GGGGSGGGGSGGGGSGGGGSGGGGS, (GGGGS)nG where n is an integer
                        from 1 to 10, (GGGGS)nG where n is an integer from 1 to 5,
                        GGGGSG, GGGGSGGGGSG, GGGGSGGGGSGGGGSG,
                        GGGGSGGGGSGGGGSGGGGSG, GGGGSGGGGSGGGGSGGGGSGGGGSG,
                        (GGGGS)nGG where n is an integer from 1 to 10, (GGGGS)nGG
                        where n is an integer from 1 to 5, GGGGSGG, GGGGSGGGGSGG,
                        GGGGSGGGGSGGGGSGG, GGGGSGGGGSGGGGSGGGGSGG, or
                        GGGGSGGGGSGGGGSGGGGSGGGGSGG
SEQUENCE: 55
```

```
APPCPPCPAP EFEGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLGSSI EKTISKAKGQ   120
PREPQVYTLP PSQEEMTKNQ VSLTCLVKGF YPSDIAVEWE SNGQPENNYK TTPPVLDSDG   180
SFFLYSRLTV DKSRWQEGNV FSCSVMHEAL HNHYTQKSLS LSLGARTXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXG GGWGIPWCTL DPGSLQCAWL GKHXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXVVCQDWE GVELCWQGG              469

SEQ ID NO: 56          moltype =    length =
SEQUENCE: 56
000

SEQ ID NO: 57          moltype =    length =
SEQUENCE: 57
000

SEQ ID NO: 58          moltype =    length =
SEQUENCE: 58
000

SEQ ID NO: 59          moltype =    length =
SEQUENCE: 59
000

SEQ ID NO: 60          moltype =    length =
SEQUENCE: 60
000

SEQ ID NO: 61          moltype =    length =
SEQUENCE: 61
000

SEQ ID NO: 62          moltype =    length =
SEQUENCE: 62
000

SEQ ID NO: 63          moltype =    length =
SEQUENCE: 63
000

SEQ ID NO: 64          moltype =    length =
SEQUENCE: 64
000

SEQ ID NO: 65          moltype =    length =
SEQUENCE: 65
000

SEQ ID NO: 66          moltype =    length =
SEQUENCE: 66
000

SEQ ID NO: 67          moltype =    length =
SEQUENCE: 67
000

SEQ ID NO: 68          moltype =    length =
SEQUENCE: 68
000

SEQ ID NO: 69          moltype =    length =
SEQUENCE: 69
000

SEQ ID NO: 70          moltype =    length =
SEQUENCE: 70
000

SEQ ID NO: 71          moltype =    length =
SEQUENCE: 71
000

SEQ ID NO: 72          moltype =    length =
SEQUENCE: 72
000

SEQ ID NO: 73          moltype =    length =
SEQUENCE: 73
```

000

SEQ ID NO: 74          moltype =     length =
SEQUENCE: 74
000

SEQ ID NO: 75          moltype =     length =
SEQUENCE: 75
000

SEQ ID NO: 76          moltype =     length =
SEQUENCE: 76
000

SEQ ID NO: 77          moltype =     length =
SEQUENCE: 77
000

SEQ ID NO: 78          moltype =     length =
SEQUENCE: 78
000

SEQ ID NO: 79          moltype =     length =
SEQUENCE: 79
000

SEQ ID NO: 80          moltype =     length =
SEQUENCE: 80
000

SEQ ID NO: 81          moltype =     length =
SEQUENCE: 81
000

SEQ ID NO: 82          moltype =     length =
SEQUENCE: 82
000

SEQ ID NO: 83          moltype =     length =
SEQUENCE: 83
000

SEQ ID NO: 84          moltype =     length =
SEQUENCE: 84
000

SEQ ID NO: 85          moltype =     length =
SEQUENCE: 85
000

SEQ ID NO: 86          moltype =     length =
SEQUENCE: 86
000

SEQ ID NO: 87          moltype =     length =
SEQUENCE: 87
000

SEQ ID NO: 88          moltype =     length =
SEQUENCE: 88
000

SEQ ID NO: 89          moltype =     length =
SEQUENCE: 89
000

SEQ ID NO: 90          moltype =     length =
SEQUENCE: 90
000

SEQ ID NO: 91          moltype =     length =
SEQUENCE: 91
000

SEQ ID NO: 92          moltype =     length =
SEQUENCE: 92
000

SEQ ID NO: 93          moltype =     length =

```
SEQUENCE: 93
000

SEQ ID NO: 94          moltype =   length =
SEQUENCE: 94
000

SEQ ID NO: 95          moltype =   length =
SEQUENCE: 95
000

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype =   length =
SEQUENCE: 99
000

SEQ ID NO: 100         moltype =   length =
SEQUENCE: 100
000

SEQ ID NO: 101         moltype = AA  length = 20
FEATURE                Location/Qualifiers
source                 1..20
                       mol_type = protein
                       organism = synthetic construct
VARIANT                1..20
                       note = This sequence may encompass 1-20 residues
SEQUENCE: 101
PPPPPPPPPP PPPPPPPPPP                                                   20

SEQ ID NO: 102         moltype = AA  length = 15
FEATURE                Location/Qualifiers
source                 1..15
                       mol_type = protein
                       organism = synthetic construct
VARIANT                1..15
                       note = This sequence may encompass 5-15 residues
SEQUENCE: 102
PPPPPPPPPP PPPPP                                                        15

SEQ ID NO: 103         moltype = AA  length = 40
FEATURE                Location/Qualifiers
source                 1..40
                       mol_type = protein
                       organism = synthetic construct
VARIANT                1..40
                       note = This sequence may encompass 1-20 PA repeating units
SEQUENCE: 103
PAPAPAPAPA PAPAPAPAPA PAPAPAPAPA PAPAPAPAPA                             40

SEQ ID NO: 104         moltype = AA  length = 30
FEATURE                Location/Qualifiers
source                 1..30
                       mol_type = protein
                       organism = synthetic construct
VARIANT                1..30
                       note = This sequence may encompass 5-15 PA repeating units
SEQUENCE: 104
PAPAPAPAPA PAPAPAPAPA PAPAPAPAPA                                        30

SEQ ID NO: 105         moltype = AA  length = 21
FEATURE                Location/Qualifiers
source                 1..21
                       mol_type = protein
                       organism = synthetic construct
VARIANT                1..20
                       note = This region may encompass 1-20 residues
SEQUENCE: 105
```

```
PPPPPPPPPP PPPPPPPPPP G                                               21

SEQ ID NO: 106          moltype = AA  length = 16
FEATURE                 Location/Qualifiers
source                  1..16
                        mol_type = protein
                        organism = synthetic construct
VARIANT                 1..15
                        note = This region may encompass 5-15 residues
SEQUENCE: 106
PPPPPPPPPP PPPPPG                                                     16

SEQ ID NO: 107          moltype = AA  length = 41
FEATURE                 Location/Qualifiers
source                  1..41
                        mol_type = protein
                        organism = synthetic construct
VARIANT                 1..40
                        note = This region may encompass 1-20 PA repeating units
SEQUENCE: 107
PAPAPAPAPA PAPAPAPAPA PAPAPAPAPA PAPAPAPAPA G                         41

SEQ ID NO: 108          moltype = AA  length = 31
FEATURE                 Location/Qualifiers
source                  1..31
                        mol_type = protein
                        organism = synthetic construct
VARIANT                 1..30
                        note = This region may encompass 5-15 PA repeating units
SEQUENCE: 108
PAPAPAPAPA PAPAPAPAPA PAPAPAPAPA G                                    31

SEQ ID NO: 109          moltype = AA  length = 22
FEATURE                 Location/Qualifiers
source                  1..22
                        mol_type = protein
                        organism = synthetic construct
VARIANT                 1..20
                        note = This region may encompass 1-20 residues
SEQUENCE: 109
PPPPPPPPPP PPPPPPPPPP GG                                              22

SEQ ID NO: 110          moltype = AA  length = 17
FEATURE                 Location/Qualifiers
source                  1..17
                        mol_type = protein
                        organism = synthetic construct
VARIANT                 1..15
                        note = This region may encompass 5-15 residues
SEQUENCE: 110
PPPPPPPPPP PPPPPGG                                                    17

SEQ ID NO: 111          moltype = AA  length = 42
FEATURE                 Location/Qualifiers
source                  1..42
                        mol_type = protein
                        organism = synthetic construct
VARIANT                 1..40
                        note = This region may encompass 1-20 PA repeating units
SEQUENCE: 111
PAPAPAPAPA PAPAPAPAPA PAPAPAPAPA PAPAPAPAPA GG                        42

SEQ ID NO: 112          moltype = AA  length = 32
FEATURE                 Location/Qualifiers
source                  1..32
                        mol_type = protein
                        organism = synthetic construct
VARIANT                 1..30
                        note = This region may encompass 5-15 PA repeating units
SEQUENCE: 112
PAPAPAPAPA PAPAPAPAPA PAPAPAPAPA GG                                   32

SEQ ID NO: 113          moltype = AA  length = 20
FEATURE                 Location/Qualifiers
source                  1..20
                        mol_type = protein
                        organism = synthetic construct
VARIANT                 1..20
                        note = This sequence may encompass 1-20 residues
```

```
SEQUENCE: 113
GGGGGGGGGG GGGGGGGGGG                                                   20

SEQ ID NO: 114          moltype = AA  length = 15
FEATURE                 Location/Qualifiers
source                  1..15
                        mol_type = protein
                        organism = synthetic construct
VARIANT                 1..15
                        note = This sequence may encompass 1-15 residues
SEQUENCE: 114
GGGGGGGGGG GGGGG                                                        15

SEQ ID NO: 115          moltype = AA  length = 40
FEATURE                 Location/Qualifiers
source                  1..40
                        mol_type = protein
                        organism = synthetic construct
VARIANT                 1..40
                        note = This sequence may encompass 1-20 GS repeating units
SEQUENCE: 115
GSGSGSGSGS GSGSGSGSGS GSGSGSGSGS GSGSGSGSGS                             40

SEQ ID NO: 116          moltype = AA  length = 30
FEATURE                 Location/Qualifiers
source                  1..30
                        mol_type = protein
                        organism = synthetic construct
VARIANT                 1..30
                        note = This sequence may encompass 1-15 GS repeating units
SEQUENCE: 116
GSGSGSGSGS GSGSGSGSGS GSGSGSGSGS                                        30

SEQ ID NO: 117          moltype = AA  length = 60
FEATURE                 Location/Qualifiers
source                  1..60
                        mol_type = protein
                        organism = synthetic construct
VARIANT                 1..60
                        note = This sequence may encompass 1-20 GGS repeating units
SEQUENCE: 117
GGSGGSGGSG GSGGSGGSGG SGGSGGSGGS GGSGGSGGSG GSGGSGGSGG SGGSGGSGGS       60

SEQ ID NO: 118          moltype = AA  length = 45
FEATURE                 Location/Qualifiers
source                  1..45
                        mol_type = protein
                        organism = synthetic construct
VARIANT                 1..45
                        note = This sequence may encompass 1-15 GGS repeating units
SEQUENCE: 118
GGSGGSGGSG GSGGSGGSGG SGGSGGSGGS GGSGGSGGSG GSGGS                       45

SEQ ID NO: 119          moltype = AA  length = 80
FEATURE                 Location/Qualifiers
source                  1..80
                        mol_type = protein
                        organism = synthetic construct
VARIANT                 1..80
                        note = This sequence may encompass 1-20 GGGS repeating units
SEQUENCE: 119
GGGSGGGSGG GSGGGSGGGS GGGSGGGSGG GSGGGSGGGS GGGSGGGSGG GSGGGSGGGS       60
GGGSGGGSGG GSGGGSGGGS                                                   80

SEQ ID NO: 120          moltype = AA  length = 60
FEATURE                 Location/Qualifiers
source                  1..60
                        mol_type = protein
                        organism = synthetic construct
VARIANT                 1..60
                        note = This sequence may encompass 1-15 GGGS repeating units
SEQUENCE: 120
GGGSGGGSGG GSGGGSGGGS GGGSGGGSGG GSGGGSGGGS GGGSGGGSGG GSGGGSGGGS       60

SEQ ID NO: 121          moltype = AA  length = 100
FEATURE                 Location/Qualifiers
source                  1..100
                        mol_type = protein
                        organism = synthetic construct
```

```
VARIANT                 1..100
                        note = This sequence may encompass 1-20 GGGGS repeating
                         units
SEQUENCE: 121
GGGGSGGGGS GGGGSGGGGS GGGGSGGGGS GGGGSGGGGS GGGGSGGGGS GGGGSGGGGS     60
GGGGSGGGGS GGGGSGGGGS GGGGSGGGGS GGGGSGGGGS                          100

SEQ ID NO: 122          moltype = AA   length = 40
FEATURE                 Location/Qualifiers
source                  1..40
                        mol_type = protein
                        organism = synthetic construct
VARIANT                 1..40
                        note = This sequence may encompass 1-8 GGGGS repeating units
SEQUENCE: 122
GGGGSGGGGS GGGGSGGGGS GGGGSGGGGS GGGGSGGGGS                           40

SEQ ID NO: 123          moltype = AA   length = 50
FEATURE                 Location/Qualifiers
source                  1..50
                        mol_type = protein
                        organism = synthetic construct
VARIANT                 1..50
                        note = This sequence may encompass 1-10 GGGGS repeating
                         units
SEQUENCE: 123
GGGGSGGGGS GGGGSGGGGS GGGGSGGGGS GGGGSGGGGS GGGGSGGGGS                50

SEQ ID NO: 124          moltype = AA   length = 25
FEATURE                 Location/Qualifiers
source                  1..25
                        mol_type = protein
                        organism = synthetic construct
VARIANT                 1..25
                        note = This sequence may encompass 1-5 GGGGS repeating units
SEQUENCE: 124
GGGGSGGGGS GGGGSGGGGS GGGGS                                           25

SEQ ID NO: 125          moltype = AA   length = 5
FEATURE                 Location/Qualifiers
source                  1..5
                        mol_type = protein
                        organism = synthetic construct
SEQUENCE: 125
GGGGS                                                                  5

SEQ ID NO: 126          moltype = AA   length = 10
FEATURE                 Location/Qualifiers
source                  1..10
                        mol_type = protein
                        organism = synthetic construct
SEQUENCE: 126
GGGGSGGGGS                                                            10

SEQ ID NO: 127          moltype = AA   length = 15
FEATURE                 Location/Qualifiers
source                  1..15
                        mol_type = protein
                        organism = synthetic construct
SEQUENCE: 127
GGGGSGGGGS GGGGS                                                      15

SEQ ID NO: 128          moltype = AA   length = 20
FEATURE                 Location/Qualifiers
source                  1..20
                        mol_type = protein
                        organism = synthetic construct
SEQUENCE: 128
GGGGSGGGGS GGGGSGGGGS                                                 20

SEQ ID NO: 129          moltype = AA   length = 25
FEATURE                 Location/Qualifiers
source                  1..25
                        mol_type = protein
                        organism = synthetic construct
SEQUENCE: 129
GGGGSGGGGS GGGGSGGGGS GGGGS                                           25

SEQ ID NO: 130          moltype = AA   length = 51
```

| | | |
|---|---|---|
| FEATURE | Location/Qualifiers | |
| source | 1..51 | |
| | mol_type = protein | |
| | organism = synthetic construct | |
| VARIANT | 1..50 | |
| | note = This region may encompass 1-10 GGGGS repeating units | |
| SEQUENCE: 130 | | |
| GGGGSGGGGS GGGGSGGGGS GGGGSGGGGS GGGGSGGGGS GGGGSGGGGS G | | 51 |
| | | |
| SEQ ID NO: 131 | moltype = AA   length = 26 | |
| FEATURE | Location/Qualifiers | |
| source | 1..26 | |
| | mol_type = protein | |
| | organism = synthetic construct | |
| VARIANT | 1..25 | |
| | note = This region may encompass 1-5 GGGGS repeating units | |
| SEQUENCE: 131 | | |
| GGGGSGGGGS GGGGSGGGGS GGGGSG | | 26 |
| | | |
| SEQ ID NO: 132 | moltype = AA   length = 6 | |
| FEATURE | Location/Qualifiers | |
| source | 1..6 | |
| | mol_type = protein | |
| | organism = synthetic construct | |
| SEQUENCE: 132 | | |
| GGGGSG | | 6 |
| | | |
| SEQ ID NO: 133 | moltype = AA   length = 11 | |
| FEATURE | Location/Qualifiers | |
| source | 1..11 | |
| | mol_type = protein | |
| | organism = synthetic construct | |
| SEQUENCE: 133 | | |
| GGGGSGGGGS G | | 11 |
| | | |
| SEQ ID NO: 134 | moltype = AA   length = 16 | |
| FEATURE | Location/Qualifiers | |
| source | 1..16 | |
| | mol_type = protein | |
| | organism = synthetic construct | |
| SEQUENCE: 134 | | |
| GGGGSGGGGS GGGGSG | | 16 |
| | | |
| SEQ ID NO: 135 | moltype = AA   length = 21 | |
| FEATURE | Location/Qualifiers | |
| source | 1..21 | |
| | mol_type = protein | |
| | organism = synthetic construct | |
| SEQUENCE: 135 | | |
| GGGGSGGGGS GGGGSGGGGS G | | 21 |
| | | |
| SEQ ID NO: 136 | moltype = AA   length = 26 | |
| FEATURE | Location/Qualifiers | |
| source | 1..26 | |
| | mol_type = protein | |
| | organism = synthetic construct | |
| SEQUENCE: 136 | | |
| GGGGSGGGGS GGGGSGGGGS GGGGSG | | 26 |
| | | |
| SEQ ID NO: 137 | moltype = AA   length = 52 | |
| FEATURE | Location/Qualifiers | |
| source | 1..52 | |
| | mol_type = protein | |
| | organism = synthetic construct | |
| VARIANT | 1..50 | |
| | note = This region may encompass 1-10 GGGGS repeating units | |
| SEQUENCE: 137 | | |
| GGGGSGGGGS GGGGSGGGGS GGGGSGGGGS GGGGSGGGGS GGGGSGGGGS GG | | 52 |
| | | |
| SEQ ID NO: 138 | moltype = AA   length = 27 | |
| FEATURE | Location/Qualifiers | |
| source | 1..27 | |
| | mol_type = protein | |
| | organism = synthetic construct | |
| VARIANT | 1..25 | |
| | note = This region may encompass 1-5 GGGGS repeating units | |
| SEQUENCE: 138 | | |
| GGGGSGGGGS GGGGSGGGGS GGGGSGG | | 27 |

```
SEQ ID NO: 139          moltype = AA   length = 7
FEATURE                 Location/Qualifiers
source                  1..7
                        mol_type = protein
                        organism = synthetic construct
SEQUENCE: 139
GGGGSGG                                                                    7

SEQ ID NO: 140          moltype = AA   length = 12
FEATURE                 Location/Qualifiers
source                  1..12
                        mol_type = protein
                        organism = synthetic construct
SEQUENCE: 140
GGGGSGGGGS GG                                                              12

SEQ ID NO: 141          moltype = AA   length = 17
FEATURE                 Location/Qualifiers
source                  1..17
                        mol_type = protein
                        organism = synthetic construct
SEQUENCE: 141
GGGGSGGGGS GGGGSGG                                                         17

SEQ ID NO: 142          moltype = AA   length = 22
FEATURE                 Location/Qualifiers
source                  1..22
                        mol_type = protein
                        organism = synthetic construct
SEQUENCE: 142
GGGGSGGGGS GGGGSGGGGS GG                                                   22

SEQ ID NO: 143          moltype = AA   length = 27
FEATURE                 Location/Qualifiers
source                  1..27
                        mol_type = protein
                        organism = synthetic construct
SEQUENCE: 143
GGGGSGGGGS GGGGSGGGGS GGGGSGG                                              27

SEQ ID NO: 144          moltype =     length =
SEQUENCE: 144
000

SEQ ID NO: 145          moltype =     length =
SEQUENCE: 145
000

SEQ ID NO: 146          moltype =     length =
SEQUENCE: 146
000

SEQ ID NO: 147          moltype =     length =
SEQUENCE: 147
000

SEQ ID NO: 148          moltype =     length =
SEQUENCE: 148
000

SEQ ID NO: 149          moltype =     length =
SEQUENCE: 149
000

SEQ ID NO: 150          moltype = AA   length = 42
FEATURE                 Location/Qualifiers
source                  1..42
                        mol_type = protein
                        organism = synthetic construct
VARIANT                 1..40
                        note = This region may encompass 1-20 GS repeating units
SEQUENCE: 150
GSGSGSGSGS GSGSGSGSGS GSGSGSGSGS GSGSGSGSGS GG                             42

SEQ ID NO: 151          moltype = AA   length = 32
FEATURE                 Location/Qualifiers
source                  1..32
                        mol_type = protein
                        organism = synthetic construct
```

| | |
|---|---|
| VARIANT | 1..30<br>note = This region may encompass 1-15 GS repeating units |

SEQUENCE: 151
```
GSGSGSGSGS GSGSGSGSGS GSGSGSGSGS GG                               32
```

| | |
|---|---|
| SEQ ID NO: 152 | moltype = AA  length = 62 |
| FEATURE | Location/Qualifiers |
| source | 1..62<br>mol_type = protein<br>organism = synthetic construct |
| VARIANT | 1..60<br>note = This region may encompass 1-20 GGS repeating units |

SEQUENCE: 152
```
GGSGGSGGSG GGGSGGSGG SGGSGGSGGS GGSGGSGGSG GSGGSGGSGG SGGSGGSGGS   60
GG                                                                62
```

| | |
|---|---|
| SEQ ID NO: 153 | moltype = AA  length = 47 |
| FEATURE | Location/Qualifiers |
| source | 1..47<br>mol_type = protein<br>organism = synthetic construct |
| VARIANT | 1..45<br>note = This region may encompass 1-15 GGS repeating units |

SEQUENCE: 153
```
GGSGGSGGSG GGGSGGSGG SGGSGGSGGS GGSGGSGGSG GSGGSGG                 47
```

| | |
|---|---|
| SEQ ID NO: 154 | moltype = AA  length = 82 |
| FEATURE | Location/Qualifiers |
| source | 1..82<br>mol_type = protein<br>organism = synthetic construct |
| VARIANT | 1..80<br>note = This region may encompass 1-20 GGGS repeating units |

SEQUENCE: 154
```
GGGSGGGSGG GSGGGSGGGS GGGSGGGSGG GSGGGSGGGS GGGSGGGSGG GSGGGSGGGS   60
GGGSGGGSGG GSGGGSGGGS GG                                          82
```

| | |
|---|---|
| SEQ ID NO: 155 | moltype = AA  length = 62 |
| FEATURE | Location/Qualifiers |
| source | 1..62<br>mol_type = protein<br>organism = synthetic construct |
| VARIANT | 1..60<br>note = This region may encompass 1-15 GGGS repeating units |

SEQUENCE: 155
```
GGGSGGGSGG GSGGGSGGGS GGGSGGGSGG GSGGGSGGGS GGGSGGGSGG GSGGGSGGGS   60
GG                                                                62
```

| | |
|---|---|
| SEQ ID NO: 156 | moltype = AA  length = 102 |
| FEATURE | Location/Qualifiers |
| source | 1..102<br>mol_type = protein<br>organism = synthetic construct |
| VARIANT | 1..100<br>note = This region may encompass 1-20 GGGGS repeating units |

SEQUENCE: 156
```
GGGGSGGGGS GGGGSGGGGS GGGGSGGGGS GGGGSGGGGS GGGGSGGGGS GGGGSGGGGS   60
GGGGSGGGGS GGGGSGGGGS GGGGSGGGGS GGGGSGGGGS GG                    102
```

| | |
|---|---|
| SEQ ID NO: 157 | moltype = AA  length = 77 |
| FEATURE | Location/Qualifiers |
| source | 1..77<br>mol_type = protein<br>organism = synthetic construct |
| VARIANT | 1..75<br>note = This region may encompass 1-15 GGGGS repeating units |

SEQUENCE: 157
```
GGGGSGGGGS GGGGSGGGGS GGGGSGGGGS GGGGSGGGGS GGGGSGGGGS GGGGSGGGGS   60
GGGGSGGGGS GGGGSGG                                                77
```

| | |
|---|---|
| SEQ ID NO: 158 | moltype = AA  length = 10 |
| FEATURE | Location/Qualifiers |
| source | 1..10<br>mol_type = protein<br>organism = synthetic construct |

SEQUENCE: 158
```
GSGSGSGSGS                                                        10
```

| | |
|---|---|
| SEQ ID NO: 159 | moltype = AA  length = 12 |

```
FEATURE                 Location/Qualifiers
source                  1..12
                        mol_type = protein
                        organism = synthetic construct
SEQUENCE: 159
GSGSGSGSGS GS                                                              12

SEQ ID NO: 160          moltype = AA  length = 14
FEATURE                 Location/Qualifiers
source                  1..14
                        mol_type = protein
                        organism = synthetic construct
SEQUENCE: 160
GSGSGSGSGS GSGS                                                            14

SEQ ID NO: 161          moltype = AA  length = 16
FEATURE                 Location/Qualifiers
source                  1..16
                        mol_type = protein
                        organism = synthetic construct
SEQUENCE: 161
GSGSGSGSGS GSGSGS                                                          16

SEQ ID NO: 162          moltype = AA  length = 18
FEATURE                 Location/Qualifiers
source                  1..18
                        mol_type = protein
                        organism = synthetic construct
SEQUENCE: 162
GSGSGSGSGS GSGSGSGS                                                        18

SEQ ID NO: 163          moltype = AA  length = 20
FEATURE                 Location/Qualifiers
source                  1..20
                        mol_type = protein
                        organism = synthetic construct
SEQUENCE: 163
GSGSGSGSGS GSGSGSGSGS                                                      20

SEQ ID NO: 164          moltype = AA  length = 22
FEATURE                 Location/Qualifiers
source                  1..22
                        mol_type = protein
                        organism = synthetic construct
SEQUENCE: 164
GSGSGSGSGS GSGSGSGSGS GS                                                   22

SEQ ID NO: 165          moltype = AA  length = 24
FEATURE                 Location/Qualifiers
source                  1..24
                        mol_type = protein
                        organism = synthetic construct
SEQUENCE: 165
GSGSGSGSGS GSGSGSGSGS GSGS                                                 24

SEQ ID NO: 166          moltype = AA  length = 26
FEATURE                 Location/Qualifiers
source                  1..26
                        mol_type = protein
                        organism = synthetic construct
SEQUENCE: 166
GSGSGSGSGS GSGSGSGSGS GSGSGS                                               26

SEQ ID NO: 167          moltype = AA  length = 28
FEATURE                 Location/Qualifiers
source                  1..28
                        mol_type = protein
                        organism = synthetic construct
SEQUENCE: 167
GSGSGSGSGS GSGSGSGSGS GSGSGSGS                                             28

SEQ ID NO: 168          moltype = AA  length = 30
FEATURE                 Location/Qualifiers
source                  1..30
                        mol_type = protein
                        organism = synthetic construct
SEQUENCE: 168
GSGSGSGSGS GSGSGSGSGS GSGSGSGSGS                                           30
```

```
SEQ ID NO: 169          moltype = AA   length = 12
FEATURE                 Location/Qualifiers
source                  1..12
                        mol_type = protein
                        organism = synthetic construct
SEQUENCE: 169
GSGSGSGSGS GG                                                               12

SEQ ID NO: 170          moltype = AA   length = 14
FEATURE                 Location/Qualifiers
source                  1..14
                        mol_type = protein
                        organism = synthetic construct
SEQUENCE: 170
GSGSGSGSGS GSGG                                                             14

SEQ ID NO: 171          moltype = AA   length = 16
FEATURE                 Location/Qualifiers
source                  1..16
                        mol_type = protein
                        organism = synthetic construct
SEQUENCE: 171
GSGSGSGSGS GSGSGG                                                           16

SEQ ID NO: 172          moltype = AA   length = 18
FEATURE                 Location/Qualifiers
source                  1..18
                        mol_type = protein
                        organism = synthetic construct
SEQUENCE: 172
GSGSGSGSGS GSGSGSGG                                                         18

SEQ ID NO: 173          moltype = AA   length = 20
FEATURE                 Location/Qualifiers
source                  1..20
                        mol_type = protein
                        organism = synthetic construct
SEQUENCE: 173
GSGSGSGSGS GSGSGSGSGG                                                       20

SEQ ID NO: 174          moltype = AA   length = 22
FEATURE                 Location/Qualifiers
source                  1..22
                        mol_type = protein
                        organism = synthetic construct
SEQUENCE: 174
GSGSGSGSGS GSGSGSGSGS GG                                                    22

SEQ ID NO: 175          moltype = AA   length = 24
FEATURE                 Location/Qualifiers
source                  1..24
                        mol_type = protein
                        organism = synthetic construct
SEQUENCE: 175
GSGSGSGSGS GSGSGSGSGS GSGG                                                  24

SEQ ID NO: 176          moltype = AA   length = 26
FEATURE                 Location/Qualifiers
source                  1..26
                        mol_type = protein
                        organism = synthetic construct
SEQUENCE: 176
GSGSGSGSGS GSGSGSGSGS GSGSGG                                                26

SEQ ID NO: 177          moltype = AA   length = 28
FEATURE                 Location/Qualifiers
source                  1..28
                        mol_type = protein
                        organism = synthetic construct
SEQUENCE: 177
GSGSGSGSGS GSGSGSGSGS GSGSGSGG                                              28

SEQ ID NO: 178          moltype = AA   length = 30
FEATURE                 Location/Qualifiers
source                  1..30
                        mol_type = protein
                        organism = synthetic construct
SEQUENCE: 178
GSGSGSGSGS GSGSGSGSGS GSGSGSGSGG                                            30
```

```
SEQ ID NO: 179          moltype = AA  length = 32
FEATURE                 Location/Qualifiers
source                  1..32
                        mol_type = protein
                        organism = synthetic construct
SEQUENCE: 179
GSGSGSGSGS GSGSGSGSGS GSGSGSGSGS GG                                  32

SEQ ID NO: 180          moltype =     length =
SEQUENCE: 180
000

SEQ ID NO: 181          moltype =     length =
SEQUENCE: 181
000

SEQ ID NO: 182          moltype =     length =
SEQUENCE: 182
000

SEQ ID NO: 183          moltype =     length =
SEQUENCE: 183
000

SEQ ID NO: 184          moltype =     length =
SEQUENCE: 184
000

SEQ ID NO: 185          moltype =     length =
SEQUENCE: 185
000

SEQ ID NO: 186          moltype =     length =
SEQUENCE: 186
000

SEQ ID NO: 187          moltype =     length =
SEQUENCE: 187
000

SEQ ID NO: 188          moltype =     length =
SEQUENCE: 188
000

SEQ ID NO: 189          moltype =     length =
SEQUENCE: 189
000

SEQ ID NO: 190          moltype =     length =
SEQUENCE: 190
000

SEQ ID NO: 191          moltype =     length =
SEQUENCE: 191
000

SEQ ID NO: 192          moltype =     length =
SEQUENCE: 192
000

SEQ ID NO: 193          moltype =     length =
SEQUENCE: 193
000

SEQ ID NO: 194          moltype =     length =
SEQUENCE: 194
000

SEQ ID NO: 195          moltype =     length =
SEQUENCE: 195
000

SEQ ID NO: 196          moltype =     length =
SEQUENCE: 196
000

SEQ ID NO: 197          moltype =     length =
SEQUENCE: 197
```

```
000

SEQ ID NO: 198          moltype =    length =
SEQUENCE: 198
000

SEQ ID NO: 199          moltype =    length =
SEQUENCE: 199
000

SEQ ID NO: 200          moltype =    length =
SEQUENCE: 200
000

SEQ ID NO: 201          moltype = AA  length = 20
FEATURE                 Location/Qualifiers
source                  1..20
                        mol_type = protein
                        organism = synthetic construct
SEQUENCE: 201
YPCWLARVGE LCDLDSGDVH                                             20

SEQ ID NO: 202          moltype = AA  length = 20
FEATURE                 Location/Qualifiers
source                  1..20
                        mol_type = protein
                        organism = synthetic construct
SEQUENCE: 202
APCWLARVGE LCDLDSGDVH                                             20

SEQ ID NO: 203          moltype = AA  length = 20
FEATURE                 Location/Qualifiers
source                  1..20
                        mol_type = protein
                        organism = synthetic construct
SEQUENCE: 203
APCALARVGE LCDLDSGDVH                                             20

SEQ ID NO: 204          moltype = AA  length = 20
FEATURE                 Location/Qualifiers
source                  1..20
                        mol_type = protein
                        organism = synthetic construct
SEQUENCE: 204
APCALAAVGE LCDLDSGDVH                                             20

SEQ ID NO: 205          moltype = AA  length = 20
FEATURE                 Location/Qualifiers
source                  1..20
                        mol_type = protein
                        organism = synthetic construct
SEQUENCE: 205
APCALAAVGA LCDLDSGDVH                                             20

SEQ ID NO: 206          moltype = AA  length = 20
FEATURE                 Location/Qualifiers
source                  1..20
                        mol_type = protein
                        organism = synthetic construct
SEQUENCE: 206
APCALAAVGA LCDLASGDVH                                             20

SEQ ID NO: 207          moltype = AA  length = 20
FEATURE                 Location/Qualifiers
source                  1..20
                        mol_type = protein
                        organism = synthetic construct
SEQUENCE: 207
APCALAAVGA LCDLAAGDVH                                             20

SEQ ID NO: 208          moltype =    length =
SEQUENCE: 208
000

SEQ ID NO: 209          moltype =    length =
SEQUENCE: 209
000

SEQ ID NO: 210          moltype =    length =
```

-continued

| | | |
|---|---|---|
| SEQUENCE: 210 000 | | |
| SEQ ID NO: 211 FEATURE source | moltype = AA length = 14 Location/Qualifiers 1..14 mol_type = protein organism = synthetic construct | |
| SEQUENCE: 211 YWCWMAQVGE LCDL | | 14 |
| SEQ ID NO: 212 FEATURE source | moltype = AA length = 14 Location/Qualifiers 1..14 mol_type = protein organism = synthetic construct | |
| SEQUENCE: 212 YHCWMAQVGE LCDL | | 14 |
| SEQ ID NO: 213 FEATURE source | moltype = AA length = 14 Location/Qualifiers 1..14 mol_type = protein organism = synthetic construct | |
| SEQUENCE: 213 YHCWMGQVGE LCDL | | 14 |
| SEQ ID NO: 214 FEATURE source | moltype = AA length = 14 Location/Qualifiers 1..14 mol_type = protein organism = synthetic construct | |
| SEQUENCE: 214 YHCWMGQMGE LCDL | | 14 |
| SEQ ID NO: 215 FEATURE source | moltype = AA length = 14 Location/Qualifiers 1..14 mol_type = protein organism = synthetic construct | |
| SEQUENCE: 215 YHCWMGQMGE LCEL | | 14 |
| SEQ ID NO: 216 FEATURE source | moltype = AA length = 14 Location/Qualifiers 1..14 mol_type = protein organism = synthetic construct | |
| SEQUENCE: 216 YHCWMGQMGE LCEM | | 14 |
| SEQ ID NO: 217 SEQUENCE: 217 000 | moltype = length = | |
| SEQ ID NO: 218 SEQUENCE: 218 000 | moltype = length = | |
| SEQ ID NO: 219 SEQUENCE: 219 000 | moltype = length = | |
| SEQ ID NO: 220 FEATURE source | moltype = AA length = 14 Location/Qualifiers 1..14 mol_type = protein organism = synthetic construct | |
| SEQUENCE: 220 KYCGFAQLGE LCVL | | 14 |
| SEQ ID NO: 221 FEATURE source | moltype = AA length = 15 Location/Qualifiers 1..15 mol_type = protein organism = synthetic construct | |
| SEQUENCE: 221 GKYCGFAQLG ELCVL | | 15 |

| | | |
|---|---|---|
| SEQ ID NO: 222<br>FEATURE<br>source<br>SEQUENCE: 222<br>GGKYCGFAQL GELCVL | moltype = AA  length = 16<br>Location/Qualifiers<br>1..16<br>mol_type = protein<br>organism = synthetic construct | 16 |
| SEQ ID NO: 223<br>FEATURE<br>source<br>SEQUENCE: 223<br>GGGKYCGFAQ LGELCVL | moltype = AA  length = 17<br>Location/Qualifiers<br>1..17<br>mol_type = protein<br>organism = synthetic construct | 17 |
| SEQ ID NO: 224<br>FEATURE<br>source<br>SEQUENCE: 224<br>KYCGFAQLGE LCVLG | moltype = AA  length = 15<br>Location/Qualifiers<br>1..15<br>mol_type = protein<br>organism = synthetic construct | 15 |
| SEQ ID NO: 225<br>FEATURE<br>source<br>SEQUENCE: 225<br>KYCGFAQLGE LCVLGG | moltype = AA  length = 16<br>Location/Qualifiers<br>1..16<br>mol_type = protein<br>organism = synthetic construct | 16 |
| SEQ ID NO: 226<br>FEATURE<br>source<br>SEQUENCE: 226<br>KYCGFAQLGE LCVLGGG | moltype = AA  length = 17<br>Location/Qualifiers<br>1..17<br>mol_type = protein<br>organism = synthetic construct | 17 |
| SEQ ID NO: 227<br>FEATURE<br>source<br>SEQUENCE: 227<br>GKYCGFAQLG ELCVLG | moltype = AA  length = 16<br>Location/Qualifiers<br>1..16<br>mol_type = protein<br>organism = synthetic construct | 16 |
| SEQ ID NO: 228<br>FEATURE<br>source<br>SEQUENCE: 228<br>GGKYCGFAQL GELCVLG | moltype = AA  length = 17<br>Location/Qualifiers<br>1..17<br>mol_type = protein<br>organism = synthetic construct | 17 |
| SEQ ID NO: 229<br>SEQUENCE: 229<br>000 | moltype =    length = | |
| SEQ ID NO: 230<br>SEQUENCE: 230<br>000 | moltype =    length = | |
| SEQ ID NO: 231<br>SEQUENCE: 231<br>000 | moltype =    length = | |
| SEQ ID NO: 232<br>SEQUENCE: 232<br>000 | moltype =    length = | |
| SEQ ID NO: 233<br>SEQUENCE: 233<br>000 | moltype =    length = | |
| SEQ ID NO: 234<br>SEQUENCE: 234<br>000 | moltype =    length = | |

| | | |
|---|---|---|
| SEQ ID NO: 235 SEQUENCE: 235 000 | moltype = | length = |
| SEQ ID NO: 236 SEQUENCE: 236 000 | moltype = | length = |
| SEQ ID NO: 237 SEQUENCE: 237 000 | moltype = | length = |
| SEQ ID NO: 238 SEQUENCE: 238 000 | moltype = | length = |
| SEQ ID NO: 239 SEQUENCE: 239 000 | moltype = | length = |
| SEQ ID NO: 240 SEQUENCE: 240 000 | moltype = | length = |
| SEQ ID NO: 241 SEQUENCE: 241 000 | moltype = | length = |
| SEQ ID NO: 242 SEQUENCE: 242 000 | moltype = | length = |
| SEQ ID NO: 243 SEQUENCE: 243 000 | moltype = | length = |
| SEQ ID NO: 244 SEQUENCE: 244 000 | moltype = | length = |
| SEQ ID NO: 245 SEQUENCE: 245 000 | moltype = | length = |
| SEQ ID NO: 246 SEQUENCE: 246 000 | moltype = | length = |
| SEQ ID NO: 247 SEQUENCE: 247 000 | moltype = | length = |
| SEQ ID NO: 248 SEQUENCE: 248 000 | moltype = | length = |
| SEQ ID NO: 249 SEQUENCE: 249 000 | moltype = | length = |
| SEQ ID NO: 250 SEQUENCE: 250 000 | moltype = | length = |
| SEQ ID NO: 251 SEQUENCE: 251 000 | moltype = | length = |
| SEQ ID NO: 252 SEQUENCE: 252 000 | moltype = | length = |
| SEQ ID NO: 253 SEQUENCE: 253 000 | moltype = | length = |
| SEQ ID NO: 254 SEQUENCE: 254 | moltype = | length = |

```
SEQ ID NO: 255          moltype =     length =
SEQUENCE: 255
000

SEQ ID NO: 256          moltype =     length =
SEQUENCE: 256
000

SEQ ID NO: 257          moltype =     length =
SEQUENCE: 257
000

SEQ ID NO: 258          moltype =     length =
SEQUENCE: 258
000

SEQ ID NO: 259          moltype =     length =
SEQUENCE: 259
000

SEQ ID NO: 260          moltype =     length =
SEQUENCE: 260
000

SEQ ID NO: 261          moltype =     length =
SEQUENCE: 261
000

SEQ ID NO: 262          moltype =     length =
SEQUENCE: 262
000

SEQ ID NO: 263          moltype =     length =
SEQUENCE: 263
000

SEQ ID NO: 264          moltype =     length =
SEQUENCE: 264
000

SEQ ID NO: 265          moltype =     length =
SEQUENCE: 265
000

SEQ ID NO: 266          moltype =     length =
SEQUENCE: 266
000

SEQ ID NO: 267          moltype =     length =
SEQUENCE: 267
000

SEQ ID NO: 268          moltype =     length =
SEQUENCE: 268
000

SEQ ID NO: 269          moltype =     length =
SEQUENCE: 269
000

SEQ ID NO: 270          moltype =     length =
SEQUENCE: 270
000

SEQ ID NO: 271          moltype =     length =
SEQUENCE: 271
000

SEQ ID NO: 272          moltype =     length =
SEQUENCE: 272
000

SEQ ID NO: 273          moltype =     length =
SEQUENCE: 273
000

SEQ ID NO: 274          moltype =     length =
```

| | | |
|---|---|---|
| SEQUENCE: 274 000 | | |
| SEQ ID NO: 275 SEQUENCE: 275 000 | moltype = | length = |
| SEQ ID NO: 276 SEQUENCE: 276 000 | moltype = | length = |
| SEQ ID NO: 277 SEQUENCE: 277 000 | moltype = | length = |
| SEQ ID NO: 278 SEQUENCE: 278 000 | moltype = | length = |
| SEQ ID NO: 279 SEQUENCE: 279 000 | moltype = | length = |
| SEQ ID NO: 280 SEQUENCE: 280 000 | moltype = | length = |
| SEQ ID NO: 281 SEQUENCE: 281 000 | moltype = | length = |
| SEQ ID NO: 282 SEQUENCE: 282 000 | moltype = | length = |
| SEQ ID NO: 283 SEQUENCE: 283 000 | moltype = | length = |
| SEQ ID NO: 284 SEQUENCE: 284 000 | moltype = | length = |
| SEQ ID NO: 285 SEQUENCE: 285 000 | moltype = | length = |
| SEQ ID NO: 286 SEQUENCE: 286 000 | moltype = | length = |
| SEQ ID NO: 287 SEQUENCE: 287 000 | moltype = | length = |
| SEQ ID NO: 288 SEQUENCE: 288 000 | moltype = | length = |
| SEQ ID NO: 289 SEQUENCE: 289 000 | moltype = | length = |
| SEQ ID NO: 290 SEQUENCE: 290 000 | moltype = | length = |
| SEQ ID NO: 291 SEQUENCE: 291 000 | moltype = | length = |
| SEQ ID NO: 292 SEQUENCE: 292 000 | moltype = | length = |
| SEQ ID NO: 293 SEQUENCE: 293 000 | moltype = | length = |

```
SEQ ID NO: 294          moltype =    length =
SEQUENCE: 294
000

SEQ ID NO: 295          moltype =    length =
SEQUENCE: 295
000

SEQ ID NO: 296          moltype =    length =
SEQUENCE: 296
000

SEQ ID NO: 297          moltype =    length =
SEQUENCE: 297
000

SEQ ID NO: 298          moltype =    length =
SEQUENCE: 298
000

SEQ ID NO: 299          moltype =    length =
SEQUENCE: 299
000

SEQ ID NO: 300          moltype = AA  length = 24
FEATURE                 Location/Qualifiers
source                  1..24
                        mol_type = protein
                        organism = synthetic construct
SEQUENCE: 300
VHRIPWCTLD PGGLQCAWLR QMGG                                          24

SEQ ID NO: 301          moltype = AA  length = 30
FEATURE                 Location/Qualifiers
source                  1..30
                        mol_type = protein
                        organism = synthetic construct
VARIANT                 1..30
                        note = This sequence may encompass 5-15 GS repeating units
SEQUENCE: 301
GSGSGSGSGS GSGSGSGSGS GSGSGSGSGS                                    30

SEQ ID NO: 302          moltype = AA  length = 32
FEATURE                 Location/Qualifiers
source                  1..32
                        mol_type = protein
                        organism = synthetic construct
VARIANT                 1..30
                        note = This region may encompass 5-15 GS repeating units
SEQUENCE: 302
GSGSGSGSGS GSGSGSGSGS GSGSGSGSGS GG                                 32
```

What is claimed is:

1. An IL-7Rαγc ligand comprising:
   an IL-7Rα ligand comprising an amino acid sequence of SEQ ID NO: 1 or an amino acid sequence having greater than 70% sequence similarity to SEQ ID NO: 1; and
   an Rγc ligand comprising an amino acid sequence of SEQ ID NO: 11 or an amino acid sequence having greater than 70% sequence similarity to SEQ ID NO: 11.

2. The IL-7Rαγc ligand of claim 1, wherein the IL-7Rαγc ligand comprises:
   an IL-7Rα ligand comprising an amino acid sequence of SEQ ID NO: 1 and
   an Rγc ligand comprising an amino acid sequence of SEQ ID NO: 11.

3. The IL-7Rαγc ligand of claim 1, wherein the IL-7Rαγc ligand comprises:
   an IL-7Rα ligand comprising an amino acid sequence having greater than 70% sequence similarity to SEQ ID NO: 1; and
   an Rγc ligand comprising an amino acid sequence having greater than 70% sequence similarity to SEQ ID NO: 11.

4. The IL-7Rαγc ligand of claim 1, wherein the IL-7Rαγc ligand comprises:
   an IL-7Rα ligand comprising an amino acid sequence based on SEQ ID NO: 1 and having from 1 to 5 amino acid substitutions; and
   an Rγc ligand comprising an amino acid sequence based on SEQ ID NO: 11 and having from 1 to 5 amino acid substitutions.

5. The IL-7Rαγc ligand of claim 1, wherein each of the IL-7Rα ligand and the Rγc ligand independently comprises from 1 to 6 glycines (G) on the N-terminus, on the C-terminus, or on both the N-terminus and the C-terminus.

6. The IL-7Rαγc ligand of claim 1, wherein the IL-7Rα ligand and the Rγc ligand are bound together through a ligand linker.

7. The IL-7Rαγc ligand of claim 6, wherein the ligand linker comprises an amino acid sequence selected from any one of SEQ ID NO: 113-136.

8. The IL-7Rαγc ligand of claim 1, wherein the IL-7Rαγc ligand comprises:
an amino acid sequence of any one of SEQ ID NO: 21-26 or an amino acid sequence having greater than 70% sequence similarity to any one of SEQ ID NO: 21-26:
WGIPWCTLDPGSLQCAWLGKH-$X^1$-VVCQDWEGVELCWQ (SEQ ID NO: 21)
GWGIPWCTLDPGSLQCAWLGKH-$X^1$-VVCQDWEGVELCWQ (SEQ ID NO: 22)
WGIPWCTLDPGSLQCAWLGKH-$X^1$-VVCQDWEGVELCWQGG (SEQ ID NO: 23)
GWGIPWCTLDPGSLQCAWLGKH-$X^1$-VVCQDWEGVELCWQGG (SEQ ID NO: 24)
GGWGIPWCTLDPGSLQCAWLGKH-$X^1$-VVCQDWEGVELCWQGG (SEQ ID NO: 25)
GGGWGIPWCTLDPGSLQCAWLGKH-$X^1$-VVCQDWEGVELCWQGG (SEQ ID NO: 26);
and wherein $X^1$ is selected from an amino acid sequence of any one of SEQ ID NO: 101-143.

9. The IL-7Rαγc ligand of claim 8, wherein $X^1$ is selected from of any one of SEQ ID NO: 137-143.

10. The IL-7Rαγc ligand of claim 8, wherein $X^1$ has an amino acid sequence of SEQ ID NO: 139.

11. The IL-7Rαγc ligand of claim 1, wherein the IL-7Rαγc ligand comprises an amino acid sequence of any one of SEQ ID NO: 27-32, or an amino acid sequence having greater than 70% sequence similarity to any one of SEQ ID NO: 27-32.

12. The IL-7Rαγc ligand of claim 1, wherein the IL-7Rαγc ligand comprises an amino acid sequence of SEQ ID NO: 32 or an amino acid sequence having greater than 70% sequence similarity to SEQ ID NO: 32.

13. An IL-7Rαγc IgG-Fc fusion fragment comprising the IL-7Rαγc ligand of claim 1 bound to an IgG-Fc fragment.

14. The IL-7Rαγc IgG-Fc fusion fragment of claim 13, wherein the IgG-Fc fragment is selected from an IgG1-Fc fragment, an IgG2-Fc fragment, and an IgG4-Fc fragment.

15. The IL-7Rαγc IgG-Fc fusion fragment of claim 13, wherein the IgG-Fc fragment is an IgG2-Fc fragment.

16. The IL-7Rαγc IgG-Fc fusion fragment of claim 13, wherein the IL-7Rαγc ligand is bound to the IgG-Fc fragment through an IgG-Fc linker.

17. The IL-7Rαγc IgG-Fc fusion fragment of claim 16, wherein the IgG-Fc linker comprises an amino acid sequence of any one of SEQ ID NO: 150-179.

18. The IL-7Rαγc IgG-Fc fusion fragment of claim 16, wherein the IgG-Fc linker comprises an amino acid sequence of SEQ ID NO: 163.

19. The IL-7Rαγc IgG-Fc fusion fragment of claim 13, wherein the IL-7Rαγc IgG-Fc fusion fragment comprises an amino acid sequence having greater than 70% sequence similarity to any one of SEQ ID NO: 44-55.

20. The IL-7Rαγc IgG-Fc fusion fragment of claim 13, wherein the IL-7Rαγc IgG-Fc fusion fragment comprises an amino acid sequence of any one of SEQ ID NO: 44-55.

21. The IL-7Rαγc IgG-Fc fusion fragment of claim 13, wherein the IL-7Rαγc IgG-Fc fusion fragment comprises an amino acid sequence having greater than 70% sequence similarity to SEQ ID NO: 45.

22. The IL-7Rαγc IgG-Fc fusion fragment of claim 13, wherein the IL-7Rαγc IgG-Fc fusion fragment comprises an amino acid sequence having SEQ ID NO: 45.

23. An IL-7Rαγc IgG-Fc fusion protein comprising:
a first IL-7Rαγc IgG-Fc fusion fragment of claim 13; and
a second IL-7Rαγc IgG-Fc fusion fragment of claim 13,
wherein the IgG-Fc of the first IL-7Rαγc IgG-Fc fusion fragment comprises a first hinge region; wherein the IgG-Fc of the second IL-7Rαγc IgG-Fc fusion fragment comprises a second hinge region; and
wherein the first IL-7Rαγc IgG-Fc fusion fragment and the second first IL-7Rαγc IgG-Fc fusion fragment are bound to each other at the first hinge region and the second hinge region through disulfide bonds.

24. The IL-7Rαγc IgG-Fc fusion protein of claim 23, wherein the first IL-7Rαγc IgG-Fc fusion fragment and the second IL-7Rαγc IgG-Fc fusion fragment have the same amino acid sequence.

25. The IL-7Rαγc IgG-Fc fusion protein of claim 23, wherein the first IL-7Rαγc IgG-Fc fusion fragment and the second IL-7Rαγc IgG-Fc fusion fragment comprise different amino acid sequences.

26. The IL-7Rαγc IgG-Fc fusion protein of claim 23, wherein the first IL-7Rαγc IgG-Fc fusion fragment and the second IL-7Rαγc IgG-Fc fusion fragment comprise a different IL-7Rα ligand.

27. The IL-7Rαγc IgG-Fc fusion protein of claim 23, wherein the first IL-7Rαγc IgG-Fc fusion fragment and the second IL-7Rαγc IgG-Fc fusion fragment comprise a different Rγc ligand.

28. A pharmaceutical composition comprising the IL-7Rαγc ligand of claim 1.

29. A pharmaceutical composition comprising the IL-7Rαγc IgG-Fc fusion protein of claim 13.

* * * * *